(12) United States Patent
Tai et al.

(10) Patent No.: US 8,071,294 B2
(45) Date of Patent: Dec. 6, 2011

(54) CANCER THERAPY SENSITIZER

(75) Inventors: Isabella T. Tai, Vancouver (CA); Lan Bo Chen, Lexington, MA (US)

(73) Assignee: Dana-Farber Cancer Institute, Boston, MA (US)

(*) Notice: Subject to any disclaimer, the term of this patent is extended or adjusted under 35 U.S.C. 154(b) by 0 days.

(21) Appl. No.: 12/625,841

(22) Filed: Nov. 25, 2009

(65) Prior Publication Data
US 2010/0151006 A1 Jun. 17, 2010

Related U.S. Application Data

(63) Continuation of application No. 11/181,115, filed on Jul. 14, 2005, now Pat. No. 7,638,272, which is a continuation of application No. PCT/US2004/000901, filed on Jan. 14, 2004.

(60) Provisional application No. 60/440,009, filed on Jan. 14, 2003.

(51) Int. Cl.
*C12Q 1/68* (2006.01)
*G01N 33/53* (2006.01)
*A61K 48/00* (2006.01)

(52) U.S. Cl. ............... 435/6; 435/7.1; 514/44 R

(58) Field of Classification Search ............... None
See application file for complete search history.

(56) References Cited

U.S. PATENT DOCUMENTS

| | | | |
|---|---|---|---|
| 5,674,743 A | 10/1997 | Ulmer | |
| 5,962,320 A | 10/1999 | Robinson | |
| 6,187,307 B1 | 2/2001 | Cohen | |
| 6,194,205 B1 | 2/2001 | Staege et al. | |
| 6,239,326 B1 | 5/2001 | Howe | |
| 6,316,193 B1 | 11/2001 | He et al. | |
| 6,387,664 B1 | 5/2002 | Ikemoto | |
| 6,406,693 B1* | 6/2002 | Thorpe et al. ............... | 424/130.1 |
| 6,475,784 B1 | 11/2002 | Papkoff | |
| 7,485,414 B2* | 2/2009 | Lorens et al. ............... | 435/4 |
| 2002/0169121 A1 | 11/2002 | Ronai | |
| 2003/0082228 A1 | 5/2003 | Flowers et al. | |
| 2003/0180306 A1 | 9/2003 | Hill et al. | |
| 2004/0229338 A1 | 11/2004 | King | |

FOREIGN PATENT DOCUMENTS

| | | |
|---|---|---|
| WO | WO 98/29138 A2 | 7/1998 |
| WO | WO 00/72679 A1 | 12/2000 |
| WO | WO 01/20989 A1 | 3/2001 |
| WO | WO 01/25397 A2 | 4/2001 |
| WO | WO 01/81631 A1 | 11/2001 |
| WO | WO 02/02771 A2 | 1/2002 |
| WO | WO 02/089772 A1 | 11/2002 |
| WO | WO 2004/005883 A2 | 1/2004 |
| WO | WO 2004/016758 A2 | 2/2004 |
| WO | WO 2005/026357 A1 | 3/2005 |

OTHER PUBLICATIONS

Alliel et al., *Eur. J. Biochem.*, 214, 347-350 (1993).
Arber et el., *Gastroenterology*, 118, 1045-1050 (2000).
Bellahcène et al., *American Journal of Pathology*, 146(1), 95-100 (Jan. 1995).
Bendik et al., *Cancer Res.*, 58 (4), 626-629 (Feb. 15, 1998).
Bornstein, *J. Cell Biol.*, 130, 503-506 (1995).
Bradshaw et al., *J. of Clinical Investigation*, 107(9), 1049-1054 (May 2001).
Bradshaw et al., *PNAS*, 100(10), 6045-6050 (May 13, 2003).
Brown et al., *Gynecologic Oncology*, 75: 25-33 (1999).
Carmichael et al., *Cancer Res.*, 47, 936-942 (Feb. 15, 1987).
Cree et al., *Curr. Opn. Invest. Drugs*, 3 (4), 641-647 (2002).
Chlenski et al., *Cancer Res.*, 62, 7357-7363 (Dec. 2002).
de las Alas et al., *J. Natl. Cancer Inst.*, 89 (20), 1537-1541 (Oct. 15, 1997).
Dhanesuan et al., *Breast Cancer Research and Treatment*, 75, 73-85 (2002).
Eltabbakh, Gamal H., *J. Surg. Oncol.*, 73, 148-152 (2000).
Fillpits et al., *Br. J. Cancer*, 75 (2), 208-212 (1997).
Folkman, Judah, *N. Engl. J. Med.*, 333 (26), 1757-1763 (1995).
Georgiou, *Current Opinion in Biotechnology*, 7, 190-197 (1996).
Gilbert et al., *Kidney International*, 48, 1216-1225 (1995).
Guermah et al., *Proc. Natl. Acad. Sci. USA*, 88, 4503-4507 (May 1991).
Hasselaar et al., *J. of Biological Chemistry*, 266(20), 13178-13184 (Jul. 15, 1991).
Hasselaar et al., *J. Cell. Biochem.*, 49, 272-283 (1992).
Hebbes et al., *Mol. Immunol.*, 26 (9), 865-873 (1989).
Hohenadl et al., *J. Biological Chemistry*, 270(40), 23415-23420 (Oct. 6, 1995).
Iruela-Arispe et al., *Mol. Biol. Cell*, 6, 327-343 (Mar. 1995).
Jendraschak et al., *Seminars in Cancer Biology*, 7, 139-146 (1996).
Johnston et al., *Neuron*, 4 (1), 165-176 (Jan. 1990).
Johnstone et al., *Cell*, 108, 153-164 (Jan. 25, 2002).
Kamesaki H., *Int. J. Hematology*, 68, 29-43 (1998).
Kelm et al., *J. Biol. Chem.*, 269 (48), 30147-30153 (1994).
Kim et al., *J. Korean Med. Sci.*, 13, 652-657 (1998).
Kupprion et al., *J. Biol. Chem.*, 273 (45), 29635-29640 (1998).
Lane et al., J. Biol. Chem., 267 (23), 16736-16745 (Aug. 1992).
Lane et al., *FASEB J.*, 8, 163-173 (Feb. 1994).
Lane et al., J. Cell Biol., 125 (4), 929-943 (May 1994).
Lankat-Buttgereit et al., *FEBS Lett.*, 236, 352-356 (Aug. 1988).
Latvala et al., *Exp. Eye Res.*, 63, 579-584 (1996).
Le Bail et al., *J. Pathol.*, 189, 46-52 (1999).
Ledda et al., *Nature Medicine*, 3 (2), 171-176 (1997).
Lehnert, Manfred, *Anticancer Res.*, 18, 2225-2226 (1998).
Li et al., *Clin. & Exp. Metastasis*, 17, 423-429 (1999).
Lin et al., *Mol. Pharm.*, 56, 390-395 (1999).

(Continued)

*Primary Examiner* — Sean Aeder
(74) *Attorney, Agent, or Firm* — Leydig, Voit & Meyer, Ltd.

(57) ABSTRACT

The present invention relates to compositions and methods for sensitizing cancer therapy. The invention provides such compositions comprising a SPARC family polypeptide or polynucleotide, as well as recombinant cells containing a SPARC family polypeptide or polynucleotide. The compositions and methods of the invention are useful in in vitro study of cancer therapy resistance, as well as ex vivo and in vivo therapy of cancer.

11 Claims, 198 Drawing Sheets

OTHER PUBLICATIONS

Lussier et al, *J. Cell. Biochem.*, 81, 463-476 (2001).
Ma et al., *Antisense & Nucleic Acid Drug Development*, 8, 415-426 (1998).
Maillard et al., *Bone*, 13, 257-264 (1992).
Makin, Guy, *Expert Opn. Ther. Targets*, 6 (1), 73-84 (2002).
Mason et al., *EMBO J.*, 5 (7),1465-1472 (Jul. 1986).
Mason et al., *EMBO J.*, 5 (8),1831-1837 (Aug. 1986).
Nair et al., *J. Immunol.*, 165 (12), 6949-6955 (2000).
Paley et al., *Gyn. Oncol.*, 78, 336-341 (2000).
Parikh et al., *Biotechniques*, 24, 428-431 (Mar. 1998).
Pichler et al., *Am. J. of Pathology*, 148(4), 1153-1167 (Apr. 1996).
Porte et al., *Int. J. Cancer*, 64, 70-75 (1995).
Porte et al., *Clin. Cancer Res.*, 4, 1375-1382 (Jun. 1998).
Porter et al., *J. Histochem. & Cytochem.* 43(8), 791-800 (1995).
Qi et al., Nuc. Acids Res., 29 (22), e116 (2001).
Raines et al., *Proc. Natl. Acad. Sci. USA*, 89, 1281-1285 (Feb. 1992).
Rempel et al., *Clinical Cancer Research*, 5, 237-241 (Feb. 1999).
Ringborg et al., *Acta Oncol.*, 76-80 (1996).
Sage et al., *J. Biol. Chem.*, 266 (23), 14831-14834 (Aug. 1991).
Sage E. Helene, *Biochem. Cell Biol.*, 70, 579-592 (1992).
Sage et al., *J. Cellular Biochemistry*, 57, 127-140 (1995).
Sage et al., *J. Biological Chemistry*, 278(39) 37849-37857 (Sep. 26, 2003).
Schulz et al., Am. J. Path, 132 (2), 233-238 (Aug. 1988).
Schwartz et al., *J. Immunol.*, 135 (4), 2598-2608 (1985).
Shea et al., *Cancer Res.*, 48, 527-533 (Feb. 1, 1988).
Shibanuma et al., *Eur. J. Biochem.*, 217, 13-19 (1993).
Skoudy et al., *Biochem. J.*, 317, 279-284 (1996).
Stein et al., *J. Natl. Cancer Inst.*, 88 (19), 1383-1392 (Oct. 2, 1996).
Stites and Terr (eds.) *Basic and Clinical Immunology*, 7$^{th}$ ed., East Norwalk, Connecticut, Appleton and Lange (1991).
St. Croix et al., *Nat. Med.*, 2, (11) 1204-1210 (Nov. 1996).
Strandjord et al., *Am. J. Respir. Cell Mol. Biol.*, 13, 279-287 (1995).
Swaroop et al., *Genomics*, 2, 37-47 (1988).
Tanigawa et al., *Cancer Res.*, 42, 2159-2164 (Jun. 1982).
Takahashi et al., *Obesity Res.*, 9(7) 388-393 (Jul. 2001).
Termine et al., *Cell*, 26, 99-104 (Oct. 1981).
Thomas et al., *Clinical Cancer Res.*, 6, 1140-1149 (Mar. 2000).
Tockman et al., *Cancer Res.*, 52, 2711s-2718s (1992).
Vannahme et al., *J. Biol. Chem.*, 277 (41), 37977-37986 (Oct. 11, 2002).
Vial et al., *Oncogene*, 19, 1772-1782 (2000).
Waldman et al., *Nature*, 381, 713-716 (Jun. 20, 1996).
Weisenthal et al., *Recent Results in Cancer Res.*, 94, 161-173 (1984).
Weisenthal et al., *Cancer Treatment Reports*, 69 (6), 615-632 (Jun. 1985).
Weisenthal, L.M., *Drug Resistance in Leukemia and Lymphoma: The Clinical Value of Laboratory Studies*, pp. 415-423, Harwood Academic Publishers (1993).
Weisenthal, *Contrib. Gyn. Obstet.* 19, 82-90 (1994).
Weisenthal, Larry M., *Chemosensitivity Testing in Gynecologic Malignancies and Breast Cancer*, v. 19, pp. 82-90, Basel, Karger (1994).
Werb, *Cell*, 91, 439-442 (Nov. 14, 1997).
Wolfsberg et al., *J. Cell Biology*, 131(2) 275-278 (Oct. 1995).
Yiu et al., *American Journal of Pathology*, 159(2): 609-622 (Aug. 2001).
Yamanaka et al., *J. Urology*, 166, 2495-2499 (Dec. 2001).
Yan et al., *J. Histochemistry & Cytochemistry*, 47(12), 1495-1505 (1999).

\* cited by examiner

TUNEL ASSAY

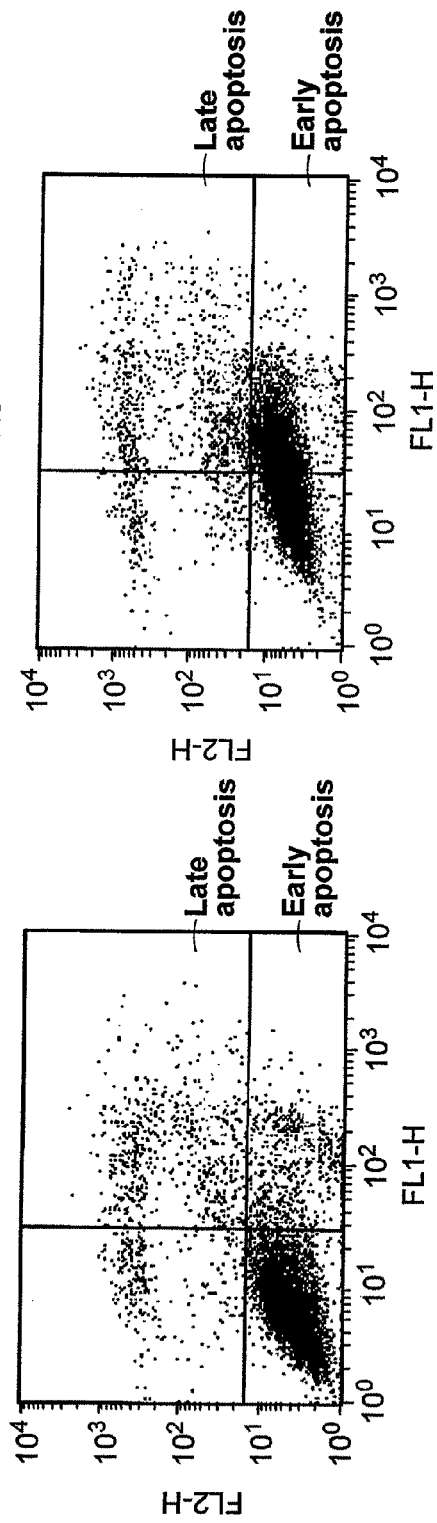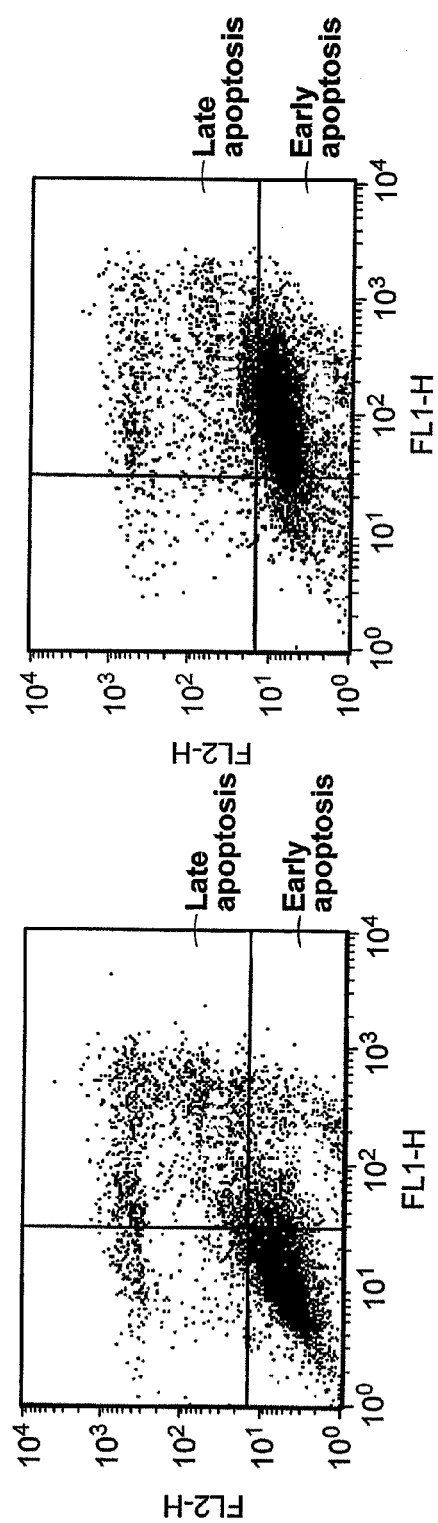

NCBI

PubMed  Nucleotide  Protein  Genome  Structure  PMC  Taxonomy  OMIM  Boo

Search Nucleotide ▽ for [                    ]  Nucleotide

Limits  Preview/Index  History  Clipboard  Details

Display default ▽  Show: 20 ▽  Send to File ▽  Get Subsequence  Clear  Links

☐ 1: NM_003118. Homo sapiens secr...[gi:4507170]

```
LOCUS       SPARC                   2133 bp    mRNA    linear   PRI 05-NOV-2002
DEFINITION  Homo sapiens secreted protein, acidic, cysteine-rich (osteonectin)
            (SPARC), mRNA.
ACCESSION   NM_003118
VERSION     NM_003118.1  GI:4507170
KEYWORDS    .
SOURCE      Homo sapiens (human)
ORGANISM    Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2133)
AUTHORS     Termine,J.D., Kleinman,H.K., Whitson,S.W., Conn,K.M., McGarvey,M.L.
            and Martin,G.R.
TITLE       Osteonectin, a bone-specific protein linking mineral to collagen
JOURNAL     Cell 26 (1 Pt 1), 99-105 (1981)
```

FIG. 12-1

```
MEDLINE    82115304
PUBMED     7034958
REFERENCE  2  (bases 1 to 2133)
AUTHORS    Swaroop,A., Hogan,B.L. and Francke,U.
TITLE      Molecular analysis of the cDNA for human SPARC/osteonectin/BM-40:
           sequence, expression, and localization of the gene to chromosome
           5q31-q33
JOURNAL    Genomics 2 (1), 37-47 (1988)
MEDLINE    88256150
PUBMED     2838412
REFERENCE  3  (bases 1 to 2133)
AUTHORS    Lankat-Buttgereit,B., Mann,K., Deutzmann,R., Timpl,R. and Krieg,T.
TITLE      Cloning and complete amino acid sequences of human and murine
           basement membrane protein BM-40 (SPARC, osteonectin)
JOURNAL    FEBS Lett. 236 (2), 352-356 (1988)
MEDLINE    88312997
PUBMED     3410046
REFERENCE  4  (bases 1 to 2133)
AUTHORS    Le Beau,M.M., Espinosa,R. III, Neuman,W.L., Stock,W., Roulston,D.,
           Larson,R.A., Keinanen,M. and Westbrook,C.A.
TITLE      Cytogenetic and molecular delineation of the smallest commonly
           deleted region of chromosome 5 in malignant myeloid diseases
JOURNAL    Proc. Natl. Acad. Sci. U.S.A. 90 (12), 5484-5488 (1993)
MEDLINE    93296163
PUBMED     8516290
REFERENCE  5  (bases 1 to 2133)
```

FIG. 12-2

```
AUTHORS    Kato,Y., Lewalle,J.M., Baba,Y., Tsukuda,M., Sakai,N., Baba,M.,
           Kobayashi,K., Koshika,S., Nagashima,Y., Frankenne,F., Noel,A.,
           Foidart,J.M. and Hata,R.I.
TITLE      Induction of SPARC by VEGF in human vascular endothelial cells
JOURNAL    Biochem. Biophys. Res. Commun. 287 (2), 422-426 (2001)
MEDLINE    21438978
PUBMED     11554745
COMMENT    PROVISIONAL REFSEQ: This record has not yet been subject to final
           NCBI review. The reference sequence was derived from J03040.1.
FEATURES           Location/Qualifiers
     source        1..2133
                   /organism="Homo sapiens"
                   /db_xref="taxon:9606"
                   /chromosome="5"
                   /map="5q31.3-q32"
     gene          1..2133
                   /gene="SPARC"
                   /note="synonym: ON"
                   /db_xref="LocusID:6678"
                   /db_xref="MIM:182120"
     CDS           58..969
                   /gene="SPARC"
                   /note="Osteonectin (secreted protein, acidic,
                   cysteine-rich)"
                   /codon_start=1
                   /product="secreted protein, acidic, cysteine-rich
                   (osteonectin)"
                   /protein_id="NP_003109.1"
```

FIG. 12-3

```
/db_xref="GI:4507171"
/db_xref="LocusID:6678"
/db_xref="MIM:182120"
/translation="MRAWIFFLLCLAGRALAAPQQEALPDETEVVEETVAEVTEVSVG
ANPVQVEVGEFDDGAEETEEVVAENPCQNHHCKHGKVCELDENNTPMCVCQDPTSCP
APIGEFEKVCSNDNKTFDSSCHFFATKCTLEGTKKGHKLHLDYIGPCKYIPPCLDSEL
TEFPLRMRDWLKNVLVTLYERDEDNNLLTEKQKLRVKKIHENEKRLEAGDHPVELLAR
DFEKNYNMYIFPVHWQFGQLDQHPIDGYLSHTELAPLRAPLIPMEHCTTRFFETCDLD
NDKYIALDEWAGCFGIKQKDIDKDLVI."  SEQ ID NO. 1
misc feature    268..339
                /gene="SPARC"
                /note="FOLN; Region: Follistatin-N-terminal domain-like"
                /db_xref="CDD:smart00274"
misc feature    340..504
                /gene="SPARC"
                /note="kazal; Region: Kazal-type serine protease inhibitor
                domain. Usually indicative of serine protease inhibitors.
                However, kazal-like domains are also seen in the
                extracellular part of agrins, which are not known to be
                protease inhibitors. Kazal domains often occur in tandem
                arrays. Small alpha+beta fold containing three
                disulphides. Alignment also includes a single domain from
                transporters in the OATP/PGT family"
                /db_xref="CDD:pfam00050"
misc feature    349..504
                /gene="SPARC"
                /note="KAZAL; Region: Kazal type serine protease
                inhibitors"
```

FIG. 12-4

```
variation          /db_xref="CDD:smart00280"
                   559
                   /gene="SPARC"
                   /allele="G"
                   /allele="C"
                   /db_xref="dbSNP:1053296"
variation          562
                   /gene="SPARC"
                   /allele="T"
                   /allele="G"
                   /allele="A"
                   /db_xref="dbSNP:707157"
variation          complement(570)
                   /allele="G"
                   /allele="C"
                   /db_xref="dbSNP:2304049"
variation          998
                   /gene="SPARC"
                   /allele="G"
                   /allele="C"
                   /db_xref="dbSNP:1053411"
variation          1117
                   /gene="SPARC"
                   /allele="T"
                   /allele="A"
                   /db_xref="dbSNP:1060151"
variation          1451
                   /gene="SPARC"
                   /allele="T"
                   /allele="G"
                   /db_xref="dbSNP:1053660"
variation          1509
                   /gene="SPARC"
                   /allele="T"
                   /allele="G"
                   /db_xref="dbSNP:3194455"
variation          1551
                   /gene="SPARC"
                   /allele="G"
                   /allele="C"
                   /db_xref="dbSNP:1054204"
variation          1655
                   /gene="SPARC"
                   /allele="T"
                   /allele="G"
```

FIG. 12-5

```
variation         /db_xref="dbSNP:1055210"
                  1724
                  /gene="SPARC"
                  /allele="T"
                  /allele="C"
                  /db_xref="dbSNP:1804455"
variation         1862
                  /gene="SPARC"
                  /allele="T"
                  /allele="C"
                  /db_xref="dbSNP:1804456"
variation         complement(1922)
                  /allele="C"
                  /allele="A"
                  /db_xref="dbSNP:1059279"
variation         2045
                  /gene="SPARC"
                  /allele="C"
                  /allele="A"
                  /db_xref="dbSNP:1064799"
variation         2072
                  /gene="SPARC"
                  /allele="T"
                  /allele="C"
                  /db_xref="dbSNP:1059829"
variation         2104
                  /gene="SPARC"
                  /allele="C"
                  /allele="A"
                  /db_xref="dbSNP:1804458"
```

FIG. 12-6

```
BASE COUNT      543 a      533 c      521 g      536 t
ORIGIN
   1 cggagagcg cgctctgcct gccgcctgcc tgcctgccac tgagggttcc cagcaccatg
  61 agggcctgga tcttcttct  cctttgcctg gcgggaggg  cctggcagc  ccctcagcaa
 121 gaagccctgc ctgatgagac agaggtggtg gaagaaactg tggcagaggt gactgaggta
 181 tctgtgggag ctaatcctgt ccaggtggaa gtaggagaat ttgatgatgg tgcagaggaa
 241 accgaagagg agtggtggc  ggaaaatccc tgccagaacc accactgcaa acacggcaag
 301 gtgtgcgagc tggatgagaa caacaccccc atgtgcgtgt gccaggaccc caccagctgc
 361 ccagccccca ttggcgagtt tgagaaggtg tgcagcaatg acaacaagac cttcgactct
 421 tcctgccact tctttgccac aaagtgcacc ctgagggca  ccaagaaggg ccacaagctc
 481 cacctggact acatcggcc  ttgcaaatac atccccccct gcctggactc tgagctgacc
 541 gaattccccc tgcgcatgcg ggactggctc aagaacgtcc tgtcaccct  gtatgagagg
 601 gatgaggaca acaaccttct gactgagaag cagaagctgc gggtgaagaa gatccatgag
 661 aatgagaagc gcctggagc  aggagaccac ccgtggagc  tgctgcccg  ggacttcgag
 721 aagaactata acatgtacat cttccctgta cactgcagt  tcgccagct  gaccagcac
 781 cccattgacg ggtacctctc ccacaccg   ctgctcctc  tgcgtgctcc cctcatccc
 841 atgagcatt  gcaccacccg cttttttgag acctgtgacc tggacaatga aggatacga  caagtacatc
 901 gccctggatg agtgggcgg  ctgcttcggc atcaagcaga aggatatcga tttaaccctc caaggatctt
 961 gtgatctaaa tccactcctt ccacagtacc ggattctctc ttgttgttct gcctggagac cccttcgtgt
1021 ttccccccaat gtttaaaatg tttggatggt tgttgttct  taaaatgaa  aattctaacc aaggtgctaa
1081 catagattta agtgaataca ttaacggtgc cttttcccaca aattctaacc caagacatga
1141 cattcttagc tgtaacttaa ctattaaggc ctttccaca  cgcattaata gtcccatttt
1201 tctcttgcca tttgtagctt tgccattgt  cttattggca catggtgga  cacggatctg
1261 ctggctctg  ccttaaacac acattgcagc ttcaactttt ctctttagtg ttctgtttga
1321 aactaatact taccgagtca gactttgtgt tcatttcatt tcagggtctt ggctgcctgt
1381 gggcttccc  agtggcctg  gaggtgggca aaggaagta  acagacacac gatgttgtca
1441 aggatggttt tgggactaga ggctcagtgg tgggagagat ccctgcagaa tccaccaacc
1501 agaacgtggt ttgcctgagg ctgtaactga gagaaagatt ctggggctgt cttatgaaaa
```

FIG. 12-7

```
1561 tatagacatt ctcacataag cccagttcat caccatttcc tcctttacct ttcagtgcag
1621 tttctttca cattaggctg ttggttcaaa cttttgggag cacggactgt cagttctctg
1681 ggaagtggtc agcgcatcct gcaggcttc  tcctcctctg tcttttggag aaccagggct
1741 cttctcaggg gctctaggga ctgccagget gtttcagcca ggaagccaa  aatcaagagt
1801 gagatgtaga aagttgtaaa atagaaaaag tggagtttggt gaatcggttg ttctttcctc
1861 acatttggat gattgtcata aggtttttag catgttcctc ctttttcttca ccctcccctt
1921 tgttcttcta ttaatcaaga gaaacttcaa agttaatggg atggtcggat ctcacaggct
1981 gagaactcgt tcacctccaa gcatttcatg aaaaagctgc ttcttattaa tcatacaaac
2041 tctcaccatg atgtgaagag tttcacaaat cttcaaaat  aaaaagtaat gacttagaaa
2101 ctgaaaaaaa aaaaaaaaaa aaa SEQ ID NO. 18
```

FIG. 12-8

```
                    NCBI                              Nucleotide

PubMed   Nucleotide   Protein   Genome   Structure   PMC   Taxonomy   OMIM   Boo
  Search Nucleotide ▽  for [                        ]
                    Limits                    Preview/Index    History         Details
  Display default ▽   Show: 20 ▽   Send to ▽   File ▽   Go   Clear
                                                         Clipboard
                                                         Get Subsequence           Links □1: NM_009242. Mus musculus secr...[gi:66780076]

LOCUS       Sparc                2079 bp   mRNA   linear   ROD 07-JAN-2002
  DEFINITION  Mus musculus secreted acidic cysteine rich glycoprotein (Sparc),
              mRNA.
  ACCESSION   NM_009242
  VERSION     NM_009242.1   GI:6678076
  KEYWORDS
  SOURCE      Mus musculus (house mouse)
  ORGANISM    Mus musculus
              Eukaryota; Metazoa; Chordata; Craniata; Vertebrata; Euteleostomi;
              Mammalia; Eutheria; Rodentia; Sciurognathi; Muridae; Murinae; Mus.
  REFERENCE   1  (bases 1 to 2079)
  AUTHORS     Mason,I.J., Taylor,A., Williams,J.G., Sage,H. and Hogan,B.L.
  TITLE       Evidence from molecular cloning that SPARC, a major product of
              mouse embryo parietal endoderm, is related to an endothelial cell
              'culture shock' glycoprotein of Mr 43,000
  JOURNAL     EMBO J. 5 (7), 1465-1472 (1986)
```

FIG. 12-9

| | | |
|---|---|---|
| MEDLINE | 86300644 | |
| PUBMED | 3755680 | |
| REFERENCE | 2 (bases 1 to 2079) | |
| AUTHORS | McVey,J.H., Nomura,S., Kelly,P., Mason,I.J. and Hogan,B.L. | |
| TITLE | Characterization of the mouse SPARC/osteonectin gene. Intron/exon organization and an unusual promoter region | |
| JOURNAL | J. Biol. Chem. 263 (23), 11111-11116 (1988) | |
| MEDLINE | 88298750 | |
| PUBMED | 3165375 | |
| REFERENCE | 3 (bases 1 to 2079) | |
| AUTHORS | Howe,C.C., Overton,G.C., Sawicki,J., Solter,D., Stein,P. and Strickland,S. | |
| TITLE | Expression of SPARC/osteonectin transcript in murine embryos and gonads | |
| JOURNAL | Differentiation 37 (1), 20-25 (1988) | |
| MEDLINE | 88255622 | |
| PUBMED | 3384223 | |
| REFERENCE | 4 (bases 1 to 2079) | |
| AUTHORS | Carninci,P., Shibata,Y., Hayatsu,N., Sugahara,Y., Shibata,K., Itoh,M., Konno,H., Okazaki,Y., Muramatsu,M. and Hayashizaki,Y. | |
| TITLE | Normalization and subtraction of cap-trapper-selected cDNAs to prepare full-length cDNA libraries for rapid discovery of new genes | |
| JOURNAL | Genome Res. 10 (10), 1617-1630 (2000) | |
| MEDLINE | 20499374 | |
| PUBMED | 11042159 | |
| REFERENCE | 5 (bases 1 to 2079) | |
| AUTHORS | Shibata,K., Itoh,M., Aizawa,K., Nagaoka,S., Sasaki,N., Carninci,P., Konno,H., Akiyama,J., Nishi,K., Kitsunai,T., Tashiro,H., Itoh,M., | |

FIG. 12-10

```
          Sumi,N., Ishii,Y., Nakamura,S., Hazama,M., Nishine,T., Harada,A.,
          Yamamoto,R., Matsumoto,H., Sakaguchi,S., Ikegami,T., Kashiwagi,K.,
          Fujiwake,S., Inoue,K. and Togawa,Y.
  TITLE   RIKEN integrated sequence analysis (RISA) system--384-format
          sequencing pipeline with 384 multicapillary sequencer
  JOURNAL Genome Res. 10 (11), 1757-1771 (2000)
  MEDLINE 20530913
   PUBMED 11076861
  COMMENT PROVISIONAL REFSEQ: This record has not yet been subject to final
          NCBI review. The reference sequence was derived from X04017.1.
FEATURES             Location/Qualifiers
     source          1..2079
                     /organism="Mus musculus"
                     /db_xref="taxon:10090"
                     /chromosome="11"
                     /map="11 29.9 cM"
     gene            1..2079
                     /gene="Sparc"
                     /note="synonym: BM-40"
                     /db_xref="LocusID:20692"
                     /db_xref="MGD:98373"
     CDS             90..998
                     /gene="Sparc"
                     /note="osteonectin"
                     /codon_start=1
                     /product="secreted acidic cysteine rich glycoprotein"
                     /protein_id="NP_033268.1"
                     /db_xref="GI:6678077"
```

FIG. 12-11

```
                 /db_xref="LocusID:20692"
                 /db_xref="MGD:98373"
                 /translation="MRAWIFFLLCLAGRALAAPQQTEVAEEIVEETVVEETGVPVGA
                 NPVQVEMGEFEDGAEETVEEVVADNPCQNHHCKHGKVCELDESNTPMCVCQDPTSCPA
                 PIGEFEKVCSNDNKTFDSSCHFFATKCTLEGTKKGHKLHLDYIGPCKYIAPCLDSELT
                 EFPLRMRDWLKNVLVTLYERDEGNNLLTEKQKLRVKKIHENEKRLEAGDHPVELLARD
                 FEKNYNMYIFPVHWQFGQLDQHPIDGYISHTELAPLRAPLIPMEHCTTRFFETCDLDN
                 DKYIALEEWAGCFGIKEQDINKDLVI" SEQ ID NO. 2
     misc_feature 297..368
                 /gene="Sparc"
                 /note="FOLN; Region: Follistatin-N-terminal domain-like"
                 /db_xref="CDD:smart00274"
     misc_feature 369..533
                 /gene="Sparc"
                 /note="kazal; Region: Kazal-type S protease inhibitor
                 domain"
                 /db_xref="CDD:pfam00050"
     misc_feature 378..533
                 /gene="Sparc"
                 /note="KAZAL; Region: Kazal type serine protease
                 inhibitors"
                 /db_xref="CDD:smart00280"
     misc_feature 432..434
                 /gene="Sparc"
                 /note="put. glycosylation signal (aa 115)"
     misc_feature 2054..2059
                 /gene="Sparc"
                 /note="polyA signal"
```

FIG. 12-12

```
BASE COUNT      526 a      552 c      518 g      483 t
ORIGIN
   1 gcattcctgc agcccttcag accgccagaa ctcttctgcc gctgcctgc ctgcctgcct
  61 gctgcctgt gccgagagtt cccagcatca tgaggcctg gatcttcttt ctcctttgcc
 121 tggccgggag ggccctggca gcccctcagc agactgaagt tgctgaggag atagtggagg
 181 aggaaaccgt ggtggaggag acagggtac ctgtgggtgc caaccagtc caggtggaaa
 241 tgggagaatt tgaggacggt gcagaggaaa cggtcgagga ggtggtggct gacaaccct
 301 gccagaacca tcattgcaaa catggcaagg tgtgtgagct ggacgagagc aacacccca
 361 tgtgtgtgtg ccagaccc accagctgcc tgcgcagttt gagaaggtat
 421 gcagcaatga caacaagacc ttcgactctt cctgccactt ctttgccacc aagtgcaccc
 481 tggagggcac caagaaggc cacaagctcc acctggacta catcgacca tgcaaataca
 541 tcgcccctg cctgattcc gagctgaccg aattccctct gcgcatgcgt gactggctca
 601 aaatgtcct ggtcaccttg tacgagagag atgaggcaa caacctcctc actgagaagc
 661 agaagctgcg tgtgaagaag atccatgaga atgagaagcg cctggaggct ggagaccacc
 721 ccgtggagct gttggccga gactttgaga agaactacaa tatgtacatc ttcctgtcc
 781 actgcagtt tggccagctg gatcagcacc ctattgatgg gtacctgtcc cacactgagc
 841 tggcccact gcgtgctccc ctcatcccca tggaacattg ttctttgaga
 901 cctgtgacct agacaacgac aagtacattg ccctggagga atgggccggc tgctttggca
 961 tcaaggagca ggacatcaac aaggatctgg tgatctaagt tcaagcctcc tgctgcagtc
1021 ctgaactctc tccctctgat gtgtcaccc tcccattacc ccctgttta aaatgttgg
1081 atggttggct gttccgcctg gggataaggt gctaacatag atttaactga atacattaac
1141 ggtgctaaaa aaaaaaaaaa aacaaagtaa gaaagaaact agaacccaag tcacagcatt
1201 ttcccacata actctgaggc catggcccat ccacagcctc ctggtccct gcactaccca
1261 gtgtctcact ggctgtgttg gaaacggagt tgcataagct caccgtccac aagcacgaga
1321 tatctctagc tttcattca attttgcatt tgactcttaa cactccacca gactctgtgc
1381 ttatttcatt tggggatg tggcttttt cccctgtgg tttggagtta ggcagaggga
1441 agttacagac acaggtacaa aatttgggta aagatactgt gagacctgag gaccaccag
1501 tcagaaccca catgccaagt cttagtagcc taggtcaagg aaagacagaa taatccagag
```

FIG. 12-13

```
1561 ctgtggcaca catgacagac tcccagcagc ccgggacctt gctgtcttct cgactcttcg
1621 ggcgtttctt tccatgtttg gctgttggtt ttagtttttgg tgagccatgg gtgggccaga
1681 acatcactca actgcaattg ggctttcagg ttcttgccgg gagctctagg cactgggagg
1741 ctgtttcagg aaagtgagac tcaagaggaa gacagaaaag gttgtaacgt agaggaagtg
1801 agactggtga attggtttga ttttttttcac atctagatgg ctgtcataaa gtttctagca
1861 tgttcccccct caccctcccc cacccccctgc cacttgaaac cttctactaa tcaagagaaa
1921 cttccaagcc aacggaatgg tcagatctca caggctgaga aattgttccc ctccaagcat
1981 ttcatgaaaa agctgcttct cattaaccat gcaaactctc acagcgatgt gaagagcttg
2041 acaagtcttt caaaataaaa agtaacaact tagaaacgg SEQ ID NO. 19
```

FIG. 12-14

```
                                                                                              Boo
                                                                       OMIM
                                                                                    Details
                                    Nucleotide
                                                                 Taxonomy
                                                              Go   Clear
                                                 PMC
                                           Structure     History
                                   Genome            ▽
                                              Preview/Index            Clipboard
                            Protein                Send to   File        Get Subsequence        Links
           NCBI  Nucleotide
  PubMed
Search Nucleotide ▽  for
                     Limits
Display default ▽ Show: 20 ▽
```

☐1: AB088113. Homo sapiens SC1,...[gi:27544421]

```
LOCUS         AB088113              14468 bp    DNA       linear   PRI 08-JAN-2003
DEFINITION    Homo sapiens SC1, OTF3 genes for transcription factor 19, POU
              domain class 5 transcription factor 1, complete cds.
ACCESSION     AB088113
VERSION       AB088113.1  GI:27544421
KEYWORDS      .
SOURCE        Homo sapiens (human)
  ORGANISM    Homo sapiens
              Eukaryota; Metazoa; Chordata; Craniata; Vertebrata; Euteleostomi;
              Mammalia; Eutheria; Primates; Catarrhini; Hominidae; Homo.
REFERENCE     1
  AUTHORS     Shiina,T., Ota,M., Katsuyama,Y., Hashimoto,N. and Inoko,H.
  TITLE       Genome diversity in HLA: A new strategy for detection of genetic
              polymorphisms in expressed genes within the HLA class III and class
              I regions
```

FIG. 12-15

```
JOURNAL     Unpublished
REFERENCE   2  (bases 1 to 14468)
AUTHORS     Shiina,T.
TITLE       Direct Submission
JOURNAL     Submitted (08-JUL-2002) Takashi Shiina, Tokai University School of
            Medicine, Molecular Life Sciense 2; Bohseidai, Isehara, Kanagawa
            259-1193, Japan (E-mail:tshiina@is.icc.u-tokai.ac.jp,
            Tel:81-463-93-1121, Fax:81-463-94-8884)
FEATURES             Location/Qualifiers
     source          1..14468
                     /organism="Homo sapiens"
                     /db_xref="taxon:9606"
                     /chromosome="6"
                     /map="6p21.31"
                     /cell_line="LKT3"
                     /cell_type="B cell"
     exon            1066..1680
                     /number=1
     gene            join(1443..1680,3384..3942,4414..4654)
                     /gene="SC1"
     CDS             join(1443..1680,3384..3942,4414..4654)
                     /gene="SC1"
                     /note="DNA binding protein required for late cell cycle
                     progression"
                     /codon_start=1
                     /product="transcription factor 19"
                     /protein_id="BAC54945.1"
                     /db_xref="GI:27544422"
```

FIG. 12-16

```
          /translation="MLPCFQLLRIGGGRGGDLYTFHPPAGAGCTYRLGHRADLCDVAL
          RPQQEPGLISGIHAELHAEPRGDDWRVSLEDHSSQGTLVNNVRLPRGHRLELSDGDLL
          TFGPEGPPGTSPSEFYFMFQQVRVKPQDFAAITIPRSRGEARVGAGFRPMLPSQGAPQ
          RPLSTFSPAPKATLILNSIGSLSKLRPQPLTFSPSWGGPKSLPVPAPPGEVGTTPSAP
          PQRNRRKSVHRVLAELDDESEPPENPPPVLMEPRKKLRVDKAPLTPTGNRRGRPRKYP
          VSAPMAPPAVGGGEPCAAPCCCLPQEETVAWVQCDGCDWFHVACVGCSIQAAREADF
          RCPGCRAGIQT" SEQ ID NO. 3
exon      3384..3942
          /gene="SC1"
          /number=2
exon      4414..5723
          /number=3
exon      6283..6805
          /number=4
gene      complement(join(6539..6805,7068..7226,7511..7641,
          7875..8115))
          /gene="OTF3"
CDS       complement(join(6539..6805,7068..7226,7511..7641,
          7875..8115))
          /gene="OTF3"
          /note="POU-type homeodomain-containing DNA-binding
          protein"
          /codon_start=1
          /product="POU domain, class 5, transcription factor 1"
          /protein_id="BAC54946.1"
          /db_xref="GI:27544423"
          /translation="MHFYRLFLGATRRFLNPEWKGEIDNWCVYVLTSLLPFKIQSQDI
          KALQKELEQFAKLLKQKRITLGYTQADVGLTLGVLFGKVFSQTTICRFEALQLSFKNM
```

FIG. 12-17

```
exon            CKLRPLLQKWVEEADNNENLQEICKAETLVQARKKRTSIENRVRGNLENLFLQCPKP
                TLQQISHIAQQLGLEKDVVRVWFCNRRQKGKRSSDYAQREDFEAAGSPFSGGPVSFP
                LAPGPHFGTPGYGSPHFTALYSSVPFPEGEAFPPVSVTTLGSPMHSN"
                7068..7226 SEQ ID NO. 35
                /number=3
exon            7511..7641
                /number=2
exon            7875..8216
                /number=1
BASE COUNT    3555 a    3859 c    3746 g    3308 t
ORIGIN
     1  tctaaggctg ttctgatctc ttcatctgtc ccttcacctg gcccctgtac cccccttcccc
    61  tttggacccc ttgaaccctc ccaggacccc cgctcagccc cttcccgccc ccaaccgact
   121  cttcccgaac gtcccttacc cccgcgaga gccccctact gcgcttggc cacacccct
   181  acgcctcgct cccggccccg ctctgcccc tgaccgcgcc ggggcccta
   241  aagtcctatt tcactctgtt gggaggaggg ggaaaggtgt acgcaggcgc agtggcgtct
   301  aaatttgggc ccactaaatg cgtcggagca tctccggcgc caggcggctc ctcctcactg
   361  cggcaacccg ggaaaacttg tgaactaatc agaaaaagtg gaaggcggga gatcttgggg
   421  cgctgtccaa tggcgcggaa gagaacaaat gagctggcca atcgggaacg gcacgggggc
   481  gggctcgctc ggcgcgaagt tcgggcccgg gaattccgaa ggaggggtag gcgctgcccg
   541  cgcgcagagg ccgcgcgccc cctgcgcccg gcttcttggc tgtcaaaacag atgcagcaac
   601  gtcggctcct gccggagagc ccaaggggtc ccggatccg ccgcacaggc tggcactgct
   661  tgaagaggag gctactcgga gactgcgccg cgcgggtaga tccgaaacgg ggctggggcg
   721  gagtgggaaa aggccgggta tgccttgcat gatcgcgggg agctccttcc tgtttttatc
   781  ccacctagag ttcttttggg agtccaatt ggattcattg cctcggagg ttcaaccagt
   841  cgtttgcact ggattggcca gaagatcggg gcgcaggcaa gcaggagtgc tctattagga
   901  tatgagtgag
```

FIG. 12-18

```
 961 taagcaagtt tgacaggaag aagctgctct tctccgaatt acacagaggt gatgtgttcg
1021 tattgcacgt agacgtgtgt ataacaggac ctccttcccc gcgccccgcc acccgacac
1081 acacaggagc tgcctaaagt atccttgcct tgcagattgg aggctcccca aatattttgt
1141 gatctgagga tccagctcaa gtgagtgcc ataggacgtg ttcctgagtt tgcattgcac
1201 ggagaccttc ctgaattttt tcatttgcaa gtcggcttaa ccaattttgc attgagtcct
1261 aggctgcttg cactctgaat ttggctatt caggtagtgt gctcaaagtt gaaaccgcat
1321 acagcacaac tcaagtttgc atcagactgg gaagcgaact taagccagcg gtgcgtggcc
1381 caggagtggg aaagaaatg gatgcctgaa gtggaagagg tggtgcagag gggcaccgc
1441 ccatgctgcc ctgcttccaa ctgctgcgca taggggcgg caggggcggt gatctctaca
1501 ccttccaccc cccgcccggg gctgctgca cctatcgctt gggccacagg gccgacctgt
1561 gtgatgtggc cctgcgcgcc cagcaggagc ctgcctcat ctctggatc cacgccgaac
1621 tgcatgccga gccccggggt gatgactgga gggtcagcct ggaagaccac agcagccaag
1681 gtgagcatta agcagggcag ctttgccct ggggttga agcgccaggc tggaatgagt
1741 aaggtctcca caagaccctg ctgcctgcct cccatactcc catcagattg gatggatagt
1801 cgtggtccag accttcatct tccaccaga agtgtgcaca gtcagaagct ctctgccaga
1861 ctgacccttt ttggtcccgt ttagctcata caggacctgg gatatcatca gaaagatatc
1921 acagtgggga tgttctgagg ccactagagg ccaagtttag acttgattca gtttccagct
1981 ttgctgaggc actctgttcc tgggttaggg cagttctatg ttgaataatg tttttaataa
2041 tctgggcatg tcttttctccg tgacttgagg cagttagcct cagaaagcct agattcacat
2101 ttgagtttttg ccactgcctc ttggtaaagt cagctgtagg agtgttatgg ttattagact
2161 atagtagcca acattcatct agtgcttact gttatgagcc aggcccatt ttaagtgtat
2221 tgaatgtagg tggtactaat attatcctca tttacagtaa aggaaaatga ggcacaaaga
2281 ggttaaggaa cttgtccagg gctggcatg gtggtttaca cctataatcc agcactttgg
2341 gaggctaagg cagggtggat cacttgagct caggagttcg agaccagcct gggcaacatg
2401 gtgaaaacct gtctctacca aaaaattaat taatttttta aaaaagcct gggcgcggtg
2461 gctcacgcct gtaatcccag cactttggga ggccgagatg ggcagatcac gaggtcagga
2521 gttcgagacc atcctgacca acatgttgaa cactttttta tgctgaaaaa aaaatacaaa
2581 aattagccag gtgtgtgc gtgcacctgt acatgtcacc acccagct accccagct acccagct actcaggagg ctgaagcagc
```

FIG. 12-19

```
2641  agaatcactt  gaacccggga  ggcggaggtt  gcagtgagct  gagatcgcac  cactgcactc
2701  cagcttgggc  gacagagcga  gactccatct  caaacaaaca  acaaaccaa   aagcttgccc
2761  aggtcacat   aactggtaag  tggtagagct  aggatctgaa  cgagctggag  ctggggaga
2821  gtgagcatgt  ttgaaaactg  gaccttaggg  cggggcacgc  tggctcacgc  ctgtaatccc
2881  agcactttgg  gaggctgagg  cggcagatc   aggaggtcag  gagtatgaga  ccagcctgc
2941  caacatggta  aaaccctgtc  tctgctaaaa  ataaaaaaat  tagccagacg  tgtggcaca
3001  tgcctgtaat  cccagctact  cagggagctg  agcaggaga   attgcttgaa  cctgggaggc
3061  ggttcaagct  tgggcaatag  agcaaaactc  catctcaaaa  aaaaaaaag   aagaaaaa
3121  aaagaagaaa  gaaagaaaat  tggaccttag  gacagtgagg  gcaggatcc   tttgtaggaa
3181  agcacaagaa  acacagactt  gttcctagct  gacaaggagt  gtactgcctg  gtacctgtca
3241  cctgctgagg  ggcttaggat  gtgaggaga   atctgactac  agtttcatat  tcttcccag
3301  aaatcataca  gatttctcca  ctcctgactc  tggtcatttc  tgttttgtc   ctccatattt
3361  gcctggtgcc  ccaccatcaa  cagtactttt  ggtcaataat  gtccgactcc  caagaggtca
3421  caggctggaa  ttgagtgatg  gagacctcct  gacctttgc   cctgaagggc  cccaggaac
3481  cagcccctcg  gagttctact  tcatgttcca  acaagtacga  gtcaagcctc  agactttgc
3541  tgccattacc  atcccacggt  ctaggggaga  agcccgggtt  gggctgtt    tcggcctat
3601  gctgccctcc  cagggggctc  cacagcggcc  tctcagcacc  ttctccctg   cccccaagc
3661  cacactgatc  ctaaactcca  taggcagcct  cagcaagctc  cggccccagc  ccctcacctt
3721  ctccccctagt  tggggtggac  caaagagcct  gcctgttccc  gccccaccctg gggaagtggg
3781  gaccacgcct  tctgctccac  cccaacgcaa  tcggaggaaa  tctgttcacc  gagtgttggc
3841  ggaactggat  gatgagagtg  agcctcctga  gaacccgcca  ccggtcctta  tggagcccag
3901  gaagaaactc  cgtgtagaca  aagcccccact  gactcccact  ggtaagtgg   agtcctcact
3961  tgcccctctc  agtgttttac  tgcttttcga  ttccttgtat  cctaggctg   tgaggagtc
4021  ccctgcctg   ggggatggg   cacggaggt   ggaatagatg  gaatgcaag   acctgggtta
4081  gctctgatag  gaaagaaaa   atatgtgcag  gagaacatga  gaggtggggt  gggcagtgc
4141  ttataaaaca  accggagtga  gcatgtcctg  ctttttacat  tcatatggct  ttaaccccat
4201  tcttctagtg  cctaaggatg  gggaacttc   aggctcacac  tagaggtttt  tagccacc
4261  ctatgtgttt  ttaaggacag  agtccaggct  caccttagtt  ctcagaccac  tgtgcctctg
```

FIG. 12-20

```
4321 tggcctcacc ctatgaccag ccataggggtg gcaaggtcta ggccttctcc tacaggtttc
4381 cggtgaccct tgtgtctgtg tcacttcctt cagaaatcga cgtggccgtc ctcggaagta
4441 cccagtgagc gctcccatgg ctccccctgc agttggggggc gggagccct gtgcagctcc
4501 ttgttgctgc ctgcccagg agagacagt ggcctgggtt cagtgtgatg gctgtgacgt
4561 ctggttccat gtggcctgtg ttggctgcag catccaggct gccaggagg ccgacttccg
4621 atgcccaggg tgccggggctg gcattcagac ctaaggtcca cgccaaggc accatcggac
4681 acacctgccc atgagtagac acagcagcga gcaaataggt ctgataaata ccccccttcc
4741 cttccctccc caagagggaa tgactacagg gaagaaggat ggattgatgt ggactcattc
4801 agggcctgga gcagaccctg gtggccaaga cagagagat ggtttcctgc caaagatatt
4861 gccacctcca ggaaattgcc agtgagctgg aagttcccac tattacaagc cataaggcca
4921 tgttgccatg gacaccagaa tatctgtagt cagagcacct atcagttgca aaagccatgc
4981 ctgcaaccga tggaaaatgt aagagggagt tcttaaggtt cttggtggca tcacccaagg
5041 cattctggga aaacctaggg cctgccccca aaacttccct actctgtggc tagtcctgct
5101 gccaacaaaa tcgtagcgac ctggcttttc acagctttgc tttattcc aagtcaagga
5161 caagccgctt cattcactcc tggcatttta ctcttcttgt ggtctgtga tattccttgc
5221 tttccaggga gaatgtgctt ggcaaggtct ggagaactaa ttcagaaatct tagggaagg
5281 ggagagatgg aaatacaaac ctgcttactg gaaaggtgca aatatatggg ttgagctgga
5341 ggtaggaata caggtaatta aggtttctag tttaagggaa aacagatcta ttgccattta
5401 aataaggtaa ctgggatttg gttaagttca caaagaagc agaagattta tttacaggct
5461 tcacctgtac tgtcagggca agagaaaagc tgtaaacca gctacagag tttaccagtg
5521 tgatggctgt gacacagctc cactccacgg gtggacacag cagaggggcaa ctgggctggc
5581 ctggttcagt gtgaatcaaa ccgcttaacc cacacatggt acatgtgatt ttcttttgtg
5641 agccttacac caagccaaac tattgtcaaa gcatcatttc tatagaaata aagccttatc
5701 ttgacctgtt ctattaaaac ctgccacatc cgcccttttcc tacctagatt taatgagccc
5761 aagttttttt acatgaaga aatgactctg gggcaaagac ccctaatgaa ctagtggcag
5821 agccaggaat aaaacttgag taactaatga gtcacttatg ggcagagtat gcaaaaacct
5881 taagtggaaa ccaaatagac cctggtatca agaaagcaca agtattaat agaagttctct
5941 ggttggggtg atctaggttc aacagaaata agatgatttc taagtataaa gccatttaag
```

FIG. 12-21

```
6001 aattccagag tagggtggga aagcaaaaag ccagctctga acaggtaaca gctacatggt
6061 gactgagtct atgggcaaaa gttcttgcat cacaggcttt tgggaactag cctatcacag
6121 ggccctgtac aaataaactt ggctgcaatc ccagctctcc ctctgatgtt gtgtgacctt
6181 aaggagtgta aatggcacct tagtttcagg gtcacttggg tatgagcatt ggatattccc
6241 atccccacct cagtaactga aggacaaacc aagataagtg tgtctatcta ctgtgtccca
6301 agctttcttta tttaagaaaa aagtgataca tgatgtggga ttaaaatcaa gagcatcatt
6361 gaacttcacc ttccctccaa ccagttgccc caaactcccc tgccccacc ctttgtgttc
6421 ccaattcctt ccttagtgaa tgaagaactt aatcccaaaa accctgcac aaactccagg
6481 ttttctttcc ctagctcctc ccctccccct gtccccatt cctagaaggg caggcacctc
6541 agtttgaatg catgggagag cccagagtgg tgacagagac aggggaaaag gcttccccct
6601 cagggaaagg gaccgaggag tacagtgcag tgaagtgagg gctcccatag cctgggtac
6661 caaaatgggg ccctgggcc agaggaaagg acactggtcc ccctgagaaa ggagaccag
6721 cagcctcaaa atcctctcgt tgtgcatagt cgctgcttga tcgcttgccc ttctgcgcc
6781 ggttacagaa ccacactcgg accacctgcc agtgaatgac agaaaggaga atgacattag
6841 acaatgagct gagagacggg cctgactctg cttgacatt ctatccaaag ccaacagccc
6901 tagagcagtt agaggaggac attagagaat gagctgagac aggcctgact gcttgacat
6961 tctgtccaaa gccaacagcc ctagagcagcc tgaggagcc agagacatgg aaagcgaggt
7021 ggtgacaggg gaaagagatg gagcccgcag agcccgcag agagacatgg cactcacatc cttctcgagc
7081 ccaagctgct gggcgatgtg gctgatctgc tgcagtgtgg gtttcgggca ctgcaggaac
7141 aaattctcca ggttgcctct cactcggttc tcgatactgg gtttcgtttct ctttcgggcc
7201 tgcacgaggg tttctgcttt gcatatctgt gcaggtggga aggggtgac aaggcaagc
7261 tttggactttg ctgagtaaca gcatcacagg ggtctgtgac tagatgtgtc agcagagcca
7321 ggtggtggtg tgaaaaggca ggatcctgga agggttggct ctgaccttta tcccagcaga
7381 actgaggaat ttcactccat cccacactgcac caaagacgga gagctacgag
7441 ccagtgatgg aagcaatgaa aattaggcca agaaagggaa ggtccccggg tatcccctc
7501 ccacccttac ctcctgaaga tttcattgt tgtcagcttc ctccacccac ttctgcagca
7561 agggccgcag cttacacatg ttcttgaagc taagctgcag agcctcaaag cggcagatgg
7621 tcgtttggct gaataccttc cctggggag gccagtcaaa agagaagcaa aatgagggag
```

FIG. 12-22

```
7681 cacgcagggc ccttgtgacc ctgagatcca agcttaccac ctcttcccag agggagctca
7741 aagcccaagc atcttctccc tctccctact cctcttcatg ggtgagggta gagtctgccc
7801 ctgcccctcc ccactaggtt caggatact  cttagaggg gagatgcggt cagaatctgc
7861 agaggggaac ccaccaaata gaaccccag ggtgagcccc acatcggcct gtgtatatcc
7921 cagggtgatc ctcttctgct tcaggagctt ggcaaattgc tcgagttctt tctgcagagc
7981 tttgatgtcc tgggactgga tttttaaaagg cagaagactt gtaagaacat aaacacacca
8041 gttatcaatc tccccttttcc attcgggatt caagaaccta cgtgtggccc caaggaatag
8101 tctgtagaag tgcatctgcc ttccaagctg cccacctaac ttctagaaat aacctaccca
8161 caaatgtcat tcacccattc cctgttcact gactcatgca tgtaacaaag gactactctt
8221 ccccagaaa ctgcacatc caaggatgc agagcatggt gaaaggacag aaagagagac
8281 cctggcctcg agagaacac ctgtcaggtt atgaaggtta gaagttcttt gctgggcgcg
8341 gtggctcatg cctataattc cagcactttg ggaggccgag gtgggcagat cacgaggtca
8401 ggagttcaag accagcatgg ccaacatggt gaaaccccgt ctctactaaa aacacaaaaa
8461 ttagctgggc acggtggcac gcacctgtaa tcccagctac tcaggaggct gaggcaggag
8521 aatcacttga acccgggagg cggagggttgc agtgagctga gatcacgcca ctgcactcca
8581 gcctgggtga cagcaaga ctctgtctca aagaaaaaa aaaagaagat agttcattta
8641 atacctgcaa aattctctca ctcaagtatc accccagtt taaggatgtt ttgagattag
8701 agaaatagat aagctgctaa gttctgggtt aattaaaaag gaagagcatc atgtctcaga
8761 agctaaattc agtatatact ctccccagct tgctttgagg gtcccacaaa ctataacatg
8821 gcatgcatac acacaaacac agcaaaaaag taacaggtgt cataagaatg gataaagtgc
8881 tttgtgtgta cttactcctc atttttaaa ttgatttttt aaattcaaga gatttatcga gcacccttcta
8941 ttcactatag aggcatccta gtggacaaag agccctgaca tccagcatga cagaagtgct
9001 taagccagcg gctatacaaa gttgcccact tggatctctt ccaagtgcac tttccttttt
9061 attcggcact tgtttcttcaa gttgcccact tggatctctt ccaagtgcac tttccttttt
9121 tccctgccct ataactttt aataataaac ttccactcct gctctgaaaa ataaaaaagt
9181 aataaaata aaaaatggcc aggcacagtg gctcatgtct gtaaatccta gcactttggg
9241 aggccaagtg gggcagactg cttgagccca agagttagaa agcagcctgg gtaacatagt
9301 gagacccgtg ccgcccccttc tcccacccct gctgcctcta tttaaaaat atatatatat
```

FIG. 12-23

```
 9361 tatggaaaaa agcaaagcag tccggggcga gtggtcatgc ctgtaatccc ttcactttgg
 9421 gaggccaagg tgggtagatc acttgaggtc aggagttcaa gactagcctg gtcaacatag
 9481 tgagactctg tctctactaa aatacaaaaa attagctggg catcatggcg ctccctata
 9541 atcccagcta ctcaggaggc tggggcagga gaattgcttg aacctaggag gtgagtttg
 9601 cagtgagcca agatcgcacc actgcactcc agcctgaggg acagagtgag actccatctc
 9661 aaaaattaaa aaaaaataa agcagtctat aggagtaggg taaaggaggg aaggagatta
 9721 tggaggaggg tgacactttt aaagacagag aaggtgattg tttgagcaaa ggacaagagt
 9781 ctaatgtggc aaggccctga agtgggcctt ccagagccca aagctggtct ggtggctagg
 9841 tagatcctgt tgcacacata gtgactttgt tttagtccaa gtgaaatgat ctctcaccct
 9901 ttttctcccc cccaagacg gaatctcgtt ctatcgccca ggctggagtg ctgtgcgtg
 9961 atcttgctc actgcaatct ccgccttctg ggttcaagct attctgcctc agccgcctga
10021 gtagctggga ctacaggcac gccaccat gccgctaa ttttttgtatt tttagtagat
10081 atgggtttc accatgttgg ccaggctggt caggagacct caagtgatct gtccaccttg
10141 gcttcccaaa gtgctgggat tacaggtgtg aaccaccgca cctagcctca ccttttttt
10201 tttttttttg agagttttcgc ttttgttgcc taggctggag tgcactggcg cgatctcggc
10261 tcaccgcaac ctacatctcc caggttcaag cgattctcct gcctcagctt cctgagtagc
10321 tgagattaca ggcatgcgtc accacgccca gctaatttttg tatttttagt agagatgggg
10381 tttcgccatg ttggtcaggc tggactcgaa ctcccaacct caggtgattc gcctgcctcg
10441 gcctcccaaa gtgcctggcc acacctttta aaacactgac tctagttgac gtgttggcca
10501 cagacagtag ggaggaagca gtataatttg agaagctact gcggtaatcc cagcagagat
10561 gatggtggct gaggccaggg ttaggttgtg attgattcag gatgttctt aaggatagga
10621 tgtaggacgt gaaagaaact gaggatgact ggtttttgcc ttgagcaact gggtgatcag
10681 ggtggagcag tcaggggagc catcacaaga gacagaaaac gcggtagtca tctgtgtct
10741 aaatgcatt taagcttga gggtgggtga gaggaaggaa gggtagatag agcagaggtt
10801 gaaggactga gccctggggc atgccatatg aggctgccgg cggacagagg tgcacagcta
10861 gtgagaaaaa acaaggcct ttttgtagtc ctgaagcctc aaggaagtgt ttcaatggtg
10921 cttgatcata tcaatttcaa ataggctgtt ttcatcccca acttctgctc agccaataac
10981 tcaaactgat aaatgccctc tgctatcctg gattttccaa attctgtttt gggtttttgg
```

FIG. 12-24

```
11041  aataaacact ggtccaaatc ctcgcttcat catttagcag ttaaacccg ttaaatagga
11101  taataatacc tccccctagg agattttgtg ctggttaatg agataatgat gtataaacgg
11161  agcacacagc caggcactta ggaagtggac cacaattgcc agccattatc attcaaggct
11221  cagcagtgac ctctgcgaa gaggttggg cttctcggtc actccagaaa ccagtcacac
11281  ctttctgtga ggtctcaagg cttagtattt aatctctaat tgcttacact tgtcgccttg
11341  gaggactgga agatacatct ttaatagtcc tcagcagggc tggatgcctt caatcccgca
11401  gcagctctat atttgcaaat ggcctggaga aatctctcac cattttttt gtttacaact
11461  ttgggaactga ggctgaagtc aatcaaaatc cagctttcta caagggtgc cagggtgtgc
11521  acctaacac agtgccagt cattggcctg agcagagat ccgggaaga caagccctat
11581  acttgactgg aggtaaaccc agctcacac ctagactttc agcacacaca caggagatcc
11641  tatcagaaac gagtcacacc ctagactttc agaacacaata atcctggaat gagcactgtt
11701  tttaccctca ggctatgctt aaccctaagg ccaaatcttt gggtctgata aggtcaaat
11761  tttcaagcag gactaagggt gggaaaaggg gctcaaacca acccaagct gggtctggtg
11821  ctgggccagt aatgagtgac cagaccctgg gcaggcctag gcagcccag agaccctgac
11881  aagggctggg ccagacagag caaaggccag cctggccag cttccgactc tcccaggccg
11941  ctctgccctc acctgcagtt gtctctctga aatccagctt ccagttccca cctgcccct
12001  gcctgccagg gctgcctgca gttgatacac acccctccct ggccaggca gctgaccctg
12061  cctgctcctc tcctgggtgc caggtctggg cagtgcagg tgaccacttc ccatccagcc
12121  tgccctgtca tgaccactc cccacaccc aaccccgtcg aagctcactt gcctcctccg
12181  ggtttttgctc cagcttctcc ttctccagct tcacggcacc agggtgacg gtgcagggct
12241  ccgggaggc cccatcggag ttgctctcca cccgactcc tgcttcgccc tcaggctgag
12301  agtctccaa gccgccttgg ggcactagcc ccactccaac ctgggccca cagtacgcca
12361  tcccccaca gaactcatac ggcggggggc ctgggccctc atgggggaat cccccacacc tcagagcctg
12421  gcccaacccc cggcccgatt cctggccctc caggagggcc ttgaagctt agccaggtcc
12481  gaggatcaac ccagccccgc tccggcccgc gccgccatc ctgcccatc acctccacca cctggagggg
12541  gcgagaaggc aaaatctgaa gccaggtgtc gccaggtgt ccgcagggc gaaggaaggc gccccaagcc
12601  ggggcctgg tgaaatgagg gcttgcgaag ggactactca acccctctct ccctcccag
```

FIG. 12-25

```
12661  tcccacccac  tagccttgac  ctctggcccc  gcccctgga   tgggtggagg  agagggaggt
12721  gggggagaa   actgaggcga  aggatgtttg  cctaatggtg  gtggcaatgg  tgtctgtgga
12781  agggaaaac   cggagacac   aactggcgcc  cctccaggac  ctcagtgcag  gtccccaca
12841  gaaacttttt  ttattttat   tttttaagac  agggtctcac  tttgttgccc  agactggagt
12901  gcagtggagt  acaatgatgg  ctcaatgtag  cctcgatcta  ctgggccaaa  gcaatcctte
12961  tgctccagcc  tcctaagtgg  ctgggactac  aggcttgac   cactgtgccc  tgttagtttt
13021  tttatttta   gtagagatgg  ggcctgcta   tgttacccag  gctggtcttg  aattcctgtc
13081  ctcaagaaat  cctcccgcct  ctgccgccca  gtgtcatgat  taaaggcgtg  agccaccaca
13141  cccaactttc  aactcccaac  ccgctccctg  gcactctctc  agctctgca   catcccagct
13201  gtctgaatc   actccacac   ctccatgttc  ttcaggaacc  caggtgcttg  acccctctc
13261  cacagacctc  tggcactgtg  ccttcagggg  ccagtcaccc  tctcagctcc  tcaaatttat
13321  tgaatgtgtg  tgtggcgcta  tccctcaatg  catccatcca  cataagcaca  atggccagct
13381  gctcccttat  gccttcccc   gatccatcca  gaatcctagg  cattccatc   ccgatactgg
13441  ccaaatccag  ccaccccgca  gcctgggtgc  ctggcaccat  ctgcccagcc  tgccaaattt
13501  cacccatct   tcaagagtag  actgccagag  aaggcctccg  tgctatatcc  cccaccccc
13561  catccccca   cccctccgtc  ttccagaatc  agactccaga  ctctcctcat  ctaacagact
13621  aagggttgg   ccctacttc   cccttcaagg  gaccagactt  tgactgatt   gggcctcagt
13681  ttccaacct   ttgctgaaac  agagtgataa  gacacccgct  ttggccccc   tccactatgg
13741  aacctgcaca  tcagttcct   tgctcccctc  tcaaccaaaa  ctcagacatc  taataccacg
13801  gtaggcccg   ttctccctcc  cccacctccc  tggccccaggc  ctccagccct  agccctggg
13861  tgggaaaac   caggggtgg   ggggtgtgga  gaaaaatat   ctgacttcag  gttcaaagaa
13921  gcctgggagg  gactggggga  agggggcagg  acaatggcct  tggctgaca   atcccggtcc
13981  ccagagggg   cagctctaac  cctaaacaag  tgctcaaccc  ttgaatgggc  ctgatgct
14041  cccctgggga  ctgcttcctg  ctcccaacc   cccagtccc   aatcccctca  cacagaatcc
14101  ccttcagaga  cgctaaaagg  agctccagca  gcccctctc   accccctct   caaagactga
14161  gcctcagacg  ggcaccaagg  gccccctaca  gggacctagg  tatctagttc  ctccttcctc
14221  tggggactc   aggcgtccag  cttcatcgtg  catccctccc  cgagcccga   agattgaggg
14281  atgtgctttg  tttagtgggg  ctggctggca  gaaagacgca  gaggaggtgg  cgagtgattt
```

FIG. 12-26

```
14341 gtggaggggt gcaggaaggc tgccctaagc tcccctttcag ggtctgtttt tctgggcctg
14401 gcctgagtat cctgaggctc atgctgctgg tctagtgctt gattctgttt gcaagagaat
14461 agccaacg SEQ ID NO. 20
```

//

Revised July 5, 2002

Disclaimer | Write to the Help Desk
NCBI | NLM | NIH

FIG. 12-27

```
                    NCBI  Nucleotide
PubMed  Nucleotide  Protein  Genome  Structure  PMC  Taxonomy  OMIM  Boo
Search Nucleotide ▽ for [                              ] Go  Clear           Details
       Limits     Preview/Index      History     Clipboard
Display default ▽ Show: 20 ▽ Send to File ▽       Get Subsequence            Links □ 1: BC033086. Homo sapiens, Sim...[gi:21620013]

LOCUS       BC033086            3021 bp    mRNA    linear   PRI 27-JUN-2002
DEFINITION  Homo sapiens, Similar to transcription factor 19 (SC1),
            transcription factor like #, clone MGC:45652 IMAGE:3160434, mRNA,
            complete cds.
ACCESSION   BC033086
VERSION     BC033086.1  GI:21620013
KEYWORDS    MGC
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 3021)
  AUTHORS   Strausberg,R.
  TITLE     Direct Submission
```

FIG. 12-28

```
JOURNAL    Submitted (25-JUN-2002) National Institutes of Health, Mammalian
           Gene Collection (MGC), Cancer Genomics Office, National Cancer
           Institute, 31 Center Drive, Room 11A03, Bethesda, MD 20892-2590,
           USA
           NIH-MGC Project URL: http://mgc.nci.nih.gov
           Contact: MGC help desk
           Email: cgapbs-r@mail.nih.gov
           Tissue Procurement: ATCC
           cDNA Library Preparation: Rubin Laboratory
           cDNA Library Arrayed by: The I.M.A.G.E. Consortium (LLNL)
           DNA Sequencing by: Genome Sequence Centre,
           BC Cancer Agency, Vancouver, BC, Canada
           info@bcgsc.bc.ca
           Steven Jones, Jennifer Asano, Ian Bosdet, Yaron Butterfield,
           Susanna Chan, Readman Chiu, Chris Fjell, Erin Garland, Ran Guin,
           Letticia Hsiao, Martin Krzywinski, Reta Kutsche, Oliver Lee, Soo
           Sen Lee, Victor Ling, Carrie Mathewson, Candice McLeavy, Steven
           Ness, Pawan Pandoh, Anna-Liisa Prabhu, Parvaneh Saeedi, Jacqueline
           Schein, Duane Smailus, Michael Smith, Lorraine Spence, Jeff Stott,
           Michael Thorne, Miranada Tsai, Natasja van den Bosch, Jill Vardy,
           George Yang, Scott Zuyderduyn, Marco Marra.

REMARK
COMMENT    Clone distribution: MGC clone distribution information can be found
           through the I.M.A.G.E. Consortium/LLNL at: http://image.llnl.gov
           Series: IRAL Plate: 43 Row: a Column: 8
           This clone was selected for full length sequencing because it
           passed the following selection criteria: matched mRNA gi: 6005891.
```

FIG. 12-29

```
FEATURES             Location/Qualifiers
     source          1..3021
                     /organism="Homo sapiens"
                     /db_xref="taxon:9606"
                     /clone="MGC:45652 IMAGE:3160434"
                     /tissue_type="Brain, neuroblastoma"
                     /clone_lib="NIH_MGC_19"
                     /lab_host="DH10B-R"
                     /note="Vector: pOTB7"
     CDS             422..1459
                     /codon_start=1
                     /product="Similar to transcription factor 19 (SC1);
                     transcription factor like #"
                     /protein_id="AAH33086.1"
                     /db_xref="GI:21620014"
                     /translation="MLPCFQLLRIGGGRGGDLYTFHPPAGAGCTYRLGHRADLCDVAL
                     RPQQEPGLISGIHAELHAEPRGDDWRVSLEDHSSQGTLVNNVRLPRGHRLELSDGDLL
                     TFGPEGPPGTSPSEFYFMFQQVRVKPQDFAAITIPRSRGEARVGAGFRPMLPSQGAPQ
                     RPLSTFSPAPKATLILNSIGSLSKLRPQPLTFSPSWGGPKSLPVPAPPGEVGTTPSAP
                     PQRNRRKSVHRVLAELDDESEPLENPPPVLMEPRKKLRVDKAPLITPTGNRRGRPRKYP
                     VSAPMAPPAVGGGEPCAAPCCCLPQEETVAWVQCDGCDVWFHVACVGCSIQAAREADF
                     RCPGCRAGIQT" SEQ ID NO.4

BASE COUNT     795 a     774 c     791 g     661 t
ORIGIN
        1 tcgtctcctg ccgagagcc caagggtcc cgggatccgc cgcacaggct ggcactgctt
       61 gaagaggagg ctactcggag actgcgccgc gcggattgga ggctccccaa atatttgcg
```

FIG. 12-30

```
 121 atctgaggat ccagctcaag tgaggtgcca taggacgtgt tcctgagttt gcattgcacg
 181 gagacctttcc tggaatttt catttgcaag tcggcttaac caatttgca ttgagtccta
 241 ggctgcttgc actctgaatt tgggctattc aggtagtgtg ctcaaagttg aaaccgcata
 301 cagcacaact caagtttgca tcagactggg aagcgaactt aagccagcgg tgcgtggccc
 361 aggagtggga aaggaaatgg atgcctgaag tggaagaggt ggtgcagagg gggcaccgcc
 421 catgctgccc tgcttccaac tgctgcgcat aggggcggc agggcggtg atctctacac
 481 ctttccacccc cccgccggg ctggctgcac ctatcgcttg ggccacaggg ccgacctgtg
 541 tgatgtggcc ctgcggcccc agcaggagcc tggcctcatc tctgggatcc acgcgcgaact
 601 gcatgccgag ccccggggtg atgactggag ggtcagcctg gaagaccaca gcagccaagg
 661 tactttggtc aataatgtcc gactcccaag aggtcacagg ctggaattga gtgatggaga
 721 cctcctgacc tttggccctg aagggccccc agaaccagc ccctcgagt tctacttcat
 781 gttccaacaa gtacgagtca agcctcagga ctttgctgcc attaccatcc cacggtctag
 841 gggagaagcc cggttggggg ctggtttccg gcctatgctg ccctcccagg gggctccaca
 901 gcggcctctc agcaccttct cccctgcccc caaggccaca ctgatcctaa actccatagg
 961 cagcctcagc aagctccggc cccagcccct cacctgggga ccctcgagt gtggaccaaa
1021 gagcctgcct gttcccgccc gttcccgccc agtgggaccc acgccttctg ctccaccca
1081 acgcaatcgg aggaaatctg ttcaccgagt gttggcggaa ctggatgatg agagtgagcc
1141 tcttgagaac ccgccaccgg tccttatgga gccaggaag aaactccgtg tagacaaagc
1201 cccactgact cccactggaa atcgacgtgg ccgtcctcgg aagtacccag tgagcgctcc
1261 catgctctcc cctgcagttg gggcggggga gccctgtgca gctccttgtt gctgctgcc
1321 ccaggaagag acagtggcct gggtttcagtg aggctgccag tgatggctgt tccatgtggc
1381 ctgtgttggc tgcagcatcc aggctgccac ggaggccgac ttccgatgcc cagggtgccg
1441 ggctggcatt cagacctccc gtccaccgcc aagcaccat cggacacacc tgcccatgag
1501 ccaggaagag agcgagcaac taggtctgat aaataccccc cttcccttcc ctccccagga
1561 ctgtgttggc tgcagcatcc aggatggatt gatgtggact cattcagggc ctggagcaga
1621 cccccttggtggc caagacagaa gagacagaga cctgccaaag atattgccac ctccaggaaa
```

FIG. 12-31

```
1681 ttgccagtga gctggaagtt cccactatta caagccataa ggccatgttg ccatggacac
1741 cagaatatct gtagtcagag cacctatcag ttgcaaaagc catgcctgca accgatggaa
1801 aatgtaagag ggagttctta agttcttga tgcatcacc caaggcattc tgggaaaacc
1861 tagggcctgg cccaaaact tccctactct gtggctagtc ctgctgccaa caaatcgta
1921 gcgacctggc ttttcacagc tttgcttta tttccaagtc aaggacaagc cgcttcattc
1981 actcctgggc atttactctt cttgtgggtc tgtgatattc cttgctttcc agggagaatg
2041 tgcttggcaa ggtctggaga actaattcag aatcttaggg gaaggggaga gatggaaata
2101 caaacctgct tactggaaag gtgcaaatat atgggttgag ctggaggtag gaatacaggt
2161 aattaaggtt tctgttttaa gggaaaacag atctattgcc atttaaataa ggtaactggg
2221 atttggttaa gttcacaaag ttagcagaag atttatttac agcttcacc tgtactgtca
2281 gggcaagaga aagcctggta aaccagctac agcagtttac cagtgtgatg gctgtgacac
2341 agctccactc cacgggtgga cacagcagag ggcaactggg ctggcctggt tcagtgtgaa
2401 tcaaaccgct taacccacac atggtacatg tgattttctt ttgtgagcct tacaccaagc
2461 caaactattg tcaaagcatc atttctatag aaataaagcc ttatctttgac ctgttctatt
2521 aaaacctgcc acatccgcc tttcctacct agatttaatg agcccaagtt tttttacatg
2581 gaagaaatga ctctggggca aagacccta atgaactagt ggcagagcca ggaataaaac
2641 ttgagtaact aatgagtcac ttatgggcag agtatgcaaa aaccttaagt ggaaaccaaa
2701 tagaccctgg tatcaagaaa gcacaaagta ttaatagaag tttctggttg gggtgatcta
2761 ggttcaacag aaataagatg atttctaagt ataaagccat tttagaattc cagagtaggg
2821 tgggaaagca aaaagccagc tctgaacagg taacagctac atggtgactg agtctatggg
2881 caaaagttct tgcatcacag gctttttggga actagcctat cacagggccc tgtacaaata
2941 aacttggctg caatcccaaa aaaaaaaaa aaaaaaaaa aaaaaaaaaa aaaaaaaaaa
3001 aaaaaaaaaa a    SEQ ID NO. 21
```

FIG. 12-32

NCBI Nucleotide

PubMed  Nucleotide  Protein  Genome  Structure  PMC  Taxonomy  OMIM  Boo

Search [Nucleotide ▼] for [                    ] [Go] [Clear]   Details

Limits   Preview/Index   History   Clipboard

Display [default ▼]  Show: [20 ▼]  [Send to ▼] [File ▼]  [Get Subsequence]   Links ☐ 1: NM_007109. Homo sapiens tran...[gi:6005891]

```
LOCUS       TCF19                   1080 bp    mRNA    linear   PRI 05-NOV-2002
DEFINITION  Homo sapiens transcription factor 19 (SC1) (TCF19), mRNA.
ACCESSION   NM_007109
VERSION     NM_007109.1  GI:6005891
KEYWORDS    
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1 (sites)
  AUTHORS   Ku,D.H., Chang,C.D., Koniecki,J., Cannizzaro,L.A.,
            Boghosian-Sell,L., Alder,H. and Baserga,R.
  TITLE     A new growth-regulated complementary DNA with the sequence of a
            putative trans-activating factor
  JOURNAL   Cell Growth Differ. 2 (4), 179-186 (1991)
  MEDLINE   91329275
```

FIG. 12-33

```
PUBMED    1868030
REFERENCE 2  (bases 1 to 1080)
AUTHORS   Krishnan,B.R., Jamry,I. and Chaplin,D.D.
TITLE     Feature mapping of the HLA class I region: localization of the
          POU5F1 and TCF19 genes
JOURNAL   Genomics 30 (1), 53-58 (1995)
MEDLINE   96129301
PUBMED    8595903
REFERENCE 3  (bases 1 to 1080)
AUTHORS   Krishnan,R.
TITLE     Molecular mapping by transposon-based nested deletion sequencing:
          the SC1 gene maps near the HLA-C locus
JOURNAL   Unpublished
COMMENT   PROVISIONAL REFSEQ: This record has not yet been subject to final
          NCBI review. The reference sequence was derived from U25826.1.
FEATURES          Location/Qualifiers
     source       1..1080
                  /organism="Homo sapiens"
                  /db_xref="taxon:9606"
                  /chromosome="6"
                  /map="6p21.3"
                  /clone="YAC B209D7, Cosmid 52, pDEL5.5"
                  /haplotype="A3 B8 C- DR3 DQw2 DRw52 and A29 Bw65 C- DR7
                  DQw2 DP4"
                  /sex="male"
                  /cell_line="B lymphoblastoid"
                  /tissue_type="blood"
                  /clone_lib="CGM1 library from the Washington University
                  School of Medicine"
```

FIG. 12-34

```
gene            1..1080
                /dev_stage="adult"
                /gene="TCF19"
                /note="synonym: SC1"
                /db_xref="LocusID:6941"
                /db_xref="MIM:600912"
CDS             1..1080
                /gene="TCF19"
                /note="transcription factor like #"
                /codon_start=1
                /product="transcription factor 19 (SC1)"
                /protein_id="NP_009040.1"
                /db_xref="GI:6005892"
                /db_xref="LocusID:6941"
                /db_xref="MIM:600912"
                /translation="MLPCFQLLRIGGGRGGDLYTFHPPAGVGCTYRLGHRADLCDVAL
                RPQQEPGLISGIHAELHAEPRGDDWRVSLEDHSSQGTLVNNVRLPRGHRLELSDGDLL
                TFGPEGPPGTSPSEFYMFQQVRVKPQDFAAITIPRSRGEARVGAGFRPMLPSQGAPQ
                RPLSTFSPAPKATLILNSIGSLSKLRPQPLTFSPSWGGPKSLPVPAPPGEVGTTPSAP
                PQRNRRKSVHRVLAELDDESEPPENPPPVLMEPRKKLRVDKAPLTPTGNARGRPRKYP
                VSAPMAPPAVGAGSPVQLLVAACPRKRQWPGFSVMAVTSGSMWPVLAAASRLPGRPTS
                DAQGAGLAFSLRSTAKAPSDTPAHE" SEQ ID NO. 5
misc_feature    88..264
                /gene="TCF19"
                /note="FHA; Region: Forkhead associated domain"
                /db_xref="CDD:smart00240"
misc_feature    91..306
                /gene="TCF19"
```

FIG. 12-35

```
conflict   /note="FHA; Region: FHA domain. The FHA
           (Forkhead-associated) domain is a phosphopeptide binding
           motif"
           /db_xref="CDD:pfam00498"
           80
           /gene="TCF19"
           /citation=[1]
           /replace="c"
variation  80
           /gene="TCF19"
           /note="WARNING: map location ambiguous"
           /allele="T"
           /allele="C"
           /db_xref="dbSNP:1065459"
           367..369
conflict   /gene="TCF19"
           /citation=[1]
           /replace="aac"
           577
conflict   /gene="TCF19"
           /citation=[1]
           /replace="a"
           631
variation  /gene="TCF19"
           /note="WARNING: map location ambiguous"
           /allele="G"
           /allele="A"
           /db_xref="dbSNP:2073721"
```

FIG. 12-36

```
variation      657
               /gene="TCF19"
               /note="WARNING: map location ambiguous"
               /allele="C"
               /allele="A"
               /db_xref="dbSNP:2073722"
variation      722
               /gene="TCF19"
               /note="WARNING: map location ambiguous"
               /allele="T"
               /allele="C"
               /db_xref="dbSNP:2073724"
conflict       802..803
               /gene="TCF19"
               /citation=[1]
               /replace="cg"
conflict       869..871
               /gene="TCF19"
               /citation=[1]
               /replace=""
variation      1042
               /gene="TCF19"
               /note="WARNING: map location ambiguous"
               /allele="G"
               /allele="A"
               /db_xref="dbSNP:1065460"
conflict       1045..1046
               /gene="TCF19"
```

FIG. 12-37

/citation=[1]
/replace="cg"

BASE COUNT      200 a      361 c      315 g      204 t
ORIGIN
    1 atgctgccct gcttccaact gctgcgcata ggggcggca ggggcggtga tctctacacc
   61 ttccacccc ccgccgggt tggctgcacc tatcgcttgg gccacagggc cgacctgtgt
  121 gatgtggccc tgcggcccca gcaggagcct ggcctcatct ctggatcca cgccgaactg
  181 catgccgagc cccggggtga tgactggagg gtcagcctgg aagaccacag cagccaaggt
  241 actttggtca ataatgtccg actcccaaga ggtcacaggc tggaattgag tgatggagac
  301 ctcctgacct ttggccctga agggccccca ggaaccagcc cctcggagtt ctacttcatg
  361 ttccaacaag tacgagtcaa gcctcaggac tttgctgcca ttaccatccc acggtctagg
  421 ggagaagccc gggttgggc tggtttccgg cctatgctgc cctcccaggg ggctccacag
  481 cggcctctca gcaccttctc ccctgccccc aaggccacac tgatcctaaa ctccataggc
  541 agcctcagca agctccggcc ccagcccctc accttctccc ctagttgggg tggaccaaag
  601 agcctgcctg ttcccgcccc acctgggaa gtggggacca cgccttctgc tccacccca
  661 cgcaatcgga ggaaatctgt tcaccgagtg ttggcggaac tggatgatga gagtgagcct
  721 cctgagaacc cgccaccggt cctatggag cccaggaaga aactccgtgt agacaaagcc
  781 ccactgactc ccactggaaa tgcacgtggc cgtcctcgga agtaccagt gagcgctccc
  841 atggctcccc ctgcagttgg ggcgggagc cctgtgcagc tcctttgttgc tgcctgcccc
  901 aggaagagac agtggcctgg gttcagtgtg atggctgtga cgtctgttc catgtggcct
  961 gtgtttggctg cagcatccag gctgccaggg aggccgactt ccgatgccca gggtgccggg
 1021 ctggcattca gcctaaggtc cacggccaag gcaccatcgg acacacctgc ccatgagtag

SEQ ID NO. 22

Revised July 5, 2002

Disclaimer | Write to the Help Desk
NCBI | NLM | NIH

FIG. 12-38

```
                                                                                  Boo
NCBI                                            Nucleotide
  PubMed    Nucleotide   Protein   Genome   Structure   PMC   Taxonomy   OMIM
Search Nucleotide  for                                        Go  Clear         Details
              Limits
Display default     Show: 20        Preview/Index    History      Clipboard     Links
                                    Send to  File                Get Subsequence
```

☐ 1: AB029519. Homo sapiens SC1(...[gi:5420470]

```
LOCUS        AB029519                4651 bp    DNA     linear   PRI 29-APR-2000
DEFINITION   Homo sapiens SC1(TCF19)-7 gene, complete cds.
ACCESSION    AB029519
VERSION      AB029519.1  GI:5420470
KEYWORDS     .
SOURCE       Homo sapiens (human)
  ORGANISM   Homo sapiens
             Eukaryota; Metazoa; Chordata; Craniata; Vertebrata; Euteleostomi;
             Mammalia; Eutheria; Primates; Catarrhini; Hominidae; Homo.
REFERENCE    1 (sites)
  AUTHORS    Teraoka,Y., Naruse,T.K., Oka,A., Matsuzawa,Y., Shiina,T.,
             Iizuka,M., Iwashita,K., Ozawa,A. and Inoko,H.
  TITLE      Genetic polymorphisms in the cell growth regulated gene, SC1
             telomeric of the HLA-C gene and lack of association of psoriasis
             vulgaris
  JOURNAL    Tissue Antigens 55 (3), 206-211 (2000)
```

FIG. 12-39

```
MEDLINE      20236853
REFERENCE    2  (bases 1 to 4651)
AUTHORS      Teraoka,Y. and Inoko,H.
TITLE        Direct Submission
JOURNAL      Submitted (02-JUL-1999) Yoshika Teraoka, Tokai University School of
             Medicine, Molecular Life Science; Bohseidai, Isehara, Kanagawa
             259-1193, Japan (E-mail:yoshika@is.icc.u-tokai.ac.jp,
             Tel:81-463-93-1121(ex.2653), Fax:81-463-94-8884)
FEATURES             Location/Qualifiers
     source          1..4651
                     /organism="Homo sapiens"
                     /db_xref="taxon:9606"
     gene            join(378..615,2320..2878,3346..3586)
                     /gene="SC1(TCF19)-7"
     CDS             join(378..615,2320..2878,3346..3586)
                     /gene="SC1(TCF19)-7"
                     /codon_start=1
                     /protein_id="BAA82327.1"
                     /db_xref="GI:5420471"
                     /translation="MLPCFQLLRIGGGRGGDLYTFHPPAGAGCTYRLGHRADLCDVAL
                     RPQQEPGLISGIHAELHAEPRGDDWRVSLEDHSSQGTLVNNVRLPRGHRLELSDGDLL
                     TFGPEGPPGTSPSEFYFMFQQVRVKPQDFAAITIPRSRGEARVGAGFRPMLPSQGAPQ
                     RPLSTFSPAPKATLILNSIGSLSKLRPQPLTFSPSWGGPKSLPVPAPPGEVGTTPSAP
                     PQRNRRKSVHRVLAELDDESEPPENPPPVLMEPRKKLRVDKAPLTPTGNRRGRPRKYP
                     VSAPMAPPAVGGEPCAAPCCCLPQEETVAWVOCDGCDVWFHVACVGCSIQAAREADF
                     RCPGCRAGIQT" SEQ ID NO. 6

BASE COUNT  1160 a    1163 c    1244 g    1084 t
```

FIG. 12-40

```
ORIGIN
   1 cgccacccc gacacacaca ggagctgcct aagtatcct tgccttgcag attggaggct
  61 cccaaatat tttgtgatct gaggatccag ccttcctga ctcaagtgag gtgccatagg acgtgttcct
 121 gagtttgcat tgcacggaga ccttcctga atttttcatt tgcaagtcgg cttaaccaat
 181 tttgcattga gtcctaggct gcttgcactc tgaatttggg ctattcaggt agtgtctca
 241 aagttgaaac cgcatacagc acaactcaag tttgcatcag actgggaagc gaacttaagc
 301 cagcggtgcg tggcccagga gtgggaaagg aatggatgc ctgaagtgga agaggtgtg
 361 cagaggggc accgcccatg ctgccctgct tccaactgct gcgcataggg ggcgcaggg
 421 gcggtgatct ctacaccttc cacccccccg ccggggctgg ctgcacctat cgcttgggcc
 481 acaggccga cctgtgtgat gtggcctgc ccgggcccca ggcccagca ggagcctggc ctcatctctg
 541 ggatccacgc cgaactgcat gccgagcccc ggggtgatga ctggagggtc agcctgaaag
 601 accacagcag ccaagtgag cattaagcag ggcagcttg cccctgggtg gttgaagcgc
 661 caggctgaa tgagtaagt ctccacaaga cctgctgcc tgcctcccat actcccatca
 721 gattggatgg atagtcgtgg tccagacctt cctttttggt ccgtttagc ccagaagtgt gcacagtcag
 781 aagctctctg ccagactgac ccttttggt gggatgttc ccgtttagc tcatacagga cctggatat
 841 catcagaaag atatcacagt gggatgttc tgaggccact agaggccaag tttagacttg
 901 attcagtttc cagctttgct gaggcactct gttcctgggt tagggcagtt ctatgttgaa
 961 taatgttttt aataatctgg gcatgtctttt ctccgtgact tgagccagtt agcctcagaa
1021 agcctagatt cacatttgag tttttgccact tttgccact gcctcttggt aaagtcagct gtaggagtgt
1081 tatgttatt agactatagt agcaacatt catctagtgc ttactgttat gagccaggcc
1141 ctatttaag tgtattgaat gtaggtgta ctaatattat cctcattac agtaaaggaa
1201 aatgaggcac aaagaggtta agaacttgt caggggctgt gcatgtgtt ttacacctat
1261 aatccagcac tttgggaggc taaggcagg tggatcactt gagctcactt gttcgagacc
1321 agcctgggca acatgtgaa acctgtctc taccaaaaaa ttaattaatt tttaaaaaa
1381 agcctgggcg cggtggctca cgcctgtaat cccagcactt tgggaggccg agatgggcag
1441 atcacgaggt caggagttcg agaccatcct gaccaacatg ttgaaaccccc atctgtctg
1501 aaaaaaaaat acaaaaatta gccaggtgtg gtggcgtgca cctgtaaccc cagctactca
1561 ggaggctgaa gcagcagaat cacttgaacc cgggaggcgg aggttgcagt gagctgagat
```

FIG. 12-41

```
1621 cgcaccactg cactccagct tgggcgacag agcgagactc catctcaaac aaacaaacaa
1681 accaaaagct tgcccagggt cacataactg gtaagtggta gagctaggat ctgaacgagc
1741 tggagctggg ggagagtgag catgttttgaa aactggacct tagggcgggg cacggtggct
1801 cacgcctgta atcccagcac tttgggaggc tgaggcgggc agatcaggag gtcaggagta
1861 tgagaccagc ctggccaaca ctggtaaaacc ctgtctctgc taaaaataaa aaaattagcc
1921 agacgtggtg gcacatgcct gtaatcccag ctactcagga ggctgaggca ggagaattgc
1981 ttgaacctgg gaggcggttc aagcttgggc aatagagcaa aactccatct caaaaaaaaa
2041 aaaaagaaag aaaaaaaaag aagaaagaaa gaaaattgaa ccttaggaca gtgaggcag
2101 ggatcctttg taggaaagca caagaaacac agacttgttc ctagctgaca aggagtgtac
2161 tgcctggtac ctgtcacctg ctgagggctg taggatgtga gggagaatct gactacagtt
2221 tcatattctt cccagaaat catacagatt tctccactcc tgactctgt catttctgtt
2281 tttgtcctcc atatttgcct ggtgcccac catcaacagg tactttggtc aataatgtcc
2341 gactcccaag aggtcacagg ctgaattga gtgatggaga cctcctgacc tttggccctg
2401 aagggcccc aggaaccagc ccctcggagt tctacttcat gttccaacaa gtacgagtca
2461 agctcagga ctttgctgcc attaccatcc cacggtctag ggagagaagcc cggttgggg
2521 ctggtttccg gcctatgctg ccctcccagg gggctccaca gcggcctctc agcaccttct
2581 ccctgcccc caagccaaca actccataga acctcatagg cagcctcagc aagctccggc
2641 cccagcccct caccttctcc cctagttggg gtggaccaaa gagcctgcct gttcccgcc
2701 cacctgggga agtgggacc acgcttctg ctccacccca acgcaatcgg aggaaatctg
2761 ttcaccgagt gttgcggaa ctgatgatg agagtgagcc tcctgagaac ccgccaccgg
2821 tccttatgga gcccaggaag aaactccgtg tagacaaagc ccactgact cccactgggt
2881 aagtgagtc ctcacttggc cctctcagtg ttttactgct tttcgattcc ttgtatccct
2941 agctgtgag gaggtccccc tgcctggggg gatgggcacg ggaggtggaa tagatggaat
3001 gcaagacct gggttagctc tgataggaaa agaaaaatat gtgcaggaga acatgagagg
3061 tggggtgggg cagtgcttat aaaacaaccg gagtgagcat gtcctgcttt ttacattcat
3121 atggctttaa ccccattctt ctagtgccta aggatgggga acttcagge tcacactaga
3181 ggttttagg cccaccctat gtgttttaa ggacagagtc caggctcacc ttagttctca
3241 gaccactgtg cctctgtggc ctcacctgc ctcaccctat gaccagccat agggtggcaa ggtctaggcc
```

FIG. 12-42

```
3301  ttctcctaca  ggtttccggt  gacccttgtg  tctgtgtcac  ttcagaaatc  gacgtgccg
3361  tcctcgaag   taccagtga   gcgctcccat  ggctcccct   gcagttgggg  gcgggagcc
3421  ctgtgcagct  ccttgttgct  gcctgccca   ggaagagaca  gtggcctggg  ttcagtgtga
3481  tggctgtgac  gtctgttcc   atgtggcctg  tgttggctgc  agcatccagg  ctgccaggga
3541  ggccgacttc  cgatgccag   ggtgccggc   tggcattcag  acctaaggtc  caccgccaag
3601  gcaccatcgg  acacacctgc  ccatgagtag  acacagcagc  gagcaaatag  gtctgataaa
3661  tacccccctt  ccctcccctc  cccaagaggg  aatgactaca  gggaagaagg  atggattgat
3721  gtgactcat   tcagggcctg  gagcagacc   tggtggccaa  gacagaagag  atggttttct
3781  gccaaagata  ttgccacctc  caggaaattg  ccagtgagct  ggaagttccc  actattacaa
3841  gccataaggc  catgttgcca  tggacaccag  aatatctgta  gtcagagcac  ctatcagttg
3901  caaaagccat  gcctgcaacc  gatggaaaat  gtaagaggga  gttcttaagg  ttcttggtgg
3961  catcacccaa  ggcattctgg  gaaaacctag  ggcctggccc  caaaacttcc  ctactcctgtg
4021  gctagtcctg  ctgccaacaa  aatcgtagcg  acctggcttt  tcacagcttt  gctttattt
4081  ccaagtcaag  gacaagccgc  ttcattcact  cctgggcatt  tactctcttt  gtgggtctgt
4141  gatattcctt  gctttccagg  gagaatgtgc  ttggcaaggt  ctggagaact  aattcagaat
4201  cttaggggaa  ggggagagat  ggaaatacaa  acctgcttac  tggaaaggtg  caaatatatg
4261  ggttgagctg  gaggtaggaa  tacaggtaat  taagttttct  agtttaaggg  aaaacagatc
4321  tattgccatt  taaataaggt  aactgggatt  tggttaagtt  cacaaagata  gcagaagatt
4381  tatttacagg  cttcacctgt  actgtcaggg  caagagaaag  cctggtaaac  cagctacagc
4441  agttaccag   tgtgatgct   gtgacacagc  tccactccac  ggtggacac   agcagaggc
4501  aactgggctg  gcctggttca  gtgtgaatca  accgcttaa   cccacacatg  gtacatgtga
4561  tttctttttg  tgagccttac  accaagccaa  actattgtca  aagcatcatt  tctatagaaa
4621  taaagcctta  tcttgacctg  ttctattaaa  a           SEQ ID NO.23
```

FIG. 12-43

```
NCBI                                          Nucleotide

PubMed   Nucleotide   Protein   Genome   Structure   PMC   Taxonomy   OMIM   Boo Search Nucleotide ▽ for [                              ]  Go  Clear
         Limits          Preview/Index   History      Clipboard      Details Display default ▽ Show: 20 ▽  Send to File ▽           Get Subsequence ☐ 1: U25826. Human transcripti...[gi:833832]                        Links LOCUS         HSU25826             5522 bp    DNA     linear   PRI 27-MAY-1995
DEFINITION    Human transcription factor (SC1) gene, complete cds.
ACCESSION     U25826
VERSION       U25826.1  GI:833832
KEYWORDS      .
SOURCE        Homo sapiens (human)
  ORGANISM    Homo sapiens
              Eukaryota; Metazoa; Chordata; Craniata; Vertebrata; Euteleostomi;
              Mammalia; Eutheria; Primates; Catarrhini; Hominidae; Homo.
REFERENCE     1  (bases 1 to 5522)
  AUTHORS     Krishnan,R.
  TITLE       Molecular mapping by transposon-based nested deletion sequencing:
              the SC1 gene maps near the HLA-C locus
  JOURNAL     Unpublished
REFERENCE     2  (sites)
```

FIG. 12-44

```
AUTHORS    Ku,D.H., Chang,C.D., Koniecki,J., Cannizzaro,L.A.,
           Boghosian-Sell,L., Alder,H. and Baserga,R.
TITLE      A new growth-regulated complementary DNA with the sequence of a
           putative trans-activating factor
JOURNAL    Cell Growth Differ. 2 (4), 179-186 (1991)
MEDLINE    91329275
 PUBMED    1868030
REFERENCE  3  (bases 1 to 5522)
AUTHORS    Krishnan,R.
TITLE      Direct Submission
JOURNAL    Submitted (27-APR-1995) Rajendra Krishnan, Dept. of Internal
           Medicine, Washington University School of Medicine, Div. Allergy &
           Immun., 660 South Euclid Avenue, St. Louis, MO 63110, USA
FEATURES           Location/Qualifiers
     source        1..5522
                   /organism="Homo sapiens"
                   /db_xref="taxon:9606"
                   /chromosome="6"
                   /map="6p23.1"
                   /clone="YAC B209D7, Cosmid 52, pDEL5.5"
                   /haplotype="A3 B8 C- DR3 DQw2 DRw52 and A29 Bw65 C- DR7
                   DQw2 DP4"
                   /sex="male"
                   /cell_line="B lymphoblastoid"
                   /tissue_type="blood"
                   /clone_lib="CGM1 library from the Washington University
                   School of Medicine"
                   /dev_stage="adult"
```

FIG. 12-45

```
gene            <933..1170
                /gene="SC1"
CDS             join(933..1170,2905..3463,3929..4211)
                /gene="SC1"
                join(933..1170,2905..3463,3929..4211)
                /gene="SC1"
                /codon_start=1
                /product="transcription factor SC1"
                /protein_id="AAB60363.1"
                /db_xref="GI:833833"
                /translation="MLPCFQLLRIGGGRGGDLYTFHPPAGVGCTYRLGHRADLCDVAL
                RPQQEPGLISGIHAELHAEPRGDDWRVSLEDHSSQGTLVNNVRLPRGHRLELSDGDLL
                TFGPEGPPGTSPSEFYFMFQQVRVKPQDFAAITIPRSRGEARVGAGFRPMLPSQGAPQ
                RPLSTFSPAPKATLILNSIGSLSKLRPQPLTFSPSWGGPKSLPVPAPPGEVGTTPSAP
                PQRNRRKSVHRVLAELDDESEPPENPPPVLMEPRKKLRVDKAPLTPTGNARGRPRKYP
                VSAPMAPPAVGAGSPVQLIVAACPRKRQWPGFSVMAVTSGSMWPVLAAASRLPGRPTS
                DAQGAGLAFSLRSTAKAPSDTPAHE"    SEQ ID NO. 7
exon            <933..1170
                /gene="SC1"
conflict        1012
                /gene="SC1"
                /citation=[2]
                /replace="c"
intron          1171..2904
                /gene="SC1"
repeat_region   1937..2238
                /rpt_family="Alu"
exon            2906..3463
                /gene="SC1"
```

FIG. 12-46

| conflict | 3033..3035 |
| | /gene="SC1" |
| | /citation=[2] |
| | /replace="aac" |
| | 3243 |
| conflict | /gene="SC1" |
| | /citation=[2] |
| | /replace="a" |
| intron | 3464..3928 |
| | /gene="SC1" |
| exon | 3929..>4211 |
| | /gene="SC1" |
| conflict | 3933..3934 |
| | /gene="SC1" |
| | /citation=[2] |
| | /replace="cg" |
| conflict | 4000..4002 |
| | /gene="SC1" |
| | /citation=[2] |
| | /replace="" |
| conflict | 4176..4177 |
| | /gene="SC1" |
| | /citation=[2] |
| | /replace="cg" |

BASE COUNT   1376 a   1368 c   1497 g   1281 t
ORIGIN
  1 gaattccgaa ggaggggtag gcgctgcccg cgcgcagagg ccgcgccct cctgcccg
 61 gcttcttggc tgtcaaacag tagcagcaac gtcggctcct gccgaggagc ccaagggtc

FIG. 12-47

```
 121 ccgggatccg ccgcacaggc tggcactgct tgaagaggag gctactcgga gactgcgccg
 181 cgcgggtaga tccgaaacgg ggctggggcg gagtgggaaa aggccgggta tgccttgcat
 241 gatcgcgggg agctccttcc tgttttttatc ccacctagag aagccggaa gtaggggttt
 301 aggtccaatt tgttggagta cttaaggact cgtttgcact ttctttttggg ggatgacagt
 361 ggattcattg ccctcggagg ttcaaccagt tatgagtgag ggattggcca gaagatcggg
 421 gcgcaggcaa gcaggagtgc tctattagga taagcaagtt tgacaggaag aagctgctct
 481 tctccgaatt acacagaggt gatgtgttcg tattgcacgt agacgtgtgt ataacaggac
 541 ctccttcccc gcgccccgcc accccgacac acacaggagc tgcctaaagt atccttgcct
 601 tgaagattgg aggctcccca aatatttgt gatctgagga tccagctcaa gtgaggtgcc
 661 ataggacgtg ttcctgagtt tgcattgcac ggagaccttc ctggaatttt tcatttgcaa
 721 gtcggcttaa ccaatttggc attgagtcct aggctgcttg cactctgaat ttggctatt
 781 cagtagtgt gctcaaagtt agaaacaac acagaacaac tcaagtttgc atcagactgg
 841 gaagcgaact taagccagcg gtgcgtggcc caggagtggg aaaggaaatg gatgcctgaa
 901 gtggaagagg tggtgcagag gggcaccgc ccatgctgcc ctgcttccaa ctgctgcgca
 961 taggggcgg caggggcggt gatctctaca ccttccaccc ccccgcgggg gttggctgca
1021 cctatcgctt gggccacagg gccgacctgt gtgatgtggc cctgcggccc cagcaggagc
1081 ctgcctcat ctctggggatc cacgccgaac tgcatgccga gccccggggt gatgactgga
1141 gggtcagcct ggaagaccac agcagccaag gtgagcatta agcaggcag ctttgcccct
1201 gggtggttga agcgccaggc tggaatgagt aaggtctcca caagacctg ctgtctgcct
1261 cccatactcc catcagattg gatgatagt cgtggtccag acctttcatct tcccaccaga
1321 agtgtgcaca gtcagaagct ctctgccaga ctgaccctt ttggtcccgt ttagctcata
1381 caggacctgg gatatcatca gaaagatatc acagtgggga tgttctgagg ccactagagg
1441 ccaagtttag acttgattca gtttccagct ttgctgagc actctgttcc tgggttaggg
1501 cagttctatg ttgaataatg ttttttaataa tctgggcatg tcttttctccg tgacttgagg
1561 cagttagcct cagaaagcct agattcacat ttgagttttgg ccactgcctc ttggtaaagt
1621 cagctgtagg agtgttatgg ttattagact atagtagcca acattcatct agtgcttact
1681 gttatgagcc aggccctatt ttaagtgtat tgaatgtagg tggtactact attatcctca
1741 tttacagaaa aggaaaatga ggcacaaaga ggttaaggaa cttgtccagg gctgggcatg
```

FIG. 12-48

```
1801 gtggtttaca cctataatcc agcactttgg gaggctaagg caggtggat cacttgagct
1861 caggagttcg agaccagcct gggcaacatg gtgaaaacct gtctctacca aaaaattaat
1921 tagtttttta aaaaaagcct ggcgcggtg ggtcacgcct gtaatcccag cactttggga
1981 ggccgagatg gcagatcac gaggtcagga gttcgagacc atcctgacca acatgttgaa
2041 accccatctg tgctgaaaaa aaaaaaccca aattaaccag gtgtggtggc gtgcacctgt
2101 aaccccagct actcaggagg ctgaagcagc agaatcactt gaacccggga ggcggaggtt
2161 ggagtgagct gagatcgcac cactgtggc cagcttggc gacagagcga gactccatct
2221 caaacaaaca aacaaaccaa aagcttgccc agggtcacat aactggtaag tggtagagct
2281 agtactgaa cgagctggag ctggggaga gtgagcatgt ttgaaaactg gaccttaggg
2341 cgggcacgg tccgtcacgc ctgtaatccc agcactttgg gaggctgagg cgggcagatc
2401 aggaggtcag gagtatgaga ccagcctggc caacatggta aaaccctgtc tctcgtaaaa
2461 ataaaaaaat tagccagacg tggtggcaca tgcctgtaat cccagctact caggaggctg
2521 aggcaggaga attgcttgaa cctgggaggc ggagtgcagt gagctgagat tgcactactg
2581 cactccagct tgggcaatag agcaaatctc catctcaaaa aaaaaaaaaa gaaagaaaaa
2641 aaaagaagaa agaaagaatt ttggccctta ggacagtgag ggcagggttc ctttgtggga
2701 aagcacaaga aacacagatt tgttcctagc tgacaaggag tgacaaggag tgtactgcct gtacctgtc
2761 acctgctgag gggcttagga tgtgagggag aatctgacca cagtttcata ttcttcccca
2821 gaaatcatac agattctcc actcctgact ctggtcaatt ctgtttttgt cctccatatt
2881 tgcctgtgc cccaccatca acaggtactt tggtcaataa tgtccgactc ccaagaggtc
2941 acaggctgga attgagtgat ggagacctcc tgaccttgg cctgaaggg ccccaggaa
3001 ccagccctc ggagttctac ttcatgttcc aacaagtacg agtcaagcct caggactttg
3061 ctgccattac catcccacgg tctaggggag aagcccgggt tggggctggt ttccggccta
3121 tgctgcctc ccagggggct ccacagcgac ctctcagcac cttctcccct gccccaagg
3181 ccacactgat cctaaactcc ataggcagcc tcagcaagct ccgccccag ccctcacct
3241 tctcccctag ttggggtgga ccaaagagcc tgcctgttcc cgccgcacct gggaagtgg
3301 ggaccacgcc ttctgctcca cccaacgca atcggaggaa atctgttcac cgagtgttgg
3361 cggaactgga tgatgagagt gagcctcctg agaacccgcc agaacccgcc accggtcctt atggagccca
3421 ggagaaact ccgtgtagac aaagcccac tgactccac tgggtaagtg gagtcctcac
```

FIG. 12-49

```
3481 ttgccctct cagtgttta ctgcttttcg attccttgta tccctaggct gtgaggaggt
3541 cccctgcct ggggatgg gcacgggagg tgaatagat ggaatgcaa gacctggtt
3601 agctctgata gggaagaaa aatatgtgca ggagaacatg agaggtgggg tgggcagtg
3661 ctataaaaca accggagtga gcatgtcctg ctttttacat tcatatggct ttaaccccac
3721 tttctagtgc ctaaggatgg ggaactttca ggctcacact agaggttttt aggcccaccc
3781 catgtgtttt taaggacaga gtccaggctc accttagttc tcagaccact gtgcctctgt
3841 ggcctcaccc tatgaccagc cataggtgg caaggtctag gccttctcag atttccggtg
3901 acccttgtgt ctctctcact tccttcagaa atgcacgtgg gccttctcgg aagtaccag
3961 tgagcgctcc catgctctcc cctgctccc cctgcagttg gggcggggag ctccttgttg
4021 ctgcctgccc caggaagaga cagtggcctg ggttcagtgt gatggctgtg acgtctgtt
4081 ccatgtggcc tgtgttggct gcagcatcca gctgccagg gaggccgact tccgatgccc
4141 agggtgccgg gctggcattc agcctaaggt ccaccgccaa ggcaccatcg gacacacctg
4201 cccatgagta gacacagcag cgagcaaata ggtctgataa atacccccct tccctccct
4261 cccaagagg gaatgactac agggaagaag gatgattga tgtggactca ttcaggcct
4321 ggagcagacc ctggtggcca agcagtgagc tggagttcc ttccaaagat attgccacct
4381 ccaggaaatt gccagtgagc tgaagttcc cactattaca agccataagg ccatgtcgcc
4441 atggacacca gaatatctgt agtcagagca ctatcagtt gcaaaagcca tgcctgcaac
4501 cgatggaaaa tgtaagaggg agttcttaag gttcttggtg gaatcaccca aggtattctg
4561 ggaaaaccta gggcctgcc ccaaaactc cctactctgt ggctagtcct gctgccaaca
4621 aaatcgtagc gacctgctt ttcacagctt tgctttttt tcaagtcaa ggacaagccg
4681 cttcattcac tcctggcat ttactcttct tgtgggtctg tgatattcct tgctttccag
4741 ggagaatgtg cttgcaagg tctggagaac taattcagaa tcttagggga agggagaga
4801 tggaaataca aacctgctta ctggaaaggt gcaaaatatg ggttgagctg gaggtaggaa
4861 tacaggtaat taaggtttct agtttaaggg aaaacagatc tatttgccat ttaaatatgg
4921 taactgggat ttgtttaagt tcacccagat agcagaagat ttatttacag gcttcacctg
4981 tactgtcagg gacagagaa aagcctggta aaccaagcta acacagcaga ccagtgtgat
5041 ggctctcaca cagctccacc ccccggggtgg acacacaga gggcacctgg gctgcctgg
5101 ttcagtgtga atcaaaccgc ttaaccacca catggtacat gtgattttct tttgtgagcc
```

FIG. 12-50

```
5161  ttacaccaag ccaaactatt gtcaaagcat catttctata gaaataaagc cttatcttga
5221  cctgttctat taaaacctgc cacatccgcc ctttcctacc tagatttaat gagcccaagt
5281  tttttacat ggaagaaatg actctggggc aaagacccct aatgaactag tggcagagcc
5341  aggaataaaa cttgagtaac ttatgagtca cttatgggca gagtatgcaa aaaccttaag
5401  tggaaccaa atagaccctg gtatcaagaa agcacaaagt attaatagaa gttctggtt
5461  ggggtgatct aggttcaaca gaaataagat gatttctaag tataaagctc aaaattgaat
5521  tc  SEQ ID NO. 24
```

FIG. 12-51

Revised July 5, 2002

| NCBI | | | | | | | | Nucleotide | | |
|---|---|---|---|---|---|---|---|---|---|---|
| PubMed | Nucleotide | Protein | Genome | Structure | PMC | Taxonomy | OMIM | | | Boo |
| Search | Nucleotide ▽ | for | | | | | | | | |
| | Limits | | Preview/Index | History | | Clipboard | | | Details | |
| Display | default ▽ | Show: | 20 ▽ | Send to | File ▽ | Go | Clear | | | |
| | | | | | Get Subsequence | | | | | Links |

☐ 1: NM_010097. Mus musculus SPAR...[gi:6753707]

```
LOCUS       Sparcl1                  2713 bp    mRNA    linear   ROD 19-SEP-2002
DEFINITION  Mus musculus SPARC-like 1 (mast9, hevin) (Sparcl1), mRNA.
ACCESSION   NM_010097
VERSION     NM_010097.1  GI:6753707
KEYWORDS
SOURCE      Mus musculus (house mouse)
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
REFERENCE   1  (bases 1 to 2713)
  AUTHORS   McKinnon,P.J., Kapsetaki,M. and Margolskee,R.F.
  TITLE     The exon structure of the mouse Scl gene is very similar to the
            mouse Sparc gene
  JOURNAL   Genome Res. 6 (11), 1077-1083 (1996)
  MEDLINE   97092869
  PUBMED    8938431
```

FIG. 12-52

```
REFERENCE    2  (bases 1 to 2713)
AUTHORS      Soderling,J.A., Reed,M.J., Corsa,A. and Sage,E.H.
TITLE        Cloning and expression of murine SC1, a gene product homologous to
             SPARC
JOURNAL      J. Histochem. Cytochem. 45 (6), 823-835 (1997)
MEDLINE      97343039
 PUBMED      9199668
COMMENT      PROVISIONAL REFSEQ: This record has not yet been subject to final
             NCBI review. The reference sequence was derived from U66166.1.
FEATURES             Location/Qualifiers
     source          1..2713
                     /organism="Mus musculus"
                     /db_xref="taxon:10090"
                     /chromosome="5"
                     /map="5 55.0 cM"
     gene            1..2713
                     /gene="Sparcl1"
                     /note="synonyms: Sc1, hevin, mast9"
                     /db_xref="LocusID:13602"
                     /db_xref="MGD:108110"
     CDS             322..2274
                     /gene="Sparcl1"
                     /note="similar to to Mus musculus Sparc and human hevin;
                     secreted glycoprotein; extracellular matrix protein 2"
                     /codon_start=1
                     /product="SPARC-like 1 (mast9, hevin)"
                     /protein_id="NP_034227.1"
                     /db_xref="GI:6753708"
```

FIG. 12-53

```
/db_xref="LocusID:13602"
/db_xref="MGD:108110"
/translation="MKAVLLLCALGTAVAIPTSTRFLSDHSNPTTATLVTPEDATVP
IAGVEATADIENHPNDKAEKPSALNSEETHEQSTEQDKTYSFEVDLKDEEDGDGDLS
VDPTEGTLTLDLQEGTSEPQQKSLPENGDFPATVSTSYVDPNQRANITKGKESQEQPV
SDSHQQPNESSKQTQDLKAEESQTQDPDIPNEEEEEEEEEEPEDIGAPSDNQ
EEGKEPLEEQPTSKWEGNREQSDDTLEESSQPTQISKTEKHQSEQGNQGQESDSEAEG
EDKASGSKEHIPHTEQQDQEGKAGLEAIGNQKDTDEKAVSTEPTDAAVVPRSHGGAGD
NGGGDDSKHGAGDDYFIPSQEFLEAERMHSLSYLLKYGGGEETTGESENQREAADNQ
EAKKAESSPNAEPSDEGNSREHSAGSCTNFQCKRGHICKTDPQGKPHCVCQDPETCPP
AKILDQACGTDNQTYASSCHLFATKCRLEGTKKGHQLQLDYFGACKSIPACTDFEVAQ
FPLRMRDWLKNILMQLYEPNPKHGGYLNEKQRSKVKKIYLDEKRLLAGDHPIELLIRD
FKKNYHMYVYPVHWQFNELDQHPADRILTHSELAPLRASLVPMEHCITRFFEECDPNK
DKHITLKEWGHCFGIKEEDIDENLLF" SEQ ID NO. 8
1573..1644
/gene="Sparcl1"
/note="FOLN; Region: Follistatin-N-terminal domain-like"
/db_xref="CDD:smart00274"
1645..1806
/gene="Sparcl1"
/note="kazal; Region: Kazal-type serine protease inhibitor
domain. Usually indicative of serine protease inhibitors.
However, kazal-like domains are also seen in the
extracellular part of agrins, which are not known to be
protease inhibitors. Kazal domains often occur in tandem
arrays. Small alpha+beta fold containing three
disulphides. Alignment also includes a single domain from
transporters in the OATP/PGT family"
```

FIG. 12-54 misc_feature    /db_xref="CDD:pfam00050"
                1654..1806
                /gene="Sparcl1"
                /note="KAZAL; Region: Kazal type serine protease
                inhibitors"
                /db_xref="CDD:smart00280"

BASE COUNT    862 a    642 c    661 g    548 t
ORIGIN
    1 cagcacggag ggagcgagat ccaggaatct gcaacagaaa ccatgacagc ctgaaacacc
   61 ctgtggtgcc aacctccaaa ttctcatctg tcacttcaga ccctgactgg ctgacagagc
  121 agcagaattt caactccaat aaacgtgaat gtgcttctag gcaaagcagc caagctgacg
  181 agggaggggg gtggaagagc tagctcctct tgggcatttg tcaaactttt acctcctggc
  241 tgtgtgcaag gagggactc aacttcggct tcaagctacc aaggctctgg atccagccac
  301 ctctccgcag atctagccag catgaaggct gtgcttctcc tcctgtgcgc cttgggaacc
  361 gctgtggcaa tcccgacaag tacaaggttt ctctcctgac actccaaccc aactactgca
  421 acactggtga caccggaaga cgctacagtc cccattgccg gggttgaagc tacagcagac
  481 atagaaaacc atcccaatga caaggctgaa aaccttcag cact-taattc agaagaggaa
  541 actcatgaac agtcaacaga gcaggacaaa acctacagct tcgaggtgga cctgaaggat
  601 gagaggatg gagatgggga tttaagtgta gatccaacgg aaggaacact aacactggat
  661 ctacaagaag gtacaagtga gcctcaacag aaaagtctcc cggagaacgg cgatttcccc
  721 gcgaccgtgt ccacttccta tgtggatcct aaccaacgcg caaacatcac aaaggaaag
  781 gagagtcagg agcaacctgt aagtgactca agaaaagccag cgaatgaaag cagcaagcaa
  841 acccaagact taaggctgaa agaaagccag acacaagatc cagacattcc caatgaagaa
  901 gaggaagaag aagaggaaga agaagaggaa gaagaggaag agccggaaga agcagcctac
  961 cccagtgata accaagagga gggaaaaagaa cctctggagg agcagcctac cagcaagtgg
 1021 gaaggaaaca gagagcaatc tgatgacacc ttagaagagt ccagtcagcc cactcagata
 1081 agcagacag agaagcatca atctgagcaa ggaaaccaag gcaggagag tgactctgag
 1141 gcagaaggag aggacaaggc ttcaggcagc aaggaacaca ttccacatac agagcagcag

FIG. 12-55

```
1201 gaccaagaag ggaaagctgg ccttgaagct attggcaacc agaaggacac tgatgagaag
1261 gccgtttcca cagaacctac cgatgctgcc gtggtgccta ggagtcacgg aggagctggt
1321 gataacgggg gcggggatga ctctaagcat ggtgcaggcg atgactactt catccccagc
1381 caggaattcc tagaggccga aaggatgcat tcccctctcct attacctcaa atatggcggc
1441 ggcgaggaga caacgactgg cgagagtgag accagaggg aaccagagga aggctgcaga caaccaagag
1501 gccaagaaag ctgagagctc accaaatgct gaaccttcag atgaggcaa ctcaagggag
1561 cacagtgctg gttcttgcac gaacttccaa tgtaaaaggg gacacatttg caaaaccgat
1621 ccacaaggga aacctcactg tgtttgccaa gatccagaga cttgtccccc tgcaaaaatc
1681 ctagatcagg cttgtggcac tgacaaccaa acctacgcca gctcctgtca cctgtttgct
1741 accaagtgca ggctgagggg gaccaaaaag ggacaccaac tgcagctgga ttacttcgga
1801 gcttgcaaat ctattcctgc ttgtacggac tttgaagtgg ctcagtttcc cctgcggatg
1861 agagactggc tcaaaaacat cctcatgcag ctttatgaac caaatcccaa acatggcggc
1921 tatctcaatg aaaagcaaag aagcaaagtc aaaaaatttt acctggatga gaagagactc
1981 ttggctggag accatcccat tgaacttctc ttgagggact ttaagaaaaa ctaccacatg
2041 tatgtgtatc ctgtgcactg gcagtttaat gaactggacc agcatcctgc agacaggatc
2101 ttgacacact ctgaacttgc tcctctgcga gcttccctgg tgcccatgga acactgcata
2161 actcgcttct ttgaggagtg tgaccccaac aaggataagc acatcacctt gaaggaatgg
2221 ggccactgct ttgaattaa agaggaggat atagatgaaa acctcctctt ttgaattaag
2281 atttgagaga atcggaactt tccatccacc tcacctgctt taaccgcttc agaaatacga
2341 gcagccatga cactatacat tcatatgtag caaaacattt gtttggcatg tgagagaaga
2401 caatggtagt aattactct tggtgatata tatatgagcc aggcacttaa tattaactta
2461 ggaaatgaaa ctttaaaatt aagtagagtc aatgtctata aaagactgtc ctgtctgggg
2521 acagttagcc accatgcaa tgtcactctg tgcatctgcg tttataattg ataattataa
2581 actattaaaa aaacaatgtt catattgtcc ataatacctt atgcatgctg aggaagtgag
2641 atactgctct tttgagataa atatgcctcc ttttcagtgt cttgatgtcc taataaaaaa
2701 tctataaaac ccc    SEQ ID NO.25
```

FIG. 12-56

| ≋ NCBI | | | | | | Nucleotide | | |
|---|---|---|---|---|---|---|---|---|
| PubMed | Nucleotide | Protein | Genome | Structure | PMC | Taxonomy | OMIM | Boo |
| Search Nucleotide ▽ for | | | | | | | | Details |
| | Limits | | Preview/Index | History | | Clipboard | | |
| Display default ▽ Show: 20 ▽ Send to File ▽ | | | | | | Go Clear | | |
| | | | | | | Get Subsequence | | |

☐ 1: U64827. Mus musculus extr...[gi:1546922]                                                                    Links

```
LOCUS       MMU64827                2734 bp    mRNA    linear   ROD 30-NOV-2000
DEFINITION  Mus musculus extracellular matrix associated protein (Scl) mRNA,
            complete cds.
ACCESSION   U64827
VERSION     U64827.1  GI:1546922
KEYWORDS
SOURCE      Mus musculus (house mouse)
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
REFERENCE   1  (bases 1 to 2734)
  AUTHORS   McKinnon,P.J., Kapsetaki,M. and Margolskee,R.F.
  TITLE     The exon structure of the mouse Scl gene is very similar to the
            mouse Sparc gene
  JOURNAL   Genome Res. 6 (11), 1077-1083 (1996)
  MEDLINE   97092869
```

FIG. 12-57

```
PUBMED      8938431
REFERENCE   2 (bases 1 to 2734)
AUTHORS     McKinnon,P.J.
TITLE       Direct Submission
JOURNAL     Submitted (22-JUL-1996) Genetics, St. Jude Children's Research
            Hospital, 332 North Lauderdale, Memphis, TN 38101, USA
FEATURES             Location/Qualifiers
     source          1..2734
                     /organism="Mus musculus"
                     /db_xref="taxon:10090"
                     /chromosome="5"
                     /map="5E4"
     gene            1..2734
                     /gene="Sc1"
     CDS             322..2274
                     /gene="Sc1"
                     /note="similar to to Mus musculus Sparc and human hevin;
                     secreted glycoprotein"
                     /codon_start=1
                     /product="extracellular matrix associated protein"
                     /protein_id="AAB08451.1"
                     /db_xref="GI:1546923"
                     /translation="MKAVLLLLCALGTAVAIPTSTRFLSDHSNPTTATLVTPEDATVP
                     IAGVEATADIENHPNDKAEKPSALNSEETHEQSTEQDKTYSFEVDLKDEEDGDGDLS
                     VDPTEGTLTLDLQEGTSEPQQKSLPENGDFPATVSTSYVDPNQRANITKGKESQEQPV
                     SDSHQQPNESSKQTQDLKAEESQTQDPDIPNEEEEEEEEEEPEDIGAPSDNQ
                     EEGKEPLEEQPTSKWEGNREQSDDTLEESSQPTQISKTEKHQSEQGNQGQESDSEAEG
                     EDKASGSKEHIPHTEQQDQEGKAGLEAIGNQKDTDEKAVSTEPTDAAVVPRSHGGAGD
```

FIG. 12-58

NGGGDDSKHGAGDDYFIPSQEFLEAERMHSLSYYLKYGGGEETTGESENQREAADNQ
EAKKAESSPNAEPSDEGNSREHSAGSCTNFQCKRGHICKTDPQGKPHCVCQDPETCPP
AKILDQACGTDNQTYASSCHLFATKCRLEGTKKGHQLQLDYFGACKSIPACTDFEVAQ
FPLRMRDWLKNILMQLYEPNPKHGGYLNEKQRSKVKKIYLDEKRLLAGDHPIELLLRD
FKKNYHMVYPVHWQFNELDQHPADRILTHSELAPLRASLVPMEHCITRFFEECDPNK
DKHITLKEWGHCFGIKEEDIDENLLF" SEQ ID NO. 9

BASE COUNT   882 a   641 c   663 g   548 t

ORIGIN
```
    1 cagcacggag ggagcgagat ccaggaatct gcaacagaaa ccatgacagc ctgaaacacc
   61 ctgtggtgcc aacctccaaa ttctcatctg tcacttcaga ccctgactgg ctgacagagc
  121 agcagaattt caactccaat aaacgtgaat gtgcttctag gcaaagcagc caagctgacg
  181 agggagggg gtggaagagc tagctcctct tgggcatttg tcaaacttt acctcctggc
  241 tgtgtgcaag gagggactc aacttcggct tcaagctacc aaggctctgg atccagccac
  301 ctctccgcag atctagccag catgaaggct gtgcttctcc tcctgtgcgc cttgggaacc
  361 gctgtgcaa tcccgacaag tacaagtttt ctctctgacc actccaacc aactactgca
  421 acactggtga caccggaaga cgctacagtc caaggctgcc cccattgccg gggttgaagc tacagcagac
  481 atagaaaacc atcccaatga caaggctgaa aaaccttcag cacttaattc agaagaggaa
  541 actcatgaac agtcaacaga gcaggacaaa acctacagct tcgaggtgga cctgaaggat
  601 gaggaggatg gagatgggga gtacaagtga tttaagtgta aggaacact aacactggat
  661 ctacaagaag gtacaagtga gcctcaacag aaaagtctcc cggaaaacg ggattttccc
  721 gcgaccgtgt ccacttccta tgtggatcct aaccaacgcg caaacatcac aaaggaaag
  781 gagagtcagg agcaacctgt aagtgactca cgaatgaaag cagacaagca cagcaagcaa
  841 acccaagact taaaggctga agaaagccag acacaagatc cagacattcc caatgaagaa
  901 gaggaagaag aagaggaaga aagaggaag agaaggaga agccggaaga cattggtgcc
  961 cccagtgata accaagagga gggaaaagaa cctctgagg agcagcctac cagcaagtgg
 1021 gaagaaaca gagagcaatc tgatgacacc ttagaagagt ccagtcagcc cactcagata
 1081 agcaagacag agaagcatca atctgagcaa ggaaaccaag ggcaggagag tgactctgag
 1141 gcagaaggag aggacaaggc ttcaggcagc aggaacaca ttccacatac agagcagcag
```

FIG. 12-59

```
1201 gaccaagaag ggaaagctgg ccttgaagct attgcaacc agaaggacac tgatgagaag
1261 gccgtttcca cagaacctac cgatgctgcc gtggtgccta ggagtcacgg aggagctggt
1321 gataacgggg gcggggatga ctctaagcat ggtgcaggcg atgactactt catccccagc
1381 caggaattcc tagaggccga aggatgcat tccctctcct attacctcaa atatggcggg
1441 ggcgagaga caacgactgg cgagagtgag aaccagaggg aggctgcaga caaccaagag
1501 gccaagaaag ctgagagctc accaaatgct gaaccttcag atgagggcaa ctcaaggag
1561 cacagtgctg gttcttgcac gaacttccaa tgtaaaaggg gacacatttg caaaccgat
1621 ccacaaggga aacctcactg tgtttgccaa gatccagaga cttgtccccc tgcaaaatc
1681 ctagatcagg cttgtggcac acctacgcca gctcctgtca cctgtttgct
1741 accaagtgca ggctggaggg gaccaaaaag ggacaccaac tgcagctgga ttacttcgga
1801 gcttgcaaat ctattcctgc ttgtacggac tttgaagtgg ctcagtttcc cctgcggatg
1861 agagactgc tcaaaaacat cctcatgcag ctttatgaac caatcccaa acatgcggc
1921 tatctcaatg aaaagcaaag aagcaaagtc aaaaaattt acctgatga gaagagactc
1981 ttggctggag accatcccat tgaacttctc ttgagggact ttaagaaaaa ctaccacatg
2041 tatgtgtatc ctgtgcactg gcagttttaat gaactggacc agcatcctgc agacaggatc
2101 ttgacacact ctgaacttgc tcctctgcga gcttccctgg tgcccatgga acactgcata
2161 actcgcttct ttgaggagtg tgacccccaac aaggataagc acatcacctt gaaggaatgg
2221 ggccactgct ttggaattaa agaggaggat atagatgaaa acctcctctt ttgaattaag
2281 atttgagaga atcggaactt tccatccacc tcacctgctt taaccgcttc agaaatacga
2341 gcagccatga cactatacat tcatatgtag caaaacattt gtttggcatg tgagagaaga
2401 caatggtagt aattacttct tggtgatata tatatgagcc aggcacttaa tattaactta
2461 ggaaatgaaa ctttaaaatt aagtagagtc aatgtctata aaagactgtc ctgtctgggg
2521 acagttagcc accatgcaa tgtcactctg tgcatctgcg tttataattg ataattataa
2581 actattaaaa aaacaatgtt catattgtcc ataatacctt atgcatgctg aggaagtgag
2641 atactgctct tttgagataa atatgcctcc ttttcagtgt cttggatgtc ctaataaaaa
2701 atctataaaa cccccaaaaa aaaaaaaaaa aaaa SEQ ID NO.26
```

FIG. 12-60

NCBI

PubMed  Nucleotide  Protein  Genome  Structure  PMC  Taxonomy  OMIM  Boo

Nucleotide

Search Nucleotide ▽ for [        ]                              Details

Limits    Preview/Index    History    Clipboard

Display default ▽  Show: 20 ▽  Send to ▽                Links

[Go] [Clear]

[Get Subsequence]

▣ 1: M58460. Human 75-kD autoa...[gi:179286]

```
LOCUS       HUMAUTOANT              1542 bp    mRNA    linear   PRI 31-DEC-1994
DEFINITION  Human 75-kD autoantigen (PM-Scl) mRNA, complete cds.
ACCESSION   M58460
VERSION     M58460.1  GI:179286
KEYWORDS    autoantigen; nucleolar protein.
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1542)
  AUTHORS   Alderuccio,F., Chan,E.K. and Tan,E.M.
  TITLE     Molecular characterization of an autoantigen of PM-Scl in the
            polymyositis/scleroderma overlap syndrome: a unique and complete
            human cDNA encoding an apparent 75-kD acidic protein of the
            nucleolar complex
  JOURNAL   J. Exp. Med. 173 (4), 941-952 (1991)
```

FIG. 12-61

```
MEDLINE    91178455
PUBMED     2007859
COMMENT    Original source text: Homo sapiens (tissue library: lambda gt11)
           lymphoblastoma cDNA to mRNA.
FEATURES             Location/Qualifiers
     source          1..1542
                     /organism="Homo sapiens"
                     /db_xref="taxon:9606"
                     /cell_line="MOLT-4"
                     /cell_type="T-cell"
                     /tissue_type="lymphoblastoma"
                     /tissue_lib="lambda gt11"
     gene            1..1542
                     /gene="PM-Scl"
     CDS             420..1487
                     /gene="PM-Scl"
                     /note="75-kD"
                     /codon_start=1
                     /product="autoantigen"
                     /protein_id="AAA58384.1"
                     /db_xref="GI:179287"
                     /translation="MAAPAFEPGRQSDLLVKLNRLMERCLRNSKCIDTESLCVVAGEK
                     VWQIRVDLHLLNHDGNIIDAASIAAIVALCHFRRPDVSVQGDEVTLYTPEERDPVPLS
                     IHHMPICVSFAFFQQGTYLLVDPNEREERVMDGLLVIAMNKHREICTIQSSGGIMLLK
                     DQVLRCSKIAGVKVAEITELILKALENDQKVRKEGGKFGFAESIANQRITAFKMEKAP
                     IDTSDVEEKAEEIIAEAEPPSEVVSTPVLWTPGTAQIGEGVENSWGDLEDSEKEDDEG
                     GGDQAIILDGIKMDTGVEVSDIGSQDAPIILDSEEEMIILEPDKNPKKIRTQTTSA
                     KQEKAPSKKPVRRKKKRAAN" SEQ ID NO. 10
```

```
BASE COUNT    494 a    283 c    355 g    410 t
ORIGIN
    1 cgaccggcac gttcacccca tccctcaggc tttattttatt ttttttcgac aggttcttt
   61 caaggctcca gtcaccgcag cagttgtcca tgctgtagtt tccacttcc tgtatgggcg
  121 ggctggttag gattccactt tcccccaagt gcttagccca gggccagaca aaaagtagtt
  181 gcttaagaaa tacttgttga aggaataaat gcttagccca atttgtgctt acagcggctg
  241 gatgcagac aaacctatga ttataggaac atcaggatct catttggaac agattacgga
  301 tgctgcattg tggaacttgg aaaaacaaga gttcttggac aggttcctg tgaacttgtg
  361 tctccaaaac tcaatcgggc aacagaaggt attcttttt taaccttgaa ctctctcaga
  421 tggccgctcc agctttcgaa cctggcaggc agtcagatct cttggtgaag ttgaatcgac
  481 tcatggaaag atgtctaaga aattcgaagt gtatagacac tgagtctctc tgtgttgttg
  541 ctggtgaaaa ggtttggcaa atacgtgtag acctacattt attaaatcat gatggaaata
  601 ttattgatgc tgccagcatt gctgcaatcg tggccttatg tcatttccga agacctgatg
  661 tctctgtcca aggagatgaa gtaacactgt atacacctga agagcgtgat cctgtaccat
  721 taagtatcca ccacatgccc atttgtgtca gttttgcctt tttccagcaa ggaacatatt
  781 tattggtgga tcccaatgaa cgagaagaac gtgtgatgaa tggctgctg gtgattgcca
  841 tgaacaaaca tcgagagatt tgtactatcc agtccagtgg tgggataatg ctactaaaag
  901 atcaagttct gagatgcagt aaaatcgctg gtgtgaaagt agcagaaatt acagagctaa
  961 tattgaaagc tttggagaat gaccaaaag taaggaaaga aggtgaaag tttggttttg
 1021 cagagtctat agcaaatcaa aggatcacag catttaaaat agcagaacct cccttcagaag
 1081 cctcgatgt agaagaaaaa gcagaaagaa tcattgctga agactccta ggagtagaaa
 1141 ttgttctac acctgtgcta tggactcctg gaactgccca aattggagag ggagtagaaa
 1201 actcctgggg tgatcttgaa gactctgaga aggaagatga tgaaggcggt ggtgatcaag
 1261 ctatcattct tgatggtata aaaatggaca ctggagtaga agtctctgat attggaagcc
 1321 aagatgctcc cataatactc tcagatagtg aagaagaaga aatgatcatt ttgaaccag
 1381 acaagaatcc aaagaaaata agaacacaga ccaccagtgc aaaacaagaa aagcaccaa
 1441 gtaaaagcc agtgaaaaga agaaaaaga agagagctgc caattaaagc taacagttgt
 1501 atatctgtat atataactat taaagggat atttattcca tt    SEQ ID NO. 27
```

Revised July 5, 2002

Disclaimer | Write to the Help Desk
NCBI | NLM | NIH

NCBI  Nucleotide

PubMed  Nucleotide  Protein  Genome  Structure  PMC  Taxonomy  OMIM  Boo

Search Nucleotide ▽ for [_____] Go Clear

Limits  Preview/Index  History  Clipboard  Details

Display default ▽ Show: 20 ▽ Send to File ▽  Get Subsequence

☐ 1: NM_004684. Homo sapiens SPAR...[gi:21359870]  Links

```
LOCUS       SPARCL1                 2808 bp    mRNA    linear   PRI 23-DEC-2002
DEFINITION  Homo sapiens SPARC-like 1 (mast9, hevin) (SPARCL1), mRNA.
ACCESSION   NM_004684
VERSION     NM_004684.2  GI:21359870
KEYWORDS    
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2808)
  AUTHORS   Girard,J.P. and Springer,T.A.
  TITLE     Cloning from purified high endothelial venule cells of hevin, a
            close relative of the antiadhesive extracellular matrix protein
            SPARC
  JOURNAL   Immunity 2 (1), 113-123 (1995)
  MEDLINE   95323677
```

FIG. 12-64

```
PUBMED      7600298
REFERENCE   2
AUTHORS     Schraml,P., Shipman,R. and Ludwig,C.U.
TITLE       An alternative PCR-based method for the direct isolation of cDNA
            ends (DICE)
JOURNAL     Unpublished
COMMENT     PROVISIONAL REFSEQ: This record has not yet been subject to final
            NCBI review. The reference sequence was derived from X86521.
            On Jun 9, 2002 this sequence version replaced gi:4758521.
FEATURES             Location/Qualifiers
     source          1..2808
                     /organism="Homo sapiens"
                     /db_xref="taxon:9606"
                     /chromosome="4"
                     /map="4q22.1"
                     /tissue_type="lung"
                     /clone_lib="human fetal lung 5'-stretch cDNA in lambda
                     gt10(Clontech)"
     gene            1..2808
                     /gene="SPARCL1"
                     /note="synonyms: HEVIN, MAST9"
                     /db_xref="LocusID:8404"
                     /db_xref="MIM:606041"
     variation       complement(139)
                     /allele="T"
                     /allele="A"
                     /db_xref="dbSNP:2615483"
     variation       161
```

FIG. 12-65 variation       /gene="SPARCL1"
                /allele="G"
                /allele="A"
                /db_xref="dbSNP:1049539"
                291
variation       /gene="SPARCL1"
                /allele="G"
                /allele="A"
                /db_xref="dbSNP:1130639"
                291
                /gene="SPARCL1"
                323..2317
CDS             /gene="SPARCL1"
                /note="mast9; hevin"
                /codon_start=1
                /product="SPARC-like 1"
                /protein_id="NP_004675.2"
                /db_xref="GI:21359871"
                /db_xref="LocusID:8404"
                /db_xref="MIM:606041"
                /translation="MKTGPFFLCLLGTAAAIPTNARLLSDHSKPTAETVAPDNTAIPS
                LWAEAEENEKETAVSTEDDSHHKAEKSSVLKSKEESHEQSAEQGKSSSQELGLKDQED
                SDGHLSVNLEYAPTEGTLDIKEDMIEPQEKKLSENTDFLAPGVSSFTDSNQQESITKR
                EENQEQPRNYSHQLNRSSKHSQGLRDQGNQEQDPNISNGEEEEKEPGEVGTHNDNQ
                ERKTELPREHANSKQEEDNTQSDDILEESDQPTQVSKMQEDEFDQGNQEQEDNSNAEM
                EEENASNVNKHIQETEWQSQEGKTGLEAISNHKETEEKTVSEALLMEPTDDGNTTPRN
                HGVDDDGDDDGDDGGTDGPRHSASDDYFIPSQAFLEAERAQSIAYHLKIEEQREKVHE
                NENIGTTEPGEHQEAKKAENSSNEEETSSEGNMRVHAVDSCMSFQCKRGHICKADQQG

FIG. 12-66

```
                KPHCVCQDPVTCPPTKPLDQVCGTDNQTYASSCHLFATKCRLEGTKKGHQLQLDYFGA
                CKSIPTCTDFEVIQFPLRMRDWLKNILMQLYEANSEHAGYLNEKQRNKVKKIYLDEKR
                LLAGDHPIDLLLRDFKKNYHMYYPVHWQFSELDQHPMDRVLTHSELAPLRASLVPME
                HCITRFFEECDPNKDKHITLKEWGHCFGIKEEDIDENLLF" SEQ ID NO. 11
misc feature   1616..1687
                /gene="SPARCL1"
                /note="FOLN; Region: Follistatin-N-terminal domain-like"
                /db_xref="CDD:smart00274"
misc feature   1688..1849
                /gene="SPARCL1"
                /note="kazal; Region: Kazal-type serine protease inhibitor
                domain. Usually indicative of serine protease inhibitors.
                However, kazal-like domains are also seen in the
                extracellular part of agrins, which are not known to be
                protease inhibitors. Kazal domains often occur in tandem
                arrays. Small alpha+beta fold containing three
                disulphides. Alignment also includes a single domain from
                transporters in the OATP/PGT family"
                /db_xref="CDD:pfam00050"
misc feature   1697..1849
                /gene="SPARCL1"
                /note="KAZAL; Region: Kazal type serine protease
                inhibitors"
                /db_xref="CDD:smart00280"
variation      336
                /gene="SPARCL1"
variation      433
                /gene="SPARCL1"
```

FIG. 12-67

```
                          /allele="T"
                          /allele="C"
                          /db_xref="dbSNP:8342"
    variation             433
                          /gene="SPARCL1"
    variation             458
                          /gene="SPARCL1"
    variation             468
                          /gene="SPARCL1"
                          /allele="C"
                          /allele="A"
                          /db_xref="dbSNP:13051"
    variation             468
                          /gene="SPARCL1"
    variation             638
                          /gene="SPARCL1"
                          /allele="G"
                          /allele="C"
                          /db_xref="dbSNP:1049544"
    variation             638
                          /gene="SPARCL1"
    variation             668
                          /gene="SPARCL1"
    variation             702
                          /gene="SPARCL1"
    variation             1577
                          /gene="SPARCL1"
                          /allele="G"
                          /allele="A"
                          /db_xref="dbSNP:3189727"
    variation             1957
                          /gene="SPARCL1"
    variation             2047
                          /gene="SPARCL1"
                          /allele="T"
                          /allele="C"
                          /db_xref="dbSNP:9933"
    variation             2047
                          /gene="SPARCL1"
    variation             2327
                          /gene="SPARCL1"
                          /allele="T"
                          /allele="A"
                          /db_xref="dbSNP:10626"
BASE COUNT        996 a      554 c       606 g       652 t
```

FIG. 12-68

```
ORIGIN
    1 cggcatgaga ggccagcctg ccaggaaat  ccaggaatct gcaacaaaaa cgatgacagt
   61 ctgaaatact ctctggtgcc aacctccaaa ttctcgtctg tcacttcaga cccccactag
  121 ttgacagagc agcagaatat caactccagt agacttgaat gtgcctctgg gcaagaagc
  181 agagctaacg aggaaaggga tttaaagagt ttttcttggg tgtttgtcaa actttattc
  241 cctgtctgtg tgcagagggg attcaacttc aattttctgc agtggctctg ggtccagccc
  301 cttacttaaa gatctgaaa  gcatgaagac tgggcttttt ttcctatgtc tcttgggaac
  361 tgcagctgca atcccgacaa atgcaagatt attatctgat cattccaaac caactgctga
  421 aacggtagca cctgacaaca ctgcaatccc cagtttatgg gctgaagctg aagaaaatga
  481 aaaagaaaca gcagtatcca cagaagacga ttcccaccat aaggctgaaa aatcatcagt
  541 actaaagtca aaagaggaaa gccatgaaca gtcagcagaa cagggcaaga gttctagcca
  601 agagctggga ttgaaggatc aagagacag  tgatgtcac  ttaagtgtga atttggagta
  661 tgcaccaact gaagttacat tggacataaa agaagatatg attgagcctc aggagaaaaa
  721 actctcagag aacactgatt ttttgctctc tggtgttagt tccttcacag attctaacca
  781 acagaaagt  atcacaaaga gagagaaaca ccaagaacaa cctagaaatt attcacatca
  841 tcagtttgaac aggagcagta aacatagcca aggcctaagg gatcaaggaa accaagagca
  901 ggatccaaat atttccaatg gagaagagga agaagaaaaa gagccaggtg aagttggtac
  961 ccacaatgat aaccaagac  attgccagg  attgccagg  gagcatgcta acagcaagca
 1021 ggaggagac  aatacccaat ctgatgatat tttggaagag tctgatcaac caactcaagt
 1081 agcaagatg  caggaggatg aatttgatca gggtaaccaa gaacaagaag ataactccaa
 1141 tgcagaaatg gaagaggaaa atgcaatcgaa cgtcaataag cacattcaag aaactgaatg
 1201 gcagagtcaa gagggtaaaa ctggcctaga agctatcagc aaccacaaag agacagagaa
 1261 aaagactgtt tctgaggctc tgctcatgga acctactgat gatggtaata ccacgcccag
 1321 aaatcatgga gttgatgatg atggcgatga tgatgcgcat gatggcggca ctgatggccc
 1381 caggcacagt gcaagtgatg actacttcat cccaagccag gccttctgg  aggccgagag
 1441 agctcaatcc attgcctatc actactcaaat tgaggagcaa agagaaaaag tacatgaaaa
 1501 tgaaatata  ggtaccactg agcctggaga gcaccaagag gccaagaaga cagaactc
 1561 atcaaatgag gagaaacgt  caagtgaagg caacatgagg gtgcatgctg tggattcttg
```

FIG. 12-69

```
1621 catgagcttc cagtgtaaaa gaggccacat ctgtaaggca gaccaacagg gaaaacctca
1681 ctgtgtctgc caggatccag tgacttgtcc tccaacaaaa cccccttgatc aagtttgtgg
1741 cactgacaat cagacctatg ctagttcctg tcatctattc gctactaaat gcagactgga
1801 ggggaccaaa aaggggcatc aactccagct ggattatttt ggagcctgca aatctattcc
1861 tacttgtacg gactttgaag tgattcagtt tcctctacgg atgagagact ggctcaagaa
1921 tatcctcatg cagcttttatg aagccaactc tgaacatgct ggttatctaa atgagaagca
1981 gagaaataaa gtcaagaaaa tttacctgga tgaaagagg cttttggctg gggaccatcc
2041 cattgatctt ctcttaaggg actttaagaa aaactaccac atgtatgtgt atcctgtgca
2101 ctgcagttt agtgaacttg accaacaccc tatgataga gtcttgacac attctgaact
2161 tgctcctctg cgagcatctc tggtgcccat ggaacactgc ataacccgtt tctttgagga
2221 gtgtgacccc aacaaggata agcacatcac cctgaaggag tggggccact gctttggaat
2281 taaagaagag gacatagatg aaaatctctt gttttgaacg aagattttaa agaactcaac
2341 tttccagcat cctcctctgt tctaaccact tcagaaaatat atgcagctgt gatacttgta
2401 gatttatatt tagcaaaatg ttagcatgta tgacaagaca atgagagtaa ttgcttgaca
2461 acaacctatg caccaggtat ttaacattaa ctttggaaac aaaaatgtac aattaagtaa
2521 agtcaacata tgcaaaatac tgtacattgt gaacagaagt ttaattcata gtaatttcac
2581 tctctgcatt gacttatgag ataattaatg attaaactat taatgataaa aataatgcat
2641 ttgtattgtt cataatatca tgtcacttc aagaaaatgg aatgctactc ttttgtggtt
2701 tacgtgtatt attttcaata tcttaatacc ctaataaaga gtccataaaa atccaaaaaa
2761 aaaaaaaaaa aaaaaaaaaa aaaaaaaa      SEQ ID NO. 28
```

Revised July 5, 2002

Disclaimer | Write to the Help Desk
NCBI | NLM | NIH

FIG. 12-70

```
                                                    NCBI
PubMed   Nucleotide   Protein   Genome   Structure   PMC   Taxonomy   OMIM   Boo Search  Nucleotide ▽  for [                                    ]
        Limits     Preview/Index    History         Clipboard          Details
Display default ▽  Show: 20 ▽  Send to File  ▽    Go  Clear
                                                  Get Subsequence      Links □ 1: X82157. H.sapiens mRNA fo...[gi:758065]

LOCUS       HSHEVIN                 2645 bp    mRNA    linear   PRI 31-MAR-1995
DEFINITION  H.sapiens mRNA for high endothelial venule.
ACCESSION   X82157
VERSION     X82157.1  GI:758065
KEYWORDS    hevin gene.
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1
  AUTHORS   Girard,J.P. and Springer,T.A.
  TITLE     Cloning from purified high endothelial venule cells of hevin, a
            close relative of the antiadhesive extracellular matrix protein
            SPARC
  JOURNAL   Immunity 2 (1), 113-123 (1995)
```

FIG. 12-71

```
MEDLINE     95323677
REFERENCE   2 (bases 1 to 2645)
AUTHORS     Girard,J.
TITLE       Direct Submission
JOURNAL     Submitted (10-OCT-1994) J. Girard, Center for Blood Research and
            Dept. of Pathology, Harvard Medical School, 200 Longwoode Avenue,
            Boston, MA 02115, USA
FEATURES             Location/Qualifiers
     source          1..2645
                     /organism="Homo sapiens"
                     /db_xref="taxon:9606"
                     /clone="HEC25"
                     /cell_line="purified high endothelial cells"
                     /cell_type="high endothelial cells"
                     /tissue_type="tonsil"
     gene            1..2645
                     /gene="hevin"
     CDS             198..2192
                     /gene="hevin"
                     /codon_start=1
                     /protein_id="CAA57650.1"
                     /db_xref="GI:758066"
                     /db_xref="SPTREMBL:Q14515"
                     /translation="MKTGLFFLCLLGTAAAIPTNARLLSDHSKPTAETVAPDNTAIPS
                     LRAEDEENEKETAVSTEDDSHHKAEKSSVLKSKEESHEQSAEQGKSSSQELGLKDQED
                     SDGDLSVNLEYAPSEGTLDIKEDMSEPQEKKLSENTDFLAPGVSSFTDSNQQESITKR
                     EENQEQPRNYSHHQLNRSSKHSQGLRDQGNQEQDPNISNGEEEEKEPGEVGTHNDNQ
```

FIG. 12-72

```
sig_peptide    198..260
               /gene="hevin"
polyA_signal   2608..2613
               /gene="hevin"

BASE COUNT  923 a   516 c   580 g   626 t
ORIGIN
    1 gagcagcaga atttcaactc cagtagactt gaatatgcct ctggcaaaag aagcagagct
   61 aacgaggaaa gggattaaa gagtttttct tgggtgtttg tcaaactttt attccctgtc
  121 tgtgtgcaga ggggattcaa cttcaatttt tctgcagtgg ctctgagtcc agccccttac
  181 ttaaagatct ggaaagcatg aagactggc agattattat ttttttcct atgtctcttg ggaactgcag
  241 ctgcaatccc gacaaatgca acaactgca atcccagtt ctgatcattc caaaccaact gctgaaacgg
  301 tagcacccga caacactgca atcccagtt taaggctga agatgaagaa aatgaaaaag
  361 aaacagcagt atccacagaa gacgattccc accataaggc cagaacaggg caagagttct agccaagagc
  421 agtcaaaaga ggaaagccat gaaagtcag gacagtgatg gtgacttaag tgtgaattg gagtatgcac
  481 tgggattgaa ggatcaagag tacattggac ataaaagaag atatgagtga gcctcaggag aaaaaactct
  541 catctgaagg tacattggac tgatttttg gctcctggtg ttagttcctt cacagattct aaccaacaag
  601 cagagaacac aaagagagag gaaaaccaag aaaaccctag aaattattca catcatcagt
  661 aaagtatcac cagtaaacat agccaaggcc taaggatca aggaaaccaa gagcaggatc
  721 tgaacaggag
```

"ERKTELPREHANSKQEEDNTQSDDILEESDQPTQVSKMQEDEFDQGNQEQEDNSNAEM
EEENASNVNKHIQETEWQSQEGKTGLEAISNHKETEEKTVSEALLMEPTDDGNTTPRN
HGVDDDGDDGDDGGTDGPRHSASDDYFIPSQAFLEARAQSIAYHLKIEEQREKVHE
NENIGTTEPGEHQEAKKAENSSNEEETSSEGNMRVHAVDSCMSFQCKRGHICKADQQG
KPHCVCQDPVTCPPTKPLDQVCGTDNQTYASSCHLFATKCRLEGTKKGHQLQLDYFGA
CKSIPTCTDFEVIQFPLRMRDWLKNILMQLYEANSEHAGYLNEKQRNKVKKIYLDEKR
LLAGDHPIDLLLRDFKKNYHMYVYPVHWQFSELDQHPMDRVLTHSELAPLRASLVPME
HCITRFFEECDPNKDKHITLKEWGHCFGIKEEDIDENLLF" SEQ ID NO. 12

FIG. 12-73

```
 781 caaatatttc caatggagaa gaggaagaag aaaaagagcc aggtgaagtt ggtacccaca
 841 atgataacca agaaagaaag acagaattgc ccagggagca tgctaacagc aagcaggagg
 901 aagacaatac ccaatctgat gatatttttg aagagtctga tcaaccaact caagtaagca
 961 agatgcagga ggatgaattt gatcagggta accaagaaca agaagataac tccaatgcag
1021 aaatgcagga ggaaagagca tcgaacgtca ataagcacat tcaagaaact gaatggcaga
1081 gtcaagaggg taaaactggc ctagaagcta tcagcaacca caaagagaca gaagaaaaga
1141 ctgtttctga ggctctgctc atggaaccta ctgatgatgg taataccacg cccagaaatc
1201 atggagttga tgatgatggc gatgatgatg gcgatgatgg cggcactgat ggccccaggc
1261 acagtgcaag tgatgactac ttcatcccaa gccaggcctt tctggaggcc gagagagctc
1321 aatccattgc ctatcacctc aaaattgagg agcaaagaga aaaagtacat gaaaatgaaa
1381 atataggtac cactgagcct ggagagcacc aagaggccaa gaaagcagag aactcatcaa
1441 atgaggaga aacgtcaagt gaagcaaca cacatctgta tgaggtgca tgctgtggat cctcactgtg
1501 gcttccagtg taaaagaggc cactctgtta aggcagacca caaacccct tgatcaagtt tgtggcactg
1561 tctgccagga tccagtgact tgtcctccaa caaaccccct tgatcaagtt tgtggcactg
1621 acaatcagac ctatgctagt tcctgtcatc tattcgctac taaatgcaga ctggagggga
1681 ccaaaaaggg gcatcaactc cagctggatt attttggagc ctgcaaatct attcctactt
1741 gtacggactt tgaagtgatt cagttcctc tacgatgag agactggctc aagaatatcc
1801 tcatgcagct ttatgaagcc aactctgaac acgctggtta tctaaatgag aagcagagaa
1861 ataaagtcaa gaaaatttac ctggatgaaa agaggctttt ggctgggac catcccattg
1921 accttctctt aagggacttt aagaaaaact accacacgta tgtgtatcct gtgcactggc
1981 agttagtga acttgaccaa caccctatgg atagagtctt gacacattct gaacttgctc
2041 ctctgcgagc atctctggtg cccatggaac actgcataac ccgtttctt gaggagtgtg
2101 acccaacaa atcctgcac atcaccctga aggagtgggg ccactgcttt ggaattaaag
2161 aagaggacat agataagaaat ctcttgtttt gaacaagat tttaaagaac tcaacttcc
2221 agcatcctcc tctgttctaa ccacttcaga aatatatgca gctgtgatac ttgtagattt
2281 atatttagca aaatgttagc atgtatgaca agacaatgag agtaattgct tgacaacaac
2341 ctatgcacca ggtattttaac attaactttg gaaacaaaaa tgtacaatta agtaaagtca
```

FIG. 12-74

```
2401 acatatgcaa aatactgtac attgtgaaca gaagtttaat tcatagtaat ttcactctct
2461 gcattgactt atgagataat taatgattaa actattaatg ataaaaataa tgcatttgta
2521 ttgttcataa tatcatgtgc acttcaagaa aatggaatgc tactcttttg tggttttacgt
2581 gtattatttt caatatctta ataccctaat aaagagtcca taaaaatcca aaaaaaaaaa
2641 aaaaa  SEQ ID NO. 29
```

Revised July 5, 2002

Disclaimer | Write to the Help Desk
NCBI | NLM | NIH

FIG. 12-75

```
TITLE      Direct Submission
JOURNAL    Submitted (26-APR-1995) P.H. Schraml, Zentrum fuer Lehre und
           Forschung (ZLF), Molecular Oncology, Laboratory 405, Kantonsspital
           Basel, Hebelstrasse 20, CH-4031 Basel, SWITZERLAND
COMMENT    Related sequences X82157 and S73397.
FEATURES         Location/Qualifiers
     source      1..2808
                 /organism="Homo sapiens"
                 /db_xref="taxon:9606"
                 /tissue_type="lung"
                 /clone_lib="human fetal lung 5'-stretch cDNA in lambda
                 gt10(Clontech)"
     gene        1..2808
                 /gene="MAST-9"
     mRNA        <1..>2808
                 /gene="MAST-9"
     variation   291
                 /gene="MAST-9"
     gene        323..2317
                 /gene="MAST 9"
     CDS         323..2317
                 /gene="MAST 9"
                 /codon_start=1
                 /product="Hevin-like protein"
                 /protein_id="CAA60386.1"
                 /db_xref="GI:809027"
                 /db_xref="SPTREMBL:Q14800"
                 /translation="MKTGPFFLCLLGTAAAIPTNARLLSDHSKPTAETVAPDNTAIPS
```

FIG. 12-77

```
LWAEAEENEKETAVSTEDDSHHKAEKSSVLKSKEESHEQSAEQGKSSSQELGLKDQED
SDGHLSVNLEYAPTEGTLDIKEDMIEPQEKKLSENTDFLAPGVSSFTDSNQQESITKR
EENQEQPRNYSHQLNRSSKHSQGLRDQGNQEQDPNISNGEEEEKEPGEVGTHNDNQ
ERKTELPREHANSKQEEDNTQSDDILEESDQPTQVSKMQEDEFDQGNQEQEDNSNAEM
EEENASNVNKHIQETEWQSQEGKTGLEAISNHKETEEKTVSEALLMEPTDDGNTTPRN
HGVDDDGDDDGDGGTDGPRHSASDDYFIPSQAFLEAERAQSIAYHLKIEEQREKVHE
NENIGTTEPGEHQEAKKAENSSNEEETSSEGNMRVHAVDSCMSFQCKRGHICKADQQG
KPHCVCQDPVTCPPTKPLDQVCGTDNQTYASSCHLFATKCRLEGTKKGHQLQLDYFGA
CKSIPTCTDFEVIQFPLRMRDWLKNILMQLYEANSEHAGYLNEKQRNKVKKIYLDEKR
LLAGDHPIDLLLRDFEKKNYHMYVYPVHWQFSELDQHPMDRVLTHSELAPLRASLVPME
HCITRFFEECDPNKDKHITLKEWGHCFGIKEEDIDENLLF"   SEQ ID NO. 13
variation  336
           /gene="MAST 9"
variation  433
           /gene="MAST 9"
variation  458
           /gene="MAST 9"
variation  468
           /gene="MAST 9"
variation  638
           /gene="MAST 9"
variation  668
           /gene="MAST 9"
variation  702
           /gene="MAST 9"
variation  1957
           /gene="MAST 9"
variation  2047
```

FIG. 12-78

```
BASE COUNT   996 a   554 c   606 g   652 t
             /gene="MAST 9"
ORIGIN
    1 cggcatgaga ggccagcctg ccagggaaat ccaggaatct gcaacaaaaa cgatgacagt
   61 ctgaaatact ctctgtgcc  aacctccaaa ttctcgtctg tcacttcaga ccccactag
  121 ttgacagagc agcagaatat caactccagt agacttgaat gtgcctctgg gcaaagaagc
  181 agagctaacg aggaaaggga tttaaagagt ttttcttggg tgttttgtcaa actttattc
  241 cctgtctgtg tgcagagggg attcaacttc aattttctgc agtggctctg ggtccagccc
  301 cttacttaaa gatctggaaa gcatgaagac tggccttttt ttcctatgtc tcttgggaac
  361 tgcagctgca atcccgacaa atgcaagatt attatctgat cattccaaac caactgctga
  421 aacggtagca cctgacaaca ctgcaatccc cagtttatgg gctgaagctg aagaaaatga
  481 aaaagaaaca gcagtatcca cagaagacga ttcccaccat aaggctgaaa aatcatcagt
  541 actaaagtca aagaggaaa  gccatgaaga caggcaaga  caggcaagga gttctagcca
  601 agagctggga ttgaaggatc tgatggtcac ttaagtgtga atttggagta
  661 tgcaccaact gaagtacat  tggacataaa agaagatatg attgagcctc aggagaaaaa
  721 actctcagag aacactgatt ttttgctcc  tggtgttagt tccttcacag attctaacca
  781 acaagaaagt atcacaaaga gagagaacaa ccaagaacaa cctagaaatt attcacatca
  841 tcagttgaac aggagcagta aacatagcca aggcctaagg gatcaaggaa accaagagca
  901 ggatccaaat atttccaatg gagaagaga  agaagaaaaa gagccaggtg aagttggtac
  961 ccacaatgat aaccaagaaa gaaagacaga attgcccagg gagcatgcta acagcaagca
 1021 ggaggaagac aatacccaat ctgatgatat tttggaagag tctgatcaac caactcaagt
 1081 aagcaagatg caggaggatg aatttgatca gggtaaccaa gaacaagaag ataactccaa
 1141 tgcagaaatg gaagaggaaa atgcatcgaa cgtcaataag cacattcaag aaactgaatg
 1201 gcagagtcaa gagggtaaaa ctgcctaga  agctatcagc aaccacaaag agacagaaga
 1261 aaagactgtt tctgaggctc tgctcatgga acctactgat gatggtaata ccacgcccag
 1321 aaatcatgga gttgatgatg atggcgatga actacttcat cccaagccag gatgcggca  ctgatggcc
 1381 caggcacagt gcaagtgatc actacttcat cccaagccag gcctttctgg aggccgagag
 1441 agctcaatcc attgcctatc acctcaaaat tgaggagcaa agagaaaaag tacatgaaaa
```

FIG. 12-79

```
1501 tgaaaatata ggtaccactg agcctggaga gccaagaaag gccaagaaag cagagaactc
1561 atcaaatgag gaggaaacgt caagtgaagg caacatgagg gtgcatgctg tggattcttg
1621 catgagcttc cagtgtaaaa gaggccacat ctgtaaggca gaccaacagg gaaaacctca
1681 ctgtgtctgc caggatccag tgacttgtcc tccaacaaaa cccttgatc aagtttgtgg
1741 cactgacaat cagacctatg ctagttcctg tcatctattc gctactaaat gcagactgga
1801 ggggaccaaa aagggcatc aactccagct ggattatttt ggagcctgca aatctattcc
1861 tacttgtacg gactttgaag tgattcagtt tcctctacgg atgagagact ggctcaagaa
1921 tatcctcatg cagcttttatg aagccaactc tgaacatgct ggttatctaa atgagaagca
1981 gagaaataaa gtcaagaaaa tttacctgga tgaaaagagg ctttggctg gggaccatcc
2041 cattgatctt ctcttaaggg acttaagaa aaactaccac atgtatgtgt atcctgtgca
2101 ctggcagttt agtgaacttg accaacaccc tatggataga gtcttgacac attctgaact
2161 tgctcctctg cgagcatctc tggtgcccat agcacatcac ggaacactgc ataacccgtt tctttgagga
2221 gtgtgacccc aacaaggata agcacatcac aaaatctctt cctgaaggag tgggccact gctttggaat
2281 taaagaagag gacatagatg cctcctctgt aaaatctctt gttttgaacg aagatttttaa agaactcaac
2341 tttccagcat cctcctctgt tctaaccact atgcagctgt gatacttgta
2401 gatttatatt tagcaaatg ttagcattaa ctttgaaaac aaaaatgtac ttgcttgaca
2461 acaacctatg caccaggtat ttaacattaa ctttgaaaac aaaaatgtac aattaagtaa
2521 agtcaacata tgcaaaatac tgtacattgt gaacagaagt ttaattcata gtaatttcac
2581 tctctgcatt gacttatgag ataattaatg attaaactat taatgataaa aataatgcat
2641 ttgtattgtt cataatatca tgtgcacttc aagaaaatgg aatgctactc ttttgtgtt
2701 tacgtgtatt attttcaata tcttaatacc ctaataaaga gtccataaaa atccaaaaaa
2761 aaaaaaaaaa aaaaaaaaaa aaaaaaaaa SEQ ID NO. 30
```

FIG. 12-80

≋ NCBI						Nucleotide

PubMed   Nucleotide   Protein   Genome   Structure   PMC   Taxonomy   OMIM   Boo Search [Nucleotide ▽] for [                    ]  [Go] [Clear]              Details Limits    Preview/Index    History    Clipboard Display [▽] Show: [20 ▽]  [Send to ▽]  [File ▽]         [Get Subsequence]      Links ☐ 1: M61908. C.coturnix japoni...[gi:213614]

```
LOCUS       QULQR1                  2678 bp    mRNA    linear   VRT 28-APR-1993
DEFINITION  C.coturnix japonica QR1 gene, complete cds.
ACCESSION   M61908
VERSION     M61908.1  GI:213614
KEYWORDS    
SOURCE      Coturnix coturnix (common quail)
  ORGANISM  Coturnix coturnix
            Eukaryota; Metazoa; Chordata; Craniata; Vertebrata; Euteleostomi;
            Archosauria; Aves; Neognathae; Galliformes; Phasianidae;
            Phasianinae; Coturnix.
REFERENCE   1  (bases 1 to 2678)
  AUTHORS   Guermah,M., Crisanti,P., Laugier,D., Dezelee,P., Bidou,L.,
            Pessac,B. and Calothy,G.
  TITLE     Transcription of a quail gene expressed in embryonic retinal cells
            is shut off sharply at hatching
  JOURNAL   Proc. Natl. Acad. Sci. U.S.A. 88 (10), 4503-4507 (1991)
```

FIG. 12-81

```
MEDLINE   91239596
PUBMED    2034690
COMMENT   Original source text: Coturnix coturnix RNA.
          entry CCQR1; dated 23-JUN-1991.
FEATURES             Location/Qualifiers
     source          1..2678
                     /organism="Coturnix coturnix"
                     /db_xref="taxon:9091"
     gene            220..2250
                     /gene="QR1"
     CDS             220..2250
                     /gene="QR1"
                     /codon_start=1
                     /protein_id="AAA49499.1"
                     /db_xref="GI:213615"
                     /translation="MKTVLLICLLGSAFTTPTDPLNYQFGAHGQKTAEKHKYTHSEM
                     PEEENTGFVNKGDVLSGHRTIKAEVPVLDTQKDEPWASRRQGQGDGEHQTKNSLRSIN
                     FLTLHSNPGLASDNQESNSGSSREQHSSEHHQPRRHRKHGNMAGQWALRGESPVDALG
                     LVRERNTWKYNKNTVGLDENNNGSEEEAGEEEEDEEWGEETDYRDMKHRARGTSHGRE
                     YRRWQNENSRPSGEFLRDSSLPVRITKRHGEKFSMEEESQEKLYKEGKLPLSKKNHNE
                     DQGEKRQSEESKEHFQVVNQRKHRAVTKRQDKEGSNAEEDDNDSGDDGEEDLGNVWRE
                     AVYEEEERMQSNDQDSITNKQKEEITAGDDSGVYREMQDYKGDKIKDVTHSEDNHYHH
                     EPPNSSSKQQLQTSSSVESMNSTEHEDEVKTTGGSYHEESARNSTGKALPDLCRNFHC
                     KRGKVCQADKQGKPSCICQDPAACPSTKDYKRVCGTDNKTYDGTCQLFGTKCQLEGTK
                     MGRQLHLDYMGACKHIPHCTDYEVNQFPLRMRDWLKNILMQYYERDQDTSAFLTEKQR
                     NKVKKIYLNEKRLVSGEHPVELLLHDFEKNYHMYLYPVHWQFYQLDQHPVDRSLTHSE
                     LAPLRASLVPMEHCITRFFQECDGDQDKLITLKEWCHCFAIKEEDINENLLF"
```

FIG. 12-82

| sig_peptide | 220..270        SEQ ID NO. 14
|             | /gene="QR1"
| mat_peptide | 271..2247
|             | /gene="QR1"
|             | /product="unnamed"
| CDS         | 220..2250
|             | /gene="QR1"
|             | /codon_start=1
|             | /protein_id="AAA49500.1"
|             | /db_xref="GI:213616"
|             | /translation="MKTVLLICLLGSAFTTPTDPLNYQFGAHGQKTAEKHKYTHSEM
|             | PEEENTGFVNKGDVLSGHRTIKAEVPVLDTQKDEPWASRRQGQGDGEHQTKNSLRSIN
|             | FLTLHSNPGLASDNQESNSGSSREQHSSEHHQPRRHRKHGNMAGQWALRGESPVDALG
|             | LVRERNTWKYNKNTVGLDENNNGSEEEAGEEEDEEWGEETDYRDMKHRARGTSHGRE
|             | YRRWQNENSRPSGEFLRDSSLPVRITKRHGEKFSMEEESQEKLYKEGKLPLSKKNHNE
|             | DQGEKRQSEESKEHFQVVNQRKHRAVTKRQDKEGSNAEEDDNDSGDDGEEDLGNVWRE
|             | AVYEEEERMQSNDQDSITNKQKEEITAGDDSGVYREMQDYKGDKIKDVTHSEDNHYHH
|             | EPPNSSSKQQLQTSSSVESMNSTEHEDEVKTTGGSYHEESARNSTGKALPDLCRNFHC
|             | KRGKVCQADKQGKPSCICQDPAACPSTKDYKRVCGTDNKTYDGTCQLFGTKCQLEGTK
|             | MGRQLHLDYMGACKHIPHCTDYEVNQFPLRMRDWLKNILMQYYERDQDTSAFLTEKQR
|             | NKVKKIYLNEKRLVSGEHPVELLLHDFEKNYHMYLYPVHWQFYQLDQHPVDRSLTHSE
|             | LAPLRASLVPMEHCITRFFQECDGDQDKLITLKEWCHCFAIKEEDINENLLF"

BASE COUNT     898 a     570 c     619 g     591 t    SEQ ID NO. 36
ORIGIN
      1 gtcagacctt cctcctcaga agctcacaga aaaacacgct ttctgaaaga ttccacactc
     61 aatgccaaaa tataccacag gaaaattttg caaggctcac ggatttccag tgcaccactg
    121 gctaaccaag taggagcacc tcttctactg ccatgaaagg aaaccttcaa acctaccac
    181 tgagccatta actaccatcc tgtttaagat ctgaaaaaca tgaagactgt attgctcctg

FIG. 12-83

```
 241 atttgtcttc taggatctgc tttcaccact ccaaccgatc cattgaacta ccaatttggg
 301 gcccatggac agaaaactgc agagaagcat aaatatactc atttctgaaat gccagaggaa
 361 gagaacacag ggtttgtaaa caaggtgat gtgctgtctg gccacaggac cataaaagca
 421 gaggtaccgg tactggatac acagaaggat gagccctggg cttccagaag acaaggacaa
 481 ggtgatggtg agcatcaaac aaaaaacagc ctgaggagca ttaacttcct tactctgcac
 541 agtaatccag ggttgcttc tgataaccag gaaagcaact ctggcagcag cagggaacag
 601 cacagctctg agcaccacca gcccaggagg cacaggaaac acggcaacat ggctggccag
 661 tgggctctga gaggagaaag tccagtggat gctcttggtc tggttcgtga gcgcaacaca
 721 tggaaataca ataaaaacac agttggccta gatgaaaaca acaatgaaag tgaagaagag
 781 gaagctgggg aggaagaga tgaggaatgg ggtgaagaaa ctgattacag ggatatgaaa
 841 cacagagccc gtgggacaag ccatggaaga gaatacagaa gatgcaaaa tgaaaacagc
 901 cggccatctg gtgaattctt gagagattcc agtctgccaa tacgtataac caagagacac
 961 ggtgagaaat tcagcatgga ggaggaaagt caggaaaagc tctacaagga aggaaaactc
1021 cctctctcaa agaaaaatca taatgaggat caagtgaaa aagacaaag tgaagaaagt
1081 aaagagcatt ttcaagtagt caatcagcgc aaacacagag cagtgacgaa aagcaggat
1141 aaggagggca gcaatgctga ggagatgat aatgatagtg gtgatgatgg tgaggaagat
1201 cttggcaatg tctggaggga agcagtctac gaggagagg aaagaatgca agcaatgac
1261 caggacagta tcactaacaa gcaaaaagag gaaataactg ctggagatga cagtggagtt
1321 tataggagag tgcaggatta caaaggtgac aaaattaaag atgttactca ctctgaagac
1381 aatcattacc accatgagcc ccctaattc agcagcaagc aacaactgca aacaagtagc
1441 tctgttgaga gcatgaattc aacagagcat gaggatgagg ttaagaccac aggaggttca
1501 tatcatgagg aagtgcaag gaacagcact gggaaggctc tcccggatct ttgtagaaac
1561 ttccactgca aagaggaaa agtctgccaa gcagacaagc aagaaaacc cagctgtatt
1621 tgccaagatc ctgctgcttg cccttccacc aagattata agcgtgtttg tggcactgat
1681 ataagactt acgatgtac gtgccaactc tttggcacca aatgtcaact tgaaggacca
1741 aaaatgggac gccagctgca cctggactat atgggtgcct gcaaacacat accccactgt
1801 actgattacg aagtgaatca gttccctctc cgtatgagag actggctcaa aaacatccta
1861 atgcaatatt atgaacgtga tcaggatacg tctgcatttc taaccgaaaa gcaaaggaat
```

FIG. 12-84

```
1921  aaggtcaaaa agatatacct gaatgagaag cgtctcgtct ctggtgagca cccagttgag
1981  cttctcctgc atgactttga gaaaaactac cacatgtatc tctatcctgt gcactggcaa
2041  ttttatcagc ttgaccagca cccagttgac agatcactga ctcattcaga gctcgctcct
2101  ttgagagcct ccctcgttcc catggaacac tgcataaccc gtttcttcca ggagtgtgat
2161  ggagaccaag acaaacttat cactttgaaa gagtggtgcc actgctttgc gattaaggaa
2221  gaagacataa atgaaaatct cctgttctga gcccacctga gcagaatccc catgcagcgc
2281  tacagcttgt caaacatgca atgcccattt atgactgcaa ttaacagctc tgttaatttt
2341  caggaataag ttggcataag attcttggag gcagaacaag tcgctcttgg ataacacaag
2401  tgcctaattg ttacaaattc attaacagca gtagtgttta agagctctaa gtagctcata
2461  cttaaagagt gtttccctct gcacgtacca ataatctctt agtaagacga ctaacttgat
2521  gactgagttg ttcacaaaac cctccgtag aattatagga tgtggatttt ataatacacc
2581  gataaaaact actttgaaat aggttttctt ttcctgtcgt ttactgtcag tagctctctg
2641  catagaaatg tcaaataaac agatcttgtt ttggttttc   SEQ ID NO. 31
```

FIG. 12-85

```
                                                      Boo
NCBI              Nucleotide                          Details PubMed  Nucleotide  Protein  Genome  Structure  PMC  Taxonomy  OMIM
Search Nucleotide ▽ for [                    ]
       Limits      Preview/Index  History          Clipboard     Links
Display default ▽ Show: 20 ▽ Send to File ▽        Get Subsequence   Go  Clear ☐ 1: NM_008047. Mus musculus foll...[gi:6679870]

LOCUS       Fstl                  2823 bp    mRNA    linear   ROD 19-SEP-2002
DEFINITION  Mus musculus follistatin-like (Fstl), mRNA.
ACCESSION   NM_008047
VERSION     NM_008047.1  GI:6679870
KEYWORDS    .
SOURCE      Mus musculus (house mouse)
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
REFERENCE   1  (bases 1 to 2823)
  AUTHORS   Shibanuma,M., Mashimo,J., Mita,A., Kuroki,T. and Nose,K.
  TITLE     Cloning from a mouse osteoblastic cell line of a set of
            transforming-growth-factor-beta 1-regulated genes, one of which
            seems to encode a follistatin-related polypeptide
  JOURNAL   Eur. J. Biochem. 217 (1), 13-19 (1993)
  MEDLINE   94039028
```

FIG. 12-86

```
PUBMED      7901004
COMMENT     PROVISIONAL REFSEQ: This record has not yet been subject to final
            NCBI review. The reference sequence was derived from M91380.1.
FEATURES             Location/Qualifiers
     source          1..2823
                     /organism="Mus musculus"
                     /db_xref="taxon:10090"
                     /chromosome="16"
                     /map="16 27.3 cM"
                     /cell_line="MC3T3-E1"
                     /cell_type="osteoblast"
     gene            1..2823
                     /gene="Fstl"
                     /note="synonyms: TSC-36, AI316791, AW107808"
                     /db_xref="LocusID:14314"
                     /db_xref="MGD:102793"
     CDS             80..1000
                     /gene="Fstl"
                     /codon_start=1
                     /product="follistatin-like"
                     /protein_id="NP_032073.1"
                     /db_xref="GI:6679871"
                     /db_xref="LocusID:14314"
                     /db_xref="MGD:102793"
                     /translation="MWKRWLALSLVTIALVHGEEPRSKSKICANVFCGAGRECAVTE
                     KGEPTCLCIEQCKPHKRPVCGSNGKTYLNHCELHRDACLTGSKIQVDYDGHCKEKKSA
                     SPSASPVVCYQANRDELRRRLIQWLEAEIIPDGWFSKGSNYSEILDKYFKSFDNGDSH
                     LDSSEFLKFVEQNETAINITTYADQENNKLLRSLCVDALIELSDENADWKLSFQEFLK
```

FIG. 12-87

```
                CLNPSFNPPEKKCALEVETYADGAETEVDCNRCVCSCGHWVCTAMTCDGKNQKGVQTH
                TEEEKTGYVQELQKHQGTAEKTKKVNTKEI"  SEQ ID NO. 15
misc_feature    233..367
                /gene="Fstl"
                /note="KAZAL; Region: Kazal type serine protease
                inhibitors"
                /db_xref="CDD:smart00280"
misc_feature    239..367
                /gene="Fstl"
                /note="kazal; Region: Kazal-type serine protease inhibitor
                domain. Usually indicative of serine protease inhibitors.
                However, kazal-like domains are also seen in the
                extracellular part of agrins, which are not known to be
                protease inhibitors. Kazal domains often occur in tandem
                arrays. Small alpha+beta fold containing three
                disulphides. Alignment also includes a single domain from
                transporters in the OATP/PGT family"
                /db_xref="CDD:pfam00050"
misc_feature    770..913
                /gene="Fstl"
                /note="VWC_out; Region: von Willebrand factor (vWF) type C
                domain"
                /db_xref="CDD:smart00215"
variation       1362
                /gene="Fstl"
                /allele="A"
                /allele="C"
                /db_xref="dbSNP:3023433"
```

FIG. 12-88

```
BASE COUNT      762 a       663 c       697 g       701 t
ORIGIN
        1 aagcgacgct cccaccttcg cctctaactc gctgccgcca ccctgccag  tgtcctccgg
       61 agtcccggac ccgagcacga tgtggaaacg atggctggcg ctctcgctgg tgaccatcgc
      121 cctggtccac ggcgaggagg aacctagaag caaatccaag atctgcgcca atgtgttttg
      181 tggagctggc agggaatgtg ccgtcacaga gaaggggag  cccacgtgcc tctgcattga
      241 gcaatgcaaa cctcacaaga ggcctgtgtg tggcagtaat ggcaagacct acctcaacca
      301 ctgtgaactt catagagatg cctgcctcac tggatccaag atccaggttg attatgatgg
      361 gcactgcaaa gaaaagaagt ctgcgagtcc atctgccagc ccagttgtct gctatcaagc
      421 taaccgcgat gagctccgac ggcgcctcat ccagtggctg gaagctgaga tcattccaga
      481 tggctggttc tctaaaggca gtaactacag tgagatccta gacaagtact ttaagagctt
      541 tgataatggc gactctcacc tggactccag tgaattcctg aaattcgtgg agcagaatga
      601 aacagccatc aacatcacca cttatgcaga tcaggagaac aacaaactgc tcagaagcct
      661 ctgtgttgac gccctcattg aactgtctga tgagaacgct gactggaaac tcagcttcca
      721 agagttcctc aagtgcctca acccctcct  caacccctcc gagaagaagt gtgccctgga
      781 ggtcgaaacc tatgcagatg gagctgagac tgaggtggac tgcaatcgct gtgtctgttc
      841 ctgtgccac  tggtctgca  cagcaatgac ctgtgatgga aagaatcaga agggggtcca
      901 gacccacaca gaggaggaga agaatcaga  tgtccaggaa ctccagaagc accaggcac
      961 agcagaaaag accaagaagg tgaacaccaa agagatctaa gaagaggcac agagcaccgt
     1021 gtccggagcc cagcgcctcc tctttcagcgc tgagccagt acacacagag tctgcagcaa
     1081 tcaccaaatc actagtattt gcttgtatgg cagcgaatct tattttgttt gttttgcaat
     1141 aaaggaaatg agggtggcca gcctagcgag ggaaggccac aaccttcacc tgtaggaatg
     1201 ctttaagaga aactaaagga caccctggga cgagaggcaa ctaaggaaac agcatcgggt
     1261 tggcagagga gcagagcag  gtttgaatga agcctttctg gggtcacagc agctgcgagg
     1321 agaatacagg aaaagcatag agaaacattg aactagccct gctgaggaa  gtgggggag
     1381 ctttgtaggg aggaaccctg ctgctttgac ccttgtcacc actgtcagca tgacagacct
     1441 gcagcaagtc tgcttctcct tttggtccca acaatcacct gaacacacag ccgcccaact
     1501 agttacctgt gtcctcagcc ttgcatggag tttcctggag gaggtgttta aatgatgcag
```

```
1561 acacttatgt acttcaagcg catggagact aaccaaattt ttaaaataca ttttttctttt
1621 ttttttttt ttgttaacca aaggtgctat ttctctgtaa aagactttt tccaagctga
1681 cttcattcct cagttattac cgttatatta ttgttgtttt ttaatatttc atttttgac
1741 tagatattaa gcttttgtaa ttattttca ttagtcctac tatttcgaga agtgaaggtg
1801 aaggggttt gggcattttt ccagggtaca gggaactctg taacacaaac agcccatacc
1861 ctgtcacata ttagaccggt tgcagttcgg agcatgcacc ccaacccaga gcttctagaa
1921 aatcagctcc atgccacgaa ggcacaagag gcccctcagc agaagccaca ggacaaagca
1981 tcttcataga cagctgttga gatccaaaca gttaatttgc ttttgtttct tgtaagaagt
2041 tccaaggatg gacgctcagg ctatcccagc ctgccagcct gctgtgatct gtggctaact
2101 ggcagagtca gccactgtgg tccttagctg ctcctgtttc taggtgtcag tttacttagt
2161 aaactgtaa gaatgaatct tggaatttaa taaatggtag tttgtggttt agccaactgg
2221 tccagaggga gctaccttct cctaggata gatgaatcta ctccataaga aaaaccagcc
2281 aggaatagca tggatgggtt ttgctttggt tgaaatgatc ctagcaggtg actggtatg
2341 aggacttcat ggtcactctg cccaggaaga gagcgtgaag gacaactagc agcttcctta
2401 gggatggtac acatgtgtgt gatctctgga gatcagaggt tgccccacac acatgatgat
2461 aaaactttc agatttagag cggttaaaac tggagatcga atctgattg agaatcagca
2521 ctggggcag aaactgttat tgaaagtcaa tccttctttt gagacactcc gaataaacta
2581 tggagattt cctgcatagg aaagtgtgga atgttgagct attgagatgg gagtggaatt
2641 cgtcctaaat agttttttcc tggtctcatc tgaacaagac aatttgctct gcctagtgtt
2701 ctgtgccctc ccttcaaaa gctctgagcc ccgctcatgc agtccagatt tcatcccct
2761 ctccaagtgc cttggagagc tcacgacagc aatgccatca tcaaaagttt tgctgctggg
2821 aag  SEQ ID NO. 32
```

FIG. 12-90

Nucleotide

PubMed  Nucleotide  Protein  Genome  Structure  PMC  Taxonomy  OMIM  Boo

Search Nucleotide ▽ for [                    ] Go Clear   Details

Limits  Preview/Index  History  Clipboard                    Links

Display default ▽ Show: 20 ▽ Send to File ▽  Get Subsequence

☐ 1: X73608. H.sapiens mRNA fo...[gi:793844]

```
LOCUS       HSTEST                  3484 bp    mRNA    linear   PRI 01-MAY-1995
DEFINITION  H.sapiens mRNA for testican.
ACCESSION   X73608
VERSION     X73608.1  GI:793844
KEYWORDS    testican.
SOURCE      Homo sapiens (human)
ORGANISM    Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 3484)
AUTHORS     Alliel,P.M., Perin,J.P., Jolles,P. and Bonnet,F.J.
TITLE       Testican, a multidomain testicular proteoglycan resembling
            modulators of cell social behaviour
JOURNAL     Eur. J. Biochem. 214 (1), 347-350 (1993)
MEDLINE     93285162
FEATURES             Location/Qualifiers
```

FIG. 12-91

```
source          1..3484
                /organism="Homo sapiens"
                /db_xref="taxon:9606"
                /clone_lib="lambda gt11"
CDS             435..1754
                /codon_start=1
                /product="testican"
                /protein_id="CAA51999.1"
                /db_xref="GI:793845"
                /db_xref="SPTREMBL:Q08629"
                /translation="MPAIAVLAAAAAWCFLQVESRHLDALAGGAGPNHGNFLDNDQW
                LSTVSQYDRDKYWNRFRDDDYFRNWNPNKPFDQALDPSKDPCLKVKCSPHKVCVTQDY
                QTALCVSRKHLLPRQKKGNVAQKHWVGPSNLVKCKPCPVAQSAMVCGSDGHSYTSKCK
                LEFHACSTGKSLATLCDGPCPCLPEPEPPKHKAERSACTDKELRNLASRLKDWFGALH
                EDANRVIKPTSSNTAQGRFDTSILPICKDSLGWMFNKLDMNYDLLLDPSEINAIYLDK
                YEPCIKPLFNSCDSFKDGKLSNNEWCYCFQKPGGLPCQNEMNRIQKLSKGKSLLGAFI
                PRCNEEGYYKATQCHGSTGQCWCVDKYGNELAGSRKQGAVSCEEEQETSGDFGSGGSV
                VLLDDLEYERELGPKDKEGKLRVHTRAVTEDDEDEDDDKEDEVGYIW" SEQ ID NO. 16
BASE COUNT    894 a    910 c    808 g    872 t
ORIGIN
        1 cactctctgt tgtccaatgg acacacctgt cgtgttttga gccagcgaga gatgcagtgg
       61 aagtgaaaag catggttaca gactcccat gcgacagtac actccttctga agtagcggac
      121 gcctggttag cttgacattc tatgcaaaga tccataatgt ggttcctgca gatgcacag
      181 ttatcaacca caatatccca ggcccagagg gctactgcat tccacttttt cacttcaaag
      241 cgcttcttgc ccgcgccgct gttggtgccg ctcggggtgg cggtgccagg cgctgcgggc
      301 tcacaaagcg gccagacgct cggcggcggc cgtgccgcgc gagctcgagc cgcgagccgg
      361 cgatcagcct tcccggcgac gcgccgcggg gcgatcgcgg gcgatgccg aactcgagc agggacccg
      421 ggccggcccc caagatgccg gcgatcgcgg gcgatgccg tgttggcggc gcgtggtgct
```

FIG. 12-92

```
 481 tcctccaagt cgagagccgg cacctgacg cgctcgccgg aggcgcggc cccaaccacg
 541 gcaatttcct agacaatgac cagtggctga gcaccgtctc ccagtacgac cggacaagt
 601 actggaaccg ctttcgagac gatgattatt tcagaaactg gaatcccaac aagcccttg
 661 accaagccct ggaccatcc aaggacccct gcctgaaggt aaaatgcagc cctcacaaag
 721 tgtgtgtgac ccaggactac cagaccgcc tgtgtgtcag ccgcaagcac ctgctcccca
 781 ggcaaaagaa ggggaacgtg gcccagaaac actgggttgg accttcgaat ttggtcaagt
 841 gcaagccctg tcccgtggca cagtcagcca tgtctgcgg ctcagatggc cactcctaca
 901 catccaagtg caaattggag ttccatgctt gttctactgg caaaagcctc gccacctct
 961 gtgatgggcc ctgtccctgt ctcccagagc ctgagccacc aaagcacaag gcagaaagga
1021 gtgcctgcac agacaaggag ttgcggaaac ttgcctcccg gctgaaggat tggtttggag
1081 ctctccacga ggatgcgaac agagtcatca agccaccag ctccaacaca gcccaaggca
1141 ggtttgacac tagcatcctg cccatctgca aggactccct gggctggatg ttcaacaagt
1201 tggacatgaa ctatgacctc ctgcttgacc cctcttttca caatgccatc tacctgata
1261 agtacgagcc ctgtatcaag cctcttttca actcgtgtga ctccttcaag gatgcaagc
1321 tttctaacaa tgagtggtgc tactgcttcc agaagctggg agtctccct tgccagaatg
1381 aaatgaacag aattcagagg ctgagtaagg ggaaaagcct gttgggggcc ttcatacctc
1441 ggtgtaatga ggaggctat tacaaagcca cacagtgcca cggcagcacg gggcagtgct
1501 ggtgtgtgga caaatatggg aatgagttgg ctggctccag gaaacaggt gctgtgagct
1561 gtgaagagga gcagaaaac tcagggatt ttggcagtgg tggtcgtg gtcctgctgg
1621 atgacctaga atatgaacgg gagctgggac gatgatgagg caaaggacaa agaggggaag ctgaggtgc
1681 acacccgagc cgtgacagag gatgatgagg caagaaagag tgacaaagag gatgaggtcg
1741 ggtacatatg gtagtgccca caagaaagtt gacacaagt ttgcacaaaa ttgcaagtca
1801 cttcctattc ctgcatttgt atctaagact ccaaggcacc aagtctctt ctccattgtt
1861 gctctctata cccgacctaa ggtttggaag acaactgctt gttcccagag gattctgatt
1921 ttgcatatgt ttgtatggga gaaaggggtgt tgtgtttttt tttttgttgt tgttttattt
1981 ttgataggg aagtcattgg cttaattaga gcctccttcc tttctgtgag attttccaa
2041 caagcatgtg atttacgtgg aattctgaca gtgcagggag cccccaccct cttaaatgtc
2101 aaagacccct tttgattacc cacactggtg gttattacag catgttccc agccttacag
```

FIG. 12-93

```
2161  tgtctaagtg cttctcttgt gtcctgtaga tgttgtgaaa aagaaaaaaa caaaaatac
2221  accacactgt acttttccc ctgcccccg ttactgccgg tgattattat taaaaattag
2281  ttttttcac atcattctat ctggcttcct ataaacaaca gccttaattc agtcaagact
2341  cctttggga attcatttta ttaaaaattg gtgtctggat acttccctgt acatgcataa
2401  atatgcatgc atgtacagaa agactgtatg tgtgtgcctt gcacacacac ccatacctct
2461  cagaaaaagt gtttgggtat cttaaaaact cgaaaaacaa tgataaattt ctcagcttgt
2521  ccagacctgg aacaaaattt ctggaataag aaatttgtat taaagtcctt ttttgcacta
2581  acagttggct cttgtagcct gcaggctgag gaagtctctt ctctgtgcat cagcagagtt
2641  actgaaaagcc tctgattgag aaaaaacctc cgtctgccta aatcactttt ctcgcagaag
2701  ccatgcgact cccacacgac acgggcagct tcacaagcca tctctttcat ttctgcttga
2761  agcccccttgg ctgcagcaat cctgtctgcc ataggtttct tccttcctta cctactcaag
2821  ggcttttttct aaggcatgca cacatatctc ctgttctctg agagtaccat ggtgttcctt
2881  aaaagaagaa aatttctaat tctgaactca atgtttttgct tttctttttt ttctactgac
2941  aaatcatgat aaggcacaa cgtaataaca catgaaagca gatttttttt tttaaccact caatcccaaa
3001  tggaggccta caaagaacat tccccctcac tcccccaagt gacaagatac aacccccgggt ttttaagagc
3061  aaattctgtc cccccctgtc aactcattgg agtctagttc taatgaagaa agttcttcac
3121  catagtgttt gttttaacta tctctcccta caaatttggt agggtcatca
3181  tctctacatt ccttaggatt ttccttcagt accagtctat caaatttggt agggtcatca
3241  gtagtctctg aagttccat ttccttcagt accagtctat aagctactgt ccgccactga
3301  ttttcatctat tcagggtgtc ctaatcagaa tcagcccacc aagcaagcct ctctgccca
3361  catatctatc ttctgccttc cccatgaac ttcagcctgt ccacacaaaa gccacataaa
3421  ctcaagcaag aaatatgttc agccaaaaca tgattatagt ggcagctgac caatacccca
3481  cccc    SEQ ID NO. 33
```

FIG. 12-94

| | | | | | | | |
|---|---|---|---|---|---|---|---|
| PubMed | Nucleotide | Protein | Genome | Structure | PMC | Taxonomy | OMIM | Boo |

Nucleotide

Search Nucleotide ▽ for [                    ]

Limits    Preview/Index    History    Clipboard    Details

Display default ▽    Show: 20 ▽    Send to File ▽    Clear

Get Subsequence

Links

☐ 1: NM_022137. Homo sapiens secr...[gi:24475656]

```
LOCUS       SMOC1                  3669 bp    mRNA    linear   PRI 05-NOV-2002
DEFINITION  Homo sapiens secreted modular calcium-binding protein 1 (SMOC1),
            mRNA.
ACCESSION   NM_022137
VERSION     NM_022137.2  GI:24475656
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1
  AUTHORS   Vannahme,C., Smyth,N., Miosge,N., Gosling,S., Frie,C., Paulsson,M.,
            Maurer,P. and Hartmann,U.
  TITLE     Characterization of SMOC-1, a Novel Modular Calcium-binding Protein
            in Basement Membranes
```

FIG. 12-95

JOURNAL   J. Biol. Chem. 277 (41), 37977-37986 (2002)
MEDLINE   22254804
COMMENT   PROVISIONAL REFSEQ: This record has not yet been subject to final
          NCBI review. The reference sequence was derived from AJ249900.1.
          On Nov 2, 2002 this sequence version replaced gi:11545872.
FEATURES         Location/Qualifiers
     source      1..3669
                 /organism="Homo sapiens"
                 /db_xref="taxon:9606"
                 /chromosome="14"
                 /map="14q24.1"
                 /tissue_type="brain"
                 /dev_stage="fetal"
                 /tissue_lib="stretch cDNA library Clontech"
     gene        1..3669
                 /gene="SMOC1"
                 /db_xref="LocusID:64093"
     CDS         255..1559
                 /gene="SMOC1"
                 /codon_start=1
                 /product="secreted modular calcium-binding protein 1"
                 /protein_id="NP_071420.1"
                 /db_xref="GI:11545873"
                 /db_xref="LocusID:64093"
                 /translation="MLPARCARLLTPHLLVLVQLSPARGHRTTGPRFLISDRDPQCN
          LHCSRTQPKPICASDGRSYESMCEYQRAKCRDPTLGVVHRGRCKDAGQSKCRLERAQA
          LEQAKKPQEAVFVPECGEDGSFTQVQCHTYTGYCWCVTPDGKPISGSSVQNKTPVCSG

FIG. 12-96

```
SVTDKPLSQGNSGRKDDGSKPTPTMETQPVFDGDEITAPTLWIKHLVIKDSKLNNTNI
RNSEKVYSCDQERQSALEEAQQNPREGIVIPECAPGGLYKPVQCHQSTGYCWCVLVDT
GRPLPGTSTRYVMPSCESDARAKTEADDPFKDRELPGCPEGKKMEFITSLLDALTTD
MVQAINSAAPTGGGRFSEPDPSHTLEERVVHWYFSQLDSNSSNDINKREMKPFKRYVK
KKAKPKKCARRFTDYCDLNKDKVISLPELKGCLGVSKEGRLV" SEQ ID NO. 37
``` sig peptide    255..332
               /gene="SMOC1"
mat peptide    333..1556
               /gene="SMOC1"
               /product="smoc-1"
misc feature   375..515
               /gene="SMOC1"
               /note="kazal; Region: Kazal-type serine protease inhibitor
               domain. Usually indicative of serine protease inhibitors.
               However, kazal-like domains are also seen in the
               extracellular part of agrins, which are not known to be
               protease inhibitors. Kazal domains often occur in tandem
               arrays. Small alpha+beta fold containing three
               disulphides. Alignment also includes a single domain from
               transporters in the OATP/PGT family"
               /db_xref="CDD:pfam00050"
misc feature   378..515
               /gene="SMOC1"
               /note="KAZAL; Region: Kazal type serine protease
               inhibitors"
               /db_xref="CDD:smart00280"
misc feature   537..728

FIG. 12-97

```
misc feature    /gene="SMOC1"
                /note="thyroglobulin_1; Region: Thyroglobulin type-1
                repeat. Thyroglobulin type 1 repeats are thought to be
                involved in the control of proteolytic degradation. The
                domain usually contains six conserved cysteines. These
                form three disulphide bridges. Cysteines 1 pairs with 2, 3
                with 4 and 5 with 6"
                /db_xref="CDD:pfam00086"
                597..737
misc feature    /gene="SMOC1"
                /note="TY; Region: Thyroglobulin type I repeats"
                /db_xref="CDD:smart00211"
                933..1130
misc feature    /gene="SMOC1"
                /note="thyroglobulin_1; Region: Thyroglobulin type-1
                repeat. Thyroglobulin type 1 repeats are thought to be
                involved in the control of proteolytic degradation. The
                domain usually contains six conserved cysteines. These
                form three disulphide bridges. Cysteines 1 pairs with 2, 3
                with 4 and 5 with 6"
                /db_xref="CDD:pfam00086"
                996..1136
misc feature    /gene="SMOC1"
                /note="TY; Region: Thyroglobulin type I repeats"
                /db_xref="CDD:smart00211"
                956
variation
```

FIG. 12-98

```
     variation      /gene="SMOC1"
                    /allele="T"
                    /allele="C"
                    /db_xref="dbSNP:3825739"
                    complement(2487)
                    /allele="T"
                    /allele="C"
                    /db_xref="dbSNP:2273780"
                    2939
     variation      /gene="SMOC1"
                    /allele="G"
                    /allele="A"
                    /db_xref="dbSNP:3742912"
                    2968
     variation      /gene="SMOC1"
                    /allele="G"
                    /allele="A"
                    /db_xref="dbSNP:3742913"
                    2993
     variation      /gene="SMOC1"
                    /allele="T"
                    /allele="C"
                    /db_xref="dbSNP:3742914"
                    3648..3653
     polyA_signal   /gene="SMOC1"
BASE COUNT       842 a    988 c   1026 g    813 t
ORIGIN
```

FIG. 12-99

```
   1 gcctgctgcc gcctgggccc cgccgagcgg agctagcgcc gcgcgcagag cacacgctcg
  61 cgctccagct cccctcctgc gcggttcatg actgtgtccc ctgaccgcag cctctgcgag
 121 ccccgcccgc aggaccacgg cccgctcccc gccgcgcga gggcccgcga cgaaggaagg
 181 aagggaggcg cgctgtgcgc ccgcggagc ccgcgaaccc cgctcgctgc cggctgccca
 241 gcctggctgg caccatgctg ccgcgcgct gcgcccgcct gctcacgcc cacttgctgc
 301 tggtgttggt gcagctgtcc cctgctcgcg gccaccgcac cacaggcccc agttttctaa
 361 taagtgaccg tgaccacag tgcaacctcc actgctccag gactcaacc aaacccatct
 421 gtgcctctga tggcaggtcc tacgagtcca tgtgtgagta ccagcgagcc aagtgccgag
 481 acccgaccct gggcgtggtg catcgagtga gatgcaaaga tgctggccag agcaagtgtc
 541 gcctggagcg ggctcaagcc ctggagcagc ccaagaagct tcaggaagct gtgtttgtcc
 601 cagagtgtgg cgaggatggc tcctttaccc agtgcagtg ccatacttac actggtact
 661 gctgtgtgt caccccgat gggaagccca tcagtggctc ttctgtgcag aataaaactc
 721 ctgtatgttc agttcagtc acgacaagc accacaagc cctgagcca gggtaactca ggaagaaag
 781 atgacgggtc taagccgaca cccacgatgg agaccagcc ggtgttcgat ggagatgaaa
 841 tcacagcccc aactctatg attaaacact tggtgatcaa ggactccaaa ctgaacaaca
 901 ccaacataag aaattcagag cgtgagggta cgtgtgacca agagaggcag agtgcctgg
 961 aagagcccca gcagaatccc cactccacc ttgtcatccc tgaatgtgcc cctggggac
1021 tctataagcc agtgcaatgc caccagtcca ctggctactg ctggtgtgtg ctgtggaca
1081 cagggcgccc gctgcctgga acctccacac gctacgtgat gcccagttgt gagagcgacg
1141 ccagggccaa gactacagag gcgatgacc ccttcaagga gcctactgga caggagcta ccaggctgtc
1201 cagaagggaa gaaaatggag tttatcacca gcctactgga tgctctcacc actgacatgg
1261 ttcaggccat taactcagca gcgcccactg gaggtgggag gttctcagag gtcctcagag ccaagcccca
1321 gccacaccct ggagagacgg gtagtgcact ggtatttcag ccagctggac agcaatagca
1381 gcaacgacat taacaagcgg gagatgaagc ccttcaaggc ctactactga aagaaagcca
1441 agcccaagaa atgtgcccgg cgtttcaccg actactgtga cctgaacaaa gacaaggtca
1501 tttcactgcc tgagctgaag ggctgcctgg gtgttagcaa agaaggacgc ctcgtctaag
1561 gagcagaaaa cccaagggca ggtggagagt ccagggaggc aggatggatc accagacacc
```

FIG. 12-100

```
1621 taaccttcag cgttgcccat ggccctgcca catcccgtgt aacataagtg gtgccacca
1681 tgtttgcact tttaataact cttacttgcg tgttttgttt ttggtttcat tttaaacac
1741 caatatctaa taccacagtg ggaaaggaa actgacaact agggaagaaa gactttattc tctctcttat
1801 tgtaagtttt tggatctgct actgacaact tttagagggt tttggggggg tggggaggg
1861 tgttgttggg gcctgagaag aaagagattt atatgctgta tataaatata tatgtaaatt
1921 gtatagttct tttgtacagg cattggcatt gctgttttgtt tatttctctc cctctgcctg
1981 ctgtgggtgg tggcactct ggacacatag tccagctttc taaaatccag gactctatcc
2041 tgggcctact aaacttctgt ttggagactg accctgtgt ataaagacg gagtcctgca
2101 attgtactgc ggactccacg agttcttttc tggtgggagg actatattgc cccatgccat
2161 tagttgtcaa aattgataag tcacttggct ctcggccttg tccagggagg ttgggctaag
2221 gagagatgga aactgccctg ggagaggaag ggagtccaga tccatgaat agcccacaca
2281 ggtaccggct ctcagagggt ccgtgcattc ctgtctccg gaccccaaa gggcccagca
2341 ttggtgggtg caccagtatc ttagtgaccc tggagcaaa ttatccacaa aggatttgca
2401 ttacgtcact cgaaacgttt tcatccatgc ttagcatcta ctctgtataa cgcatgagag
2461 gggagcaaa gaagaaaagg acacacgaa gggcctttaa aaaagtagat atttaatatc
2521 taagcagggg agggacagg acagaaaagc tgcactgagg ggtgcggtgc caacaggaa
2581 actcttcacc tccctgcaaa cctaccagtg aggctcccag agacgcagct gtctcagtgc
2641 ccaggggcag attgggtgtg acctctccac tcctccatct cctgctgttg tcctagtggc
2701 tatccacaggc ctgggtgggt gggttggggg aagtgtcagt caccttgttg gtaacactaa
2761 agtttgtttg ttggtttttt aaaaacccaa tactgaggtt cttcctgttc cctcaagttt
2821 tcttatggc ttccaggctt taagctaatt ccagaagtaa aactgatctt gggtttccta
2881 ttctgcctcc cctagaaggg caggggtgat aacccagcta caggaaatc ccggcccagc
2941 tttccacagg catcacaggc atcttccgcg gattctaggg tgggctgccc agccttctgg
3001 tctgaggcgc agctccctct gcccagtgc tgtgcctatt caagtggcct tcaggcagag
3061 cagcaagtgg cccttagcgc cccttcccat ctcctcagat aagcagctgt ggtggcagtg agggaggttg
3121 ggtagccctg gactggtccc ctcctcagat caccccttgca aatctggcct catcttgtat
3181 tccaacccga catcccctaaa agtacctcca ccgttccgg gtctgaagg cgttggcacc
```

FIG. 12-101

```
3241 acaagcactg tccctgtggg aggagcacaa ccttctcggg acaggatctg atggggtctt
3301 gggctaaagg agtccctgc tgtcctggag aaagtcctag aggttatctc aggaatgact
3361 ggtggccctg cccaacgtg gaaaggtggg aaggaagcct tctcccatta gccccaatga
3421 gagaactcaa cgtgccggag ctgagtgggc cttgcacgag acactggccc cactttcagg
3481 cctggaggaa gcatgcacac atggagacgg cgcctgcctg tagatgtttg gatcttcgag
3541 atctccccag gcatcttgtc tcccacagga tcgtgtgtgt aggtggtgtt gtgtggtttt
3601 cctttgtgaa ggagagaggg aaactatttg tagcttgttt tataaaaaat aaaaaatggg
3661 taaatcttg SEQ ID NO. 38
```

FIG. 12-102

```
                          Nucleotide

PubMed  Nucleotide  Protein  Genome  Structure  PMC  Taxonomy  OMIM  Boo

Search Nucleotide ▽ for [                    ]  Go   Clear           Details

Limits      Preview/Index   History    Clipboard
Display default ▽ Show: 20 ▽  Send to  File ▽    Get Subsequence      Links
```

☐ 1: BC004617. Mus musculus, Sim...[gi:13435493]

```
LOCUS       BC004617                1611 bp    mRNA    linear   ROD 20-SEP-2002
DEFINITION  Mus musculus, Similar to transcription factor 19 (SC1), clone
            MGC:6711 IMAGE:3585301, mRNA, complete cds.
ACCESSION   BC004617
VERSION     BC004617.1  GI:13435493
KEYWORDS    MGC.
SOURCE      Mus musculus (house mouse)
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
REFERENCE   1  (bases 1 to 1611)
  AUTHORS   Strausberg,R.
  TITLE     Direct Submission
  JOURNAL   Submitted (21-MAR-2001) National Institutes of Health, Mammalian
            Gene Collection (MGC), Cancer Genomics Office, National Cancer
```

FIG. 12-103

```
          Institute, 31 Center Drive, Room 11A03, Bethesda, MD 20892-2590,
          USA
REMARK    NIH-MGC Project URL: http://mgc.nci.nih.gov
COMMENT   Contact: MGC help desk
          Email: cgapbs-r@mail.nih.gov
          Tissue Procurement: Gilbert Smith, Ph.D.
          cDNA Library Preparation: Life Technologies, Inc.
          cDNA Library Arrayed by: The I.M.A.G.E. Consortium (LLNL)
          DNA Sequencing by: Baylor College of Medicine Human Genome
          Sequencing Center
          Center code: BCM-HGSC
          Web site: http://www.hgsc.bcm.tmc.edu/cdna/
          Contact: amg@bcm.tmc.edu
          Gunaratne, P.H., Garcia, A.M., Lu, X., Hulyk, S.W., Hale, S.M.,
          Yoon, V.S., Kowis, C.R., Lawrence, S., Martin, R.G., Muzny, D.M.,
          Richards, S., Gibbs, R.A.

Clone distribution: MGC clone distribution information can be found
          through the I.M.A.G.E. Consortium/LLNL at: http://image.llnl.gov
          Series: IRAK Plate: 10 Row: 1 Column: 11
          This clone was selected for full length sequencing because it
          passed the following selection criteria: GenomeScan gene
          prediction, similarity but not identity to protein.
FEATURES           Location/Qualifiers
     source        1..1611
                   /organism="Mus musculus"
                   /strain="FVB/N"
                   /db_xref="taxon:10090"
```

FIG. 12-104

```
          /clone="MGC:6711 IMAGE:3585301"
          /tissue_type="Mammary tumor. Metallothionien-TGF alpha
          model. 10 month old virgin mouse. Taken by biopsy."
          /clone_lib="NCI_CGAP_Mam1"
          /lab_host="DH10B"
          /note="Vector: pCMV-SPORT6"
     CDS  360..1151
          /codon_start=1
          /product="Similar to transcription factor 19 (SC1)"
          /protein_id="AAH04617.1"
          /db_xref="GI:13435494"
          /translation="MLPCFQLLRIGGGRGGDLYTFHPPSKSGCTYGLGCRADLCDVAL
          RPQQEPGLISGVHAELHAELQGDDWRVSLEDHSSQGTLVNNVRLPRGHRLELSDGDLL
          TFGPQGQAGTSSSSEFYFMFQQVRVKPQDFAAITVPRSKGEAGGGFQPMLPPQGAPQR
          PLSTLSSAPKATLILNSIGSLSKLQAQPLTFSRGGGRPQGLAIPSQHGEAQVSPAPPT
          RNRRKSAHKVLAELDDEVSPGPLSVLTEPRKRLRVEKAALIASGE" SEQ ID NO. 17
BASE COUNT   393 a   456 c   417 g   345 t
ORIGIN
     1 ggaatcccctt cctcagttta ccccgcgagc gaaaaaaaga aaggattgtc ggaggctccc
    61 ggatgttgag ccgcctgagg atccggcttc actgaggtgc cacaagacgt cttcctgtt
   121 ttgcatcgca tcaggacttt actggaattg ctttttaaac ctcatcttga cagcctctgt
   181 cttggtgcat atccaggcct ctggcgctct gaatctgcac tgcttaagtt ggcattaggc
   241 acaatactta gctgttgaca tcagagagaa ctgaattgaa gcccacggtg catgaccccag
   301 gagtaggaga gggaatggac ttctgaggtg ggcgaagtgg tgcagagggg gcaccccca
   361 tgctgccctg tttccagctg ctgcgtatag ggggcggcag gggcggtgac ctctacacct
   421 tccaccccc gtccaagtct ggctgcacct atggattggg gcctcatctc gacctgtgtg
   481 atgtggccct gcggccccag caggagcccg ggctcatctc tggagtccat gcggaattgc
   541 atgctgaact ccaaggggac gactggaggg tcagcctgga ggatcacagc agccaaggga
```

FIG. 12-105

```
 601 ctttggtcaa taatgtccga cttccaagag gccacagact ggagttgagt gatggtgacc
 661 ttctgacctt tgcccccaa  ggtcagcag gaaccagctc ctcctcagag ttctacttca
 721 tgtttcaaca agtccgggtt aaacctcagg actttgcagc cataaccgtc cctcggtcta
 781 agggagaagc tggggcggt  ttccaaccta tgctgccccc ccaaggggca cctcagaggc
 841 cactccagcac tctctcctct gccccaagg  cctctcacct tctcaattcc atcggcagcc
 901 tcagcaaact ccaggcccag gggaagcgc  tctcccgtgg tggtggcagg ccacagggcc
 961 tggctattcc ctctcagcat gtgttggcag aagtttcgcc tgctccaccc acaagaaacc
1021 ggaggaaatc agctcataaa gtgttggcag cgaggtctcc ccaggccccc
1081 tgtccgtcct gacggagccc aggaagaggc tccgggtgga gaaagctgct ctgatagcca
1141 gtggggaatg accacaggga aggtccatt  gctaaagact gactcaaggc tggagaatgc
1201 ttgcaaatga agtgacagaa aagatggttt cctgccaaag atgttgcagc ctccaagttt
1261 ccagtgagct acaagcccag tcacaaggaa taaagccttg cctccatga  tgccaggata
1321 cctgcagtta gagcaccggt cccagaaacc attcctagaa ggtatggttt tattttgctg
1381 aagccagcat ataccaggca agtgctctgc cacaataccc taaccctact catgttcttg
1441 aatggcatcg gctaaagcac cctgaaggac ccagagcaca ttcccaaggc atcctcatgc
1501 caccgctagc tagtatcacc accagctgag tctctgggac tagcttttca gagcttagtc
1561 tttattccca aataaagaat aaactgtttc atccaaaaaa aaaaaaaaaa a SEQ ID NO. 34
```

```
                      ATCAG-------TAATAGCC-AAGGA-   Majority

398                   AT----------------------GACA   4507170-SPARC.seq
498                   AACAA-AAA-ACAGCCTGAGGA------   213614-QR-1.seq
535                   ATCAG-TACTAAAGTCAAAGA-------   21359870-Hevin.seq
801                   ATCAAGCCCACCAGCTCCAACAGCCCAAGGCAGGTTTG   15451924-SPOCK.seq
258                   --CAG---------TAAT----------G   13242264-FRP.seq ---------GCAAGACCT--TG   Majority 404                   ----------ACAAGACCT--TC   4507170-SPARC.seq
518                   ----------GCATTAACT--TC   213614-QR-1.seq
556                   ----------GGAAAGCCA--TC   21359870-Hevin.seq
841                   ACACTAGCATCCTGCCCATCTGCAAGGACTCCCTGGCTG   15451924-SPOCK.seq
266                   ----------GCAAGACCT--   13242264-FRP.seq
```

```
                                                                    Majority
AAC--TCATTGTTTGGTTTG-TGAGGTGAGCTCATTGGCA 520        530       540
516  ----CCCTTGCCTTGGACTC-TGAGCTGACCGAATTC----   4507170-SPARC.seq
688  GATGCTCTTGGTCTGGTTCG-TGAGCGCAAACAT--GGA    213614-QR-1.seq
731  AACACTGATTTTTGGCTCC-TGGTGTAGTTCTTCACA       21359870-Hevin.seq
1121 GGCCTTCATACCTCGGTGTAATGAGGAGGGCTATTACAAA   15451924-SPOCK.seq
361  AA----------GTCTG-TGAG-------TCCATCCGCC     13242264-FRP.seq Majority
GACCC-CAACGAATGCG-GGGGTAGC-CAGATG-A 550       560
547  CCC----CTGCGCATGCG-GGACTGGC-----------     4507170-SPARC.seq
725  AATAC---AATAAAAACA-CAGTTGGCCTAGATGAA       213614-QR-1.seq
770  GATTC---TAACCAACAAG-AAAGTATTCACAAAGAGA     21359870-Hevin.seq
1161 GCCACACAGCCACGGCACGGCCAGTGCTGGTGTG          15451924-SPOCK.seq
382  AGCCC----CGTGTCTTGC---------TATTC          13242264-FRP.seq
```

|   | Majority |
|---|---|
| 606 | ----TGGGGCCAAGGACCTG--ATGACC |
| 808 | ----------------------CTGACT 4507170-SPARC.seq |
| 863 | ----------------------ATTA-C 213614-QR-1.seq |
| 1281 | GATTTGGCAGTGGTGGGATC---GGGATC 21359870-Hevin.seq |
| 443 | TGGAA---------------GCC 15451924-SPOCK.seq |
|   | GCC 13242264-FRP.seq |

|   | Majority |
|---|---|
| 625 | GAGAATATGAA--GAGCAGGGTCCAAATGGCT |
| 829 | GAGAA-------------GCAGAAGCTG 4507170-SPARC.seq |
| 885 | AGGGATATGAA-ACACAGAGCCCG--TGGGA 213614-QR-1.seq |
| 1321 | AAGGAAACCAA-GAGCAGGATCCAAATATTT 21359870-Hevin.seq |
| 451 | TAGAATATGAAGGGAGCTGGGACCAAAAGGACAAAGAGG 15451924-SPOCK.seq |
|   | GAGATCAT----TCCAGATGGCT 13242264-FRP.seq |

FIG. 13-18

```
          CACCCGTGGTGACCAC-AGAGAGA------TAC  Majority
                     |                  |
                    690                700

688  CACCCCG-TG-------------GAGC------TGC  4507170-SPARC.seq
905  CATG--TG-TGGTGAATTCTTGAGAGA------TTC  213614-QR-1.seq
962  CACAATGATAACCAAGAAAGAAA----------GAC  21359870-Hevin.seq
1441 TATGGTAGTGCCCACAAGAAAGAGGACACAAGTTTGCAC  15451924-SPOCK.seq
490  TACAGTG------------------AGA-----TGC  13242264-FRP.seq TAGATTGC--CCAGTACTTATA-CTAA  Majority
                         |
                        710

704  TG---GC------CCGGGACTT------CGA  4507170-SPARC.seq
930  CAGTCTGC-----C-AGTACGTATAACCAA  213614-QR-1.seq
988  AGAATTGC-----CCAGGGAGCATG-CTAA  21359870-Hevin.seq
1481 AAAATTGCAAGTCACTTCCTATTCCTGTATTCTAA  15451924-SPOCK.seq
503  TAGA---------CAAGTACTT------TAA  13242264-FRP.seq
```

```
                                      Majority          4507170-SPARC.seq
                                                        213614-QR-1.seq
                                                        21359870-Hevin.seq
                                                        15451924-SPOCK.seq
                                                        13242264-FRP.seq

- - CATAAAGA - G - - ATGGA - AGGAAGACTG  Majority
                                       |
                                      860

860  - - - - - - - - - - - - - - - - - - - - - - - -    - G C T T    4507170-SPARC.seq
1177  - - - - - - - - - - - - - - AGTGGTGATG - - - -    - G C T T    213614-QR-1.seq
1244  - - - - - - - - - - - - - - CACAAAGA - G - - - -  - G C T T    21359870-Hevin.seq
2081  CTGTACATGCATAAATATGCATGCAGAAGAAAAGATCT             ATGGTGAGGAAGATCT 15451924-SPOCK.seq
 629  - - - - - - - - - - - - - - - - - - - - - - - -    - AACTG    13242264-FRP.seq Majority
        - - CGATGCCTCT - - G - - - - - - - - - - - -  Majority
                          |
                         870

864  T T T - - - - - - - - - - - - - - - - - - - -    - CGAGACCT         4507170-SPARC.seq
1203  T G G - - - - - - - - - - - - - - - - - - - -    - CAATGTCTGG - AGGG 213614-QR-1.seq
1269  T T T - - - - - - - - - - - - - - - - - - - -    - CTGAGGCTCT - GCTC 21359870-Hevin.seq
2121  TATGTGTGTGCCTTGCACACACCCATACCTCTCAGAA              15451924-SPOCK.seq
 634  C T C - - - - - - - - - - - - - - - - - - - -    - AGAGGCCTCT - G    13242264-FRP.seq

```
          ....TCTCTGGTA.....CCTAT-GGAACA Majority
AGCG

1595 ATTT-...-----CCTCCTTTA-----CCTTT-...CA  4507170-SPARC.seq
2106 AGCC-...-----TCCCCTCGTT----COCAT-GGAACA  213614-QR-1.seq
2173 AGCA-...-----TCTCTGGTG-----CCCAT-GGAACA  21359870-Hevin.seq
3601 ATTGAAAAATTGCACTTAGAAAACTAGGAACA  15451924-SPOCK.seq
1049 AGCG-...-----TCTGTGGCA-----ATCA  13242264-FRP.seq G--TGCATAACCCGTTTC---TTTTCGGAGT-----GTGA Majority 1615 G-...--GTTTC------TTTTCACATT----AGGC  4507170-SPARC.seq
2130 C--TGCATAACCCGTTTC---TTCCAGGAGT----GTGA  213614-QR-1.seq
2197 C--TGCATAACCCGTTTC---TTTGAGGAGT----GTGA  21359870-Hevin.seq
3641 GGGTGAACCACTGATTTTAATTGCCTAATTATCTTATGA  15451924-SPOCK.seq
1066 C--CGAATCACCAGTATT---TGCT-...GT--A  13242264-FRP.seq
```

FIG. 13-46

| | | Majority |
|---|---|---|
| | CG------GCAACTAAGATAA-ACTTA-------- | |
| | 1640  1650 | |
| 1639 | TG------TTGGTT-------CAA-ACTTT------- | 4507170-SPARC.seq |
| 2160 | TG----GAGACCAAGACAA-ACTTA-------- | 213614-QR-1.seq |
| 2227 | CC---T--CCAACAAGGATAA-GCACA-------- | 21359870-Hevin.seq |
| 3681 | CAAGTATCAAATTAAGATGACACTTAAAGATTCCTTAGCAT | 15451924-SPOCK.seq |
| 1090 | CG-----GCAGCA------AA-TCTTA-------- | 13242264-TRP.seq |

| | | Majority |
|---|---|---|
| | TCACTT--TGA--GAGAGTGGTGC---------CAGTGGTT | |
| | 1660  1670 | |
| 1655 | TGG------GA--GCACGGACTGT---------CAGTTCTC | 4507170-SPARC.seq |
| 2180 | TCACTT--TGA--AAGAGTGGTGC---------CACTGCTT | 213614-QR-1.seq |
| 2247 | TCACCC--TGA--AGGAGTGGGGC---------CACTGCTT | 21359870-Hevin.seq |
| 3721 | TAACTTAAATGATGGAGAAGAGTGCTCAACAGACAGTTCCC | 15451924-SPOCK.seq |
| 1105 | TC---------T--TGT---------T--TGTTT | 13242264-TRP.seq |

```
                          . . . . . . . . . . . . . . . . . . . . T C C A T G A A T A T T T A A G G C  Majority
                                               |
                                              1760
1743 . T C T C A G G G C . . . . . . . . . . . T C T A G G G A C - T G C C A G G C  4507170-SPARC.seq
2290 - T C - A A A C A T . . . . . . . . . . . - G C A A T G C C C A T T T A T G A C  213614-QR-1.seq
2360 . T T C T A A C C A C . . . . . . . . . . . T T C A G A A A T A T A T G C A G C  21359870-Hevin.seq
3921 T T T T A A A G A T C T T T A A T A C T T T A A T A C T T C C A T G A G T A C T A A A G A T  15451924-SPOCK.seq
1174 - T T C T A G G A A T . . . . . . . . . . . . . . . . . . . . . . . . . T G C  13242264-FRP.seq T G T A A T - A G C T A . . . . . . . . . . . . . . . . . . . . G T A T G T T T A T T  Majority
              |                                       |
             1770                                    1790
1770 T G T T - T C A G C C A . . . . . . . . . . . . . . . . . . . . G G A A G G C C A A A  4507170-SPARC.seq
2316 T G C A A T T A A A C A G . . . . . . . . . . . . . . . . . . . C T C T G T T A A T T  213614-QR-1.seq
2388 T G T G A T - - A C T T . . . . . . . . . . . . . . . . . . . . G T A G A T T T A T A  21359870-Hevin.seq
3961 T G T A A T G A G T T A C C T T A T C C T T A G A A G T A G A A T G T T T G C T  15451924-SPOCK.seq
1186 . . . . . . . . . . . . . . . . . . . . . . . . . . . . . . . . . . . . . . . . . .  13242264-FRP.seq
```

| Position | Majority | 4507170-SPARC.seq | 213614-QR-1.seq | 21359870-Hevin.seq | 15451924-SPOCK.seq | 13242264-FRP.seq |
|---|---|---|---|---|---|---|
| | C-TTAATGT----CCTGATAAA- | | | | | |
| 2053 | | G-TGAAGAG | | | | |
| 2620 | | T--TTACTGT- | C--AGTA- | | | |
| 2722 | | C--TTAATAC- | | CCTAATAAA- | | |
| 4561 | | CACTGATGTTTGTCCTGTTAAATGTATAGCATTGTAATG | | | | |
| 1333 | | --GC- | | CCTGCTGGA- | | |

| Position | Majority | 4507170-SPARC.seq | 213614-QR-1.seq | 21359870-Hevin.seq | 15451924-SPOCK.seq | 13242264-FRP.seq |
|---|---|---|---|---|---|---|
| | -GAGTCCATTCAAAAATCT--- | | | | | |
| 2070 | | T--TCTTTCAAAAT- | | | | |
| 2633 | | --GCTC-- | TCT- | | | |
| 2739 | | -GAGTCCCATAAAAATCC- | | | | |
| 4601 | | AGAGCCCATCAAAATCCTGAGTGTCAGTTTGTCCTAT | | | | |
| 1344 | | -GG- | | --AAAT- | | |

```
              AFDNTAIP---EEEKET--AVSTED-DSHHKAE Majority
              |----+----|----+----|----+----|
                   40        50        60

36  APDNTAIPSLWAEAEENEKET--AVSTED-DSHHKAE  SPARC.pro
   8  AFEDVT------------ETQAC--TDKELR------  TESTICAN.pro
  36  APDNTAIPSLWAEAEENEKET--AVSTED-DSHHKAE  HEVIN.pro
  11  LFQLTP--------TRTRCDLVIFSGGENE-------  FRP.pro
  30  KYTHSEMP------EEENTG--FVNKGDVLSGHRTI-  QR1.pro KSSVLLAS--EESH--EASAEQGK93---KDQ Majority
              |----+----|----+----|----+----|
                   70        80        90       100

70  KSSVLKSK--EESH--EQSAEQGKSSSQELGLKDQ  SPARC.pro
  25  -NLASRLKDWFGALKE--DANRVIKPTS--SDT   TESTICAN.pro
  70  KSSVLKSK--EESH--EQSAEQGKSSSQELGLKDQ  HEVIN.pro
  33  --KLAS-----GIFQ--PPVTHLKSVS--DQI    FRP.pro
  66  KAEVPVLD--TQKDEPWASRRQGQGD------GEH  QR1.pro
```

FIG. 13-62

```
       EDGDGHLSVNLLYAP-SEGTLDIKEDMIEP-QEKKLSEST Majority
                      |         |         |
                     110       120       130

101    EDSDGHLSVNLEYAP-TEGTLDIKEDMIEP-QEKKLSENT SPARC.pro
 53    TQGRF--DTSILPICKDSLGWMFNKLDMN-YDLLDHSE   TESTICAN.pro
101    EDSDGHLSVNLEYAP-TEGTLDIKEDMIEP-QEKKLSENT HEVIN.pro
 54    SKGGY--SVTLRPS-SVGVPW-FTKVTLQREFVTTPE    FRP.pro
 93    QTKNSLRSINFLTLH-SNPGLASDNQE9NS-GSSREQHS5 QR1.pro D------------------------------FLA-     Majority
                                  |
                                 140

139    D-----------------------------FLAP      SPARC.pro
 89    INAIYLDKYEPCIKPLENSCDBFKDGKLSNNEWCYCFQ-  TESTICAN.pro
139    D-----------------------------FLAP      HEVIN.pro
 89    V-----------------------------LE        FRP.pro
131    E-----------------------------WHQ       QR1.pro
```

FIG. 13-63

```
                    -FTDSNQQESIT---KREENQEQPRNYSHHQL-NR$ Majority
                           150         160         170
144 GVSgFTDSNQQESIT---KREENQEQPRNYSHHQL-NR$ SPARC.pro
127 -------------------------------------- TESTICAN.pro
144 GVSSFTDSNQQESIT---KREENQEQPRNYSHHQL-NR$ HEVIN.pro
 92 -------------------------------------- FRP.pro
135 ---PRRHRKHGNMAGQWALRGESPVPALGLVRERNTWKY QR1.pro SKHSQG-LREQGNIEQ--ISNGEEEEKEPGEVGTHND Majority
            180         190         200         210

179 SKHSQG-LRDQGNQEQDPNISNGEEEEKEPGEVGTHND SPARC.pro
127 -KPGGLPCQNEMNRIQK----LSKG------------- TESTICAN.pro
179 SKHSQG-LRDQGNQEQDPNISNGEEEEKEPGEVGTHND HEVIN.pro
 92 -RSVTL-EKEIEQIEP--SIQA---------------- FRP.pro
171 NKNTVG--LDENNGSE--EEAGEEEDEWGEETDYRD-- QR1.pro
```

FIG. 13-64

```
                                  RATELPGEHA---------GS  Majority
                                            220        230
217 NQE--------------------------RKTELPREHA----------NS  SPARC.pro
147 ---------------------------KSLLGAFIPRCNEEGYYKATQCWCVDKYGN  TESTICAN.pro
217 NQE--------------------------RKTELPREHA----------NS  HEVIN.pro
110 ---------------------------------NAAALAGEAE------GN  FRP.pro
206 MKH-----------------------RARGTSHGRE-------------YR  QR1.pro EQEE---SNTQSDDILEESDQPTQVSKMQEDEFDQGNEE  Majority
                 240         250         260
232 -KQEE---DNTQSDDILEESDQPTQVSKMQEDEFDQGNQE  SPARC.pro
184 -ELAG---LSRKQGTV---------------SCEE     TESTICAN.pro
232 -KQEE---DNTQSDDILEESDQPTQVSKMQEDEFDQGNQE  HEVIN.pro
122 -ELGGTWTSQKSTAL----------------SRTK     FRP.pro
221 RWQNE---NRPSGEFLRDSSLPVRITKRHGEKFSMEEES  QR1.pro
```

FIG. 13-65

```
                                            ----EDNSNAEMEESNASLV-------N Majority
                                                         |         |
                                                        270       280

268 Q-----------EDNSNAEMEENASNV-----N SPARC.pro
                                        199 E-----------QETSGDFGSGGSVVL----- TESTICAN.pro
                                        268 Q-----------EDNSNAEMEENASNV----N HEVIN.pro
                                        140 G-----------ETDGDTVEENSKVGL----- FRP.pro
                                        258 QEKLYKEGKLPLSKKNHNEDQGEKRQSEESKEHFQVVNQR QR1.pro KHIQETEWQSQEGKTGLEAISNHKETEETV---SEALL Majority
                                                    |         |         |
                                                   290       300       310      320

286 KHIQETEWQSQEGKTGLEAISNHKETEEKTV--SEALL SPARC.pro
                                        215 -----------LDDLDDEREIGPKD------------- TESTICAN.pro
                                        286 KHIQETEWQSQEGKTGLEAISNHKETEEKTV--SEALL HEVIN.pro
                                        156 -----------QRVLENRKAALCKE------------- FRP.pro
                                        298 KHRAVTKRQDKEGSNAEEDDNSGDDGEEDLGNVWREAV- QR1.pro
```

```
                    IGTTEPGEHQEAKKAENSSNE  Majority
    EKVQENEV
         |         |         |
        390       400       410

388 EKVHENEN------IGTTEPGEHQEAKKAENSSNE    SPARC.pro
301 E--QNARVSSGWKEVANTREAMAS-----------    TESTICAN.pro
388 EKVHENEN------IGTTEPGEHQEAKKAENSSNE    HEVIN.pro
218 E--DRMWV------DQTTA----------------    FRP.pro
401 QQLQTSSS------VESMNSTEHEDEVKTTGGSYH    QR1.pro EETSSEGNMRVH-VDSCMSFQCKRGHICKADQQGKPHCVC  Majority
         |         |         |
        420       430       440       450

417 EETSSEGNMRVH-VDSCMSFQCKRGHICKADQQGKPHCVC  SPARC.pro
323 ---------VNKLI-DK----------------------  TESTICAN.pro
417 EETSSEGNMRVH-VDSCMSFQCKRGHICKADQQGKPHCVC  HEVIN.pro
229 -------MQAFP-RP------------------------  FRP.pro
430 EESARNSTGKAL-PDLCRNFHCKRGKVCQADKQGKPSCIC  QR1.pro
```

FIG. 13-68

```
         Q D P V T C P P T K P L D Q V C G T D N Q T Y A S S C H L F A T K C R L E G T K   Majority
                    |              |              |              |
                   460            470            480            490

457  Q D P V T C P P T K P L D Q V C G T D N Q T Y A S S C H L F A T K C R L E G T K   SPARC.pro
329  Q D P V T C P P T K P L D Q V C G T D N Q T Y A S S C H L F A T K C R L E G T K   TESTICAN.pro
457  Q D P V T C P P T K P L D Q V C G T D N Q T Y A S S C H L F A T K C R L E G T K   HEVIN.pro
235  Q D P A A C P S T K D Y K R V C G T D N K T Y D G T C Q L F G T K C Q L E G T K   FRP.pro
469  Q D P A A C P S T K D Y K R V C G T D N K T Y D G T C Q L F G T K C Q L E G T K   QR1.pro K G H Q L Q L D Y F G A C K S I P T C T D F E V I Q F P L R M R D W L K N I L M   Majority
                    |              |              |              |
                   500            510            520            530

497  K G H Q L Q L D Y F G A C K S I P T C T D F E V I Q F P L R M R D W L K N I L M   SPARC.pro
329  K G H Q L Q L D Y F G A C K S I P T C T D F E V I Q F P L R M R D W L K N I L M   TESTICAN.pro
497  K G H Q L Q L D Y F G A C K S I P T C T D F E V I Q F P L R M R D W L K N I L M   HEVIN.pro
235  K G H Q L Q L D Y F G A C K S I P T C T D F E V I Q F P L R M R D W L K N I L M   FRP.pro
509  M G R Q L H L D Y M G A C K H I P R C T D Y E V N Q F P L R M R D W L K N I L M   QR1.pro
```

FIG. 13-69

```
                 QLYEANSEHAGYLNEKQRNKVKKIYLDEKRLLAGDHPIDL  Majority

|         |         |
                        540       550       560       570

537  QLYEANSEHAGYLNEKQRNKVKKIYLDEKRLLAGDHPIDL  SPARC.pro
    329                                            TESTICAN.pro
    537  QLYEANSEHAGYLNEKQRNKVKKIYLDEKRLLAGDHFIDL  NEVIN.pro
    235                                            FRP.pro
    549  QYYERDQDTSAFLTEKQRNKVKKIYLNEKRLVSGEHPVEL  QR1.pro LLRDFKKNYHMYVVPVHWQFSELDQHPMDRVLTHSELAPL  Majority

|         |         |
                        580       590       600       610

577  LLRDFKKNYHMYVVPVHWQFSELDQHPMDRVLTHSELAPL  SPARC.pro
    329                                            TESTICAN.pro
    577  LLRDFKKNYHMYVVPVHWQFSELDQHPMDRVLTHSELAPL  NEVIN.pro
    235                                            FRP.pro
    589  LLRDFKKNTHMYLVPVHWQFYQLDQHPVDRSLTHSELAPL  QR1.pro
```

FIG. 13-70

NORMAL COLON

ADENOCARCINOMA

MUCINOUS ADENOCARCINOMA

MIVER METASTASIS

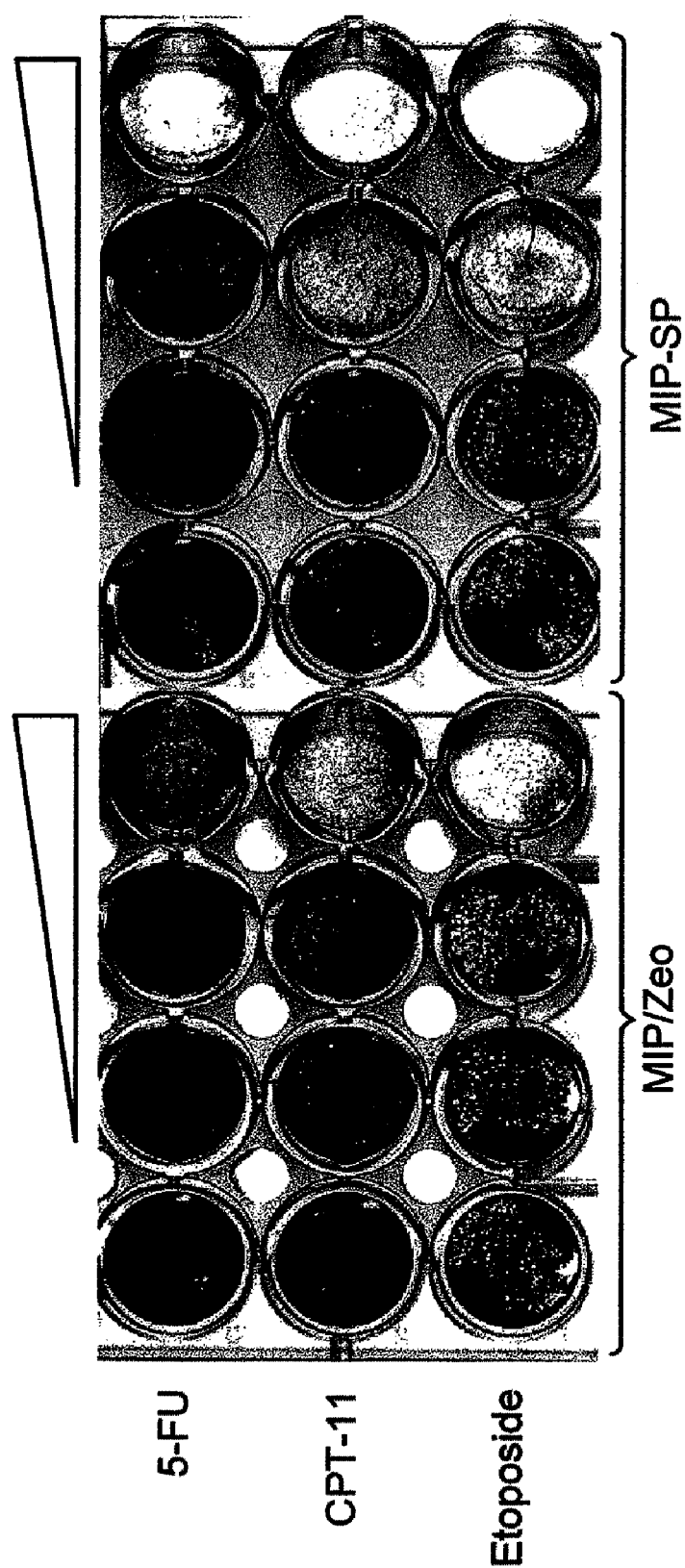

: # CANCER THERAPY SENSITIZER

RELATED APPLICATION(S)

This application is a continuation of U.S. application Ser. No. 11/181,115, filed on Jul. 14, 2005, which is a continuation of PCT/US04/000901, filed Jan. 14, 2004, and claims the benefit of U.S. Provisional Application No. 60/440,009, filed on Jan. 14, 2003. The entire teachings of the above applications are incorporated herein by reference.

FIELD OF THE INVENTION

The invention relates to cancer therapy sensitizing compositions and methods.

BACKGROUND

The reason for cancer treatment failures following induction with chemotherapy or radiation therapy is still unclear. Many factors have been implicated in therapeutic resistance, such as upregulation of efflux pumps from multidrug resistance family (MDR) p-glycoprotein and other non-classical MDR proteins (multidrug resistance-associated protein, MRP; lung resistance protein, LRP) have been described in a variety of cancers (Lehnert, M. Anticancer Res 1998; 18:2225-2226; Ringborg, U. and Platz, A. Acta Oncol 1996; 5:76-80; Shea, T. C., Kelley, S. L., and Henner, W. D. Cancer Res 1998; 48:527-533). Unfortunately, many tumors that are intrinsically resistant to chemotherapy, such as the gastrointestinal malignancies, have relatively low levels of expression of the MDR genes. For example, only 23% of primary colorectal tumors express MRP and 65% express p-glycoprotein (Filipits M, Suchomel R W, Dekan G, Stigilbauer W, Haider K, Depisch D, Pirker R. Br. J Cancer 1997; 75: 208-212). Therefore, resistance to therapeutic agents cannot be explained solely on the basis of activation and up-regulation of known MDR genes. Studies have also shown that genetic mutations responsible for tumorigenesis may also contribute to drug resistance. For example, loss of DNA mismatch repair (MMR) genes found in hereditary non-polyposis colorectal cancer (HNPCC), have been associated with a more rapid emergence of clinical drug resistance (de las Alas MM, S Aebi, D Fink, S B Howell, G Los. J Natl Canc Inst 1997; 89:1537-41; Lin X, Howell S B (1999). Mol Pharmacol 56:390-5). Mutations in the K-ras gene, detected in approximately 40% of adenomatous polyps and adenocarcinomas, are associated with an increased relapse rate, mortality and a poor chemotherapeutic response (Arber N, I. Shapira, J. Ratan et al. Gastroenterology 2000; 118:1045-1050). Genes involved in cell cycle regulation, such as p21 and p27, have been shown to protect tumors from undergoing apoptosis elicited by various anticancer agents (Waldman T, Lengauer C, Kinzler K W, Vogelstein B. Nature 1996, 381:713-716; St. Croix B, Florenes V A, Rak J W, Flanagan M, Bhattacharya N, slingerland J M, Kerbel R S. Nature Med 1996, 2:1204-1210). In addition, cell adhesion molecules, such as E-cadherin, confer resistance to cells when exposed to chemotherapeutic agents (Skoudy A, Llosas M D, Garcia de Herreros A. Biochem J 1996).

The mechanisms involved in therapeutic resistance therefore appear to be very complex. Recent evidence suggests that the selectivity of chemotherapy for the relatively few tumors ever cured by drugs depends, to a large extent, upon their easy susceptibility to undergo apoptosis, i.e., to kill themselves (Makin G, Expert Opin Ther Targets. 2002 6(1):73-84; Johnstone R W, Ruefli A A, Lowe S W, Cell. 2002 108(2): 153-64; Kamesaki H, Int J Hematol. 1998 68(1):29-43).

Secreted protein acidic and rich in cystein (SPARC) belongs to a family of extracellular proteins, called matricellular proteins. Since its identification and cloning, the functional role of SPARC remains unclear. Its high evolutionary conservation suggests an important physiological role for this protein (Iruela-Arispe M L, Lane T F, Redmond D, Reilly M, Bolender R P, Kavanagh T J, Sage E H. Mol Biol Cell. 1995 March; 6(3):327-43). Initial studies showed that SPARC is important in bone mineralization (Termine J D, Kleinman H K, Whitson S W, Conn K M, McGarvey M L, Martin G R. Cell. 1981 October; 26(1 Pt 1):99-105). While SPARC is expressed at high levels in bone tissue, it is also distributed widely in other tissues and cell types (Maillard, C., et al., Bone, 13:257-264 (1992)). Its role has been expanded to include tissue remodeling (Latvala T, Puolakkainen P, Vesaluoma M, Tervo T. Exp Eye Res. 1996 November; 63(5):579-84; Kelm R J Jr, Swords N A, Orfeo T, Mann K G. J Biol Chem. 1994 Dec. 2; 269(48):30147-53); endothelial cell migration (Hasselaar P, Sage E H. J Cell Biochem. 1992 July; 49(3):272-83), morphogenesis (Mason L T, Murphy D, Munke M, Francke U, Elliott R W, Hogan B L. EMBO J. 1986 August; 5(8):1831-7; Strandjord T P, Sage E H, Clark J G. Am J Respir Cell Mol Biol. 1995 September; 13(3):279-87), and angiogenesis (Kupprion C, Motamed K, Sage E H. J Biol Chem. 1998 Nov. 6; 273(45):29635-40; Lane T F, Iruela-Arispe M L, Johnson R S, Sage E H. J Cell Biol. 1994 May; 125(4):929-43). SPARC has also been shown to have an antiproliferative effect on endothelial cells, mesangial cells, fibroblasts and smooth muscle cells (Sage E H. Biochem Cell Biol. 1992 July; 70(7):579-92).

Experiments in vitro have also identified SPARC in tumors (Schulz, A., et al., Am. J. Pathol., 132:233-238 (1988); Porter, P. L., et al., J. Histochem. Cytochem., 43:791-800 (1995)). There is conflicting evidence that SPARC can function either as an oncogene, as suggested by studies in melanoma (Ledda M F, Adris S, Bravo A T, Kairiyama C, Bover L, Chernajovsky Y, Mordoh J, Podhajcer O L. Nat Med. 1997 February; 3(2):171-6) or as a tumor suppressor, as demonstrated by its strong inhibition of growth in vJun-ml and v-Src-transformed chicken embryo fibroblasts (Vial E, Castellazzi M. Oncogene. 2000 Mar. 30; 19(14):1772-82). Although the growth inhibitory properties of SPARC have been mainly shown in primary cells, such as endothelial, fibroblast, mesangial and smooth muscle cells, this may also contribute to the role of SPARC in tumorigenesis. SPARC has also been shown to have tumor invasive properties. Variable SPARC expression has been observed in a variety of cancers. Higher levels of expression have been detected in breast cancer (Bellahcene A, Castronovo V. Am J Pathol. 1995 January; 146(1):95-100), esophageal cancer (Porte H, Triboulet J P, Kotelevets L, Carrat F, Prevot S, Nordlinger B, DiGioia Y, Wurtz A, Comoglio P, Gespach C, Chastre E. Clin Cancer Res. 1998 June; 4(6): 1375-82), hepatocellular carcinoma (Le Bail B, Faouzi S, Boussarie L, Guirouilh J, Blanc J F, Caries J, Bioulac-Sage P, Balabaud C, Rosenbaum J. J Pathol. 1999 September; 189 (1):46-52), and prostate (Thomas R, True L D, Bassuk J A, Lange P H, Vessella R L. Clin Cancer Res 2000; 6:1140-1149). However, conflicting results have been seen with ovarian cancers (Brown T J, Shaw P A, Karp X, Huynh M H, Begley, Ringuette M J. Gynecol Oncol 1999; 75: 25-33; Paley P J, Goff B A, Gown A M, Greer B E, Sage E H. Gynecol Oncol 2000; 78: 336-341; Yiu G K, Chan W Y, Ng S W, Chan P S, Cheung K K, Berkowitz R S, Mok S C. Am J Pathol 2001; 159:609-622), and colorectal cancers (Porte H, Chastre E, Prevot 5, Nordlinger B, Empereur S, Basset P, Chambon P, Gespach C. Int J Cancer 1995; 64: 70-75; Lussier C, Sodek J, Beaulieu J F. J Cell Biochem. 2001; 81(3):463-76).

Recently, SPARC has been suggested to be involved in inducing apoptosis of ovarian cancer cells (Yiu G K, Chan W Y, Ng S W, Chan P S, Cheung K K, Berkowitz R S, Mok S C. Am J Pathol 2001; 159:609-622). Yiu et al. (2001, supra) has showed that there was downregulation of SPARC expression following malignant transformation, and that there were antiproliferative properties of SPARC on both normal ovarian and cancer cells. Yiu et al. (2001, supra) further provided additional evidence that exogenous exposure to SPARC alone was capable of inducing apoptosis in ovarian cancer cells. However, human pathological specimens of tumors with high SPARC expression levels have not been shown to have higher number of apoptotic cells.

WO0202771 discloses a novel hSPARC-h1 polypeptide and its potential applications in tissue remodeling, tissue repair and general modulation of various growth factor activities.

U.S. Pat. No. 6,387,664 provides a SPARC fusion protein obtainable by fusing SPARC to thioredoxin which can be used for basic research in neurobiology and/or for treating various neuropathologies.

U.S. Pat. No. 6,239,326 provides a SPARC-deficient transgenic mouse model for testing drugs in promoting or retarding wound healing and treating or preventing cataracts, diabetes mellitus or osteoporosis.

All references cited herein above and throughout the specification, including patents, patent applications, are hereby incorporated by reference in their entirety.

SUMMARY OF THE INVENTION

The invention is based on the discovery that SPARC sentitizes cancer therapy.

The present invention provides compositions and methods for sensitizing cancer therapeutic treatment.

The present invention provides a composition comprising a SPARC family polypeptide and a chemotherapy agent.

The present invention provides a composition comprising a SPARC family polypeptide and a chemotherapy-resistant cell.

The present invention provides a chemotherapy-resistant cell comprising a recombinant SPARC family polynucleotide.

The present invention provides a recombinant cell comprising a heterologous transcription control region operatively associated with a SPARC family polynucleotide.

In another aspect, the present invention provides a method for in vivo sensitizing a mammal to a therapeutic treatment, the method comprising administrating to the mammal diagnosed with cancer an effective amount of a SPARC family polypeptide or a polynucleotide encoding a SPARC polypeptide.

The present invention provides a method for ex vivo sensitizing a mammal diagnosed with cancer to a therapeutic treatment, the method comprising: administering to a mammal an effective amount of a cell comprising a SPARC family polypeptide or a polynucleotide encoding a SPARC family polypeptide; wherein the cell produces an increased amount of the SPARC polypeptide.

The present invention also provides a method for ex vivo sensitizing a mammal diagnosed with cancer to a therapeutic treatment, the method comprising: (1) Obtaining a cancer sample from the mammal; (2) contacting the cancer sample with an effective amount of a composition comprising a SPARC family polypeptide or a polynucleotide encoding a SPARC polypeptide; and (3) returning the cancer sample after the contacting of (2) to the mammal.

The present invention further provides a method for sensitizing a cancer sample to a therapeutic treatment, the method comprising contacting the cancer sample with an effective amount of a composition comprising a SPARC family polypeptide or a polynucleotide encoding a SPARC polypeptide.

In one embodiment of the invention, the cancer sample is a cell or tissue sample.

In another embodiment of the invention, the cancer sample is transfected or infected with the polynucleotide of (e)-(f).

The present invention provides a method for evaluating a first cancer cell for its resistance to a therapeutic treatment, comprising: (a) measuring the expression level of a SPARC family mRNA or polypeptide, or the extracellular level of a SPARC family polypeptide in the first cancer cell; and (b) comparing the expression level or the extracellular level obtained in (a) with the expression level of the SPARC family mRNA or polypeptide, or the extracellular level of the SPARC family polypeptide in a second cancer cell which does not exhibit resistance to the therapeutic treatment; wherein a lower level of expression or extracellular level in (a) is indicative of the first cancer cell being resistant to the therapeutic treatment.

The present invention provides a method for evaluating a first cancer cell for its resistance to a therapeutic treatment, comprising: (a) measuring expression level of a SPARC family mRNA or polypeptide, or extracellular level of a SPARC family polypeptide in the first cancer sample; (b) measuring expression level of the SPARC family mRNA or polypeptide, or extracellular level of the SPARC family polypeptide in a second cancer sample which does not exhibit resistance to the therapeutic treatment; (c) comparing the expression levels or the extracellular levels obtained in (a) and (b), where a lower level of expression or extracellular level in (a) is indicative of the first cancer sample being resistant to the therapeutic treatment.

In one embodiment, the first sample is from a first mammal and the lower level of expression or extracellular level in (a) is further indicative of the first mammal being resistant to the therapeutic treatment.

In another embodiment, the second cancer sample is from a first mammal who provides the first cancer sample.

In yet another embodiment, the second cancer sample is from a second mammal who is different from the first mammal providing the first cancer sample.

Preferably, the first mammal and the second mammal are diagnosed with the same cancer.

In one embodiment, the expression level of the SPARC family mRNA is measured by polymerase chain reaction, DNA microarray or northern blot.

In one embodiment, the expression or extracellular level of the SPARC family polypeptide is measured by Immuno Blotting or Enzyme-Linked Immunosorbent Assay (Elisa).

The present invention provides a method for identifying an agent which modulates a SPARC family mRNA or polypeptide expression, or a SPARC family polypeptide secretion, comprising: (a) measuring expression level of the SPARC family mRNA or polypeptide, or extracellular level of the SPARC family polypeptide in a sample; (b) contacting a candidate agent with the sample; (c) after the contacting of (b), measuring expression or extracellular level of the SPARC family mRNA or polypeptide, or extracellular level of the SPARC family polypeptide in the sample of (b); (d) comparing the expression levels or the extracellular levels in (a) and (c), where a differential level of expression or extracellular level in (a) and (c) indicates the candidate agent being an agent which modulates the SPARC family mRNA or polypeptide expression, or the SPARC family polypeptide secretion.

The present invention also provides a method for identifying an agent which sensitizes a cancer sample to a therapeutic treatment, comprising: (a) measuring expression level of a SPARC family mRNA or polypeptide, or extracellular level of a SPARC family polypeptide in the cancer sample; (b) contacting a candidate agent with the cancer sample; (c) after the contacting of (b), measuring expression level of the SPARC family mRNA or polypeptide, or extracellular level of the SPARC family polypeptide in the cancer sample of (b); (d) comparing the expression levels or the extracellular levels obtained in (a) and (c), where an increased level of expression or extracellular level in (c) indicates the candidate agent being an agent which sensitizes a cancer sample to a therapeutic treatment.

In one embodiment, the cancer sample of the subject method is from a mammal diagnosed with cancer, and the increased level of expression or extracellular level is further indicative of the candidate agent being an agent which sensitizes the mammal to a therapeutic treatment.

The present invention provides a method for determining a therapeutic treatment protocol for a first mammal diagnosed with cancer, comprising: (a) determining if expression of a SPARC family mRNA or polypeptide or extracellular level of a SPARC family polypeptide is lower in a first sample from the first mammal than a second sample which does not exhibit resistance to the therapeutic treatment; and (b) if (a) is positive, increasing the strength of the therapeutic treatment to the first mammal so as to increase the response to the treatment.

Preferably, the polynucleotide of (e) or (f) of the subject composition and method is an expression vector.

More preferably, the expression vector is a plasmid or a viral vector.

In one embodiment, the plasmid vector is pcDNA3.1.

The SPARC family polypeptide or a polynucleotide encoding a SPARC family polypeptide of the present invention include: (a) a SPARC polypeptide which is selected from the group consisting of SEQ ID Nos. 1-17; (b) a polypeptide having an amino acid sequence of at least 60% homology to the SPARC family polypeptide in (a); (c) a polypeptide fragment of (a)-(b) where the fragment is at least 50 amino acids in length; (d) a fusion polypeptide comprising the polypeptide of (a), (b), or (c); (e) a polynucleotide encoding the polypeptide of (a), (b), (c) or the fusion polypeptide of (d); or (f) a polynucleotide hybridizing to the polynucleotide of (e) under a stringent hybridization condition.

Preferably, the SPARC family polypeptide or polynucleotide of the present invention is selected from: SMOC-1, SPARC, hevin, SC1, QR-1, follistatin-like proteins (TSC-36), testican.

Preferably, the therapeutic agent of the subject composition and method is a chemotherapy agent or a radiation therapy agent.

More preferably, the therapeutic agent is selected from the group consisting of the agents listed in Table 1.

In one embodiment, the mammal of the subject method exhibits resistance to the therapeutic treatment.

In one embodiment, the therapeutic treatment is chemotherapy or radiation therapy.

In one embodiment, the cancer sample of the subject method is a cell or a tissue sample.

Preferably, the cell or tissue sample is lysed before the measuring of the expression or extracellular level of a SPARC family polypeptide or polynucleotide (e.g., mRNA).

More preferably, a polynucleotide or polypeptide extract is obtained from the cell or tissue sample before the measuring of the expression or extracellular level of a SPARC family polypeptide or polynucleotide (e.g., mRNA).

BRIEF DESCRIPTION OF THE DRAWINGS

The foregoing features of the invention will be more readily understood by reference to the following detailed description, taken with reference to the accompanying drawings.

DETAILED DESCRIPTION

Figure 1:
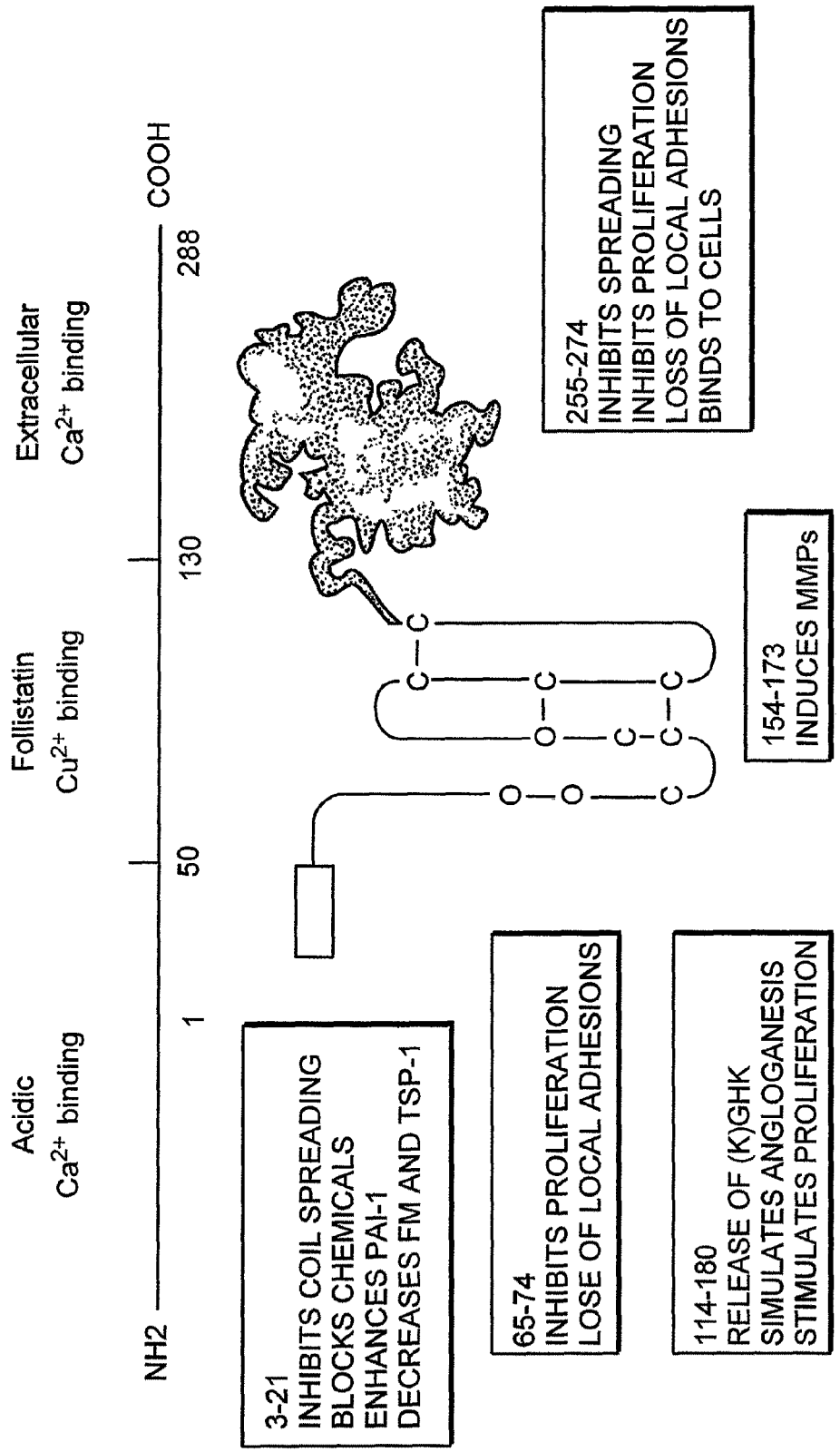
FIG. 1 is a modular structure of human SPARC and the location and functions of synthetic peptides. Three domains and their residue numbers are shown as described in Yan and Sage, 1999, J. Histochem. & Cytochem. 47(12):1495-1505.
Figure 2:
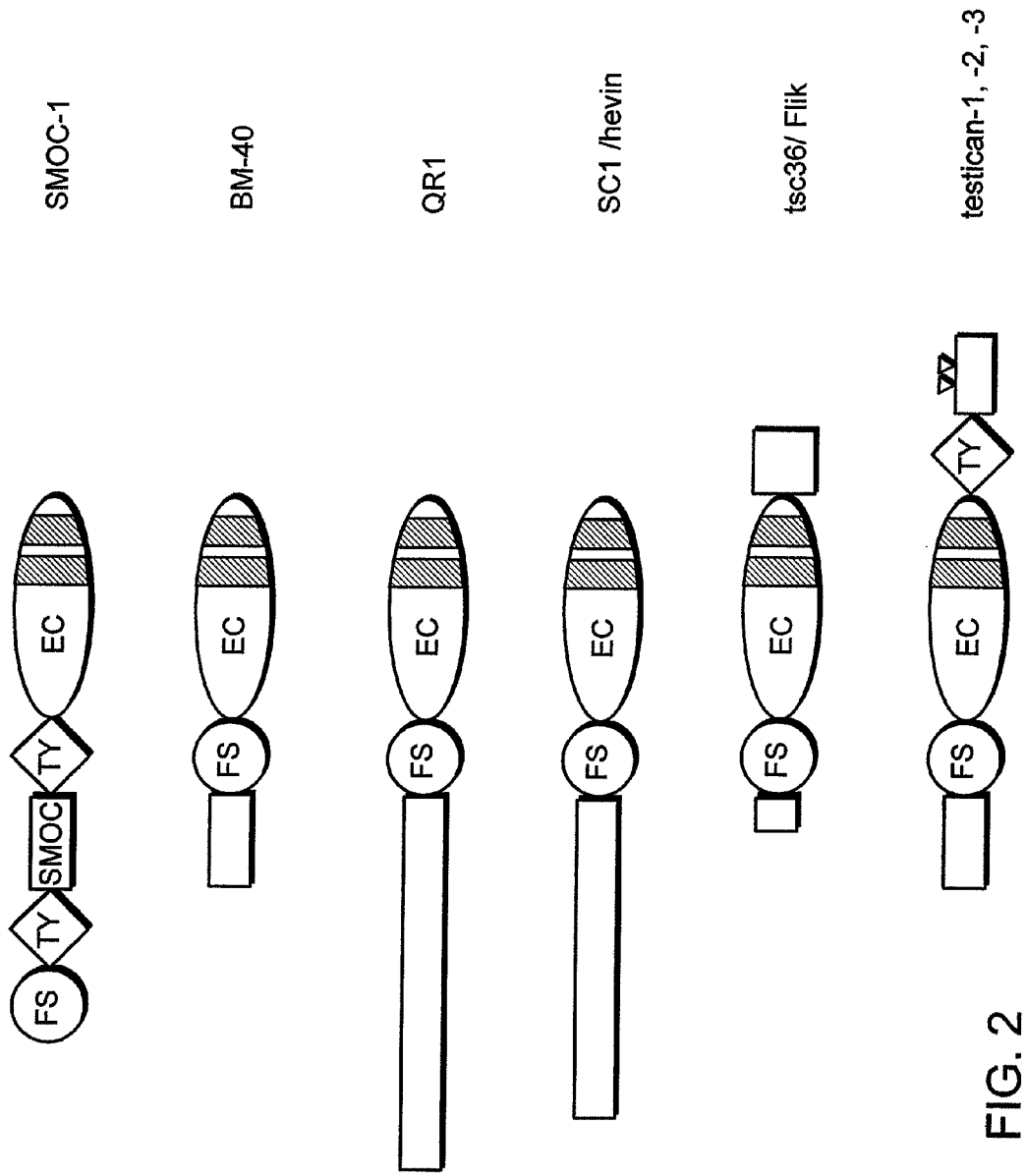
FIG. 2 is a domain organization of various SPARC family proteins. FS represents the follistatin-like domain, TY the thyroglobulin-like domain, EC the extracellular calcium-binding domain as described in Vannahme et al., 2002, J. Biol. Chem. 277(41):37977-37986. Domains with no homology to other proteins are shown as open boxes. Signal peptides are not shown.

The invention is based on the SPARC family and sensitization to cancer therapy.

Definitions

As used herein, a "SPARC family polypeptide" refers to a polypeptide (including a fragment or variant thereof) of a family of extracellular proteins. This family of extracellular proteins include SPARC and other members of the family, such as SMOC-1, hevin, SC1, QR-1, follistatin-like proteins (TSC-36) and testican (see for example, Vannahme et al., (2002), J. Biol. Chem. 277(41): 37977-37986; Johnston, I. G., Paladino, T., Gurd, J. W., and Brown, I. R. (1990) Neuron 2, 165-176; Guermah, M., Crisanti, P., Laugier, D., Dezelee, P., Bidou, L., Pessac, B., and Calothy, G. (1991) Proc. Natl. Acad. Sci. U.S.A. 88, 4503-4507; Shibanuma, M., Mashimo, J., Mita, A., Kuroki, T., and Nose, K. (1993) Eur. J. Biochem. 217, 13-19; Alliel, P. M., Perin, J. P., Jolles, P., and Bonnet, F. J. (1993) Eur. J. Biochem. 214, 347-350, hereby incorporated by reference.) A SPARC family polypeptide is typically composed of three independently folded domains (Yan and Sage, 1999, J. Histochem. & Cytochem., 47(12):1495-1505, hereby incorporated by reference). The N-terminal domain (e.g., two adjacent N-terminal $Glu_3$ and $Glu_4$ in SPARC) is negatively charged, the second domain (e.g., residues 53-137 in SPARC) is homologous to follistatin (FS)1 with 10 cysteines in a typical pattern, the C-terminal extracellular calcium-binding (EC) domain (e.g., residues 138-286 in SPARC) has two EF-hand calcium-binding motifs, each with a bound calcium ion in the x-ray structure (Maurer, P., Hohenadl, C., Hohenester, E., Göhring, W., Timpl, R., and Engel, J. (1995) J. Mol. Biol. 253, 347-357; Hohenester, E., Maurer, P., Hohenadl, C., Timpl, R., Jansonius, J. N., and Engel, J. (1996) Nat. Struct. Biol. 3, 67-73).

The term "SPARC family polypeptide", according to the present invention, includes the full length polypeptide or a fragment thereof, a wild-type polypeptide or any variant thereof. A "SPARC family polynucleotide" is a polynucleotide (e.g., DNA or mRNA) molecule encoding a SPARC polypeptide, or a fragment thereof. (a) a SPARC family polypeptide or gene selected from the group consisting of SEQ ID Nos. 1-17; (b) a polypeptide having an amino acid sequence of at least 60% homology to the SPARC family polypeptide in (a) or a gene encoding the polypeptide of at least 60% homology; (c) a polypeptide fragment of (a)-(b) wherein the fragment is at least 50 amino acids in length; (d) a fusion polypeptide comprising the polypeptide of (a), (b), or (c); (e) a polynucleotide encoding the polypeptide of (a), (b), (c) or the fusion polypeptide of (d); or (f) a polynucleotide hybridizing to the polynucleotide of (e) under a stringent hybridization condition.

The term "SPARC" polypeptide refers to SEQ ID Nos. 1-17, and the term "SPARC gene" to SEQ ID Nos. 18-34, the corresponding nucleotide sequences of SEQ ID Nos. 1-17. It is contemplated that variations of these sequences which retain the biological activity of SPARC are equivalents of these sequences. The biological activity of the SPARC gene is that it is downregulated in chemotherapy resistant cells. The gene also may be overexpressed in cells that are sensitive to chemotherapy. The biological activity of the SPARC polypeptide is that it sensitizes chemotherapy resistant cells to chemotherapy.

With respect to a SPARC family polypeptide member, it is contemplated that variations of their sequences which retain the biological activity of the family member are equivalents of these sequences. The biological activity of a SPARC gene family member is that the gene is downregulated in chemotherapy resistant cells, i.e., expression decreased by at least 25%, for example, 30%, 40%, 50%, 75%, 100% (1-fold), 2-fold, 4-fold, or 5-fold or more, compared to chemotherapy sensitive cells. The gene also may be overexpressed in cells that are sensitive to chemotherapy. The biological activity of the SPARC family polypeptide member is that it sensitizes chemotherapy resistant cells to chemotherapy, i.e., increase the response to chemotherapy by at least 25%, for example, 30%, 40%, 50%, 60%, 70%, 80%, or more, to 2-fold, 3-fold, 4-fold, 5-fold, 10-fold, 15-fold, 20-fold or more, compared to treatment sensitivity in the absence of the SPARC family polypeptide.

As defined herein, a "tissue" is an aggregate of cells that perform a particular function in an organism. The term "tissue" as used herein refers to cellular material from a particular physiological region. The cells in a particular tissue may comprise several different cell types. A non-limiting example of this would be brain cells that further comprise neurons and glial cells, as well as capillary endothelial cells and blood cells.

The term "cell type" or "tissue type" refers to the tissue of origin, for example, from which a tumor develops. Such tissues (cells types) include, for example, without limitation, blood, colorectal, breast, esophageal, hepatocellular, prostate, ovarian, thyroid, pancreas, uterus, testis, pituitary, kidney, stomach, esophagus and rectum.

As used herein, the term "cancer" refers to a proliferative disorder disease caused or characterized by the proliferation of cells which have lost susceptibility to normal growth control. The term "cancer," as used in the present application, includes tumors and any other proliferative disorders. Cancers of the same tissue type originate in the same tissue, and may be divided into different subtypes based on their biological characteristics. The cancer may be selected from one or more from the group consisting of: melanoma, leukemia, astocytoma, glioblastoma, lymphoma, glioma, Hodgkins lymphoma, chronic lymphocyte leukemia and cancer of the pancreas, breast, thyroid, ovary, uterus, testis, pituitary, kidney, stomach, esophagus and rectum.

As used herein, the term "sensitizing" refers to an increased sensitivity or reduce the resistance of a cancer sample or a mammal responding to a therapeutic treatment. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician.

As used herein, the term "administer" or "administering" refers to introduce by any means a composition (e.g., a therapeutic agent) into the body of a mammal in order to prevent or treat a disease or condition (e.g., cancer).

As used herein, the terms "treating", "treatment", "therapy" and "therapeutic treatment" as used herein refer to curative therapy, prophylactic therapy, or preventative therapy. An example of "preventative therapy" is the prevention or lessening of a targeted disease (e.g., cancer) or related condition thereto. Those in need of treatment include those already with the disease or condition as well as those prone to have the disease or condition to be prevented. The terms "treating", "treatment", "therapy" and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

By "therapeutically effective amount" is meant an amount that relieves (to some extent, as judged by a skilled medical practitioner) one or more symptoms of the disease or condition in a mammal. Additionally, by "therapeutically effective amount" is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. The determination of amount of a composition that must be administered to be therapeutically effective is routine in the art and within the skill of an ordinarily skilled clinician.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug may be purified, substantially purified or partially purified. An "agent", according to the present invention, also includes a radiation therapy agent.

As used herein, "modulation" or "modulating" means that a desired/selected response is more efficient (e.g., at least 10%, 20%, 40%, 60% or more), more rapid (e.g., at least 10%, 20%, 40%, 60% or more), greater in magnitude (e.g., at least 10%, 20%, 40%, 60% or greater), and/or more easily induced (e.g., at least 10%, 20%, 40%, 60% or more) in the presence of an agent than in the absence of the agent.

As used herein, the term "resistance to a therapeutic treatment" refers to an acquired or natural resistance of a cancer sample or a mammal to a therapy, i.e., being nonresponsive to or having reduced or limited response to the therapeutic treatment, e.g., having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response is measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi drug-resistant microorganism or a combination of microorganisms. The determination of resistance to a therapeutic treatment is routine in the art and within the skill of an ordinarily skilled clinician, for example, can be measured by cell proliferative assays and cell death assays as described herein above under "sensitizing".

As used herein, the term "chemotherapy" refers to the use of drugs to destroy cancer cells (including leukaemias and lymphomas). There are over 50 different chemotherapy drugs and some are given on their own, but often several drugs may be combined (known as combination chemotherapy). Chemotherapy may be used alone to treat some types of cancer. Sometimes it can be used together with other types of treatment such as surgery, radiotherapy, immunotherapy, or a combination thereof.

As used herein, "radiotherapy", also called "radiation therapy", refers to the treatment of cancer and other diseases with ionizing radiation. Ionizing radiation deposits energy that injures or destroys cells in the area being treated (the "target tissue") by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or uterine cervix. It can also be used to treat leukemia and lymphoma (cancers of the blood-forming cells and lymphatic system, respectively).

As used herein, the term "treatment protocol" refers to the process of informing the decision making for the treatment of a disease. As used herein, treatment protocol is based on the comparative levels of one or more cell growth-related polypeptides in a patient's tissue sample relative to the levels of the same polypeptide(s) in a plurality of normal and diseased tissue samples from mammals for whom patient information, including treatment approaches and outcomes is available.

As used herein, the term "biological characteristics" refers to the phenotype and/or genotype of one or more cells or tissues, which can include cell type, and/or tissue type from which the cell was obtained, morphological features of the cell(s)/tissue(s), and the expression of biological molecules within the cell(s)/tissue(s).

As used herein, the term "sample" refers to material derived from the body of a mammal, including, but not limited to, blood, serum, plasma, urine, nipple aspirate, cerebrospinal fluid, liver, kidney, breast, bone, bone marrow, testes or ovaries and brain, colon, and lung. A "sample," according to the present invention, may also be cultured cells and tissues.

As used herein, a "cancer sample" refers to a sample which originates from a cancer, i.e., from a new growth of different or abnormal tissue. A "cancer sample" may be a cell or tissue sample. The cancer cells may exist as part of the cancer tissue, or may exist as free-floating cells detached from the cancer tissue from which they originate. A cancer sample, according to the present invention, may be used for in vitro or ex vivo testing of cancers.

As used herein, the term "non-cancer sample" refers to cell or tissue sample obtained from a normal tissue. A sample may be judged a non-tumor sample by one of skill in the art on the basis of morphology and other diagnostic tests.

As used herein, the term "mammal" refers to a human or other animal, such as farm animals or laboratory animals (e.g. guinea pig or mice).

As used herein, "specific hybridization" or "selective hybridization" or "hybridization under a stringent condition" refers to hybridization which occurs when two polynucleotide sequences are substantially complementary, i.e., there is at least about 60% and preferably, at least about 80% or 90% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). Typically, stringent conditions will be those in which the salt concentration is at least about 0.01 to 1.0 M Na ion concentration (or other salts) at pH 7.0 to 8.3 and the temperature is at least about 30° C. for short probes (e.g., about 6 to 50 nucleotides). Stringent conditions may also be achieved with the addition of destabilizing agents such as formamide. Generally, stringent conditions are selected to be about 5° C. lower than the thermal melting point (Tm) for the specific sequence at a defined ionic strength and pH, as calculated using methods routine in the art.

As used herein, the term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. "Homology", with respect to polypeptides (i.e., amino acids), may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue. A "homology of 60% or higher" includes a homology of, for example, 60%, 70%, 75%, 80%, 85%, 90%, 95%, and up to 100% (identical) between two or more nucleotide or amino acid sequences.

As used herein, the term "polynucleotide" includes RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

As used herein, the term "mutation" refers to a change in nucleotide sequence within a gene, or outside the gene in a regulatory sequence compared to wild type. The change may be a deletion, substitution, point mutation, mutation of multiple nucleotides, transposition, inversion, frame shift, nonsense mutation or other forms of aberration that differentiate the polynucleotide or protein sequence from that of a normally expressed gene in a functional cell where expression and functionality are within the normally occurring range.

"Polypeptide" and "protein" are used interchangeably herein to refer to a polymer of amino acid residues. The term "recombinant protein" refers to a protein that is produced by expression of a recombinant DNA molecule that encodes the amino acid sequence of the protein. Polynucleotides and recombinantly produced polypeptide, and fragments or analogs thereof, may be prepared according to methods known in the art and described in Maniatis et al., Molecular Cloning: A Laboratory Manual, 2nd Ed., (1989), Cold Spring Harbor, N.Y., and Berger and Kimmel, Methods in Enzymology, Volume 152, Guide to Molecular Cloning Techniques (1987), Academic Press, Inc., San Diego, Calif., which are incorporated herein by reference.

As used herein, the term "fragment" when in reference to a polypeptide (as in "a fragment of a given protein") refers to a shorter portion of the polypeptide. The fragment may range in size from four amino acid residues to the entire amino acid sequence minus one amino acid. In one embodiment, the present invention contemplates "functional fragments" of a polypeptide. Such fragments, according to the present invention, are "functional" in that they retain the ability to sensitize a cancer sample or cancer mammal to a therapeutic treatment, albeit with perhaps lower sensitizing activity than that observed for the full-length polypeptide. Such "fragment" of a polypeptide is preferably greater than 10 amino acids in length, and more preferably greater than 50 amino acids in length, and even more preferably greater than 100 amino acids in length. A "fragment" of a SPARC family polypeptide, according to the present invention, may contain one or more of the three conserved domains of the SPARC family members, i.e., the Acidic N-terminal domain, the follistatin-like domain, and the extracellular calcium-binding EC domain.

As used herein, a "variant" of a specific polypeptide refers to a polypeptide substantially similar to either the entire specific peptide or a fragment thereof. By "substantially similar", it means that the variant is made to arrive at a final construct which possesses the desired function, i.e., sensitizing a cancer sample or a mammal to a therapeutic treatment, albeit with perhaps lower sensitizing activity of the variant than that observed for the wild-type polypeptide. Such variants include, for example, deletions, insertions, or substitutions of residues within the amino-acid sequence of the specific polypeptide. In addition, a "variant" may also be a fusion polypeptide between a SPARC family polypeptide and a second polypeptide. Any combination of deletion, insertion, substitution, and fusion may also be made.

As used herein, "isolated" or "purified" when used in reference to a polynucleotide or a polypeptide means that a naturally occurring nucleotide or amino acid sequence has been removed from its normal cellular environment or is synthesized in a non-natural environment (e.g., artificially synthesized). Thus, an "isolated" or "purified" sequence may be in a cell-free solution or placed in a different cellular environment. The term "purified" does not imply that the nucleotide or amino acid sequence is the only polynucleotide or polypeptide present, but that it is essentially free (about 90-95%, up to 99-100% pure) of non-polynucleotide or polypeptide material naturally associated with it.

As used herein the term "encoding" refers to the inherent property of specific sequences of nucleotides in a polynucleotide, such as a gene in a chromosome or an mRNA, to serve as templates for synthesis of other polymers and macromolecules in biological processes having a defined sequence of nucleotides (i.e., rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. A polynucleotide that encodes a protein includes any polynucleotides that have different nucleotide sequences but encode the same amino acid sequence of the protein due to the degeneracy of the genetic code. Polynucleotides and nucleotide sequences that encode proteins may include introns and may be genomic DNA.

As used herein, the term "vector" refers to a polynucleotide compound used for introducing exogenous or endogenous polynucleotide into host cells. A vector comprises a nucleotide sequence which may encode one or more polypeptide molecules. Plasmids, cosmids, viruses and bacteriophages, in a natural state or which have undergone recombinant engineering, are non-limiting examples of commonly used vectors to provide recombinant vectors comprising at least one desired isolated polynucleotide molecule.

As used herein, the term "transformation" or the term "transfection" refers to a variety of art-recognized techniques for introducing exogenous polynucleotide (e.g., DNA) into a cell. A cell is "transformed" or "transfected" when exogenous DNA has been introduced inside the cell membrane. The terms "transformation" and "transfection" and terms derived from each are used interchangeably.

As used herein, an "expression vector" refers to a recombinant expression cassette which has a polynucleotide which encodes a polypeptide (i.e., a protein) that can be transcribed and translated by a cell. The expression vector can be a plasmid, virus, or polynucleotide fragment.

The term "expression" refers to the production of a protein or nucleotide sequence in a cell or in a cell-free system, and includes transcription into an RNA product, post-transcriptional modification and/or translation into a protein product or polypeptide from a DNA encoding that product, as well as possible post-translational modifications.

As used herein, the term "comparing the expression level" refers to comparing the deferential expression of a polynucleotide or a polypeptide in two or more samples.

As used herein, the term "differential expression" refers to both quantitative, as well as qualitative, differences in a polynucleotide or a polypeptide expression patterns among two or more samples. A polynucleotide or a polypeptide is said to be "differentially expressed" if its expression is detectable in one sample, but not in another sample, by known methods for polynucleotide or polypeptide detection (e.g., electrophoresis). A polynucleotide or a polypeptide is also said to be "differentially expressed" if the quantitative difference of its expression (i.e., increase or decrease, measured in µg, µmol or copy number) between two samples is about 20%, about 30%, about 50%, about 70%, about 90% to about 100% (about two-fold) or more, up to and including about 1.2 fold, 2.5 fold, 5-fold, 10-fold, 20-fold, 50-fold or more. A "differentially expressed" gene transcript means a mRNA transcript that is found in different numbers of copies between two or more samples.

As used herein, an "increased amount of a SPARC family polypeptide or polynucleotide" refers to a greater level of expression of at least 20%, e.g., 30%, 40%, 50%, 60%, 70%, 80%, or 90%, or 2-fold, 3-fold, 4-fold, 5-fold or more in a cell, compared to a control cell. A cell expressing a SPARC family polypeptide or polynucleotide is said to have an increase amount of such polypeptide or polynucleotide if the expression is as defined herein above when compared with a chemotherapy resistant cell.

The term "secreted protein" refers to a protein having at least a portion which is extracellular and includes proteins which are completely extracellular (i.e., not attached to a cell). "Level of secretion" refers to the level (i.e., amount) of a secreted protein in the extracellular compartment.

As used herein, the term "proliferation" refers to the rate of cell division and the ability of a cell to continue to divide. One complete cell division process is referred to as a "cycle". By an "increase in cell proliferation" is meant to increase the cell division rate so that the cell has a higher rate of cell division compared to normal cells of that cell type, or to allow the cell division to continue for more cycles without changing the rate of each cell division, e.g., increase by 10% or higher (e.g., 20%, 30%, 40% 50%, up to 2 fold, 5 fold, 10 fold or higher. By an "decrease in cell proliferation" is meant to decrease the cell division rate so that the cell has a lower rate of cell division compared to normal cells of that cell type, or to reduce the number of cycles of the cell division without changing the rate of each cell division, e.g., decrease by 10% or higher (e.g., 20%, 30%, 40% 50%, up to 2 fold, 5 fold, 10 fold or higher).

The present invention provides compositions and methods for sensitizing cancer therapeutic treatments. Such sensitizing compositions and methods are particularly useful in enhancing the response of patients who are resistant to a treatment. They are also useful in reducing the side-effects of cancer therapy, for example, by enhancing the response of a patient to a smaller strength (i.e., dosage) of the treatment. The composition of the present invention may reduce the dosage of a therapeutic treatment agent by at least 20%, for example, 30%, 40%, 50%, and up to 60%.

The SPARC Family Polypeptides and Polynucleotides

In one embodiment, the present invention provides (a) a SPARC family polypeptide selected from the group consisting of SEQ ID Nos. 1-17; (b) a polypeptide having an amino acid sequence of at least 60% homology to said SPARC family polypeptide in (a); (c) a polypeptide fragment of (a)-(b) wherein said fragment is at least 50 amino acids in length, and (d) a fusion polypeptide comprising the polypeptide of (a)-(c).

A SPARC family polypeptide provided by the present invention may be a wild-type polypeptide or a variant thereof, it may be the full length polypeptide or a fragment thereof. A SPARC family polypeptide is within the scope of the present invention so long as it retains the function of sensitizing a cancer sample or a patient to a therapeutic treatment, albeit that a lower activity may exist for a variant or a fragment polypeptide when compared to the wile-type or full length polypeptide.

Based on sequence homology, several members of the SPARC family have been identified, such as SMOC-1 (Vannahme et al., 2002, J. Biol. Chem. 277(41):37977-37986), hevin (Bendik I, Schraml P, Ludwig C U, Cancer Res. 1998; 58(4):626-9), SC1 (Johnston I G, Paladino T, Gurd J W, Brown I R, Neuron. 1990 4(1):165-76), QR-1, follistatin-like proteins (TSC-36) (Shibanuma, M., Mashimo, J., Mita, A., Kuroki, T. and Nose, K, 1993, Eur. J. Biochem. 217 (1) 13-19) and testican (Alliel, P. M., Perin, J. P., Jolles, P. and Bonnet, F. J, 1993, Eur. J. Biochem. 214 (1), 347-350). A SPARC family polypeptide of the present invention includes, but is not limited to, SPARC and any of its identified family members known in the art or as described herein.

The alignment of the various polynucleotide sequences permit one skilled in the art to select conserved portions of the proteins (i.e. those portions in common between two or more sequences) as well as unconserved portions (i.e. those portions unique to two or more sequences). In one embodiment, the present invention contemplates conserved fragments 10 amino acids in length or greater, and more typically greater than 50 amino acids in length. Preferably, the SPARC family polypeptide of the present invention contains one or two or three domains (i.e. the Acidic N-terminal domain, the follistatin-like domain, and/or the EC domain), conserved among the SPARC family members.

The therapy-sensitizing fragment or a variant of a wild-type SPARC family protein may be delineated by routine sequence manipulations known to those skilled in the art, including, but not limited to, deletion mutations, point mutations, fusions as described herein below and as described in J. Sambrook, E. F. Fritsch, and T. Maniatis, Molecular Cloning: A. Laboratory Manual, 2 Ed., Cold Spring Harbor Laboratory Press, Cold Spring Harbor, N.Y., 1989, and Ausubel et al., Current Protocols in Molecular Biology, 1994, incorporated by reference herein.

A mutation in the DNA encoding the variant polypeptide must not alter the reading frame and preferably will not create complementary regions that could produce secondary mRNA structures. At the genetic level these variants are prepared by site directed mutagenesis of nucleotides in the DNA encoding the peptide molecule thereby producing DNA encoding the variant, and thereafter expressing the DNA in recombinant cell culture.

In Vitro Production and Purification of a SPARC Family Polypeptide

A SPARC family polypeptide provided by the present invention may be produced in a prokaryotic or eukaryotic cell using any known method, for example, recombinant DNA techniques. Recombination techniques may be conducted as described herein below, or for example, by the methods disclosed in T. Maniatis et al., "Molecular Cloning", 2nd Ed., Cold Spring Harbor Laboratory, Cold Spring Harbor, N. T. (1989); Nippon Seikagaku Kai (Biochemical Society of Japan) ed., "Zoku-Seikagaku Jikken Kouza 1, Idenshi Kenkyuho II (Lectures on Biochemical Experiments (Second Series; 1), Methods for Gene Study II)", Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinant DNA Technique))", Tokyo Kagaku Dojin, Japan (1992); R. Wu (ed.), "Methods in Enzymology", Vol. 68, Academic Press, New York (1980); R. Wu et al. (ed.), "Methods in Enzymology", Vols. 100 & 101, Academic Press, New York (1983); R. Wu et al. (ed.), "Methods in Enzymology", Vols. 153, 154 & 155, Academic Press, New York (1987), etc. as well as by techniques disclosed in the references cited therein, the disclosures of which are hereby incorporated by reference. Such techniques and means may also be those which are individually modified/improved from conventional techniques depending upon the object of the present invention.

A SPARC family polypeptide may be expressed and purified from a recombinant host cell. Recombinant host cells may be prokaryotic or eukaryotic, including but not limited to bacteria such as E. coli, fungal cells such as yeast, insect cells including but not limited to drosophila and silkworm derived cell lines, and mammalian cells and cell lines.

In certain embodiments, when expressing and purifying a SPARC family polypeptide of the present invention, techniques for improving protein solubility are employed to prevent the formation of inclusion body (which are insoluble fractions), and therefore obtaining large quantities of the polypeptide. SPARC accumulated in inclusion bodies is an inactive-type SPARC not retaining its physiological activities.

Solubility of a purified SPARC family polypeptide may be improved by methods known in the art, and as described herein below.

For example, solubility may also be improved by expressing a functional fragment, but not the full length SPARC family polypeptide. The fragment expressed should retain the sensitizing activity as described herein, albeit the activity may be lower than that of a full length polypeptide.

In one embodiment, a fragment containing one or two or three domains of the three conserved domains of the SPARC family members is expressed.

In addition, to increase the solubility of an expressed protein (e.g., in E. coli), one can reduce the rate of protein synthesis by lowering the growth temperature, using a weaker promoter, using a lower copy number plasmid, lowering the inducer concentration, changing the growth medium as described in Georgiou, G. & Valax, P. (1996, Current Opinion Biotechnol. 7, 190-197). This decreases the rate of protein synthesis and usually more soluble protein is obtained. One can also add prostethic groups or co-factors which are essential for proper folding or for protein stability, or add buffer to control pH fluctuation in the medium during growth, or add 1% glucose to repress induction of the lac promoter by lactose, which is present in most rich media (such as LB, 2xYT). Polyols (e.g. sorbitol) and sucrose may also be added to the media because the increase in osmotic pressure caused by these additions leads to the accumulation of osmoprotectants in the cell, which stabilize the native protein structure. Ethanol, low molecular weight thiols and disulfides, and NaCl may be added. In addition, chaperones and/or foldases may be co-expressed with the desired polypeptide. Molecular chaperones promote the proper isomerization and cellular targeting by transiently interacting with folding intermediates. The best characterized E. coli chaperone systems are: GroES-GroEL, DnaK-DnaJ-GrpE, ClpB. Foldases accelerate rate-limiting steps along the folding pathway. Three types of foldases play an important role: peptidyl prolyl cis/trans isomerases (PPI's), disulfide oxidoreductase (DsbA) and disulfide isomerase (DsbC), protein disulfide isomerase (PDI) which is an eukaryotic protein that catalyzes both protein cysteine oxidation and disulfide bond isomerization. Co-expression of one or more of these proteins with the target protein could lead to higher levels of soluble protein.

A SPARC family polypeptide of the present invention may be produced as a fusion protein in order to improve its solubility and production. The fusion protein comprises a SPARC family polypeptide and a second polypeptide fused together in frame. The second polypeptide may be a fusion partner known in the art to improve the solubility of the polypeptide to which it is fused, for example, NusA, bacterioferritin (BFR), GrpE, thioredoxin (TRX) and glutathione-S-transferase (GST). Madison, Wis.-based Novagen Inc. provides the pET 43.1 vector series which permit the formation of a NusA-target fusion. DsbA and DsbC have also shown positive effects on expression levels when used as a fusion partner, therefore can be used to fuse with a SPARC polypeptide for achieving higher solubility.

In one embodiment, a SPARC family polypeptide is produced as a fusion polypeptide comprising the SPARC family polypeptide and a fusion partner thioredoxin, as described in U.S. Pat. No. 6,387,664, hereby incorporated by reference in its entirety. The thioredoxin-SPARC fusion can be produced in *E. coli* as an easy-to-formulate, soluble protein in a large quantity without losing the physiological activities of SPARC. Although U.S. Pat. No. 6,387,664 provides a fusion SPARC protein with SPARC fused to the C-terminus of thioredoxin, it is understood, for the purpose of the present invention, a SPARC family polypeptide may be fused either to the N-terminus or the C-terminus of a second polypeptide, so long as its sensitizing function is retained.

In addition to increase solubility, a fusion protein comprising a SPARC family polypeptide may be constructed for the easy detection of the expression of the SPARC family polypeptide in a cell. In one embodiment, the second polypeptide which fused to the SPARC family polypeptide is a reporter polypeptide. The reporter polypeptide, when served for such detection purpose, does not have to be fused with the SPARC family polypeptide. It may be encoded by the same polynucleotide (e.g., a vector) which also encodes the SPARC family polypeptide and be co-introduced and co-expressed in a target cell.

Preferably, the reporter polypeptide used in the invention is an autofluorescent protein (e.g., GFP, EGFP). Autofluorescent proteins provide a ready assay for identification of expression of a polynucleotide (and the polypeptide product) of interest. Because the activity of the reporter polypeptide (and by inference its expression level) can be monitored quantitatively using a flow sorter, it is simple to assay many independent transfectants either sequentially or in bulk population. Cells with the best expression can then be screened for or selected from the population. This is useful when selecting a recombinant cell comprising a SPARC family polypeptide or polynucleotide for sensitizing treatment according to the present invention. Quantitative parameters such as mean fluorescence intensity and variance can be determined from the fluorescence intensity profile of the cell population (Shapiro, H., 1995, Practical Flow Cytometry, 217-228). Non-limiting examples of reporter molecules useful in the invention include luciferase (from firefly or other species), chloramphenicol acetyltransferase, β-galactosidase, green fluorescent protein (GFP), enhanced green fluorescent protein (EGFP), and dsRed.

Expression of the SPARC polypeptide (either by itself, or as a fusion protein) can also be directly determined by an immunoassay such as an ELISA (enzyme-linked immunoabsorbent assay) (see e.g., U.S. Pat. No. 5,962,320; U.S. Pat. No. 6,187,307; U.S. Pat. No. 6,194,205), western blot, or by other methods routine in the art. The expression of a SPARC family polypeptide can be indirectly detected by detecting the transcript of the protein (e.g., by hybridization analysis such as Northern blot or DNA Microarray, or by PCR).

In one embodiment, a polynucleotide encoding a second polypeptide is fused to a polynucleotide encoding a SPARC family polypeptide through an intervening linker sequence which encodes for a linker polypeptide.

In another embodiment, the linker polypeptide comprises a protease cleavage site comprising a peptide bond which is hydrolyzable by a protease. As a result, the SPARC family polypeptide can be separated from the second polypeptide after expression by proteolysis. The linker can comprise one or more additional amino acids on either side of the bond to which the catalytic site of the protease also binds (see, e.g., Schecter and Berger, 1967, Biochem. Biophys. Res. Commun. 27, 157-62). Alternatively, the cleavage site of the linker can be separate from the recognition site of the protease and the two cleavage site and recognition site can be separated by one or more (e.g., two to four) amino acids. In one aspect, the linker comprises at least 2, 3, 4, 5, 6, 7, 8, 9, 10, 20, 30, 40, 50 or more amino acids. More preferably the linker is between 5 and 25 amino acids in length, and most preferably, the linker is between 8 and 15 amino acids in length.

Some proteases useful according to the invention are discussed in the following references: V. Y. H. Hook, *Proteolytic and cellular mechanisms in prohormone and proprotein processing*, RG Landes Company, Austin, Tex., USA (1998); N. M. Hooper et al., 1997, Biochem. J. 321:265-279; Werb, 1997, Cell 91: 439-442; Wolfsberg et al., 1995, J. Cell Biol. 131: 275-278; Murakami and Etlinger, 1987, Biochem. Biophys. Res. Comm. 146: 1249-1259; Berg et al., 1995, Biochem. J. 307: 313-326; Smyth and Trapani, 1995, Immunology Today 16: 202-206; Talanian et al., 1997, J. Biol. Chem. 272: 9677-9682; and Thornberry et al., 1997, J. Biol. Chem. 272: 17907-17911. Suitable proteases include, but are not limited to, those listed in Table 1 below.

TABLE 1

| Proteases and Their Cleavage Signals | |
|---|---|
| Protease | Cleavage Signal (Exemplary Linker Polynucleotide Sequence) |
| subtilisn/kexin family (furin, PC1, PC2, PC4, PACE4, PC5, PC) | RXKR (SEQ ID NO. 49) (CGC NNN AAG CGC) (SEQ ID NO. 50) |
| MMP-2 | PLGLWA (SEQ ID NO. 51) (CCC CTG GGC CTG TGG GCC) (SEQ ID NO. 52) |
| MT1-MMP | PLGLWA (SEQ ID NO. 51) (CCC CTG GGC CTG TGG GCC) (SEQ ID NO. 52) |
| Protease | Cleavage Signal-Amino Acid Sequence (Exemplary Linker Polynucleotide Sequence) |

TABLE 1-continued

Proteases and Their Cleavage Signals

| Protease | Cleavage Signal (Exemplary Linker Polynucleotide Sequence) |
|---|---|
| caspase-1 | YEVDGW (SEQ ID NO. 53) (TAC GAG GTG GAC GGC TGG) (SEQ ID NO. 54) |
| caspase-2 | VDVADGW (SEQ ID NO. 55) (GTG GAC GTG GCC GAC GGC TGG) (SEQ ID NO. 56) |
| caspase-3 | VDQMDGW (SEQ ID NO. 57) (GTG GAC CAG ATG GAC GGC TGG) (SEQ ID NO. 58) |
| caspase-4 | LEVDGW (SEQ ID NO. 59) CTG GAG GTG GAC GGC TGG) (SEQ ID NO. 60) |
| caspase-6 | VQVDGW (SEQ ID NO. 61) (GTG CAG GTG GAC GGC TGG) (SEQ ID NO. 62) |
| caspase-7 | VDQVDGW (SEQ ID NO. 63) (GTG GAC CAG GTG GAC GGC TGG) (SEQ ID NO. 64) |
| caspase-8 | DXXD (SEQ ID NO. 65) (GAC NNN NNN GAC) (SEQ ID NO. 66) |
| caspase-9 | DXXD (SEQ ID NO. 65) (GAC NNN NNN GAC) |
| alpha-secretase | amyloid precursor protein (APP) |
| proprotein convertase (subtilisin/kexin isozyme SKI-1 | RGLT (SEQ ID NO. 67) (CGC GGC CTG ACC) (SEQ ID NO. 68) |
| proprotein convertases | cleavage at hydrophobic residues (e.g., Leu, Phe, Val, or Met) or at small acid residues such as Ala or Thr |
| foot and mouth disease virus, protease 2A | NFDLLKLAGDVESNPGP (SEQ ID NO. 69) (AAC TTC GAC CTG CTG AAG CTG GCC GGC GAC GTG GAG AGC AAC CCC GGC CCC) (SEQ ID NO. 70) |
| signal peptidase | A-X-A-X (SEQ ID NO. 71) (GCC NNN GCC NNN) (SEQ ID NO. 72) |
| aminopeptidases (e.g., arginine aminopeptidase, lysine aminopeptidase, aminopeptidase B, trypsin) | LTK (SEQ ID NO. 73) (CTG ACC AAG) (SEQ ID NO. 74) |
| insulin degrading enzyme | GGFLRKVGQ (SEQ ID NO. 75) (GGC GGC TTC CTG CGC AAG GTG GGC CAG) (SEQ ID NO. 76) |

Additional linker polypeptides can be obtained from the substrates for proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); prolyl endopeptidase; and high molecular weight protease.

Cell surface proteases also can be used with cleavable linkers according to the invention and include, but are not limited to: Aminopeptidase N; Puromycin sensitive aminopeptidase; Angiotensin converting enzyme; Pyroglutamyl peptidase II; Dipeptidyl peptidase IV; N-arginine dibasic convertase; Endopeptidase 24.15; Endopeptidase 24.16; Amyloid precursor protein secretases alpha, beta and gamma; Angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; Urokinase plasminogen activator; Tissue plasminogen activator; Plasmin; Thrombin; BMP-1 (procollagen C-peptidase); ADAM 1, 2, 3, 4, 5, 6, 7, 8, 9, 10, and 11; and, Granzymes A, B, C, D, E, F, G, and H.

An alternative to relying on cell-associated proteases is to use a a self-cleaving linker. For example, the foot and mouth disease virus (FMDV) 2A protease may be used as a linker. This is a short polypeptide of 17 amino acids that cleaves the polyprotein of FMDV at the 2A/2B junction. The sequence of the FMDV 2A propeptide is NFDLLKLAGDVESNPGP (SEQ ID NO. 77). Cleavage occurs at the C-terminus of the peptide at the final glycine-proline amino acid pair and is independent of the presence of other FMDV sequences and cleaves even in the presence of heterologous sequences.

Insertion of this sequence between two protein coding regions (i.e., between the SPARC family polypeptide and the second polypeptide of a fusion protein according to the invention) results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (see, e.g., P. deFelipe et al., Gene Therapy 6: 198-208 (1999)). Self-cleaving linkers and additional protease-linker combinations are described further in WO 0120989, the entirety of which is incorporated by reference herein.

Polynucleotides encoding linker sequences described above can be cloned from sequences encoding the natural substrates of an appropriate protease or can be chemically synthesized using methods routine in the art.

When expressing a SPARC family polypeptide in a human cell, e.g., in vitro or in vivo, the codons selected for such the polynucleotide encoding the SPARC family polypeptide are preferably those which are most frequently used in humans, such as those listed in Table 2 below. The exemplary polynucleotide sequences shown in Table 4 rely on codons which are most frequently used in humans.

TABLE 2

Preferred DNA Codons For Human Use

| Amino Acids | 3 Letter Code | 1 Letter Code | Codons Preferred in Human Genes |
|---|---|---|---|
| Alanine | Ala | A | GCC |
| | | | GCT |
| | | | GCA |
| | | | GCG |
| Cystein | Cys | C | TGC |
| | | | TGT |
| Aspartic Acid | Asp | D | GAC |
| | | | GAT |
| Glutamic Acid | Glu | E | GAG |
| | | | GAA |
| Phenylalanine | Phe | F | TTC |
| | | | TTT |
| Glycine | Gly | G | GGC |
| | | | GGG |
| | | | GGA |
| | | | GGT |
| Histidine | His | H | CAC |
| | | | CAT |
| Isoleucine | Ile | I | ATC |
| | | | ATT |
| | | | ATA |
| Lysine | Lys | K | AAG |
| | | | AAA |
| Leucine | Leu | L | CTG |
| | | | TTG |
| | | | CTT |
| | | | CTA |
| | | | TTA |
| Methionine | Met | M | ATG |
| Asparagine | Asn | N | AAC |
| | | | AAT |
| Proline | Pro | P | CCC |
| | | | CCT |
| | | | CCA |
| | | | CCG |
| Glutamine | Gln | Q | CAG |
| | | | CAA |
| Arginine | Arg | R | CGC |
| | | | AGG |
| | | | CGG |
| | | | AGA |
| | | | CGA |
| | | | CGT |
| Serine | Ser | S | AGC |
| | | | TCC |
| | | | TCT |
| | | | AGT |
| | | | TCA |
| | | | TCG |
| Threonine | Thr | T | ACC |
| | | | ACA |
| | | | ACT |
| | | | ACG |

TABLE 2-continued

Preferred DNA Codons For Human Use

| Amino Acids | 3 Letter Code | 1 Letter Code | Codons Preferred in Human Genes |
|---|---|---|---|
| Valine | Val | V | GTG |
| | | | GTC |
| | | | GTT |
| | | | GTA |
| Tryprophan | Trp | W | TGG |
| Tyrosine | Tyr | Y | TAC |
| | | | TAT |

The uppermost codons represent those most preferred for use in human genes. Underlined codons are almost never used in human genes and are therefore not preferred.

In another embodiment, the present invention provides (a) a polynucleotide encoding the polypeptide of a SPARC family polypeptide or a fusion polypeptide comprising a SPARC family polypeptide; and (b) a polynucleotide hybridizing to the polynucleotide of (a) under a stringent hybridization condition.

Techniques for polynucleotide manipulation to perform the above embodiments of the invention are well known in the art. (See, e.g., Sambrook et al., 1989; Ausubel et al. 1987 and in Annual Reviews of Biochemistry, 1992, 61:131-156). Reagents useful in applying such techniques, such as restriction enzymes and the like, are widely known in the art and commercially available from a number of vendors.

Polynucleotide sequences for use in the present invention may also be produced in part or in total by chemical synthesis, e.g. by the phosphoramidite method described by Beaucage, et al., 1981, Tetra. Letts., 22:1859-1862, or the triester method (Matteucci et al., 1981, J. Am. Chem. Soc., 103: 3185), which may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

In one embodiment, the SPARC family polynucleotide provided by the present invention exists as a vector, preferably, an expression vector.

Expression Vectors

A polynucleotide coding for a SPARC family polypeptide sequence may be incorporated into vectors capable of introduction into and replication in a prokaryotic or eukaryotic cell to produce a SPARC family polypeptide of the present invention for sensitizing treatment, or it can be used to transfect or infect a cell or tissue and achieve the sensitizing function directly by expressing the SPARC family polypeptide. The vectors may or may not integrate within the genome of the transfected or infected cell.

Useful polynucleotide molecules encoding a SPARC family polypeptide of the present invention may be cloned into an expression vector before they are introduced into an appropriate cell and may be passage in cells to generate useable quantities of these polynucleotides.

Suitable vectors for the invention may be plasmid or viral vectors. Plasmid expression vectors include, but are not limited to, plasmids including pBR322, pUC, pcDNA3.1 or Bluescript™. Viral vectors include, but are not limited to baculoviruses, adenoviruses, poxviruses, adenoassociated viruses (AAV), and retrovirus vectors (Price et al, 1987, Proc. Natl. Acad. Sci. USA, 84:156-160) such as the MMLV based replication incompetent vector pMV-7 (Kirschmeier et al., 1988, DNA, 7:219-225), as well as human and yeast modified chromosomes (HACs and YACs).

The expression vectors may comprise one or more regulatory elements to drive and/or enhance expression of upstream or downstream polynucleotides. These regulatory sequences are selected on the basis of the cells to be used for introduction and/or expression, and are operatively linked to a polynucleotide sequence to be expressed. The term "regulatory elements" is intended to include promoters, enhancers and other expression control elements (e.g., polyadenylation signals). Such regulatory elements are described, for example, in Goeddel; 1990, *Gene Expression Technology: Methods in Enzymology* 185, Academic Press, San Diego, Calif.

Regulatory elements include those which direct expression of a nucleotide sequence in many types of subject cells as well as those which direct expression of the nucleotide sequence only in certain subject cells (e.g., tissue-specific regulatory sequences).

Regulatory elements also include those which direct constitutive expression of an operatively linked polynucleotide sequence and those which direct inducible expression of the polynucleotide sequence.

Preferably, suitable promoters may be used. For example, such promoters may include tryptophan (trp) promoter, lactose (lac) promoter, tryptophan-lactose (tac) promoter, lipoprotein (lpp) promoter, λ phage $P_L$ promoter, etc. in the case of plasmids where *Escherichia coli* is used as a host; and GAL1, GAL10 promoters, etc. in the case of plasmids where yeast is used as a host.

Some eukaryotic promoters and enhancers have a broad range of cells in which they can activate and/or modulate transcription while others are functional only in a limited subset of cell types (See e.g., Voss et al., 1986, Trends Biochem. Sci., 11:287; and Maniatis et al., supra, for reviews). For example, the SV40 early gene enhancer is very active in a wide variety of cell types from many mammalian species and has been widely used for the expression of proteins in mammalian cells (Dijkema et al., 1985, EMBO J. 4:761). Two other examples of promoter/enhancer elements active in a broad range of mammalian cell types are those from the human elongation factor 1α gene (Uetsuki et al., 1989, J. Biol. Chem., 264:5791; Kim et al., 1990, Gene, 91:217; and Mizushima, et al., 1990, Nagata, Nuc. Acids. Res., 18:5322) and the long terminal repeats of the Rous sarcoma virus (Gorman et al., 1982, Proc. Natl. Acad. Sci. USA, 79:6777) and the human cytomegalovirus (Boshart et al., 1985, Cell, 41:521).

Suitable promoters for eukaryotic cell expression include, but are not limited to, TRAP promoters, adenoviral promoters, such as the adenoviral major late promoter; the cytomegalovirus (CMV) promoter; the respiratory syncytial virus (RSV) promoter; inducible promoters, such as the MMT promoter, the metallothionein promoter, heat shock promoters; the albumin promoter; the ApoAI promoter; human globin promoters; viral thymidine kinase promoters, such as the Herpes Simplex thymidine kinase promoter; retroviral LTRs; ITRs; the β-actin promoter; and human growth hormone promoters. The promoter also may be the native promoter that controls the polynucleotide encoding the polypeptide and the sequences of native promoters may be found in the art (see Agrawal et al., 2000, J. Hematother. Stem Cell Res., 795-812; Cournoyer et al., 1993, Annu. Rev. Immunol., 11:297-329; van de Stolpe et al., 1996, J. Mol. Med., 74:13-33; Herrmann, 1995, J. Mol. Med., 73:157-63).

A variety of enhancer sequences can be used in the instant invention including but not limited to: Immunoglobulin Heavy Chain enhancer; Immunoglobulin Light Chain enhancer; T-Cell Receptor enhancer; HLA DQ α and DQ β enhancers; β-Interferon enhancer; interleukin-2 enhancer; Interleukin-2 Receptor enhancer; MHC Class II $5_a^k$ enhancer; MHC Class II HLA-DRα enhancer; β-Actin enhancer; Muscle Creatine Kinase enhancer; Prealbumin (Transthyretin) enhancer; Elastase I enhancer; Metallothionein enhancer; Collagenase enhancer; Albumin Gene enhancer; α-Fetoprotein enhancer; β-Globin enhancer; c-fos enhancer; c-HA-ras enhancer; Insulin enhancer; Neural Cell Adhesion Molecule (NCAM) enhancer; $α_1$-Antitrypsin enhancer; H2B (TH2B) Histone enhancer; Mouse or Type I Collagen enhancer; Glucose-Regulated Proteins (GRP94 and GRP78) enhancer; Rat Growth Hormone enhancer; Human Serum Amyloid A (SAA) enhancer; Troponin I (TN I) enhancer; Platelet-Derived Growth Factor enhancer; Duchenne Muscular Dystrophy enhancer; SV40 Polyoma enhancer; Retrovirusal enhancer; Papilloma Virus enhancer; Hepatitis B Virus enhancer; Human Immunodeficiency enhancer; Cytomegalovirus enhancer; and Gibbon Ape Leukemia Virus enhancer.

Exemplary inducible promoter/enhancer sequences and their inducers are listed below.

TABLE 3

Useful Inducible Promoters/Enhancers

| Element | Inducer |
|---|---|
| MTII | PhorbolEster(TFA) Heavymetals |
| MMTV (mouse mammary tumor virus) | Glucocorticoids |
| β-Interferon | poly(rI) × poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TFA) |
| Murine MX Gene | Interferon, Newcastle Disease Virus |
| GRP78 Gene | A23187 |
| α-2-Macroglobulin | IL-6 |
| Vimentin | Serum |
| MHC ClassI Gene H-2kB | Interferon |
| HSP70 | E1a, SV40 Large T Antigen |
| Proliferin | Phorbol Ester (TPA) |
| Tumor Necrosis Factor | FMA |
| Thyroid Stimulating Hormone α Gene | Thyroid Hormone |

Additional Eukaryotic regulatory sequences may be obtained from the Eukaryotic Promoter Data Base EPDB) also can be used to drive expression of a polynucleotide.

In certain embodiments of the invention, the delivery of a vector in a cell may be identified in vitro or in vivo by including a selection marker in the expression construct, such as described herein above. The marker would result in an identifiable change to the modified cell permitting easy identification of expression. Usually the inclusion of a drug selection marker aids in cloning and in the selection of transformants. Genes which can be used as selectable markers in Eukaryotic cells are known in the art and include, examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et al., 1989, Molecular Cloning: A Laboratory Manual, 2nd ed., Cold Spring Harbor Laboratory Press, New York pp. 16.9-16.15.

Alternatively, genes encoding enzymes, such as herpes simplex virus thymidine kinase (tk) (eukaryotic) or chloramphenicol acetyltransferase (CAT) (prokaryotic) may be employed to provide selectable markers. Immunologic markers also can be employed. The exact type selectable marker employed is not believed to be important, so long as it is capable of being expressed simultaneously with the polynucleotide encoding a polypeptide of interest. Further examples of selectable markers are well known to one of skill in the art.

Where a cDNA insert is employed to express a SPARC family polypeptide of the invention, one typically will desire to include a polyadenylation signal to effect proper polyadenylation of the polynucleotide transcript. The nature of the polyadenylation signal is not believed to be crucial to the successful practice of the invention, and any such sequence may be employed. These elements can serve to enhance message levels and to minimize read through from the expression cassette into other sequences.

Recombinant Cell Production: —Introducing a SPARC family Polynucleotide Into a Cell for Expression and/or Sensitization As described above, a SPARC family polynucleotide of the invention may be introduced into a cell in order to express the SPARC family polypeptide for purification or to express and achieve the sensitizing effect of the invention according to methods well known in the art, for example, in Current Protocols in Molecular Biology, Ausubel, F. M. et al. (eds.), 1989, Greene Publishing Associates, Section 9.1 and in Molecular Cloning: A Laboratory Manual, 2nd Edition, Sambrook et al., 1989, Cold Spring Harbor Laboratory Press.

Several non-viral methods for the transfer of vectors into cultured mammalian cells are contemplated by the present invention. These include calcium phosphate precipitation (Graham, et al., 1973; Chen, et al., 1987; Rippe, et al., 1990) DEAE-dextran (Gopal, 1985), electroporation (Tur-Kaspa et al., 1986; Potter et al., 1984), direct microinjection (Harland, et al., 1985), DNA-loaded liposomes (Nicolau, et al., 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu, et al., 1987; Wu, et al., 1988). Some of these techniques may be successfully adapted for in vivo or ex vivo use.

Once the vector has been delivered into the cell, the polynucleotide encoding a SPARC family polypeptide may be positioned and expressed at different sites. In certain embodiments, the polynucleotide encoding a SPARC family polypeptide may be stably integrated into the genome of the cell. This integration may be via homologous recombination (gene replacement) or it may be integrated in a random, non-specific location (gene augmentation), see Holmes-Son et al., 2001, Adv. Genet. 43: 33-69. In yet further embodiments, the polynucleotide encoding a SPARC family polypeptide may be stably maintained in the cell as a separate, episomal segment of DNA. Such polynucleotide segments or "episomes" encode sequences sufficient to permit maintenance and replication independent of or in synchronization with the subject cell cycle. How the expression construct is delivered to a cell and where in the cell the polynucleotide remains is well known in the art and is dependent on the type of expression construct employed.

Cell lines derived from mammalian species which may be suitable for transfection and infection of a SPARC family polynucleotide and for expression and purification of a recombinant polypeptide, may be commercially available. These cell lines include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, HEK-293 (ATCC CRL1573), NS0 (ECACC85110503) and HT1080.

Cell cultures may be prepared in various ways for gene transfer in vitro. In order for the cells to be kept viable while in vitro and in contact with the expression construct, it is necessary to ensure that the cells maintain contact with the correct ratio of oxygen and carbon dioxide and nutrients but are protected from microbial contamination.

Transfer of the construct may be performed by any of the methods known in the art and as described herein below. Some methods may be particularly applicable for transfer in vitro but it may be applied to in vivo use as well.

Transfection Mediated by $CaPO_4$

A polynucleotide encoding a SPARC family polypeptide can be introduced into cells by forming a precipitate containing the polynucleotide and calcium phosphate. For example, a HEPES-buffered saline solution can be mixed with a solution containing calcium chloride and polynucleotide to form a precipitate and the precipitate is then incubated with cells. A glycerol or dimethyl sulfoxide shock step can be added to increase the amount of polynucleotide taken up by certain cells. $CaPO_4$-mediated transfection can be used to stably (or transiently) transfect cells and is only applicable to in vitro modification of cells. Protocols for $CaPO_4$-mediated transfection can be found in *Current Protocols in Molecular Biology*, Ausubel, F. M. et al. (eds.), 1989, Greene Publishing Associates, Section 9.1 and in *Molecular Cloning: A Laboratory Manual, 2nd Edition*, Sambrook et al., 1989, Cold Spring Harbor Laboratory Press Sections 16.32-16.40 or other standard laboratory manuals.

Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. Thus the polynucleotide encoding a SPARC family polypeptide may also be transferred in a similar manner in vivo to express a desired SPARC family polypeptide as described above.

Transfection Mediated by DEAE-Dextran

A polynucleotide encoding a SPARC family polypeptide can be introduced into cells by forming a mixture of the polynucleotide and DEAE-dextran and incubating the mixture with the cells. A dimethylsulfoxide or chloroquine shock step can be added to increase the amount of polynucleotide uptake. Protocols for DEAE-dextran-mediated transfection can be found in *Current Protocols in Molecular Biology*, Ausubel, F. M. et al. (eds.), 1989, Greene Publishing Associates, Section 9.2 and in *Molecular Cloning: A Laboratory*

*Manual*, 2nd Edition, Sambrook et al., 1989, Cold Spring Harbor Laboratory Press, Sections 16.41-16.46 or other standard laboratory manuals.

Electroporation

A polynucleotide encoding a SPARC family polypeptide can also be introduced into cells by incubating the cells and the polynucleotide together in an appropriate buffer and subjecting the cells to a high-voltage electric pulse. The efficiency with which polynucleotide is introduced into cells by electroporation is influenced by the strength of the applied field, the length of the electric pulse, the temperature, the conformation and concentration of the polynucleotide and the ionic composition of the media. Electroporation can be used to stably (or transiently) transfect a wide variety of cell types. Protocols for electroporating cells can be found in Ausubel, F. M. et al. (eds.), supra, Section 9.3 and in Sambrook et al., supra, Sections 16.54-16.55 or other standard laboratory manuals.

Liposome-Mediated Transfection ("Lipofection")

A polynucleotide encoding a SPARC family polypeptide also can be introduced into cells by mixing the polynucleotide with a liposome suspension containing cationic lipids. The polynucleotide/liposome complex is then incubated with cells. Liposome mediated transfection can be used to stably (or transiently) transfect cells in culture in vitro. Protocols can be found in Ausubel, F. M. et al. (eds.), supra, Section 9.4 and other standard laboratory manuals. Additionally, gene delivery in vivo has been accomplished using liposomes. See for example Nicolau et al., 1987, *Meth. Enz.*, 149:157-176; Wang, et al., 1987, *Proc. Natl. Acad. Sci. USA*, 84:7851-7855; Brigham et al., 1989, *Am. J. Med. Sci.*, 298:278; and Gould-Fogerite et al., 1989, *Gene*, 84:429-438.

Direct Injection

A polynucleotide encoding a SPARC family polypeptide can be introduced into cells by directly injecting the polynucleotide into the cells. For an in vitro culture of cells, polynucleotide can be introduced by microinjection. Since each cell is microinjected individually, this approach is very labor intensive when modifying large numbers of cells. However, a situation where microinjection is a method of choice is in the production of transgenic animals (discussed in greater detail below). In this situation, the polynucleotide is stably introduced into a fertilized oocyte which is then allowed to develop into an animal. The resultant animal contains cells carrying the polynucleotide introduced into the oocyte. Direct injection may be used to introduce the polynucleotide encoding a SPARC family polypeptide into cells in vivo (see e.g., Acsadi et al., 1991, *Nature*, 332: 815-818; Wolff et al., 1990, *Science*, 247:1465-1468). A delivery apparatus (e.g., a "gene gun") for injecting DNA into cells in vivo can be used. Such an apparatus is commercially available (e.g., from BioRad).

Receptor-Mediated DNA Uptake

A polynucleotide encoding a SPARC family polypeptide also can be introduced into cells by complexing the polynucleotide to a cation, such as polylysine, which is coupled to a ligand for a cell-surface receptor (see for example Wu, et al., 1988, *J. Biol. Chem.*, 263:14621; Wilson et al., 1992, *J. Biol. Chem.*, 267:963-967; and U.S. Pat. No. 5,166,320). Binding of the polynucleotide-ligand complex to the receptor facilitates uptake of the polynucleotide by receptor-mediated endocytosis. Receptors to which a polynucleotide-ligand complex have targeted include the transferrin receptor and the asialoglycoprotein receptor. A polynucleotide-ligand complex linked to adenovirus capsids which naturally disrupt endosomes, thereby releasing material into the cytoplasm can be used to avoid degradation of the complex by intracellular lysosomes (see for example Curiel et al., 1991, *Proc. Natl. Acad. Sci. USA*, 88:8850; Cristiano et al., 1993, *Proc. Natl. Acad. Sci. USA*, 90:2122-2126). Receptor-mediated polynucleotide uptake can be used to introduce the polynucleotide encoding a SPARC family polypeptide into cells either in vitro or in vivo and, additionally, has the added feature that polynucleotide can be selectively targeted to a particular cell type by use of a ligand which binds to a receptor selectively expressed on a target cell of interest.

Viral-Mediated Gene Transfer

Another approach for introducing a polynucleotide encoding a SPARC family polypeptide into a cell is by use of a viral vector containing the polynucleotide encoding a SPARC family polypeptide. Infection of cells with a viral vector has the advantage that a large proportion of cells receive the polynucleotide, which can obviate the need for selection of cells which have received the polynucleotide. Additionally, molecules encoded within the viral vector, e.g., by a cDNA contained in the viral vector, are expressed efficiently in cells which have taken up viral vector polynucleotide and viral vector systems can be used either in vitro or in vivo.

Nonreplicating viral vectors can be produced in packaging cell lines which produce virus particles which are infectious but replication-defective, rendering them useful vectors for introduction of polynucleotide into a cell lacking complementary genetic information enabling encapsidation (Mann et al., 1983, cell, 33:153; Miller and Buttimore, Mol. Cell. Biol., 1986, 6:2895 (PA317, ATCC CRL9078). Packaging cell lines which contain amphotrophic packaging genes able to transform cells of human and other species origin are preferred.

Retroviruses

The retroviruses are a group of single-stranded RNA viruses characterized by an ability to convert their RNA to double-stranded DNA in infected cells by a process of reverse-transcription (Coffin, 1990, in Fields et al., Ceds, *Virology*, Raven Press, New York, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, functions as a signal for packaging of the genome into virions. Two long terminal repeat (LTR) sequences are present at the 5' and 3' ends of the viral genome. These contain strong promoter and enhancer sequences and are also required for integration in the subject cell genome (Coffin, supra).

Defective retroviruses are well characterized for use in gene transfer for gene therapy purposes (for a review see Miller, 1990, Blood 76:271).

Protocols for producing recombinant retroviruses and for infecting cells in vitro or in vivo with such viruses can be found in *Current Protocols in Molecular Biology*, Ausubel, F. M. et al. (eds.), 1989, Greene Publishing Associates, Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al., 1985, *Science*, 230:1395-1398; Danos, et al., 1988, Proc. Nail. Acad. Sci. USA, 85:6460-6464; Wilson et al., 1988, Proc. Natl. Acad. Sci. USA, 85:3014-3018; Armentano et al., 1990, Proc. Natl. Acad. Sci. USA, 87:6141-6145;

Huber et al., 1991, Proc. Natl. Acad. Sci. USA, 88:8039-8043; Ferry et al., 1991, Proc. Natl. Acad. Sci. USA, 88:8377-8381; Chowdhury et al., 1991, Science, 254:1802-1805; van Beusechem et al., 1992, Proc. Natl. Acad. Sci. USA, 89:7640-7644; Kay et al., 1992, Human Gene Therapy, 3:641-647; Dai et al., 1992, Proc. Natl. Acad. Sci. USA, 89:10892-10895; Hwu et al., 1993, J. Immunol., 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign polynucleotide inserted into it) to be integrated into the subject genome to stably introduce polynucleotide into the cell. Thus, it may be necessary to stimulate replication of the target cell.

Adenovirus

Knowledge of the genetic organization of adenovirus, a 36 kB, linear and double-stranded DNA virus, allows substitution of a large piece of adenoviral DNA with foreign sequences up to 7 kB (Grunhaus, et al., 1992, Seminar in Virology, 3:237-252). In contrast to retrovirus, the infection of adenoviral DNA into subject cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target-cell range, and high infectivity. Both ends of the viral genome contain 100-200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5' tripartite leader (TL) sequence which makes them preferred mRNAs for translation.

The genome of an adenovirus can be manipulated such that it encodes and expresses a gene product of interest but is inactivated in terms of its ability to replicate in a normal lytic viral life cycle. See for example Berkner, et al., 1988, BioTechniques, 6:616; Rosenfeld, et al., 1991, Science, 252:431-434; and Rosenfeld, et al., 1992, Cell, 68:143-155. Suitable adenoviral vectors derived from the adenovirus strain Ad type 5 d1324 or other strains of adenovirus (e.g., Ad2, Ad3, Ad7, etc.) are well known to those skilled in the art. Recombinant adenoviruses are advantageous in that they do not require dividing cells to be effective gene delivery vehicles and can be used to infect a wide variety of cell types, including airway epithelium (Rosenfeld, et al., 1992, cited supra), endothelial cells (Lemarchand, et al., 1992, Proc. Natl. Acad. Sci. USA, 89:6482-6486), hepatocytes (Herz, et al., 1993, Proc. Natl. Acad. Sci. USA, 90:2812-2816) and muscle cells (Quantin, et al., 1992, Proc. Natl. Acad. Sci. USA, 89:2581-2584). Additionally, introduced adenoviral polynucleotide (and foreign DNA contained therein) is not integrated into the genome of a subject cell but remains episomal, thereby avoiding potential problems that can occur as a result of insertional mutagenesis in situations where introduced polynucleotide becomes integrated into the subject genome (e.g., retroviral DNA). Moreover, the carrying capacity of the adenoviral genome for foreign DNA is large (up to 8 kilobases) relative to other gene delivery vectors (Berkner, et al. cited supra; Haj-Ahmand, et al., 1986, J. Virol., 57:267). Most replication-defective adenoviral vectors currently in use are deleted for all or parts of the viral E1 and E3 genes but retain as much as 80% of the adenoviral genetic material.

Recombinant adenovirus may be generated by methods known in the art, e.g., as described in U.S. Pat. No. 6,194,191, incorporated herein by reference.

Generation and propagation of the adenovirus vectors, which are replication deficient, depend on a unique helper cell line, designated 293, which was transformed from human embryonic kidney cells by Ad5 DNA fragments and constitutively expresses E1 proteins (Graham, et al., 1977). Since the E3 region is dispensable from the adenovirus genome (Jones, et al., 1978), the current adenovirus vectors, with the help of 293 cells, carry foreign DNA in either the E1, the E3 or both regions (Graham, et al., 1991). In nature, adenovirus can package approximately 105% of the wild-type genome (Ghosh-Choudhury, et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication-defective and will not have an adenovirus E1 region. Thus, it will be most convenient to introduce the polynucleotide encoding a polypeptide of interest at the position from which the E1 coding sequences have been removed. However, the position of insertion of the coding region of a selected polynucleotide within the adenovirus sequences is not critical to the present invention.

Adenovirus is easy to grow and manipulate and exhibits broad subject range in vitro and in vivo. This group of viruses can be obtained in high titers, e.g., $10^9$-$10^{11}$ plaque-forming unit (PFU)/ml, and they are highly infective. The life cycle of adenovirus does not require integration into the subject cell genome.

Adenovirus vectors have been used in eukaryotic gene expression (Levrero, et al., 1991, Gene, 101:195-202; Gomez-Foix, et al., 1992, J. Biol. Chem., 267:25129-25134) and vaccine development (Grunhaus, et al., 1992, Seminar in Virology, 3:237-252; Graham, et al., 1992, Biotechnology, 20:363-390). Animal studies suggested that recombinant adenovirus could be used for gene therapy (Stratford-Perricaudet, et al., 1991, in: Human Gene Transfer, O. Cohen-Haguenauer, Ceds), John Libbey Eurotext, France; Stratford-Perricaudet, et al., 1990, Hum. Gene Ther., 1:241-256; Rich, et al., 1993, Nature, 361:647-650). Experiments in administering recombinant adenovirus to different tissues include trachea instillation (Rosenfeld, et al., 1991, Science, 252: 431-434; Rosenfeld, et al., 1992, Cell, 68:143-155), muscle injection (Ragot, et al., 1993, Nature, 361:647-650), peripheral intravenous injection (Herz, et al., 1993, Proc. Nat'l. Acad. Sci. USA 90:2812-2816), and stereotactic inoculation into the brain (Le Gal La Salle et al., 1993, Science, 259:988-990).

Other Viral Vectors as Expression Vectors

Other viral vectors may be employed as expression constructs in the present invention. Vectors derived from viruses such as vaccinia virus (Ridgeway, 1988, in: Rodriguez R L, Denhardt D T, ed. *Vectors: A Survey of Molecular Cloning Vectors and Their Uses*. Stoneham: Butterworth, pp. 467-492; Baichwal, et al., 1986 In: Kucherlapati R, ed. Gene Transfer. New York: Plenum Press, pp. 117-148; Coupar, et al., 1988, Gene, 68:1-10), adeno-associated virus (AAV) (Baichwal, et al., 1986, supra; Hermonat, et al., 1984, Proc. Natl. Acad. Sci. USA, 81:6466-6470) and herpesviruses may be employed. They offer several attractive features for various mammalian cells (Friedmann, 1989, Science, 244:1275-1281; Baichwal, et al., 1986, supra; Coupar, et al., 1988, supra; Horwich, et al., 1990, J. Virol., 64:642-650).

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol., 158:97-129). It is also one of the few viruses that may integrate its DNA into non-dividing cells, and exhibits a high frequency of stable integration (see, for example, Flotte et al., 1992, Am. J. Respir. Cell. Mol. Biol., 7:349-356; Samulski et al., 1989, J. Virol., 63:3822-3828; and McLaughlin et al., 1989, J. Virol., 62:1963-1973). Vectors containing as little as 300 base pairs of AAV can be packaged and can integrate. Space for exogenous polynucleotide is limited to about 4.5 kb. An AAV vector such as that described in Tratschin et al., 1985, Mol. Cell. Biol., 5:3251-3260 can be used to introduce polynucleotide into cells. A variety of polynucleotides have been introduced into different cell types using AAV vectors (see for example Hermonat, et al., 1984, Proc. Natl. Acad. Sci. USA, 81:6466-6470; Tratschin, et al., 1985, Mol. Cell. Biol., 4:2072-2081; Wondisford, et al., 1988, Mol. Endocrinol., 2:32-39; Tratschin, et al., 1984, J. Virol., 51:611-619; and Flotte, et al., 1993, J. Biol. Chem., 268:3781-3790).

After the transfer of a polynucleotide encoding a SPARC family polypeptide into cells, the cells may be selected and used for sensitizing treatment according to the present invention. The efficacy of a particular expression vector system and method of introducing polynucleotide into a cell can be assessed by standard approaches routinely used in the art. For example, polynucleotide introduced into a cell can be detected by a filter hybridization technique (e.g., Southern blotting) and RNA produced by transcription of introduced polynucleotide can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. Alternatively, an expression system can first be optimized using a reporter gene linked to the regulatory elements and vector to be used as described herein above. The reporter gene encodes a separate gene product which is easily detectable and, thus, can be used to evaluate the efficacy of the system.

Since a SPARC family polypeptide is a secreted protein, its extracellular level may also be detected to determine its expression using methods known in the art, such as Immunoblotting or Elisa.

Another way of increase the expression of a SPARC polynucleotide or polypeptide in a cell is by endogenous gene activation, i.e., inserting a strong promoter before the natural SPARC family gene sequence in the genome of the cell. Endogenous gene activation is a method of introducing, by homologous recombination with genomic DNA, DNA sequences (e.g., strong promoters) which are not normally functionally linked to the endogenous gene and (1) which, when inserted into the host genome at or near the endogenous gene, serve to alter (e.g., activate) the expression of the endogenous gene, and further (2) allow for selection of cells in which the activated endogenous gene is amplified. Expression of proteins by endogenous gene activation is well known in the art and is disclosed, for example in U.S. Pat. Nos. 5,733,761, 5,641,670, and 5,733,746, and international patent publication Nos. WO 93/09222, WO 94/12650, WO 95/31560, WO 90/11354, WO 91/06667 and WO 91/09955, the contents of each of which are incorporated herein by reference in its entirety.

In one embodiment, a endogenous SPARC family gene expression is activated (e.g., increased) by inserting a tetracycline-inducible tetracycline promoter/operator to control its expression.

The methods described above to transfer polynucleotide into cells and to make recombinant cells of the invention are merely for purposes of illustration and are typical of those that might be used. However, other procedures may also be employed to obtain expression of a SPARC family polypeptide in cells, as is understood in the art.

Cancer Therapy

Cancer is typically treated by surgery, chemotherapy or radiation therapy. Biological therapies such as immunotherapy and gene therapy are also being developed. Other therapies include hyperthermic therapy, photodynamic therapy, etc. (see National Cancer Institute home page at world wide web nci.nih.gov).

Chemotherapy

Chemotherapy is the use of anti-cancer (cytotoxic) drugs to destroy cancer cells. There are over 50 different chemotherapy drugs and some are given on their own, but often several drugs may be combined (this is known as combination chemotherapy). An example list of chemotherapy agents, as described at World wide web cancerbacup.org.uk/info/actinomycin.htm, include: Actinomycin D, Adriamycin, Altretamine, Asparaginase, Bleomycin, Busulphan, Capecitabine, Carboplatin, Carmustine, Chlorambucil, Cisplatin, CPT-11, Cyclophosphamide, Cytarabine, Dacarbazine, Daunorubicin, Doxorubicin, Epirubicin, Etoposide, Fludarabine, Fluorouracil, Gemcitabine, Hydroxyurea, Idarubicin, fosfamide, Irinotecan, Liposomal Doxorubicin, Lomustine, Melphalan, Mercaptopurine, Methotrexate, Mitomycin, Mitozantrone, Oxaliplatin, Procarbazine, Steroids, Streptozocin, Taxol, Taxotere, Taxotere—the TACT trial, Tamozolomide, Thioguanine, Thiotepa, Tomudex, Topotecan, Treosulfan, UFT (Uracil-tegufur), Vinblastine, Vincristine, Vindesine, Vinorelbine.

Because cancer cells may grow and divide more rapidly than normal cells, many anticancer drugs are made to kill growing cells. But certain normal, healthy cells also multiply quickly, and chemotherapy can affect these cells, too. This damage to normal cells causes side effects. The fast-growing, normal cells most likely to be affected are blood cells forming in the bone marrow and cells in the digestive tract (mouth, stomach, intestines, esophagus), reproductive system (sexual organs), and hair follicles. Some anticancer drugs may affect cells of vital organs, such as the heart, kidney, bladder, lungs, and nervous system.

The kinds of side effects one has and how severe they are depend on the type and dose of chemotherapy one gets and how its body reacts. Side effects of chemotherapy include fatigue, nausea and vomiting, pain, hair loss, anemia, central nervous system problems, infection, blood clotting problems, mouth, gum, and throat problems, diarrhea, constipation, nerve and muscle effects, effects on skin and nails, radiation recall, kidney and bladder effects, flu-like symptoms, and fluid retention.

Radiation Therapy

One type of radiation therapy commonly used involves photons, "packets" of energy. X-rays were the first form of photon radiation to be used to treat cancer. Depending on the amount of energy they possess, the rays can be used to destroy cancer cells on the surface of or deeper in the body. The higher the energy of the x-ray beam, the deeper the x-rays can go into the target tissue. Linear accelerators and betatrons are machines that produce x-rays of increasingly greater energy. The use of machines to focus radiation (such as x-rays) on a cancer site is called external beam radiotherapy.

Gamma rays are another form of photons used in radiotherapy. Gamma rays are produced spontaneously as certain elements (such as radium, uranium, and cobalt 60) release radiation as they decompose, or decay. Each element decays at a specific rate and gives off energy in the form of gamma rays and other particles. X-rays and gamma rays have the same effect on cancer cells.

Another technique for delivering radiation to cancer cells is to place radioactive implants directly in a tumor or body cavity. This is called internal radiotherapy. (Brachytherapy, interstitial irradiation, and intracavitary irradiation are types of internal radiotherapy.) In this treatment, the radiation dose is concentrated in a small area, and the patient stays in the hospital for a few days. Internal radiotherapy is frequently used for cancers of the tongue, uterus, and cervix.

Several new approaches to radiation therapy are being evaluated to determine their effectiveness in treating cancer. One such technique is intraoperative irradiation, in which a large dose of external radiation is directed at the tumor and surrounding tissue during surgery.

Another investigational approach is particle beam radiation therapy. This type of therapy differs from photon radiotherapy in that it involves the use of fast-moving subatomic particles to treat localized cancers. A sophisticated machine is needed to produce and accelerate the particles required for this procedure. Some particles (neutrons, pions, and heavy ions) deposit more energy along the path they take through tissue than do x-rays or gamma rays, thus causing more damage to the cells they hit. This type of radiation is often referred to as high linear energy transfer (high LET) radiation.

Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

Radioactive seed implants can be used as the sole treatment modality for adenocarcinoma of the prostate for appropriate patients with early stage disease. The two most common sources are Iodine-125 and Palladium-103 with no compelling clinical data that one is superior to the other. The radioactive seed implant can be individually customized to a patient's prostate to maximize the dose to the gland while minimizing the dose to the surrounding normal structures. Prostate brachytherapy offers the highest level of conformal radiation therapy for adenocarcinoma of the prostate. The prostate brachytherapy team at Thomas Jefferson University has extensive experience in prostate brachytherapy and has presented work at national and international forums.

Prostate brachytherapy or radioactive seed implant is a highly technical, operator dependent method delivers the radiation energy by placing many small radioactive seeds directly inside the prostate, effectively delivering the treatment "from the inside-out". This is done in the operating room under general anesthesia, as a one-time procedure. These seeds can deliver high doses of radiation directly to the tumor, with little harm to the normal, healthy tissue around the prostate. This may be combined with 3-dimensional conformal radiation therapy in some settings.

Other recent radiotherapy research has focused on the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells. The success of this technique will depend upon both the identification of appropriate radioactive substances and determination of the safe and effective dose of radiation that can be delivered in this way.

Radiation therapy may be used alone or in combination with chemotherapy or surgery. Like all forms of cancer treatment, radiation therapy can have side effects. Possible side effects of treatment with radiation include temporary or permanent loss of hair in the area being treated, skin irritation, temporary change in skin color in the treated area, and tiredness. Other side effects are largely dependent on the area of the body that is treated.

Hyperthermia Therapy

Hyperthermia, a procedure in which body tissue is exposed to high temperatures (up to 106° F.), is under investigation to assess its effectiveness in the treatment of cancer. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (radiation therapy, chemotherapy, and biological therapy) to try to increase their effectiveness.

Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes.

In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally.

Whole-body heating is used to treat metastatic cancer that has spread throughout the body. It can be accomplished using warm-water blankets, hot wax, inductive coils (like those in electric blankets), or thermal chambers (similar to large incubators).

Hyperthermia does not cause any marked increase in radiation side effects or complications. Heat applied directly to the skin, however, can cause discomfort or even significant local pain in about half the patients treated. It can also cause blisters, which generally heal rapidly. Less commonly, it can cause burns.

Photodynamic Therapy

Photodynamic therapy (also called PDT, photoradiation therapy, phototherapy, or photochemotherapy) is a treatment for some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent.

In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells.

The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer.

An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs.

Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath.

In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

Laser Therapy

Laser therapy involves the use of high-intensity light to destroy cancer cells. This technique is often used to relieve symptoms of cancer such as bleeding or obstruction, especially when the cancer cannot be cured by other treatments. It may also be used to treat cancer by shrinking or destroying tumors.

The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel).

Although there are several different kinds of lasers, only three kinds have gained wide use in medicine:

Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers.

Neodymium: yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers.

Argon laser—This laser can pass through only superficial layers of tissue and is therefore useful in dermatology and in eye surgery. It also is used with light-sensitive dyes to treat tumors in a procedure known as photodynamic therapy (PDT).

Lasers have several advantages over standard surgical tools, including:

Lasers are more precise than scalpels. Tissue near an incision is protected, since there is little contact with surrounding skin or other tissue.

The heat produced by lasers sterilizes the surgery site, thus reducing the risk of infection.

Less operating time may be needed because the precision of the laser allows for a smaller incision.

Healing time is often shortened; since laser heat seals blood vessels, there is less bleeding, swelling, or scarring.

Laser surgery may be less complicated. For example, with fiber optics, laser light can be directed to parts of the body without making a large incision.

More procedures may be done on an outpatient basis.

There are also disadvantages with laser surgery:
Relatively few surgeons are trained in laser use.
Laser equipment is expensive and bulky compared with the usual surgical tools, such as scalpels.
Strict safety precautions must be observed in the operating room. (For example, the surgical team and the patient must use eye protection.)

Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells.

CO2 and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread.

Lasers are used to treat many types of cancer. Laser surgery is a standard treatment for certain stages of glottis (vocal cord), cervical, skin, lung, vaginal, vulvar, and penile cancers.

In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer.

Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

Gene Therapy

Gene therapy is an experimental medical intervention that involves modifying the genetic material of living cells to fight disease. Gene therapy is being studied in clinical trials (research studies with humans) for many different types of cancer and for other diseases.

One of the goals of gene therapy is to supply cells with healthy copies of missing or altered genes. Instead of giving a patient a drug, doctors attempt to correct the problem by altering the genetic makeup of some of the patient's cells. Examples of diseases that could be treated this way include cystic fibrosis and hemophilia.

Gene therapy is also being studied as a way to change how a cell functions; for example, by stimulating immune system cells to attack cancer cells.

In general, a gene is delivered to the cell using a "vector." The most common types of vectors used in gene therapy are viruses. Viruses used as vectors in gene therapy are genetically disabled; they are unable to reproduce themselves. Most gene therapy clinical trials rely on mouse retroviruses to deliver the desired gene. Other viruses used as vectors include adenoviruses, adeno-associated viruses, poxviruses, and the herpes virus.

A gene therapy can be done both ex vivo and in vivo. In most ex vivo gene therapy clinical trials, cells from the patient's blood or bone marrow are removed and grown in the laboratory. The cells are exposed to the virus that is carrying the desired gene. The virus enters the cells, and the desired gene becomes part of the cells' DNA. The cells grow in the laboratory and are then returned to the patient by injection into a vein. In in vivo gene therapy, vectors or liposomes are used to deliver the desired gene to cells inside the patient's body.

Immunotherapy

Cancer may develop when the immune system breaks down or is not functioning adequately. Immunotherapy uses the body's immune system, either directly or indirectly, to fight cancer or to lessen the side effects that may be caused by some cancer treatments. Immunotherapy is designed to repair, stimulate, or enhance the immune system's responses.

Immune system cells include the following: Lymphocytes are a type of white blood cell found in the blood and many other parts of the body. Types of lymphocytes include B cells, T cells, and Natural Killer cells. B cells (B lymphocytes) mature into plasma cells that secrete antibodies (immunoglobulins), the proteins that recognize and attach to foreign substances known as antigens. Each type of B cell makes one specific antibody, which recognizes one specific antigen. T cells (T lymphocytes) directly attack infected, foreign, or cancerous cells. T cells also regulate the immune response by signaling other immune system defenders. T cells work primarily by producing proteins called lymphokines. Natural Killer cells (NK cells) produce powerful chemical substances that bind to and kill any foreign invader. They attack without first having to recognize a specific antigen. Monocytes are white blood cells that can swallow and digest microscopic organisms and particles in a process known as phagocytosis. Monocytes can also travel into tissue and become macrophages.

Cells in the immune system secrete two types of proteins: antibodies and cytokines. Antibodies respond to antigens by latching on to, or binding with, the antigens. Specific antibodies match specific antigens, fitting together much the way a key fits a lock. Cytokines are substances produced by some immune system cells to communicate with other cells. Types of cytokines include lymphokines, interferons, interleukins, and colony-stimulating factors. Cytotoxic cytokines are released by a type of T cell called a cytotoxic T cell. These cytokines attack cancer cells directly.

Nonspecific immunomodulating agents are substances that stimulate or indirectly augment the immune system. Often, these agents target key immune system cells and cause secondary responses such as increased production of cytokines and immunoglobulins. Two nonspecific immunomodulating agents used in cancer treatment are *bacillus* Calmette-Guerin (BCG) and levamisole. BCG, which has been widely used as a tuberculosis vaccine, is used in the treatment of superficial bladder cancer following surgery. BCG may work by stimulating an inflammatory, and possibly an immune, response. A solution of BCG is instilled in the bladder and stays there for about 2 hours before the patient is allowed to empty the bladder by urinating. This treatment is usually performed once a week for 6 weeks. Levamisole is used along with fluorouracil (5-FU) chemotherapy in the treatment of stage III (Dukes' C) colon cancer following surgery. Levamisole may act to restore depressed immune function.

Some antibodies, cytokines, and other immune system substances can be produced in the laboratory for use in cancer treatment. These substances are often called biological response modifiers (BRMs). They alter the interaction between the body's immune defenses and cancer cells to boost, direct, or restore the body's ability to fight the disease. BRMs include interferons, interleukins, colony-stimulating factors, monoclonal antibodies, and vaccines. Immunotherapy may be used to stop, control, or suppress processes that permit cancer growth; make cancer cells more recognizable, and therefore more susceptible, to destruction by the immune system; boost the killing power of immune system cells, such as T cells, NK cells, and macrophages; alter cancer cells' growth patterns to promote behavior like that of healthy cells; block or reverse the process that changes a normal cell or a precancerous cell into a cancerous cell; enhance the body's ability to repair or replace normal cells damaged or destroyed by other forms of cancer treatment, such as chemotherapy or radiation; and prevent cancer cells from spreading to other parts of the body.

Some BRMs are a standard part of treatment for certain types of cancer, while others are being studied in clinical trials. BRMs are being used alone or in combination with each other. They are also being used with other treatments, such as radiation therapy and chemotherapy.

Interferons (IFNs) are types of cytokines that occur naturally in the body. They were the first cytokines produced in the laboratory for use as BRMs. There are three major types of interferons—interferon alpha, interferon beta, and interferon gamma; interferon alpha is the type most widely used in cancer treatment. Interferons can improve the way a cancer patient's immune system acts against cancer cells. In addition, interferons may act directly on cancer cells by slowing their growth or promoting their development into cells with more normal behavior. Some interferons may also stimulate NK cells, T cells, and macrophages, boosting the immune system's anticancer function. The U.S. Food and Drug Administration (FDA) has approved the use of interferon alpha for the treatment of certain types of cancer, including hairy cell leukemia, melanoma, chronic myeloid leukemia, and AIDS-related Kaposi's sarcoma. Studies have shown that interferon alpha may also be effective in treating other cancers such as metastatic kidney cancer and non-Hodgkin's lymphoma.

Like interferons, interleukins (IL) are cytokines that occur naturally in the body and can be made in the laboratory. Many interleukins have been identified; interleukin-2 (IL-2 or aldesleukin) has been the most widely studied in cancer treatment. IL-2 stimulates the growth and activity of many immune cells, such as lymphocytes, that can destroy cancer cells. The FDA has approved IL-2 for the treatment of metastatic kidney cancer and metastatic melanoma.

Colony-stimulating factors (CSFs) (sometimes called hematopoietic growth factors) usually do not directly affect tumor cells; rather, they encourage bone marrow stem cells to divide and develop into white blood cells, platelets, and red blood cells. Bone marrow is critical to the body's immune system because it is the source of all blood cells. The CSFs' stimulation of the immune system may benefit patients undergoing cancer treatment. Because anticancer drugs can damage the body's ability to make white blood cells, red blood cells, and platelets, patients receiving anticancer drugs have an increased risk of developing infections, becoming anemic, and bleeding more easily. By using CSFs to stimulate blood cell production, doctors can increase the doses of anticancer drugs without increasing the risk of infection or the need for transfusion with blood products. CSFs are particularly useful when combined with high-dose chemotherapy. Some examples of CSFs and their use in cancer therapy are as follows: G-CSF (filgrastim) and GM-CSF (sargramostim) can increase the number of white blood cells, thereby reducing the risk of infection in patients receiving chemotherapy. G-CSF and GM-CSF can also stimulate the production of stem cells in preparation for stem cell or bone marrow transplants; Erythropoietin can increase the number of red blood cells and reduce the need for red blood cell transfusions in patients receiving chemotherapy; and Oprelvekin can reduce the need for platelet transfusions in patients receiving chemotherapy.

CSFs are used in clinical trials to treat some types of leukemia, metastatic colorectal cancer, melanoma, lung cancer, and other types of cancer.

Monoclonal Antibodies (MOABs) are also being evaluated in cancer therapy. These antibodies are produced by a single type of cell and are specific for a particular antigen. MOABs specific to the antigens found on the surface of the cancer cell being treated are being created.

MOABs are made by injecting human cancer cells into mice so that their immune systems will make antibodies against these cancer cells. The mouse cells producing the antibodies are then removed and fused with laboratory-grown cells to create "hybrid" cells called hybridomas. Hybridomas can indefinitely produce large quantities of these pure antibodies, or MOABs. MOABs may be used in cancer treatment in a number of ways: MOABs that react with specific types of cancer may enhance a patient's immune response to the cancer. MOABs can be programmed to act against cell growth factors, thus interfering with the growth of cancer cells. MOABs may be linked to anticancer drugs, radioisotopes (radioactive substances), other BRMs, or other toxins. When the antibodies latch onto cancer cells, they deliver these poisons directly to the tumor, helping to destroy it. MOABs may help destroy cancer cells in bone marrow that has been removed from a patient in preparation for a bone marrow transplant. MOABs carrying radioisotopes may also prove useful in diagnosing certain cancers, such as colorectal, ovarian, and prostate.

Rituxan® (rituximab) and Herceptin® (trastuzumab) are examples of monoclonal antibodies that have been approved by the FDA. Rituxan is used for the treatment of B-cell non-Hodgkin's lymphoma that has returned after a period of improvement or has not responded to chemotherapy. Herceptin is used to treat metastatic breast cancer in patients with tumors that produce excess amounts of a protein called HER-2. (Approximately 25 percent of breast cancer tumors produce excess amounts of HER-2.) MOABs are begun tested in clinical trials to treat lymphomas, leukemias, colorectal cancer, lung cancer, brain tumors, prostate cancer, and other types of cancer.

Cancer vaccines are another form of immunotherapy currently under study. Vaccines for infectious diseases, such as measles, mumps, and tetanus, are effective because they expose the body's immune cells to weakened forms of antigens that are present on the surface of the infectious agent. This exposure causes the immune cells to produce more plasma cells, which make antibodies. T cells that recognize the infectious agent also multiply. These activated T cells later remember the exposure. The next time the agent enters the body, cells in the immune system are already prepared to respond and stop the infection.

For cancer treatment, researchers are developing vaccines that may encourage the patient's immune system to recognize cancer cells. These vaccines may help the body reject tumors and prevent cancer from recurring. In contrast to vaccines against infectious diseases, cancer vaccines are designed to be injected after the disease is diagnosed, rather than before it develops. Cancer vaccines given when the tumor is small may be able to eradicate the cancer. Early cancer vaccine clinical trials (research studies with people) involved mainly patients with melanoma. Currently, cancer vaccines are also being studied in the treatment of many other types of cancer, including lymphomas and cancers of the kidney, breast, ovary, prostate, colon, and rectum. Researchers are also investigating ways that cancer vaccines can be used in combination with other BRMs.

Like other forms of cancer treatment, biological therapies can cause a number of side effects, which can vary widely from patient to patient. Rashes or swelling may develop at the site where the BRMs are injected. Several BRMs, including interferons and interleukins, may cause flu-like symptoms including fever, chills, nausea, vomiting, and appetite loss. Fatigue is another common side effect of BRMs. Blood pressure may also be affected. The side effects of IL-2 can often be severe, depending on the dosage given. Patients need to be closely monitored during treatment. Side effects of CSFs may include bone pain, fatigue, fever, and appetite loss. The side effects of MOABs vary, and serious allergic reactions may occur. Cancer vaccines can cause muscle aches and fever.

Sensitizing Compositions and Methods—Dosage, Mode of Administration, and Pharmaceutical Formulations The present invention provides for a composition comprising a SPARC family polypeptide or a polynucleotide encoding such polypeptide and a therapeutic agent. The SPARC polypeptide or polynucleotide is provided as a therapeutically effective amount so as to sensitize a cancer cell or patient to the treatment by said therapeutic agent.

The therapeutic agent may be any suitable agent for a specific therapy as described herein and as known in the art. It may be a chemotherapy agent, i.e., a drug, for example, 5-fluorouracil; it may be a radiation agent, such as a radiolabeled antibody, a radiosensitizer, or a radioactive seed implant. The therapeutic agent may also be a photosensitizing agent, such as porfimer sodium; or a gene therapy agent (e.g., a vector), or it may be an immunotherapy agent, such as a immune cell, an antibody, or cytokine.

The present invention provides a composition comprising a SPARC family polypeptide and a chemotherapy-resistant cell.

The present invention also provides a recombinant cell comprising a heterologous transcription control region operatively associated with a SPARC family polynucleotide.

In addition to sensitizing a sample or a mammal to cancer therapy, the use of the subject compositions of the present invention can reduce the dosage of a therapy, therefore reducing the side effects caused by cancer therapy.

The above compositions may be a pharmaceutical composition which includes a pharmaceutically acceptable carrier or excipient.

As used herein, a "carrier" refers to any substance suitable as a vehicle for delivering an APC to a suitable in vitro or in vivo site of action. As such, carriers can act as an excipient for formulation of a therapeutic or experimental reagent containing an APC. Preferred carriers are capable of maintaining an APC in a form that is capable of interacting with a T cell. Examples of such carriers include, but are not limited to water, phosphate buffered saline, saline, Ringer's solution, dextrose solution, serum-containing solutions, Hank's solution and other aqueous physiologically balanced solutions or cell culture medium. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer.

A composition comprising a SPARC family polypeptide and a therapeutic agent may be used to sensitize a cancer in vitro by directly contacting the cancer sample with an effective amount of the purified SPARC family polypeptide. A mammal (e.g., a cancer patient) can be administered a composition comprising a SPARC family polypeptide to achieve the sensitizing effect in vivo. In addition, a cancer sample, either cells or tissue, may be obtained from the mammal and sensitized using the SPARC family polypeptide ex vivo before being returned back to the mammal.

A SPARC family polynucleotide of the present invention may be introduced into a cancer cell in vitro to sensitizing the response of the cancer cell, or it may be delivered to a mammal in vivo through an appropriate vector as known in the art and as described herein above. In addition, the polynucleotide may be introduced ex vivo into cancer cells or tissue obtained from a mammal in need, and the cells or tissue then returned to the mammal in need. Being a secreted protein, a SPARC family polypeptide made by such ex vivo introduced cells may function in the local environment to sensitize not only the modified cells, but also the neighboring non-modified cancer cells.

A composition comprising a recombinant cell may be introduced into a mammal for sensitizing treatment.

Subject dose size, number of doses, frequency of dose administration, and mode of administration can be determined and optimized using methods known in the art (see, e.g., Hardman et al., Ceds 1995, Goodman & Gilman's *The Pharmacological Basis of Therapeutics*, Ninth Edition, McGraw-Hill).

Dosages of each therapy in treating various cancer patients are known in the art and can be determined by a skilled physician. For example, a suitable SPARC polypeptide dose may be in the range of 0.01 to 100 mg SPARC polypeptide per kilogram body weight of the recipient per day, preferably in the range of 0.2 to 10 mg per kilogram body weight per day. A SPARC polynucleotide of the present invention may be administered at a suitable dose in the range of 0.01 to 100 mg polynucleotide per kilogram body weight of the recipient per day, preferably in the range of 0.2 to 10 mg per kilogram body weight per day. The cells comprising a recombinant SPARC polynucleotide may be administered at a dosage in the range of 104-1010 per kilogram body weight of the recipient, preferably in the range of 106-108 per kilogram body weight of the recipient. The desired dose is preferably presented once daily, but may be dosed as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of the SPARC family polypeptide per unit dosage form. Dosages of the SPARC family polypeptide or the SPARC family polynucleotide, or the cells comprising a recombinant SPARC family polynucleotide useful according to the invention will vary depending upon the condition to be treated or prevented and on the identity of the SPARC family polypeptide or polynucleotide being used. Estimates of effective dosages and in vivo half-lives for the individual composition encompassed by the invention can be made on the basis of in vivo testing using an animal model, such as the mouse model described herein or an adaptation of such method to larger mammals.

In Vitro/Ex Vivo Applications

Compositions provided by the present invention may be used to sensitize a cancer cell in vitro using methods known in the art, and as described herein before. Thus the present invention provides a method for sensitizing a cancer cell to a therapeutic treatment, the method comprising contacting the cancer sample with an effective amount of a composition comprising a SPARC family polypeptide or a polynucleotide encoding a SPARC family polypeptide. The present invention also provides a method for ex vivo sensitizing a mammal diagnosed with cancer to a therapeutic treatment, the method comprising: (1) Obtaining a cancer sample from the mammal; (2) contacting the cancer sample with an effective amount of a composition comprising a SPARC family polypeptide or a polynucleotide encoding a SPARC family polypeptide; and (3) returning the cancer sample after the contacting of (2) to the mammal.

Ex vivo gene therapy refers to the isolation of cells from an animal, the delivery of a polynucleotide into the cells, in vitro, and then the return of the modified cells back into the animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods. This method is applicable because a SPARC family polypeptide is a secreted polypeptide. The return of the modified cells back to a mammal may increase the extracellular concentration of a SPARC family polypeptide locally and therefore sensitizing the unmodified cancer cells which are in proximity with the modified cells.

When tissue sample needs to be taken from a mammal for ex vivo application, cellular extracts may be prepared from tissue biopsies of patients including, but not limited to brain, heart, lung, lymph nodes, eyes, joints, skin and neoplasms associated with these organs. "Tissue biopsy" also encompasses the collection of biological fluids including but not limited to blood, plasma, sputum, urine, cerebrospinal fluid, lavages, and leukophoresis samples. In a preferred embodiment, "tissue biopsies" according to the invention are taken from tumors of the breast, ovary or prostate. "Tissue biopsies" are obtained using techniques well known in the art including needle aspiration and punch biopsy of the skin.

Generally, when a polynucleotide is introduced into cells in culture (e.g., by one of the transfection techniques described above) only a small fraction of cells (about 1 out of $10^5$) typically integrate the transfected polynucleotide into their genomes (i.e., the polynucleotide is maintained in the cell episomally). Thus, in order to identify cells which have taken up exogenous polynucleotide, it is advantageous to transfect polynucleotide encoding a selectable marker into the cell along with the polynucleotide(s) of interest, i.e., a SPARC family polynucleotide, as described herein before.

In Vivo Applications

The composition provided by the present invention can be administered to a mammal, e.g., in a method of sensitizing a therapeutic treatment. Thus the present invention provides a method for in vivo sensitizing a mammal diagnosed with cancer to a therapeutic treatment, the method comprising administrating to the mammal an effective amount of a composition comprising a SPARC family polypeptide or a polynucleotide encoding a SPARC family polypeptide.

The manner of administration of a composition of the present invention can depend upon the particular purpose for the delivery, the overall health and condition of the patient and the judgment of the physician or technician administering the target vehicle. A composition of the present invention can be administered to an animal using a variety of methods. Such delivery methods can include parenteral, topical, oral or local administration, such as intradermally. A composition can be administered in a variety of unit dosage forms depending upon the method of administration. Preferred delivery methods for a composition of the present invention include intravenous administration, local administration (e.g., intra-tumoral) by, for example, injection, intradermal injection, intramuscular injection, intraperitoneal injection and inhalation. For particular modes of delivery, a composition of the present invention can be formulated in an excipient of the present invention. A composition of the present invention can be administered to any animal, preferably to mammals, and more preferably to humans.

Injection: The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration: Pharmaceutical compositions for oral administration are formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use are obtained through a combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which are used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Nasal administration: For nasal administration, penetrants appropriate to the particular barrier to be permeated are used in the formulation. Such penetrants are generally known in the art.

Subcutaneous and intravenous use: For subcutaneous and intravenous use, the composition of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The composition useful according to the invention may also be presented as liposome formulations.

Gene therapy using the compositions provided by the present invention may be carried out according to generally accepted methods, for example, as described by Friedman in "Therapy for Genetic Disease," T. Friedman, ed., Oxford University Press (1991), pp. 105-121, hereby incorporated by reference.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

After pharmaceutical compositions comprising a therapeutic agent of the invention formulated in a acceptable carrier have been prepared, they are placed in an appropriate container and labeled for treatment of an indicated condition with information including amount, frequency and method of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state (e.g., location of the disease, age, weight, and gender of the patient, diet, time and frequency of administration, drug combination(s), reaction sensitivities, and tolerance/response to therapy). Long acting pharmaceutical compositions might be administered every 3 to 4 days, every week, or once every two weeks depending on half-life and clearance rate of the particular formulation. General guidance as to particular dosages and methods of delivery for other applications is provided in the literature (see U.S. Pat. Nos. 4,657,760; 5,206,344; and 5,225,212, herein incorporated by reference). Those skilled in the art will typically employ different formulations for oligonucleotides and gene therapy vectors than for proteins or their inhibitors. Similarly, delivery of polynucleotides or polypeptides will be specific to particular cells, conditions, locations, and the like.

The composition provided by the present invention may be formulated as described in U.S. Pat. No. 6,187,330 (hereby incorporated by reference in its entirety) which provides a composition for the controlled release of a peptide or protein comprising a biocompatible, bioerodable polymer having dispersed therein a glassy matrix phase comprising the peptide or protein and a thermoprotectant, said glassy matrix phase having a glass transition temperature above the melting point of the polymer. Since the peptide or protein drug is stable within the composition, it can conveniently be formed, in its melt stage, into suitably shaped devices to be used as drug delivery implants, e.g. in the form of rods, films, beads or other desired shapes.

Determining Resistance or Sensitivity to a Therapeutic Treatment

The determination of a cancer sample (e.g., cells or tissue) responding to a therapeutic treatment can be carried out by any methods known in the art. For example, by a cell culture drug resistance testing (CCDRT). CCDRT refers to testing a cancer sample (e.g., taken from a mammal patient) in the laboratory to drugs that may be used to treat the patient's cancer. The testing can identify the cancer sample is sensitive to which drugs and resistant to which drugs, which indicates which drugs are more likely to work and which drugs are less likely to work in the patient. The sensitivity of the cancer sample (therefore, the patient) can be sensitized by treatment with the composition provided by the present invention. CCDRT can be performed again with the sensitizing treatment and determine if a sensitizing composition provided by the present invention can sensitize the response of the cancer sample to a specific treatment or not. A composition can be said to sensitize a therapeutic treatment if the response as measured by CCDRT is increased by at least 20%, e.g., 30%, 40%, 50% 80%, 100% (2-fold), or 3-fold, 4-fold, 5-fold, or more when compared to the response in the absence of the sensitizing composition.

CCDRT typically include the cell proliferation assays and cell death assays.

The cell proliferation assay measures the proliferation of cells. It can be done by the radioactive thymidine incorporation assay originally described by Tanigawa and Kern (supra). In this assay, applied only to solid tumors and not to hematologic neoplasms, tumor cells suspended in soft agarose are cultured for 4-6 days in the continuous presence of antineoplastic drugs. At the end of the culture period, radioactive thymidine is introduced and differences in putative thymidine incorporation into DNA are compared between control and drug-treated cultures. Kern and Weisenthal analyzed the clinical correlation data and defined the concept of "extreme drug resistance," or EDR [Kern D H, Weisenthal L M. J Natl Cancer Inst 1990; 82: 582-588]. This was defined as an assay result which was one standard deviation more resistant than the median result for comparison, database assays. Patients treated with single agents showing EDR in the assay virtually never enjoyed a partial or complete response. Kern and Weisenthal also defined "low drug resistance" (LDR) as a result less resistant than the median and "intermediate drug resistance" (IDR) as a result more resistant than the median but less resistant than EDR (in other words, between the median and one standard deviation more resistant than the median).

The principles and clinical correlation data with the thymidine "EDR" assay were reviewed in 1992 (Weisenthal L M, Kern D H. Oncology (USA) 1992; 5: 93-103]. There have been only a few follow-up studies published since this time. One such study showed that EDR to one or more of the single agents used in a two drug combination is not apparently associated with a lower probability of response to the two drug combination in the setting of intraperitoneal chemotherapy of appendiceal and colon cancers (Fernandez-Trigo V, Shamsa F, Vidal-Jove J, Kern D H, Sugarbaker P H. Am J Clin Oncol 1995; 18: 454-460). It is, however, possible that response to the high drug concentrations achievable with intraperitoneal chemotherapy may be more closely associated with drug penetration to the tumor than to intrinsic drug resistance of the tumor cells. It was also shown that EDR to paclitaxel does not appear to be a prognostic factor in ovarian cancer patients or in patients with primary peritoneal carcinoma treated with paclitaxel plus platinum (Eltabbakh G H, Piver M S, Hempling R E, et al. Gynecol Oncol 1998; 70: 392-397; Eltabbakh G H. J Surg Oncol 2000; 73: 148-152). However, it was recently reported that EDR to platinum in ovarian cancer may have prognostic implications (Fruehauf, J., et al. Proc ASCO, v. 20, Abs 2529, 2001). It was also reported that previously-untreated breast cancer patients with tumors showing LDR (defined above) had superior times to progression and overall survivals than patients with tumors showing either IDR or EDR (Mehta, R. S., et al, Breast Cancer Res Treat 66:225-37, 2001).

The thymidine "EDR" assay has a very high specificity (>98%) for the identification of inactive single agents, but a low sensitivity (<40%). In other words, a drug with assay-defined "EDR" is predicted to be almost certain to be inactive as a single agent (high specificity for identifying inactive drugs), but many drugs without "EDR" will also be inactive (low sensitivity for identifying inactive drugs).

A second form of cell proliferation assay is the adhesive tumor cell culture system, based on comparing monolayer growth of cells over a proprietary "cell adhesive matrix" (Ajani J A, Baker F L, Spitzer G, et al. J Clin Oncol 1987). Positive clinical correlations were also described in this publication.

In some embodiments, colony formation assays are used to measure cell proliferation. In this test cells are grown in vitro in soft agar (tissue culture medium containing agar as a gelling agent; also referred to as semi-solid agar) or other highly viscous media, containing, for example, methylcellulose, plasma gel or fibrin clots. These semi-solid media reduce cell movement and allow individual cells to develop into cell clones that are identified as single colonies. These assays are also generally referred to as Clonogenic assays. The colony formation assays are well known in the art, for example, see Rizzino, A Soft agar growth assays for transforming growth factors and mitogenic peptides. Methods in Enzymology 146: 341-53 (1987) and In some embodiments, apoptosis is measured by a terminal deoxynucleotide transferase-mediated dUTP nick end labeling (TUNEL) assay which is well known in the art and Materials and Methods available as supporting online material on Science Online.

As opposed to measuring cell proliferation, there is a closely-related family of assays based on the concept of total cell kill, or, in other words, cell death occurring in the population of tumor cells (Weisenthal L M, Shoemaker R H, Marsden J A, Dill P L, Baker J A, Moran E M. Recent Results Cancer Res 1984; 94: 161-173; Weisenthal L M, Lippman M E. Cancer Treat Rep 1985; 69: 615-632; Weisenthal L M. *Cell culture assays for hematologic neoplasms based on the concept of total tumor cell kill*. In: Kaspers G J L, Pieters R, Twentyman P R, Weisenthal L M, Veerman A J P, eds. *Drug Resistance in Leukemia and Lymphoma*. Langhorne, Pa.: Harwood Academic Publishers, 1993: 415-432; Weisenthal L M. Contrib Gynecol Obstet 1994; 19: 82-90). The concepts underlying cell death assays are relatively simple, even though the technical features and data interpretation can be very complex.

The basic technology concepts are straightforward. For example, a fresh specimen is obtained from a viable neoplasm. The specimen is most often a surgical specimen from a viable solid tumor. Less often, it is a malignant effusion, bone marrow, or peripheral blood specimen containing "tumor" cells (a word used to describe cells from either a solid or hematologic neoplasm). These cells are isolated and then cultured in the continuous presence or absence of drugs, most often for 3 to 7 days. At the end of the culture period, a measurement is made of cell injury, which correlates directly with cell death. There is evidence that the majority of available anticancer drugs may work through a mechanism of causing sufficient damage to trigger so-called programmed cell death, or apoptosis (Hickman J A. Cancer Metastasis Rev 1992; 11: 121-139; Zunino F, Perego P, Pilotti S, Pratesi G, Supino R, Arcamone F. Pharmacol Ther 1997; 76: 177-185).

Although there are methods for specifically measuring apoptosis which can be applied to cultured cells, there are practical difficulties in applying these methods to mixed (and clumpy) populations of tumor cells and normal cells. Thus, more general measurements of cell death have been applied. These include: (1) delayed loss of cell membrane integrity (which has been found to be a useful surrogate for apoptosis), as measured by differential staining in the DISC assay method, which allows selective drug effects against tumor cells to be recognized in a mixed population of tumor and normal cells (Weisenthal L M, Kern D H. Oncology (USA) 1992; 5: 93-103; Weisenthal L M, Marsden J A, Dill P L, Macaluso C K. Cancer Res 1983; 43: 749-757), (2) loss of mitochondrial Krebs cycle activity, as measured in the MTT assay (Carmichael J, DeGraff W G, Gazdar A F, Minna J D, Mitchell J B. Cancer Res 1987; 47: 936-942), (3) loss of cellular ATP, as measured in the ATP assay (Kangas L, Gronroos M, Nieminen A L. Med Biol 1984; 62: 338-343; Garewal H S, Ahmann F R, Schifman R B, Celniker A. J Natl Cancer Inst 1986; 77: 1039-1045; Sevin B-U, Peng Z L, Perras J P, Ganjei P, Penalver M, Averette H E. Gynecol Oncol 1988; 31: 191-204), and (4) loss of cell membrane esterase activity and cell membrane integrity, as measured by the fluorescein diacetate assay (Rotman B, Teplitz C, Dickinson K, Cozzolino J P. In vitro Cell Dev Biol 1988; 24: 1137-1138; Larsson R, Nygren P, Ekberg M, Slater L. Leukemia 1990; 4: 567-571; Nygren P, Kristensen J, Jonsson B, et al. Leukemia 1992; 6: 1121-1128).

In some embodiments, apoptosis is measured by a terminal deoxynucleotide transferase-mediated dUTP nick end labeling (TUNEL) assay which is well known in the art and for example as described in Materials and Methods available as supporting online material on Science Online.

In addition, the sensitivity or resistance of an animal to a treatment may be directly determined by measuring tumor size before and after treatment and/or over a period of time of treatment. If tumor size is decreased by 50%, preferably 75%, more preferably 85%, most preferably 100% with a treatment, than the animal is said to be sensitive (not resistant) to the treatment. Otherwise, the animal is considered to be resistant to the treatment. If the tumor size is reduced by at least 25%, preferably 50%, more preferably 75%, most preferably 100% after the administering of a treatment sensitizing composition of the present invention compared to the tumor after treatment but in the absence of the a composition of the present invention, then the composition is said to be effective in sensitizing the treatment in the animal. In human, the tumor size may be compared over a window of 6 month period of treatment, in other animals, this window varies for example a 4-6 week window may be used for mouse. It is understood that the actual time window for comparing tumor size may be determined according to knowledge in the art and the particular tumor to be treated.

Furthermore, whether a cell is resistant to a treatment may be also determined by measuring the expression of a SPARC family polypeptide or polynucleotide as described herein before. Thus the present invention provides a method for evaluating a first cancer sample for its resistance to a therapeutic treatment, comprising: (a) measuring expression level of a SPARC family mRNA or polypeptide, or extracellular level of a SPARC family polypeptide in the first cancer sample; (b) measuring expression level of the SPARC family mRNA or polypeptide, or extracellular level of the SPARC family polypeptide in a second cancer sample which does not exhibit resistance to the therapeutic treatment; (c) comparing the expression levels or the extracellular levels obtained in (a) and (b), wherein a lower level of expression or extracellular level in (a) is indicative of the first cancer sample being resistant to the therapeutic treatment.

The present invention further provides a method for identifying an agent which modulates a SPARC family mRNA or polypeptide expression, or a SPARC family polypeptide secretion, comprising: (a) measuring expression level of the SPARC family mRNA or polypeptide, or extracellular level of the SPARC family polypeptide in a sample; (b) contacting a candidate agent with the sample; (c) after the contacting of (b), measuring expression or extracellular level of the SPARC family mRNA or polypeptide, or extracellular level of the SPARC family polypeptide in the sample of (b); (d) comparing the expression levels or the extracellular levels in (a) and (c), wherein a differential level of expression or extracellular level in (a) and (c) indicates the candidate agent being an agent which modulates the SPARC family mRNA or polypeptide expression, or the SPARC family polypeptide secretion.

Expression levels of a SPARC polypeptide or a polynucleotide and the secretion levels of a SPARC polypeptide can be measured as described herein before and by any method known in the art.

An agent, which enhances the expression or secretion of a SPARC family member, may itself be used as a therapy sensitizing agent as described in the present invention. The agent may be a chemical, or a biological molecule (e.g., a protein, or a polynucleotide, etc.)

Animal Models

The therapeutic effects of the compositions provided by the present invention may be tested in various animal models. This may be done in vitro, ex vivo, or in vivo as described herein before.

Mouse models for proliferative disorders are known in the art and can be found, for example, on Jackson laboratory mouse database at world wide web www.jax.org and The Jackson Laboratory catalog—Jax-Mice—June 2001-May 2003, or Jackson-Grusby L. 2002, Oncogene. 12; 21(35): 5504-14; Ghebranious N, Donehower L A., 1998, Oncogene. 24; 17(25):3385-400; Palapattu G S, Bao S, Kumar T R, Matzuk M M. 1998, Cancer Detect Prey. 22(1):75-86). For example, tumor mouse models include those used for the study of Chronic Myelogenous Leukemia (CML), defects in cell cdhesion molecules, genes regulating growth and proliferation, growth factors/receptors/cytokines, increased tumor incidence, oncogenes, toxicology and tumor suppressor genes.

EXAMPLES

The invention is based on the observation that SPARC was found to be significantly underexpressed in chemotherapy resistant cells, that SPARC polypeptide sensitizes cancer therapy resistant cells to cancer treatment, that SPARC encoding DNA sensitizes cells to cancer therapy, and that animals engrafted with SPARC transfectant cells show a dramatic reduction in tumor growth compared to animals engrafted with a control.

Example 1

Materials and Methods

Cell Culture—The colorectal cell line MIP-101 was maintained in Dulbecco's modified Eagle's medium (DMEM) (Invitrogen) supplemented with 10% fetal bovine serum (FBS) (Invitrogen), 1% penicillin/streptomycin (Invitrogen) at 37° C. and 5% CO2. Resistant MIP101 cells were developed following long-term incubation with incremental concentrations of 5-fluorouracil (5-FU), irinotecan (CPT-11), cisplatin (CIS), and etoposide (ETO). Stable MIP101 cells transduced with SPARC (MIP/SP) were maintained in DMEM supplemented with 10% FBS, 1% penicillin/streptomycin, and 0.1% Zeocin at 37° C. and 5% $CO_2$.

Analytical Reverse Transcription-Polymerase Chain Reaction—Total RNA was extracted from cultured cells ($2 \times 10^6$ cells, 75% confluence) using TRIZOL reagent (Invitrogen) according to the manufacturer's protocol. RT-PCR was performed using a commercially available kit (BD Biosciences) following the manufacturer's protocol using 1 ug of total RNA. The specific primers used to amplify SPARC: 5'CGA AGA GGA GGT GGT GGC GGA AA-3' (sense) (SEQ ID NO. 78) and 5'GGT TGT TGT CCT CAT CCC TCT CAT AC-3' (antisense) (SEQ ID NO. 79). GAPDH: 5'-CTC TCT GCT CCT CCT GTT CGA CAG-3' (sense) (SEQ ID NO. 80) and 5'-AGG GGT CTT ACT CCT TGG AGG CCA-3' (antisense) (SEQ ID NO. 81) was used as internal control and to normalize the gene expression levels. The following settings were used for the reaction: 50° C.×1 hr, followed by 37 cycles of 94° C.×1 min, 65° C.×1 min, 72° C.×2 min, followed by 72° C.×10 min and incubation at 4° C. The PCR products were separated on 1% agarose gel in TAE buffer (stained with ethidium bromide 0.5 ug/ml) by electrophoresis for 1 hr at 100 V and subsequently photographed.

Quantitation of Apoptosis—For the TUNEL assay, cells were plated onto glass coverslips in 6-well plates at 250,000 cells/plate overnight prior to any induction study 24 hours later. For the assessment of apoptosis following exogenous SPARC (Haematologic Technologies Inc), cells were incubated with SPARC 5 µg/ml for 24 hrs followed by a 12-hr exposure to 5-FU 1000 µM. Cells were then processed for labeling by Apoptosis Detection Kit (Promega) according to the manufacturer's instructions. For quantitation of apoptosis, cells were plated at 250,000 cells/plate in 6-well plates overnight, followed by 12-hr incubation with the following chemotherapy agents: 5-FU 1000 µM, CPT-11 200 µM, cisplatin 100p4, and etoposide 10 µM. Cells were collected by using a nonenzymatic cell dissociation medium (Sigma), washed with phosphate-buffered saline and subsequently stained for Annexin V and propidium iodide using an Apoptosis detection kit (R & D Research) according to the manufacturer's protocol. The proportion of cells labeled with Annexin V and propidium iodide was analyzed by XL Flow Cytometry Analyzer. Data was collected from 100,000 events.

Transfection and Selection of Clone—The SPARC cDNA was cloned into pcDNA3.1 expression vector. Transfections were performed with 2.0 µg of the gene/expression vector construct using the polyethylenimine method of Boussiff et al. (1995) with minor modifications (Tai et al., 2002). After transfection, cells were washed with phosphate-buffered saline (PBS, pH 7.4) and maintained in culture medium for 24 hours, followed by a change to an appropriate selection medium containing 1% Zeocin. Cells were selected based on Zeocin resistance and individual colonies and clones from these colonies were then propagated for further verification. Stably transduced clones (MIP/SP) were screened for SPARC mRNA expression by reverse-transcription polymerase chain reaction (RT-PCR) analysis. MIP/SP clones with the highest expression of SPARC mRNA (by RT-PCR) and protein (by Western blot) were selected for subsequent in-vitro and in-vivo studies. Control cell lines used for this study included MIP101 cells stably transduced with pcDNA3.1 empty vector only (MLP/Zeo) and selected based on Zeocin resistance.

Western Blot Analysis—Total protein was extracted from cell lines cultured on 10-cm plates using CHAPS lysis buffer. 10-30 ug of total protein were electrophoresed using SDS-PAGE and transferred to PVDF membrane. After blocking with 5% nonfat milk solution, the membranes were incubated with anti-SPARC antibody (1:1000, Haematologic Technologies Inc) overnight at 4° C. The membrane was subsequently incubated with rabbit anti-mouse HRP-conjugated secondary antibody (1:2000) for 1-hr at room temperature and detected by Extendi-Dura chemiluminescence kit (Pierce). The same membrane was stripped using Western Blot Restore Stripping Buffer (Pierce) and subsequently re-probed for tubulin with a primary anti-tubulin mouse antibody (Sigma) and rabbit anti-mouse HRP-conjugated secondary antibody (1:2000) as an internal control.

Immunohistochemistry—Paraffin sections of human colorectal cancers or normal colonic epithelium were kindly provided by Dr. Maximo Loda (Dana Farber Cancer Institute, Boston). Prior to staining, the sections were washed with 0.1% Tris-buffered saline (TBS) containing 0.1% Triton X-100 (Sigma), treated with 1% $H_2O_2$ for 30 min, washed in TBS/0.1% Triton for 30 min (×3) at room temperature, blocked with 3% BSA in TBS/0.1% Triton for 1 hr. Sections were then incubated with mouse anti-SPARC antibody (1:50) overnight at 4° C. (Haematologic Technologies Inc.), washed several times with TBS/Triton and counterstained with avidin-biotin-peroxidase (ABC) complex solution (Vecstain ABC kits, Vector Laboratories Inc, Burlingame, Calif.) for 1 hr, followed by incubation in DAB solution. Sections were mounted using Permount.

Colony forming Assay—For clonogenic cell survival studies, MIP101 parental cells and MIP/SP cells were plated at 1,000 cells/plate in 48-well plates and incubated with increasing concentrations of 5-FU (0, 10 µM, 100 µM, 1000 µM), CPT-11 (0, 1 µM, 10 µM, 100 µM), or etoposide (0, 10 µM, 100 µM, 1000 µM) for 4 days. Cells were then washed with PBS and incubated in fresh medium containing the appropriate concentrations of chemotherapy for an additional 7 days. Each well was stained with crystal violet and the colonies with more than 50 cells were counted. The number of colonies formed in the treated group was calculated based on the colonies formed from the control, untreated cells.

Concentrated SPARC-containing supernatant [SPARC(s)]—MIP/SP cells were plated at $1 \times 10^6$ cells in 100 cm flasks in DMEM (10% FBS, 1% penicillin/streptomycin, 0.1% Zeocin) for 24 hrs. Cells were subsequently washed with PBS twice and incubated in serum-free VP-SFM medium supplemented with glutamine 4 mM (Invitrogen) for 72 hrs. This medium was concentrated from 500 ml to 2 ml using Centricon Filter units (Millipore) at 4° C. All media collected and processed by this method were used for subsequent animal studies.

Animal Studies—Tumor xenograft animal models were used to assess the effect of SPARC on tumor progression in-vivo. NIH nude mice (6 weeks old, Taconic Laboratories) were engrafted following subcutaneous injection of $2 \times 10^6$ cells into the left flank. Treatment regimens were initiated once the average tumor size was 50-75 $mm^3$ in size. Tumor measurements were performed using a hand-held caliper (Fisher) twice weekly and weight measurements were made concurrently until the completion of the study. Chemotherapy was provided using a 3-week cycle regimen for a total of 6 cycles: 5-FU 25 mg/kg or CPT-11 25 mg/kg intraperitoneal injections three times on week 1 of each cycle, followed by 2 weeks of treatment-free periods. Dosing schedule for SPARC(s) was 100 µL of SPARC(s) three times per week until the completion of the chemotherapy cycle.

Example 2

SPARC Expression in Chemotherapy Resistant Cells

Figure 3:
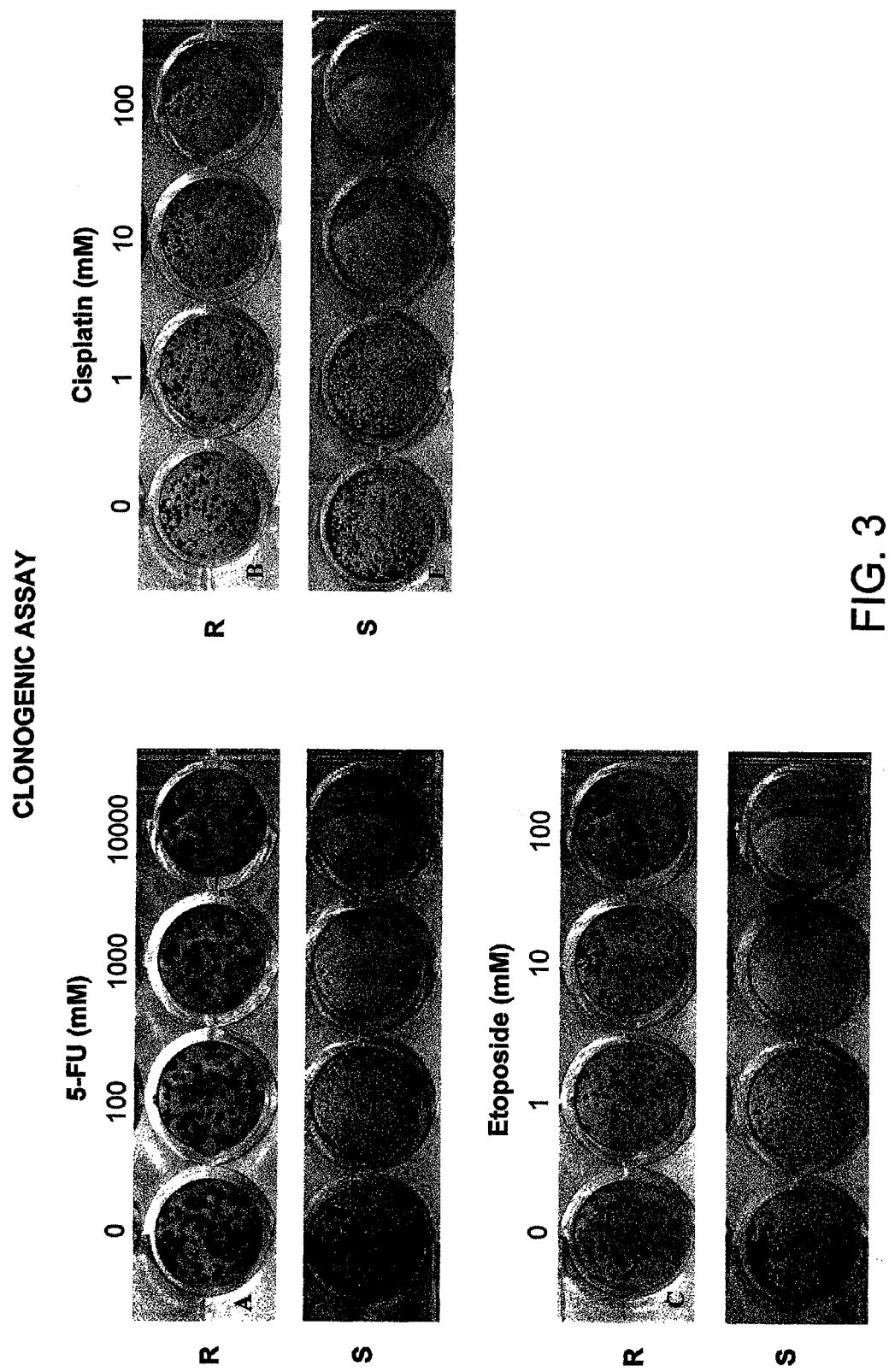
FIG. 3 is a picture showing colony formation assays of chemotherapy sensitive and resistant cells according to one embodiment of the invention.
Figure 4:
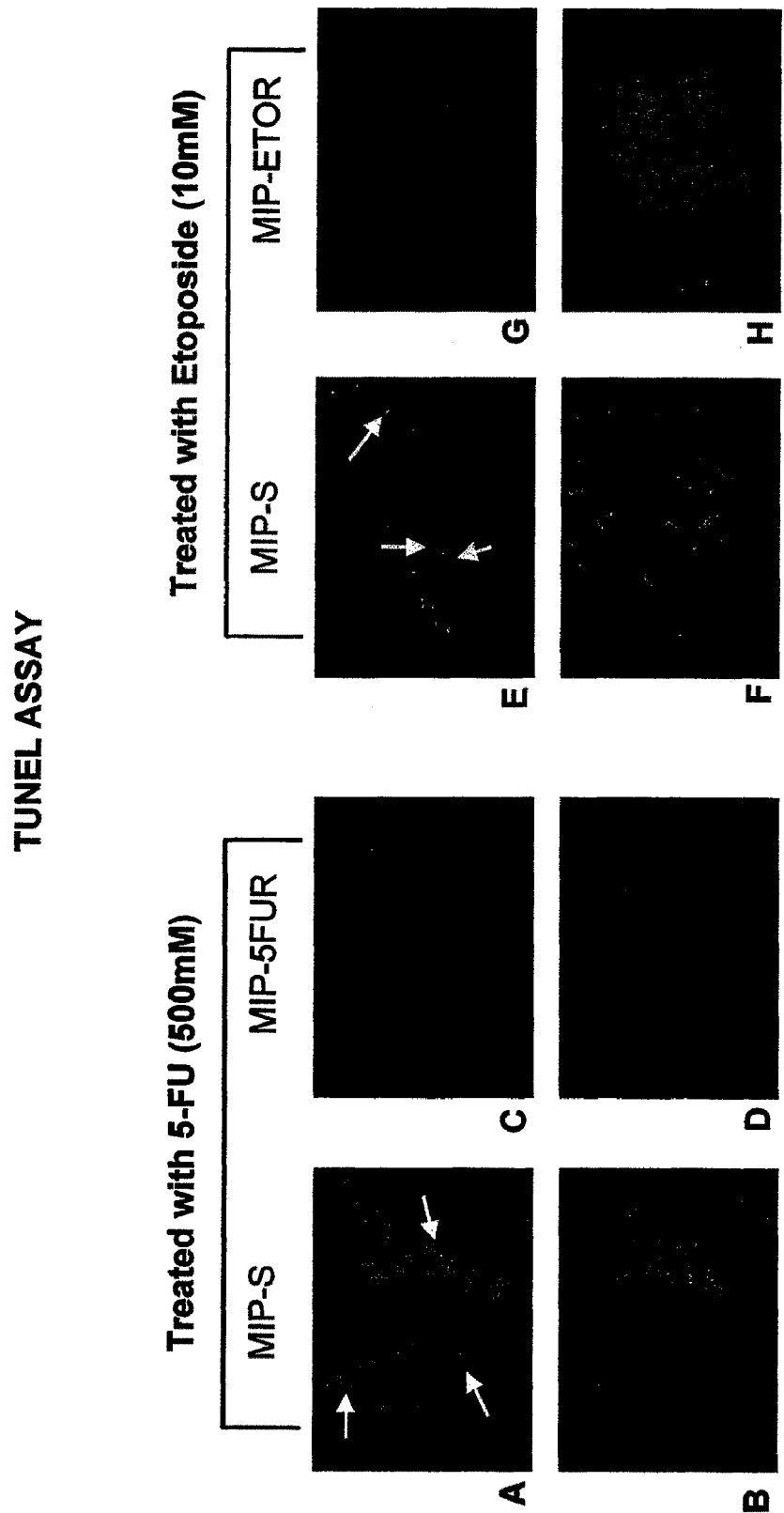
FIG. 4 is a picture showing TUNEL assays of chemotherapy sensitive and resistant cells according to one embodiment of the invention.

Two chemotherapy resistant clones (MIP-5FUR and MIP-ETOR), as supported by colony formation assays (FIG. 3) and TUNEL assay (FIG. 4), were used for the detection of SPARC in chemotherapy resistant cells. Microarray analysis identified a number of genes underexpressed in the resistant cells, including SPARC.

Figure 5A:
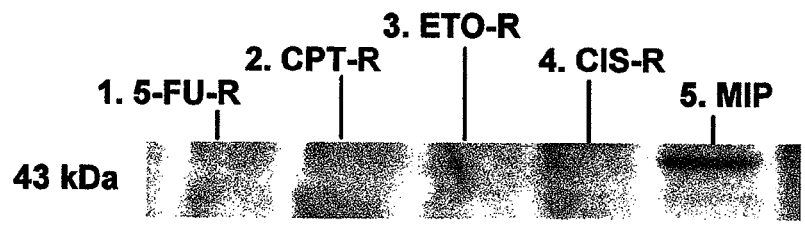
FIGS. 5 (A and B) is a picture showing the decreased level of SPARC polypeptide in chemotherapy resistant cell lines according to one embodiment of the invention.
Figure 5B:
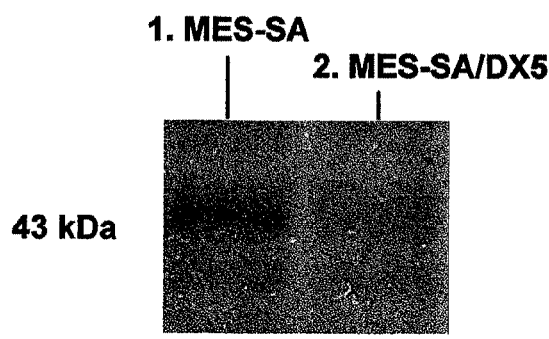

Underexpression at the gene expression level also translated into lower levels of SPARC protein levels in the chemotherapy resistant cell lines (FIG. 5A). This feature was not unique to the resistant cell lines developed solely for the purposes of the current study, since another well established uterine sarcoma cell line, MES-SA, also showed decreased expression of SPARC when it is resistant to a different chemotherapeutic agent, doxorubicin. (FIG. 5B). Furthermore, in normal human pathological samples, SPARC protein expression appears to be highest in the villi, with a decreasing gradient towards colonic crypts. This variable expression is lost in malignancy, with a general decrease in expression of SPARC in colorectal adenocarcinoma of various stages.

Figures 2, 13:
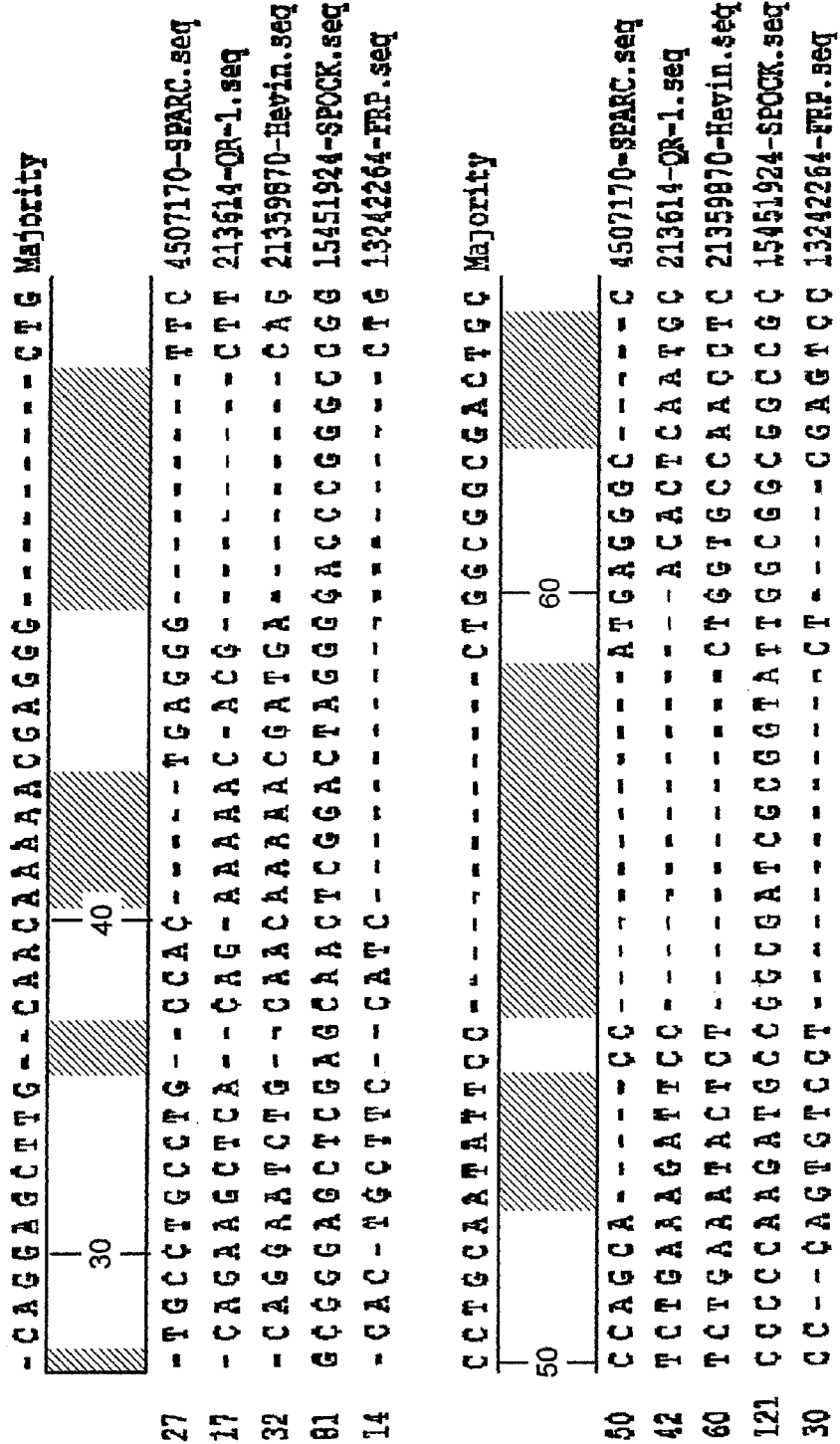
FIG. 13 is a figure showing the sequence alignment among different SPARC family polypeptides and polynucleotides according to one embodiment of the invention.
Figures 3, 13:
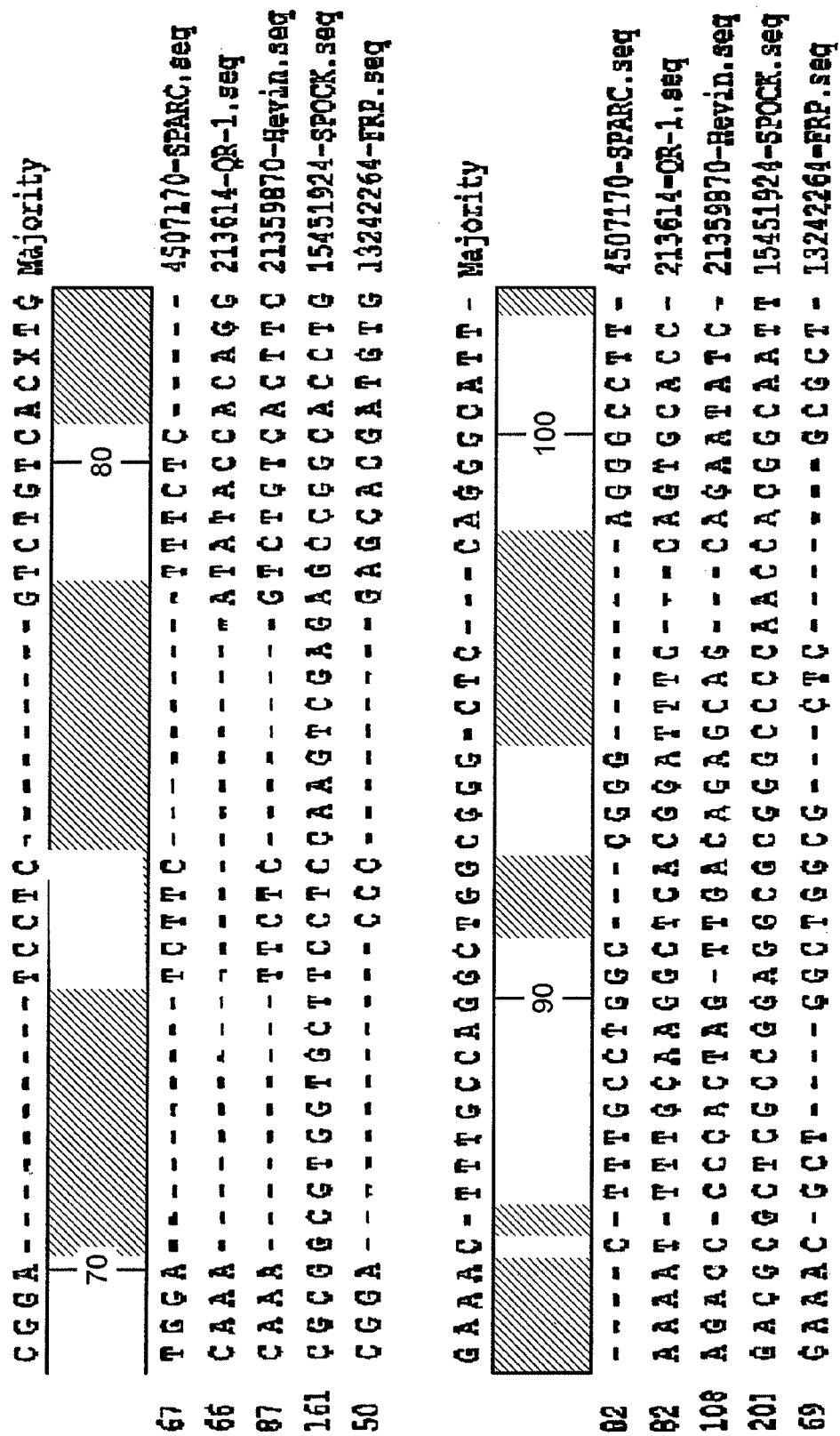
Figures 4, 13:
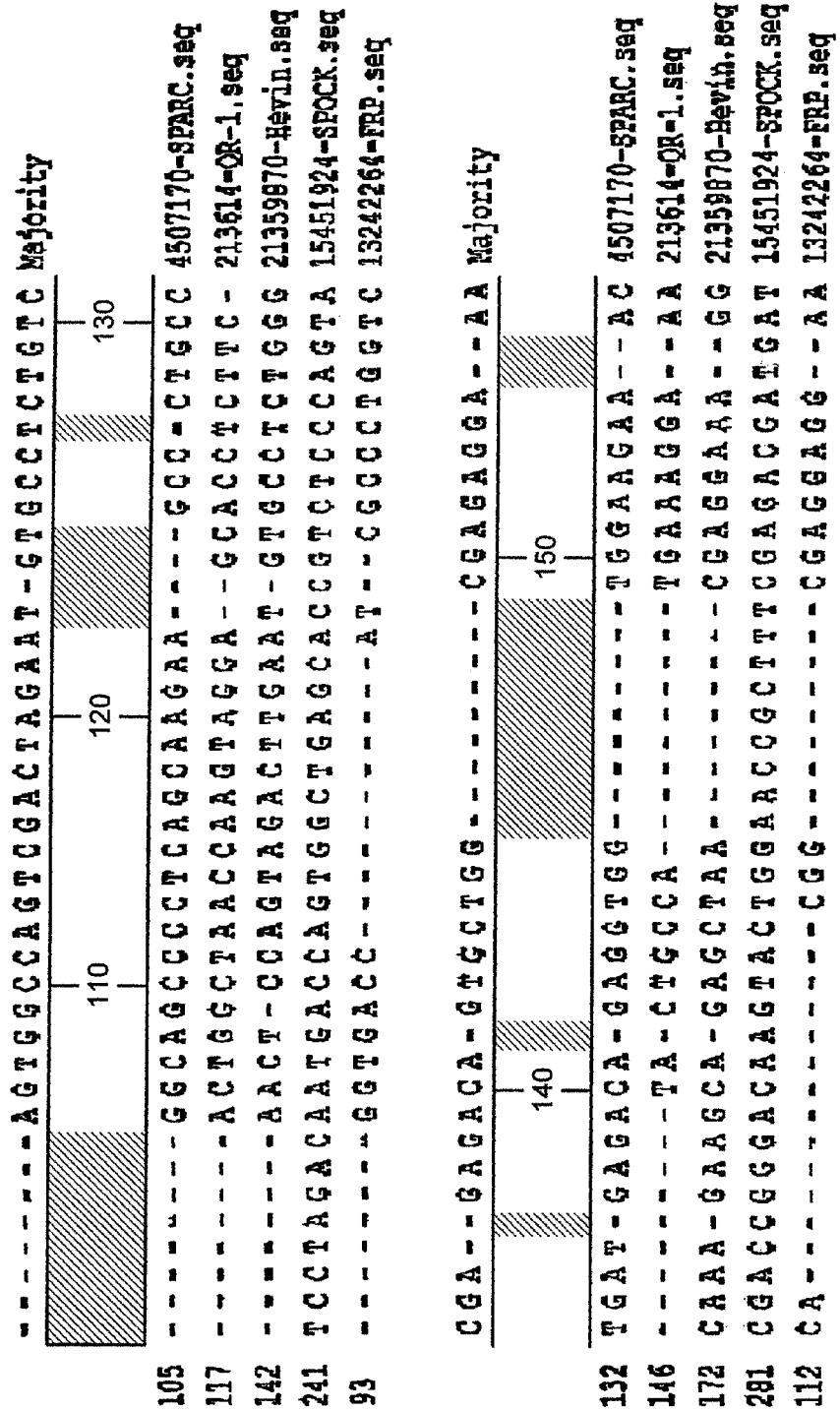
Figures 8, 13:
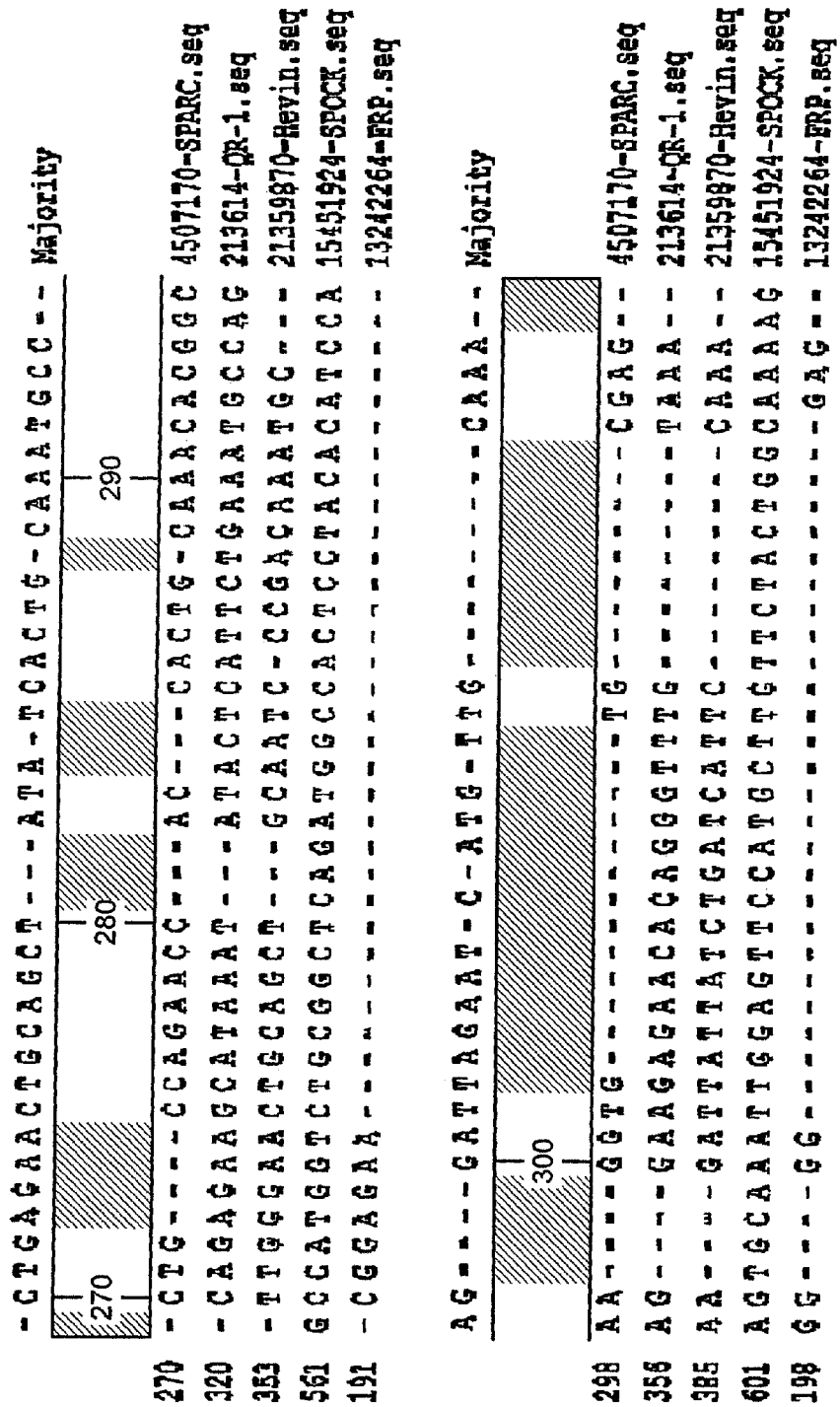
FIG. 8 is a FACS analysis showing cell populations induced to undergo apoptosis following exposure to chemotherapeutic agents according to one embodiment of the invention.
Figures 13, 14:
FIG. 14 shows effect of chemotherapy on tumor xenografts of SPARC-overexpressing cells according to one embodiment of the invention.
Figures 13, 14, 15, 16, 17, 18, 19, 20, 21, 22, 23, 24, 25, 26, 27, 28:
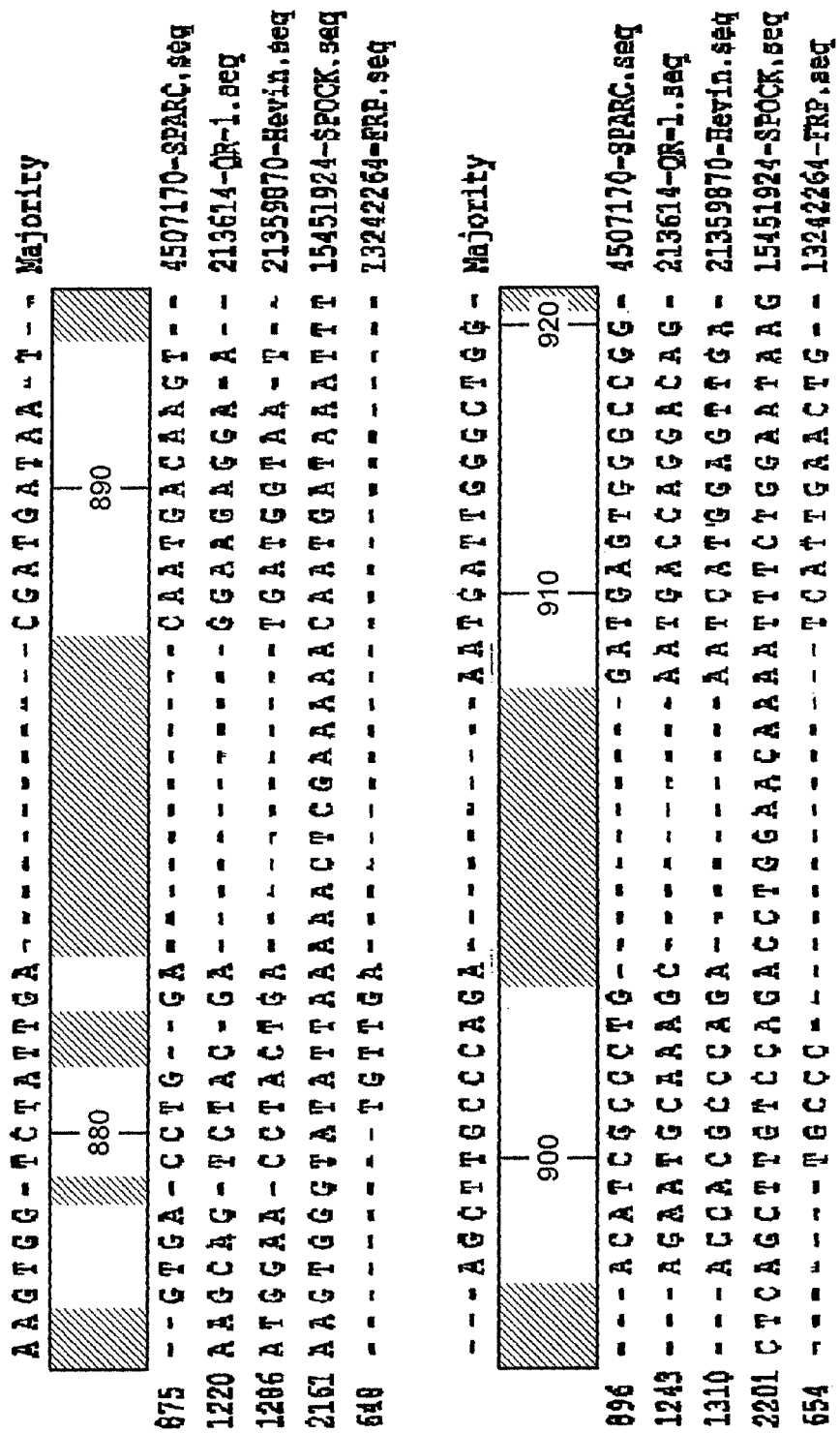
FIG. 15 shows effect of radiation therapy on tumor xenografts of SPARC-overexpressing cells according to one embodiment of the invention.
FIG. 16 shows treatment of MIP101 tumor xenografts with combination therapy with SPARC(s) intraperitoneally according to one embodiment of the invention.
FIG. 17 shows treatment of MIP101 tumor xenografts with combination therapy with SPARC(s) subcutaneously according to one embodiment of the invention.
FIG. 18 shows treatment of MIP/5FU tumor xenografts with combination therapy with SPARC(s) according to one embodiment of the invention.
FIG. 19 shows human SPARC mRNA and protein levels in colorectal cancer cell lines sensitive and resistant to chemotherapy according to one embodiment of the invention.
FIG. 20 shows SPARC protein expression in human colonic epithelium according to one embodiment of the invention.
FIG. 21 shows assessment of the effect of SPARC in influencing the sensitivity of cells to chemotherapy according to one embodiment of the invention.
Figures 13, 14, 15, 16, 17, 18, 19, 20, 21, 22, 23, 24, 25, 26, 27, 28, 29, 30, 31:
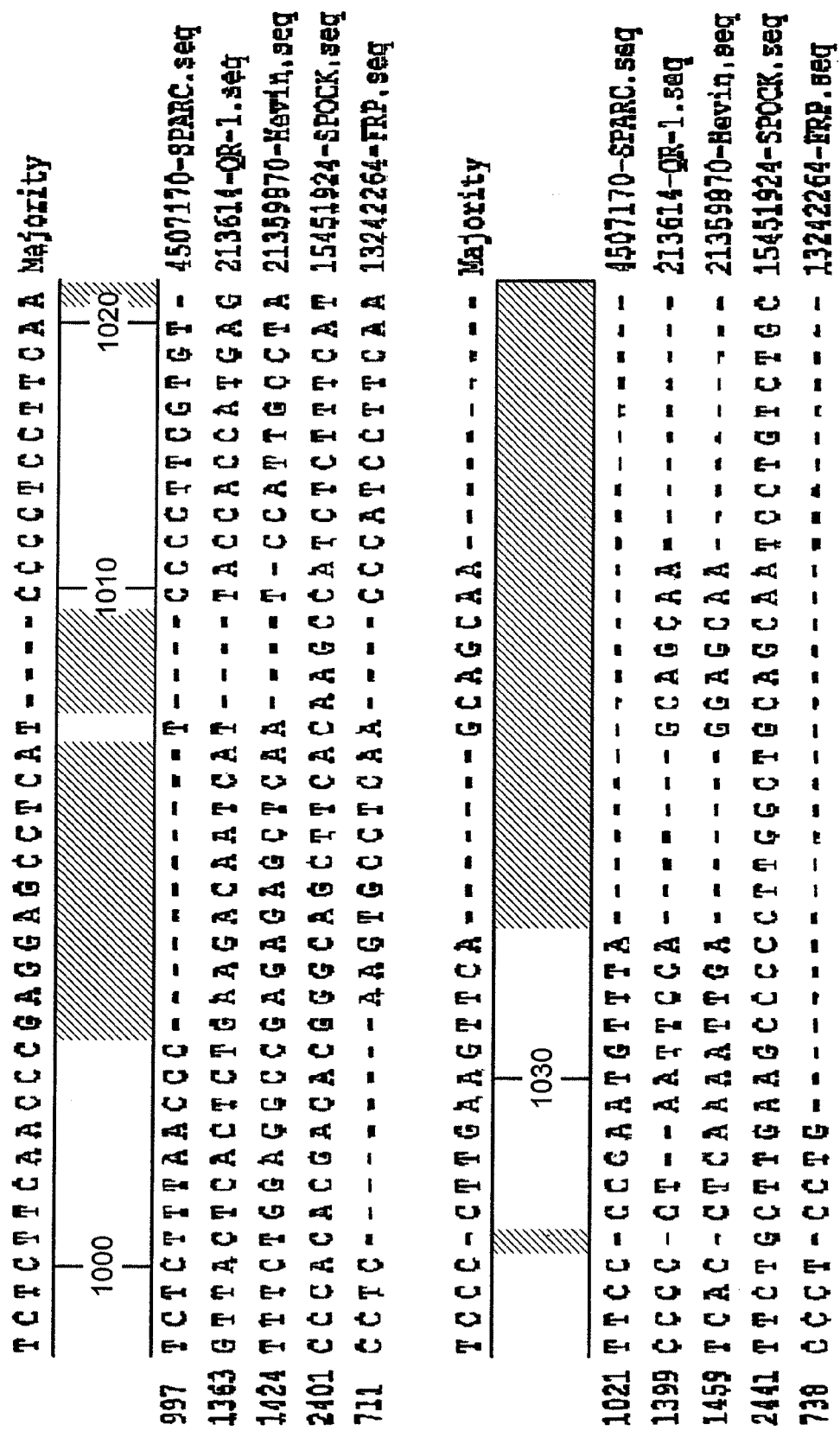
Figures 13, 14, 15, 16, 17, 18, 19, 20, 21, 22, 23, 24, 25, 26, 27, 28, 29, 30, 31, 32, 33:
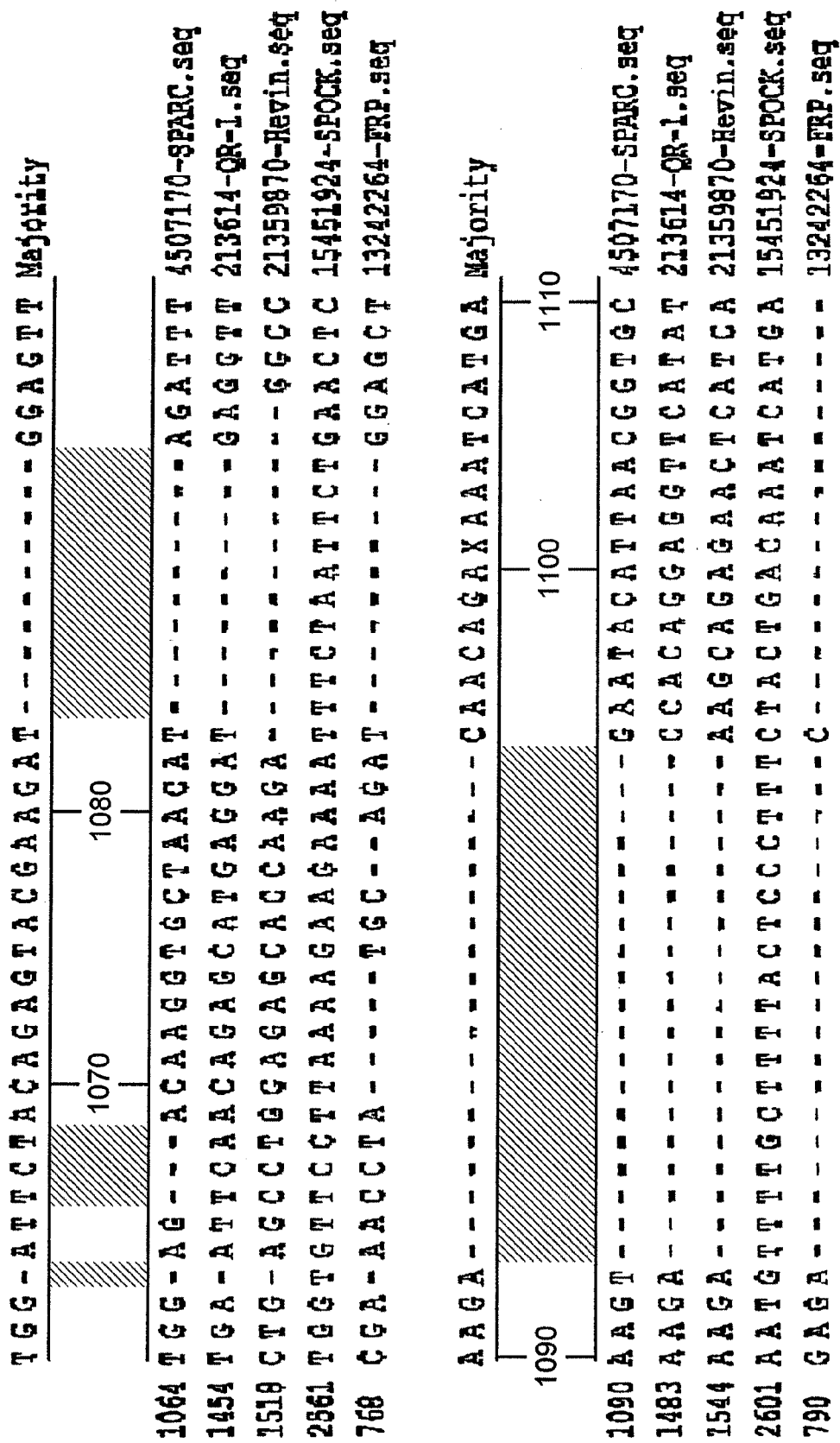
Figures 13, 14, 15, 16, 17, 18, 19, 20, 21, 22, 23, 24, 25, 26, 27, 28, 29, 30, 31, 32, 33, 34:
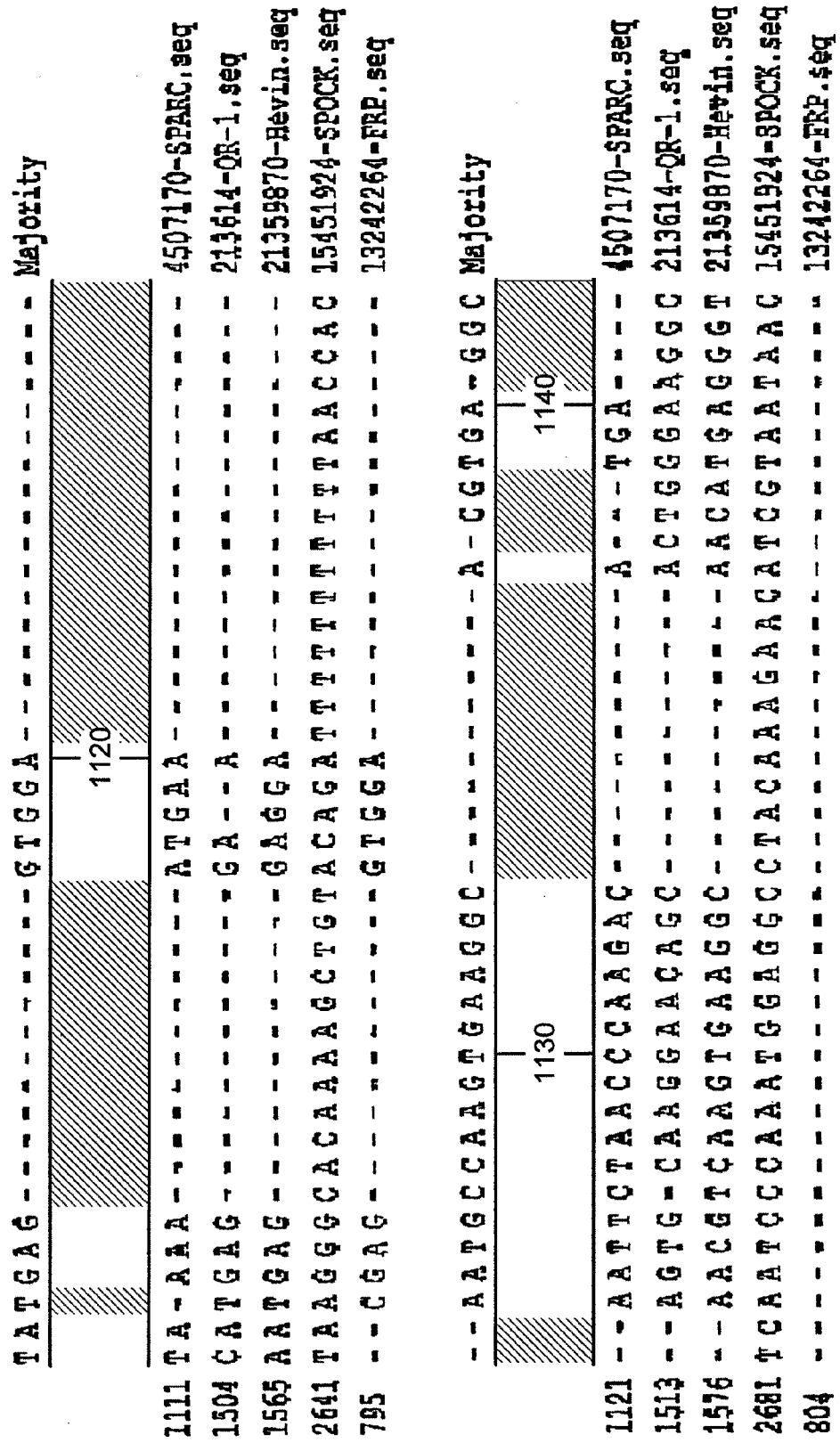
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
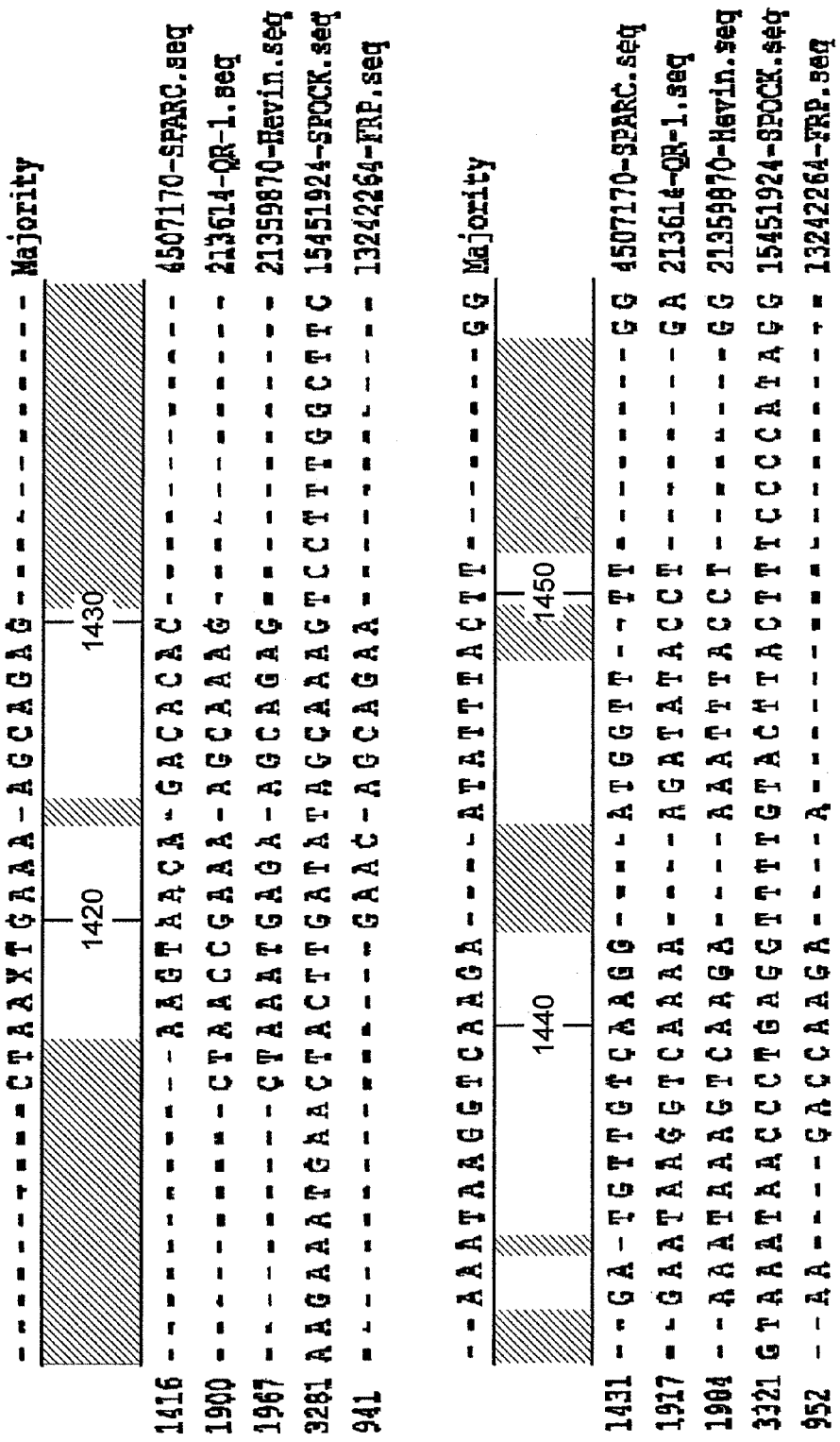
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
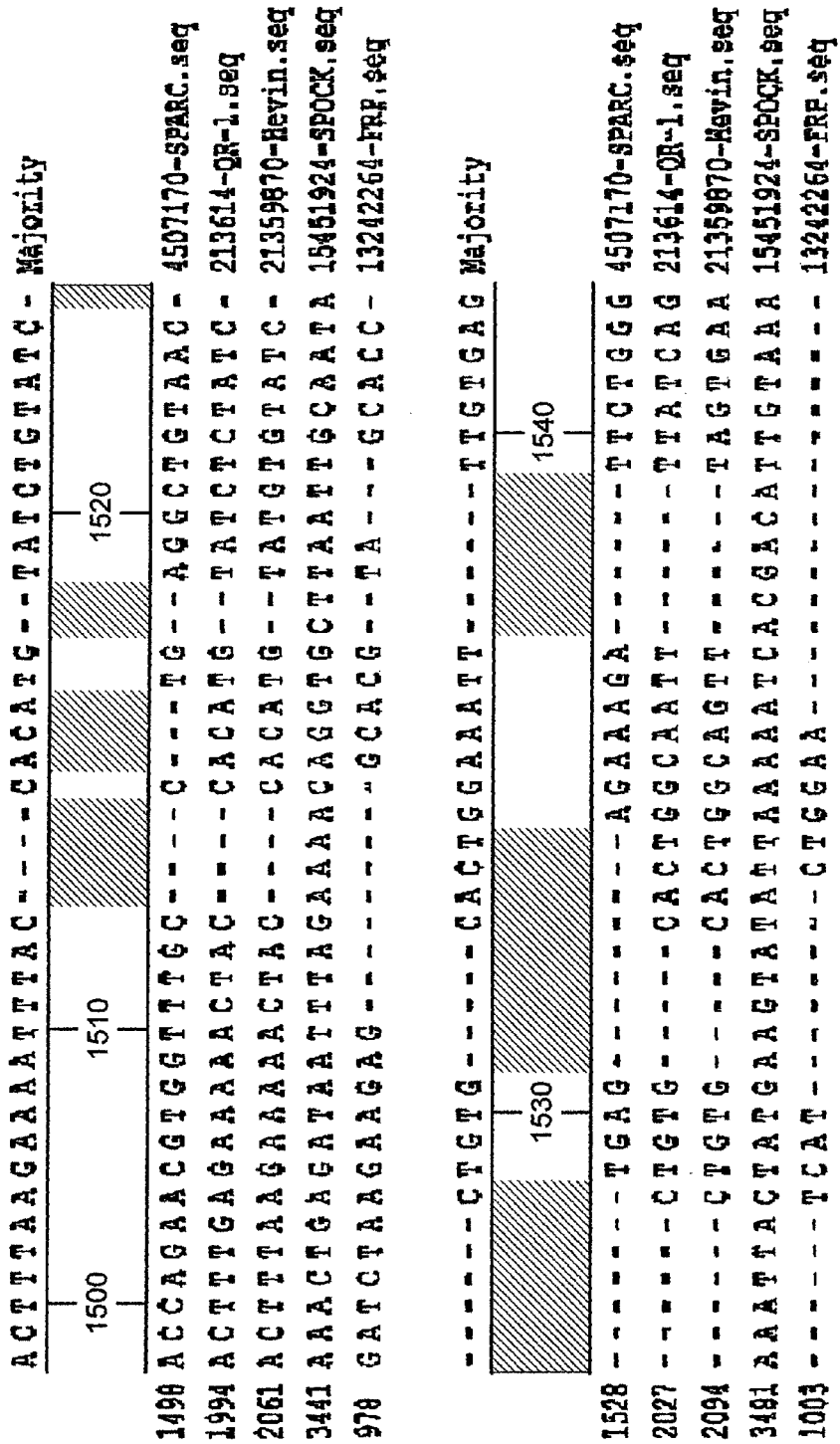
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
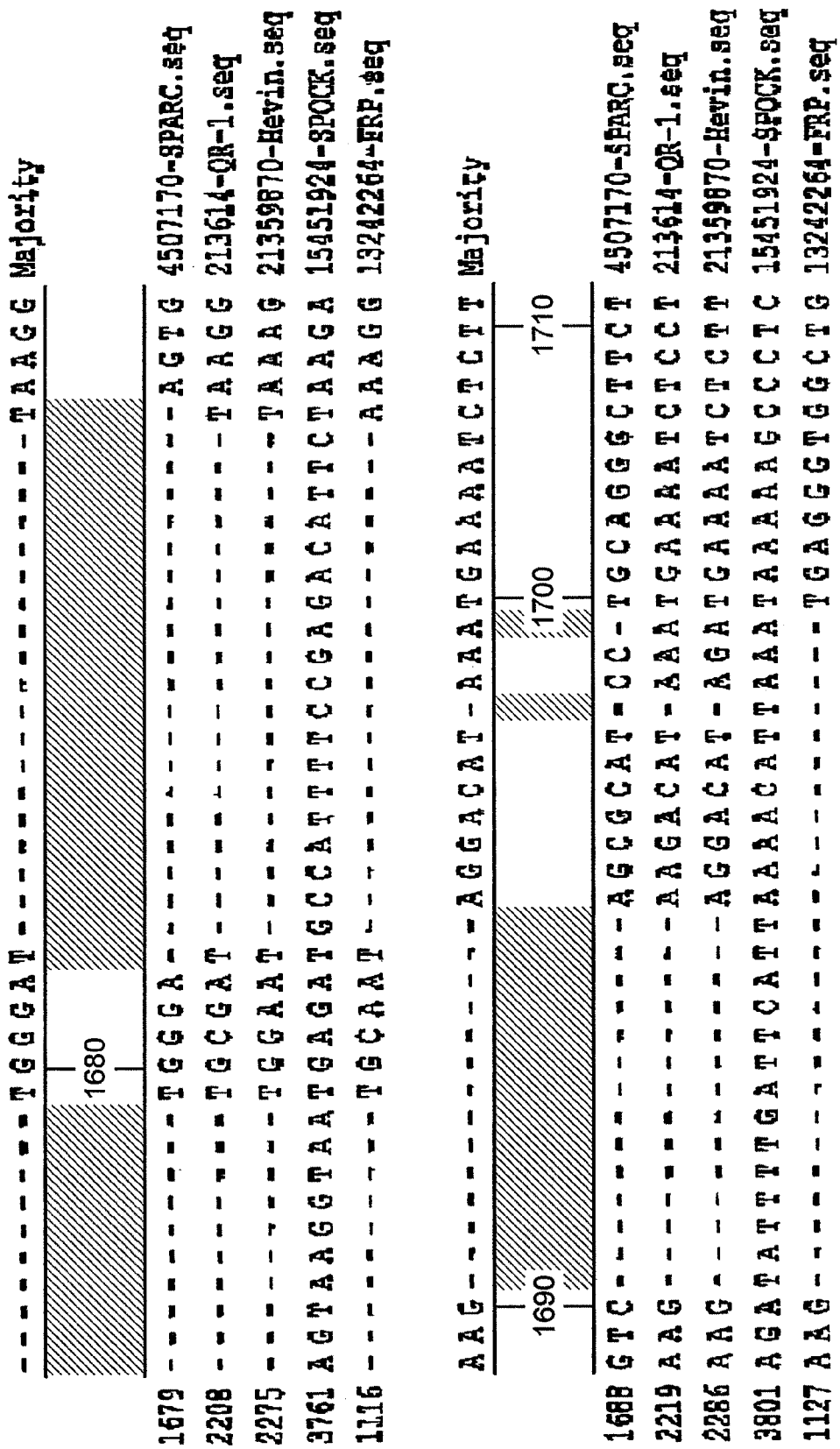
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
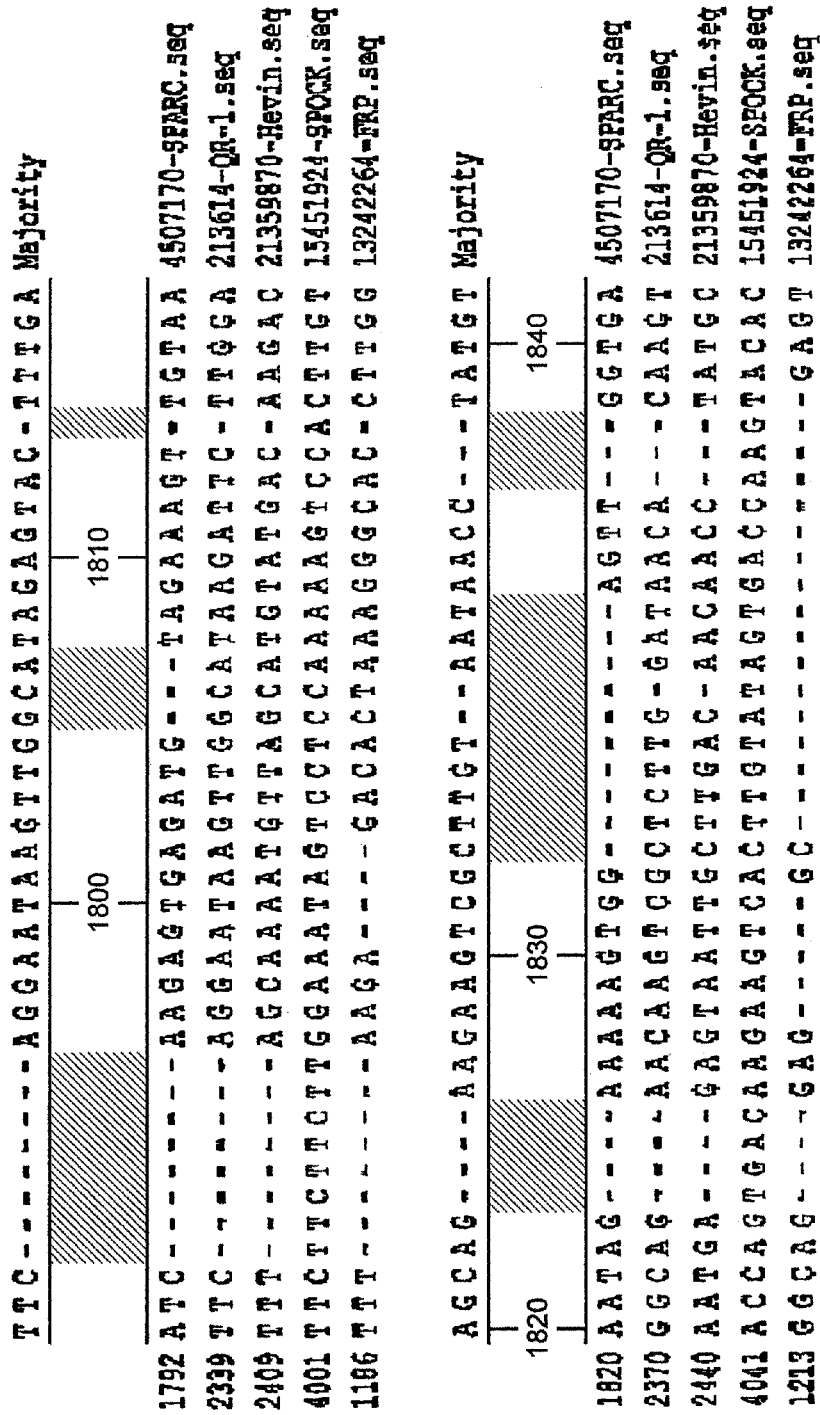
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
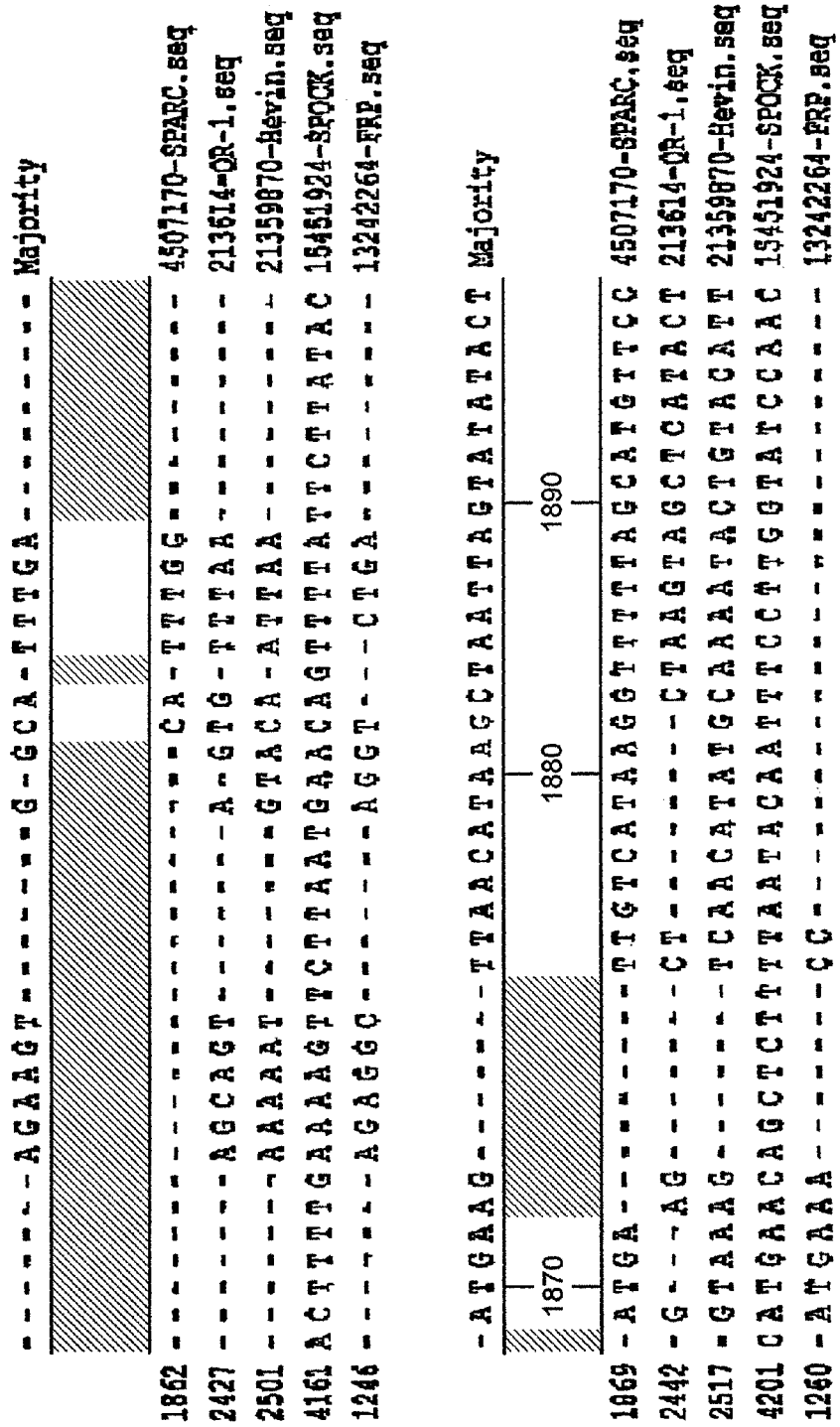
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
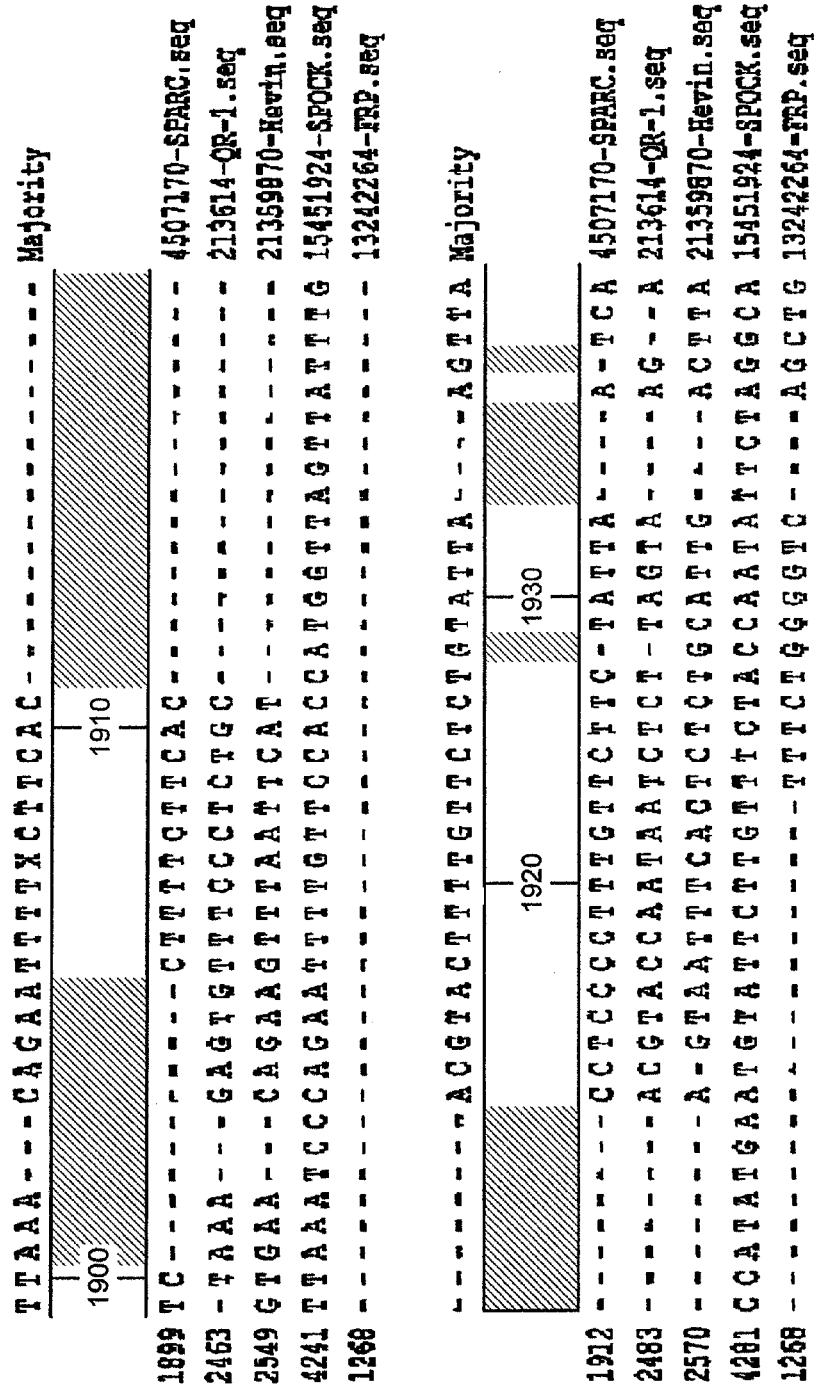
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55:
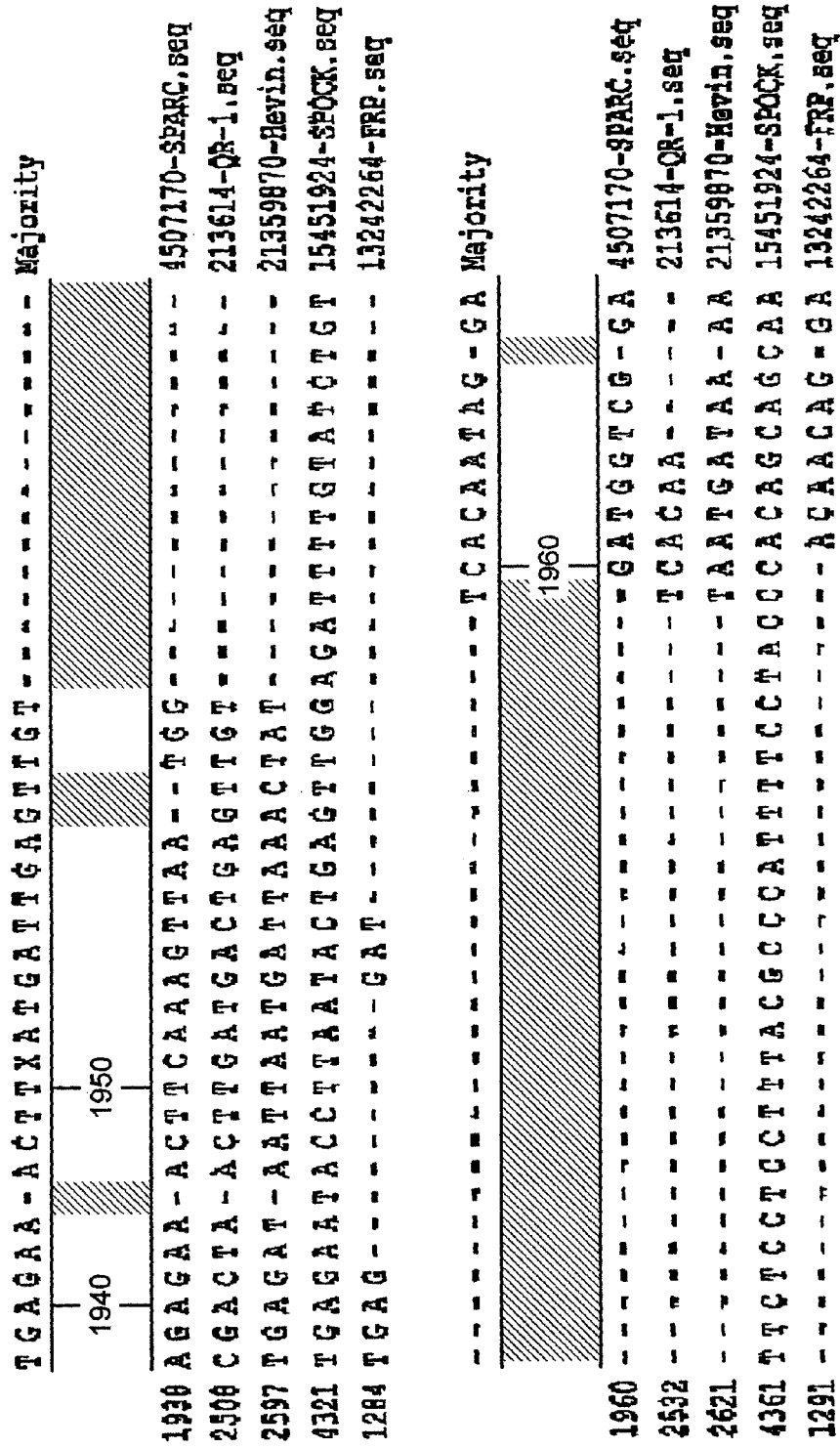
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56:
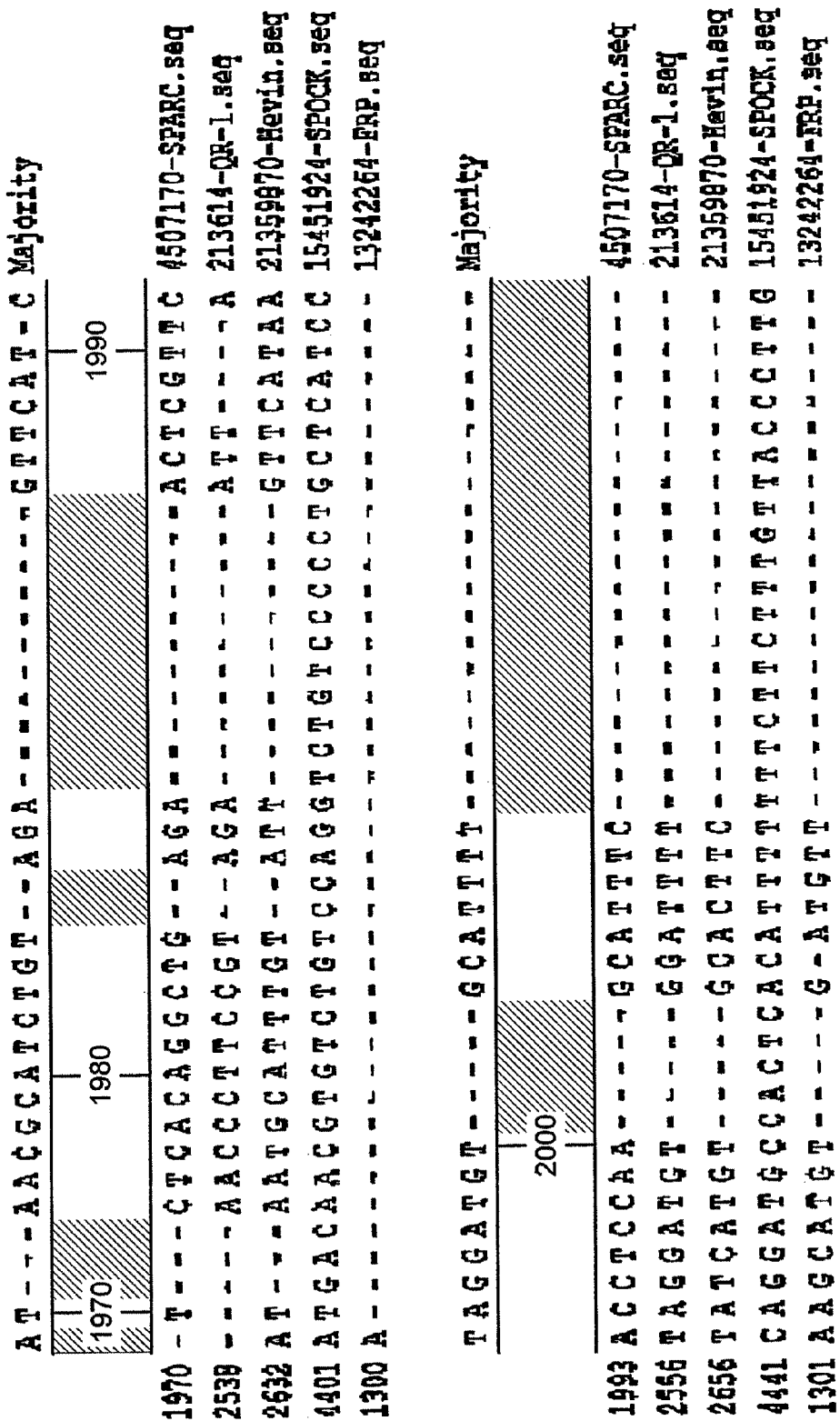
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57:
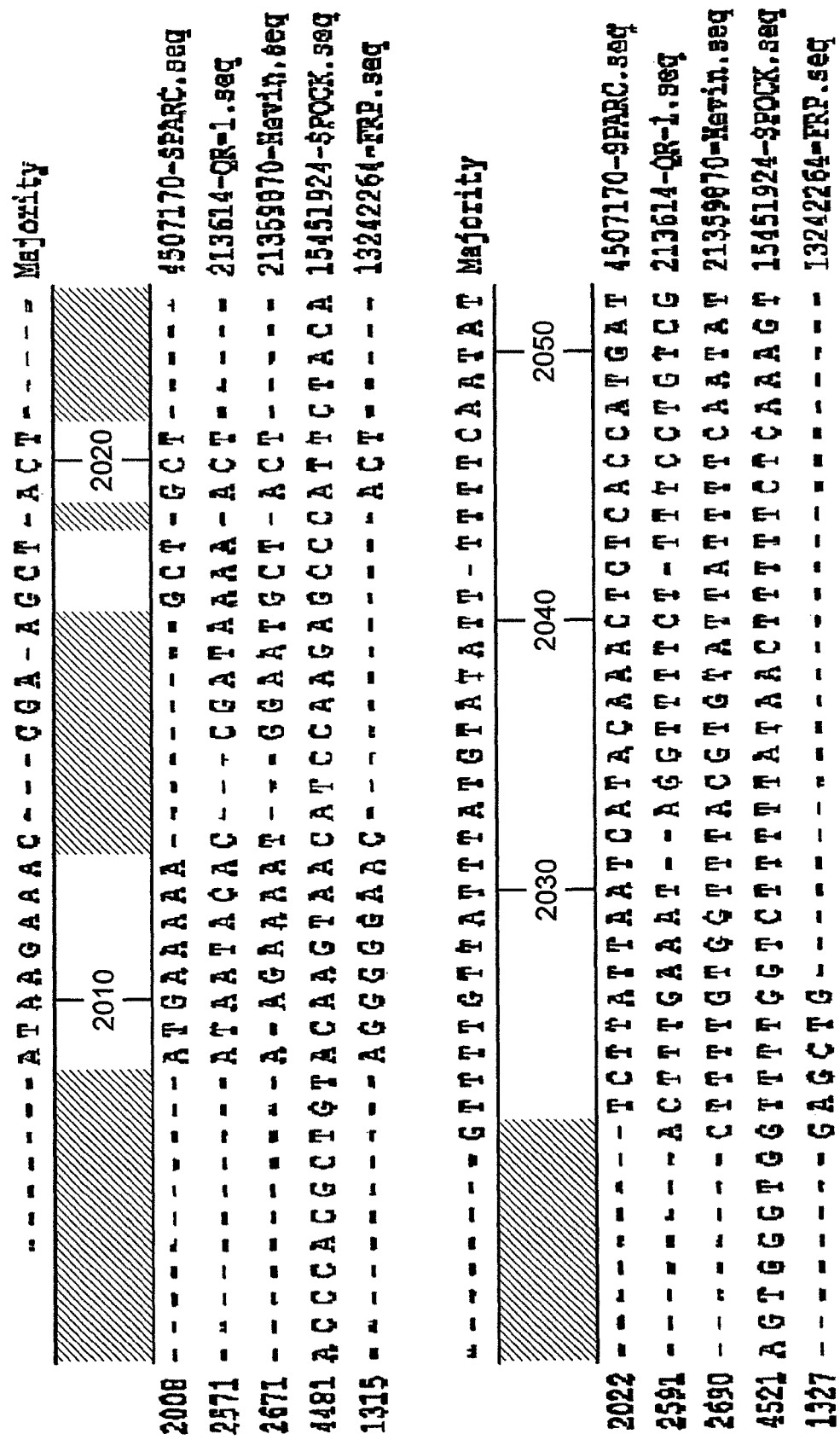
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59:
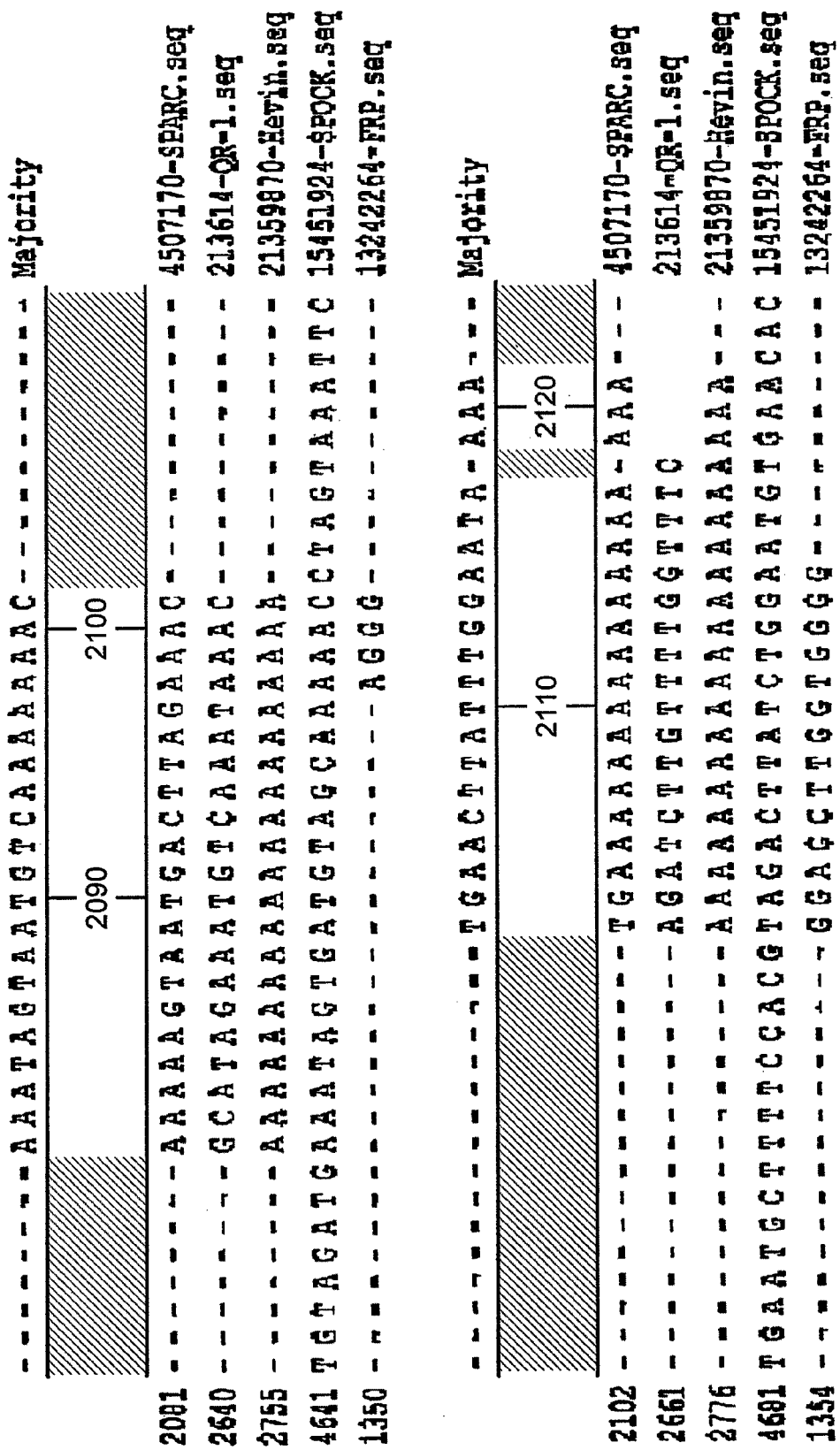
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60:
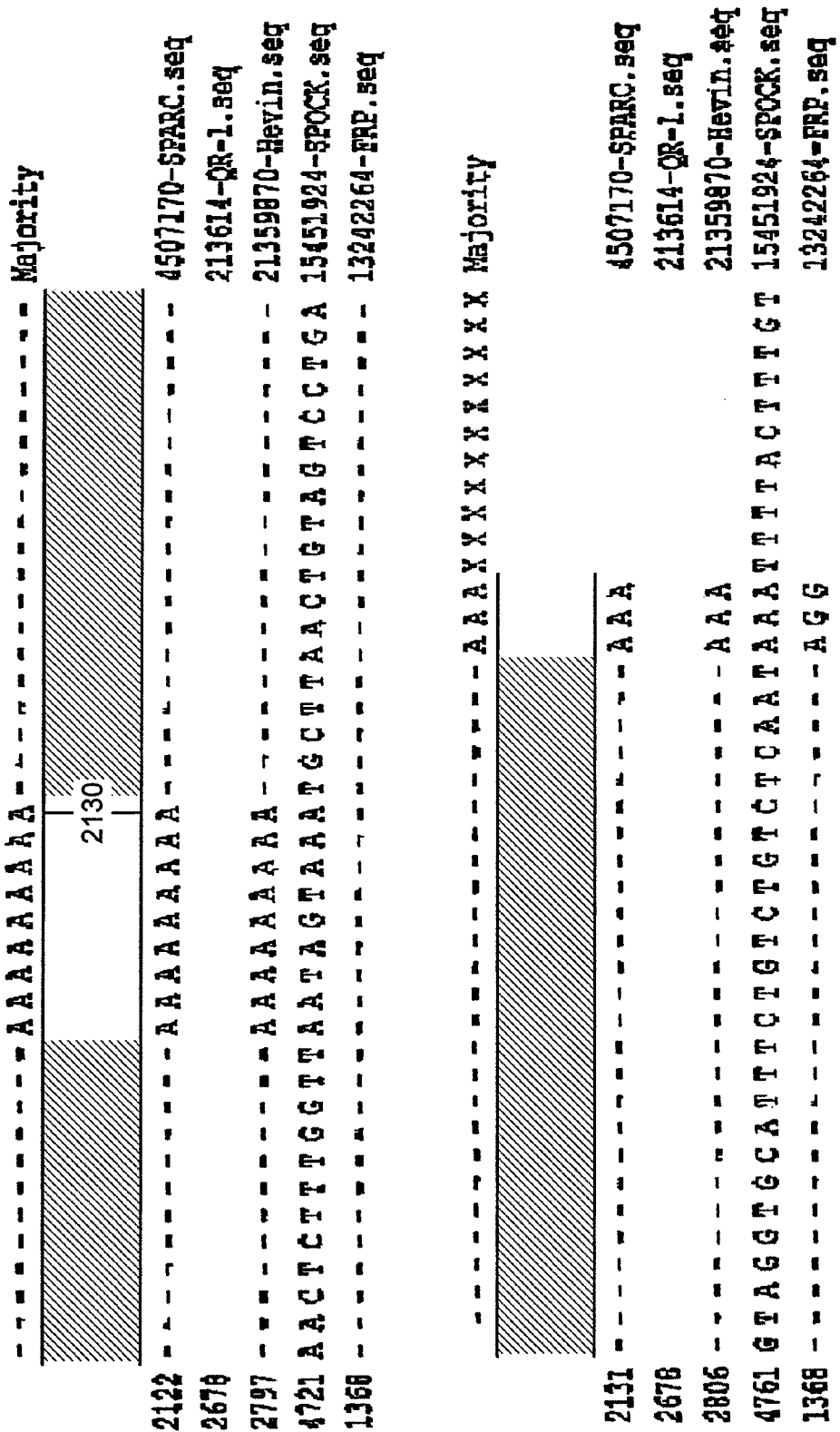
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61:
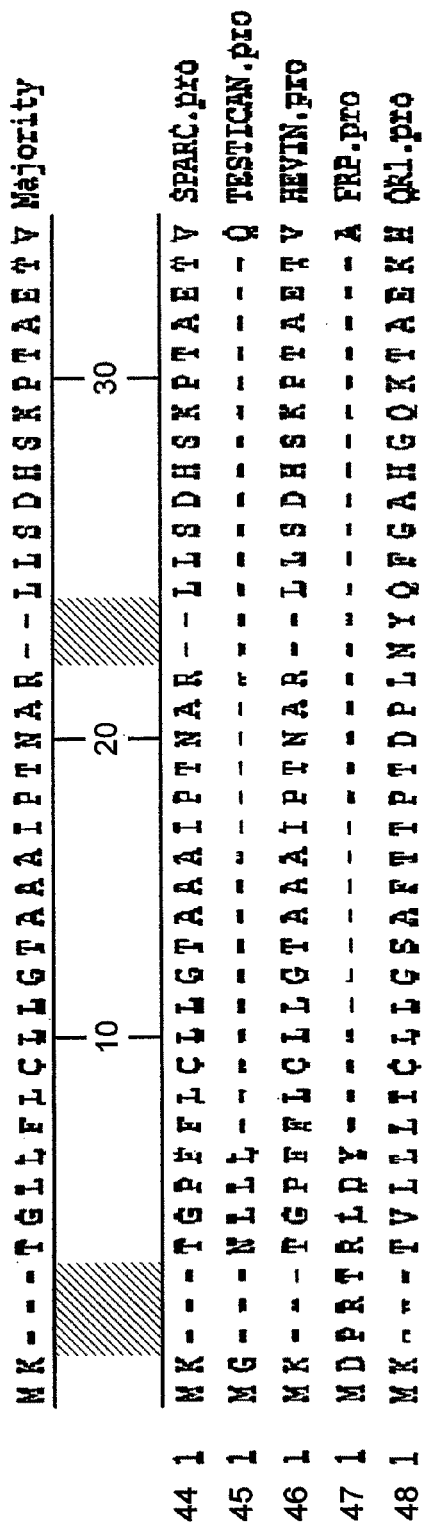
Figures 13, 71:
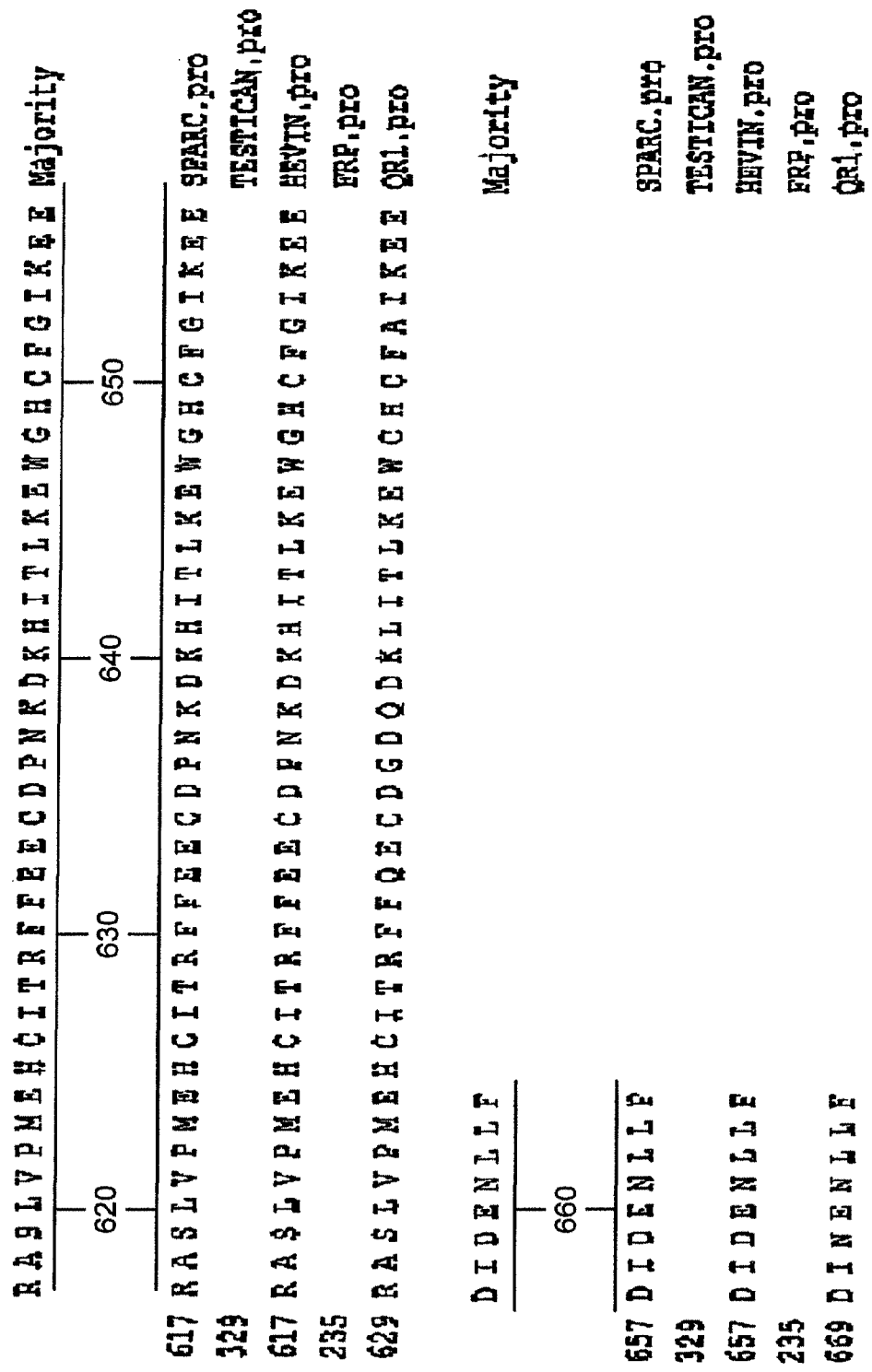
Figure 14:
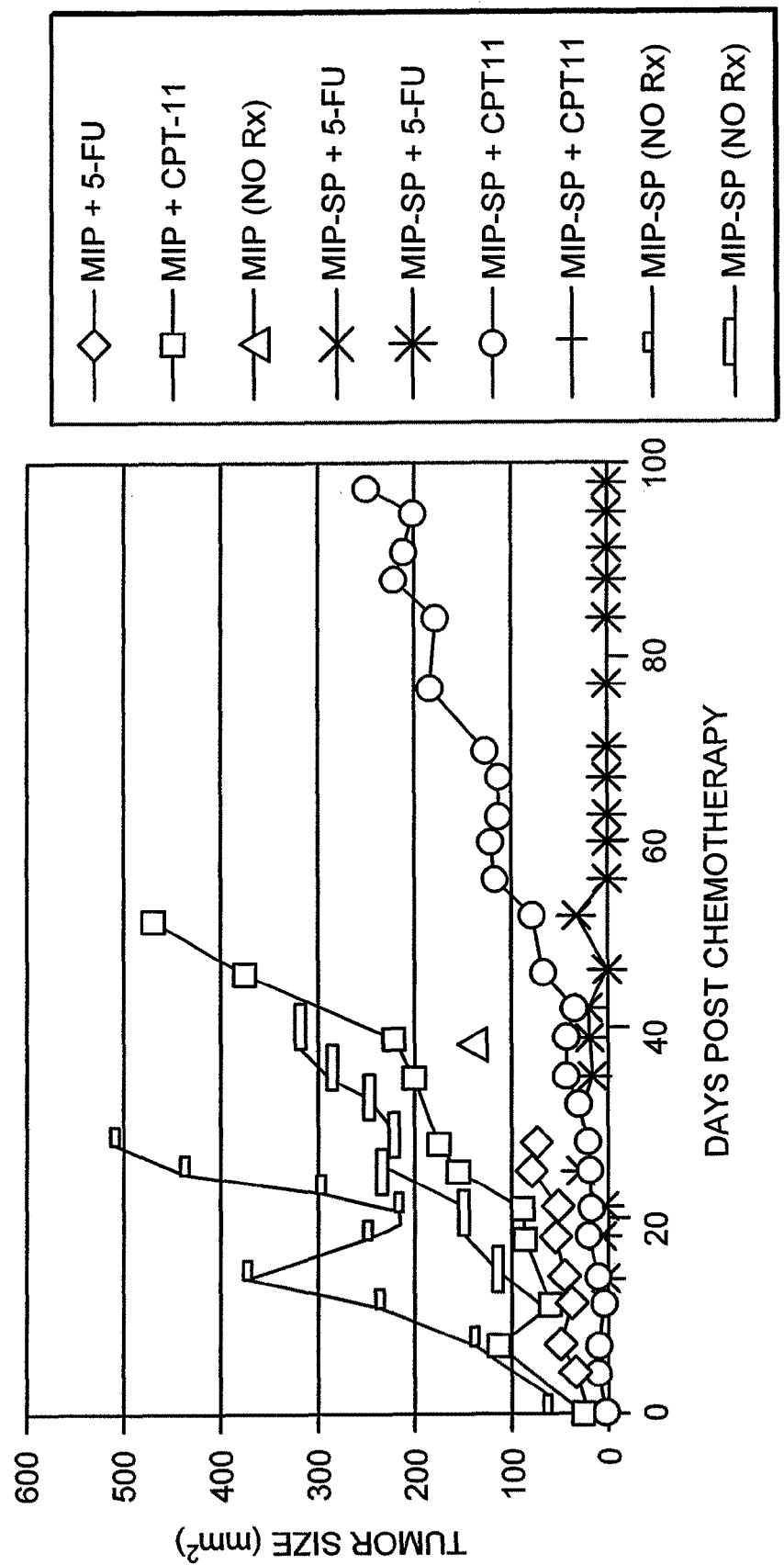
Figure 15:
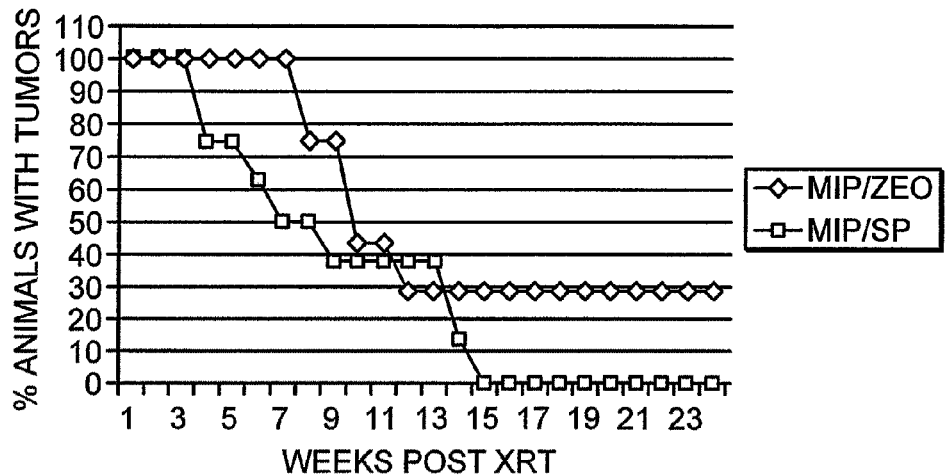
Figure 16:
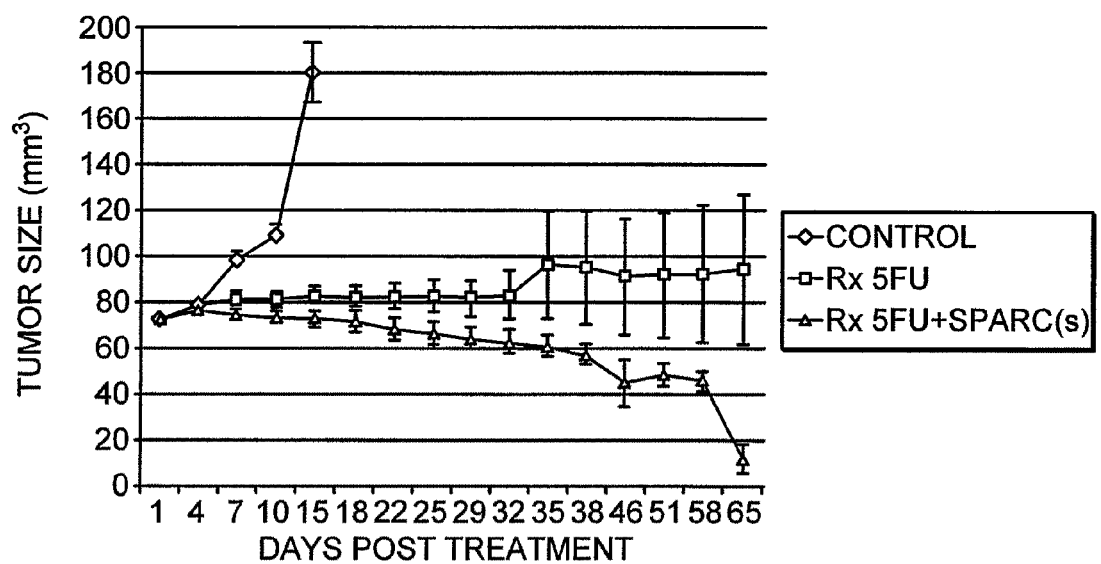
Figure 17:
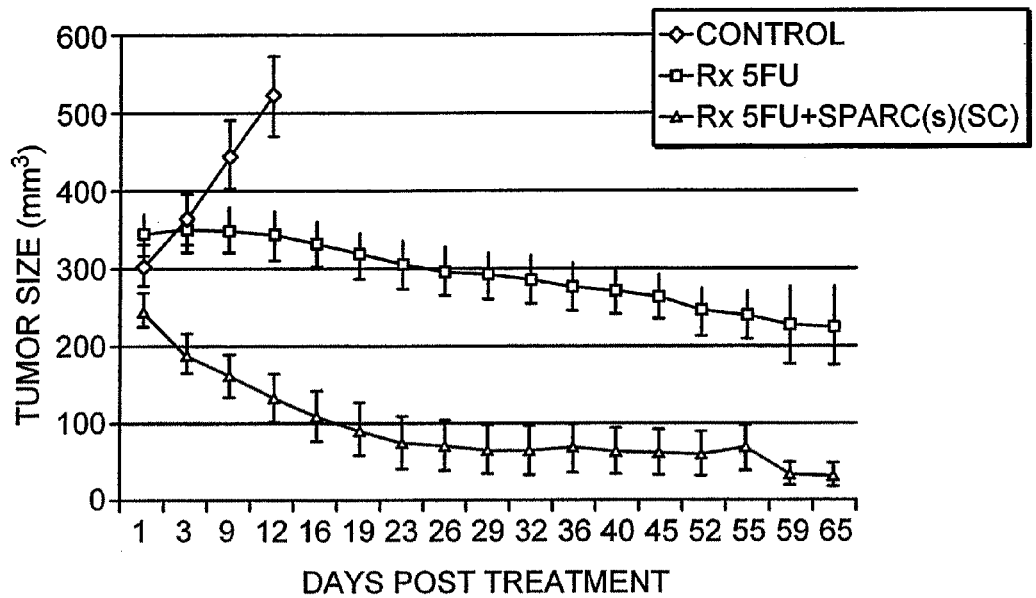
Figure 18:
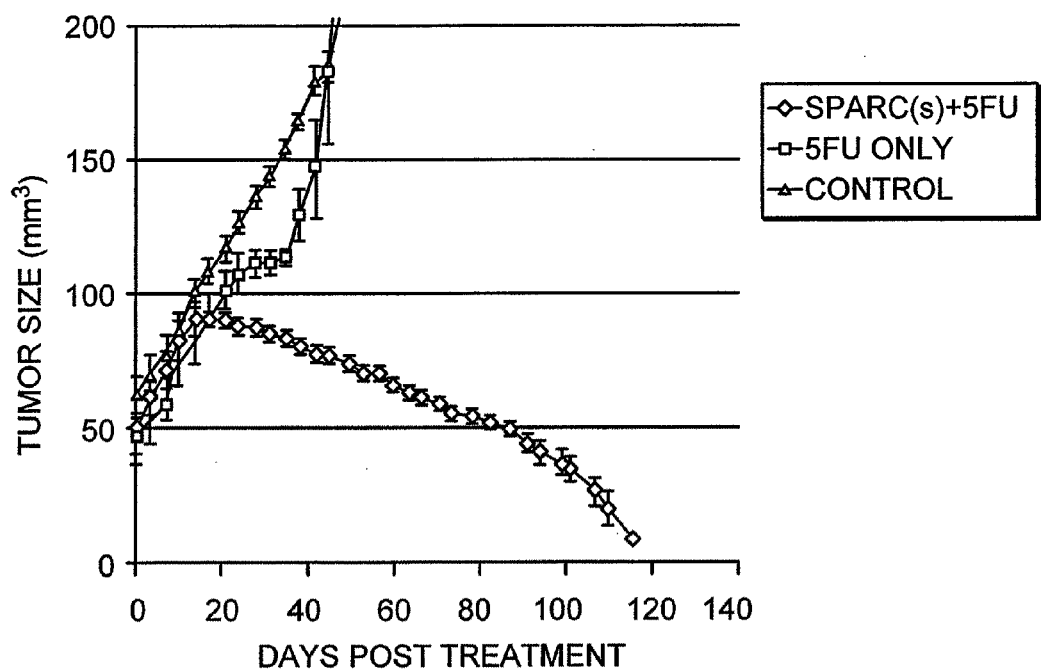
Figure 19A:
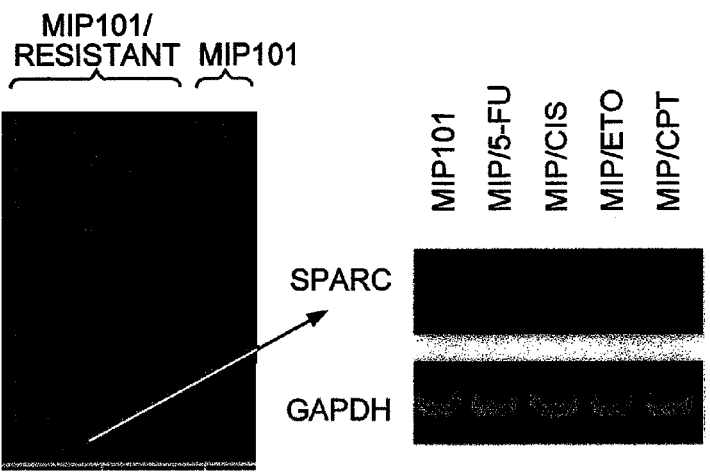
Figure 19B:
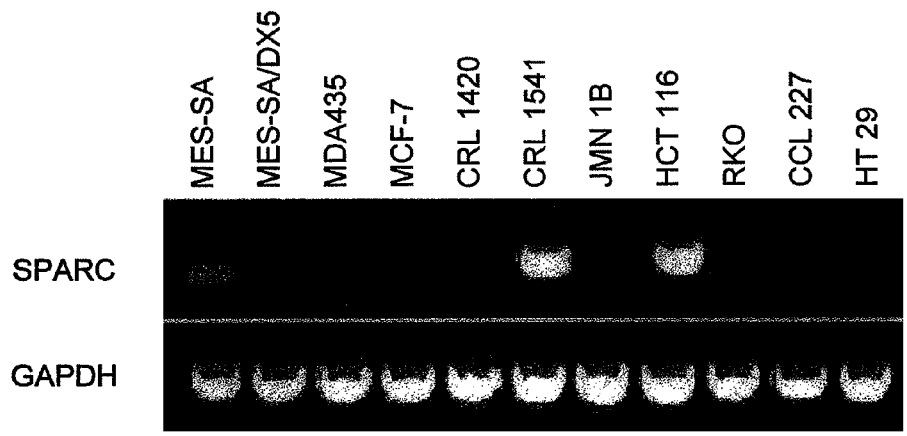
Figure 19C:
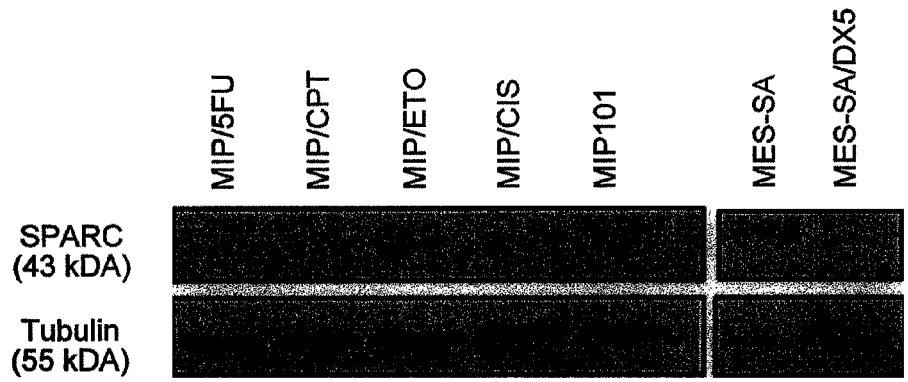
Figure 20A:
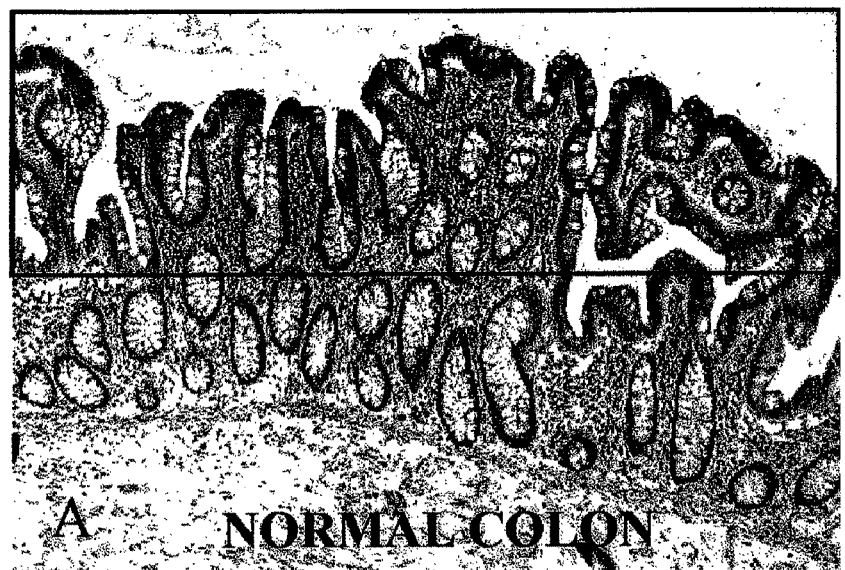
Figure 20B:
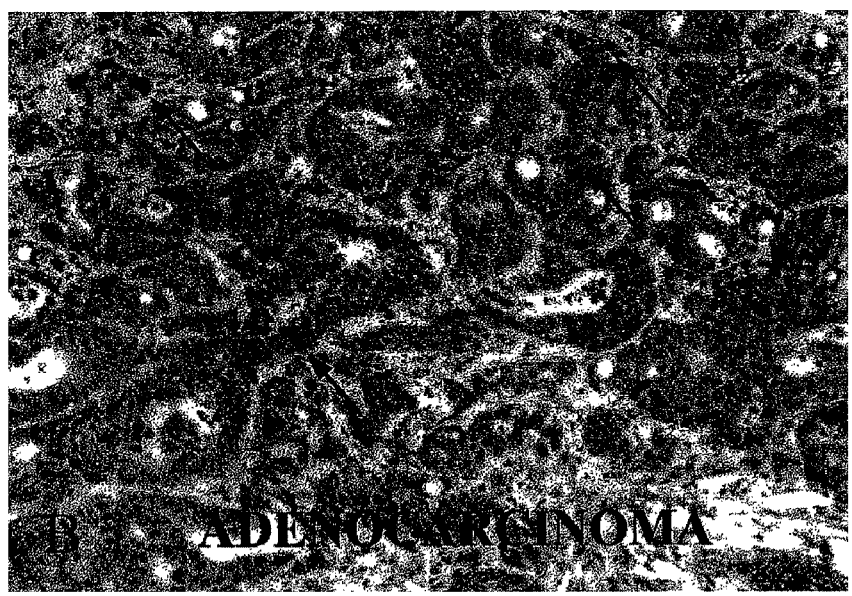
Figure 20C:
Figure 20D:
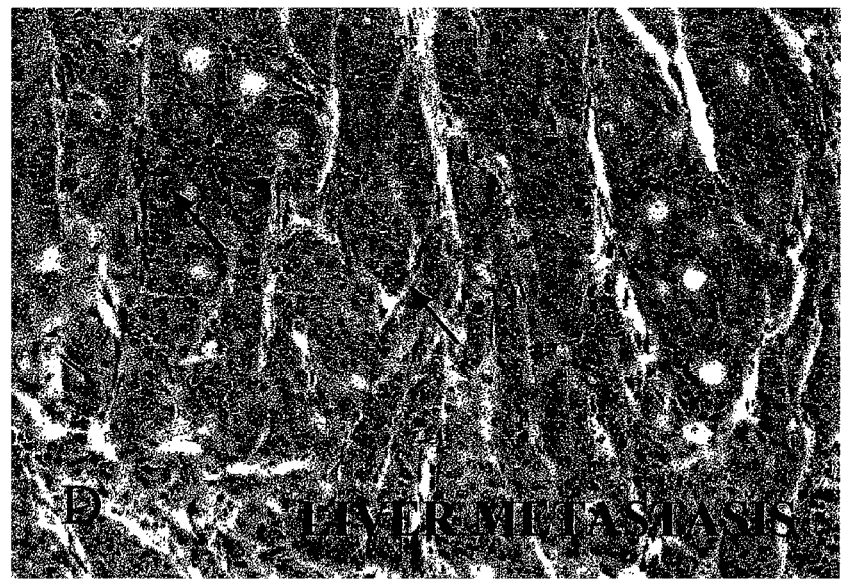
Figure 21A:
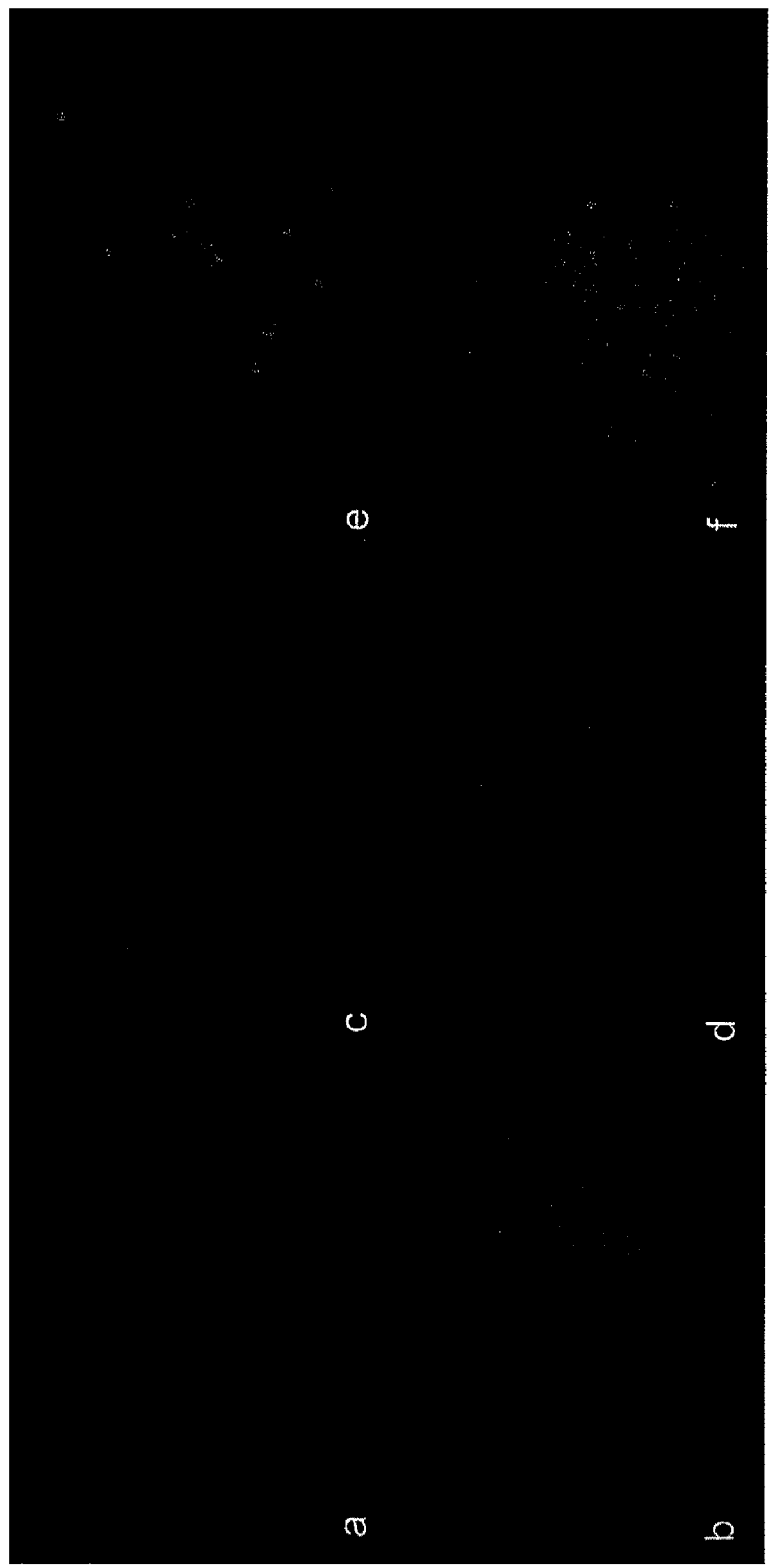
Figure 21C:
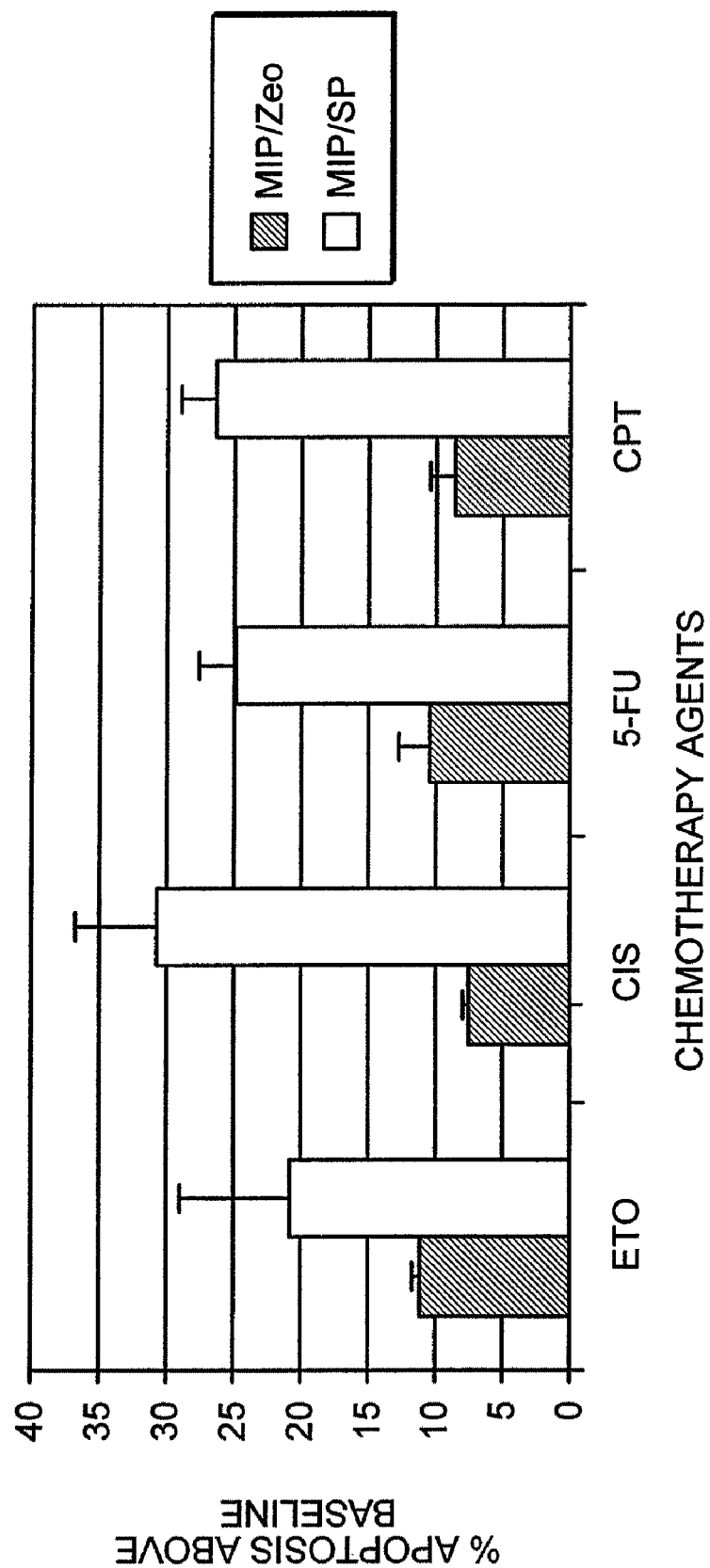

FIG. 19 shows human SPARC mRNA and protein levels in colorectal cancer cell lines sensitive and resistant to chemotherapy. (A) Oligonucleotide microarray cluster analysis diagram (left panel) reveals that SPARC gene expression is significantly lower in cell lines resistant to chemotherapy, which was confirmed by semi-quantitative RT-PCR (right panel). (B) Detection of SPARC expression levels in a paired uterine sarcoma cell line sensitive to chemotherapy (MES-SA) and resistant to doxorubicin (MES-SA/DX5) shows a similar decrease in expression in the resistant cell line. In breast cancer cell lines, MDA435 had slightly higher levels of SPARC expression than MCF-7. Low levels of expression were detected in pancreatic cancer cell line (CRL 1420), lung cancer cell line (JMN 1B), colorectal cancer lines (RKO, CCL 227, HT 29). High levels of SPARC expression was detected in normal colon cell line (CRL 1541) and a colon cancer cell line (HCT 116). (C) SPARC protein expression verifies that there is a significant decrease in this protein in the MIP101 resistant clones (resistant cell lines: MIP/5FU, MIP/CPT, MIP/ETO, MIPT/CIS) in comparison to the normal parental cell line (lane 5, MIP101). Similarly, another set of resistant cell line of uterine sarcoma origin (MES-SA/DX5, uterine sarcoma resistant to doxorubicin) shows decreased expression of SPARC in comparison to the parental sensitive cell lines (MES-SA, parental uterine sarcoma).

FIG. 20 shows SPARC protein expression in human colonic epithelium. (A) Normal colon shows a differential pattern of SPARC protein expression with higher levels of the protein within the superficial cells proximal of the lumen and a gradient of decreasing expression towards the crypts. SPARC protein levels in (B) Adenocarcinoma of the colon, (C) mucinous adenocarcinoma and (D) adenocarcinoma of the colon metastatic to liver show low level of SPARC protein diffusely within the malignant epithelium. Sections 6 µm cross sections, ×20 magnification.

Example 3

SPARC Polypeptide Sensitizes Resistant Cells to 5-FU Treatment

Figure 6:
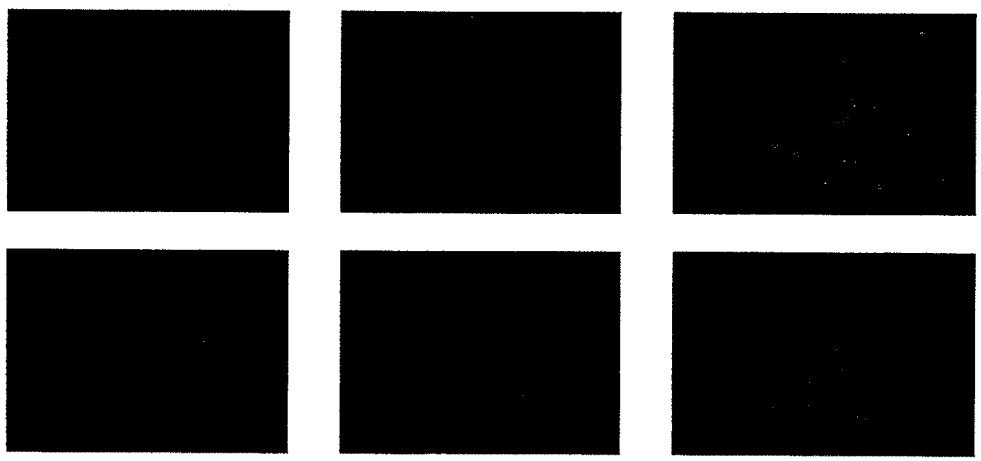
FIG. 6 is a Tunel assay showing the response of the resistant MIP101 cells to exogenous SPARC in reversing the resistant phenotype according to one embodiment of the invention.

In order to further delineate this potential role, we assessed the response of the resistant MIP101 cells (FIG. 6) to exogenous SPARC in reversing the resistant phenotype. As indicated by initial experiments, MIP101 cells resistant to 5-FU (MIP-5FUR) could not be triggered to undergo apoptosis with 5-FU at a concentration of 500 uM, while a significant number of cells from the parental, sensitive cell line underwent apoptosis following exposure to a similar concentration of 5-FU. A significant finding was observed with exogenous exposure of resistant cells with SPARC: incubation of the resistant clones with SPARC for a 24-hr period followed by a 12-hr exposure to a chemotherapeutic agent was sufficient in reversing the resistant phenotype, as apoptotic cells were once again detected by TUNEL assay in cells exposed to concentrations of chemotherapy that previously did not stimulate cell death. Incubation with exogenous SPARC alone without subsequent exposure to chemotherapy did not induce apoptosis in either the parental MIP 101 or the resistant cells.

FIG. 21 shows assessment of the effect of SPARC in influencing the sensitivity of cells to chemotherapy. (A) Effect of exposure of MIP/5FU cells to exogenous SPARC in combination with 5-FU in-vitro. Assessment of apoptosis by TUNEL assay shows positively stained cells in sensitive MIP101 cells exposed to 5-FU 1000 uM (a, TUNEL stain; b, DAPI stain) but lack of apoptosis in the resistant phenotype (c, TUNEL stain; d, DAPI stain) following exposure to a similar concentration of 5-FU. However, following a 24 hr exposure to SPARC (5 ug/ml), 5-FU resistant cells once again became sensitive to 5-FU 1000 uM as shown by TUNEL-positive stained cells (e; f, DAPI stain), indicating the presence of apoptotic cells. This is the first indication that exogenous exposure to SPARC reverses the resistant phenotype of the 5-FU resistant cells and thereby suggesting that SPARC may function as a chemotherapy sensitizer. (B) Stably transduced MIP101 cell lines overexpressing SPARC (MIP/SP) and control (MIP/Zeo) exposed to increasing concentrations of chemotherapy (5-FU, CPT-11 and etoposide) showed fewer cell colonies of MIP/SP cells when exposed to lower drug concentrations than MIP/Zeo cells, thereby indicating increased sensitivity of the SPARC overexpressing clones to chemotherapy as fewer cells survived at relatively lower concentrations of chemotherapy. (B) Greater number of MIP101 overepressing SPARC (MIP/SP) undergo apoptosis following a 12-hr exposure to various chemotherapeutic agents (ETO=etoposide, CIS=cisplatin, 5-FU=5-fluorouracil, CPT=CPT-11) in comparison to control cells (MIP/Zeo) ($p<0.05$). Analysis of apoptosis following Annexin V labeling by flow cytometry represent results of three independent studies performed in triplicate. Results of the clonogenic assay (B) is a representative experiment that was repeated three times with similar results.

Example 4

Figure 7:
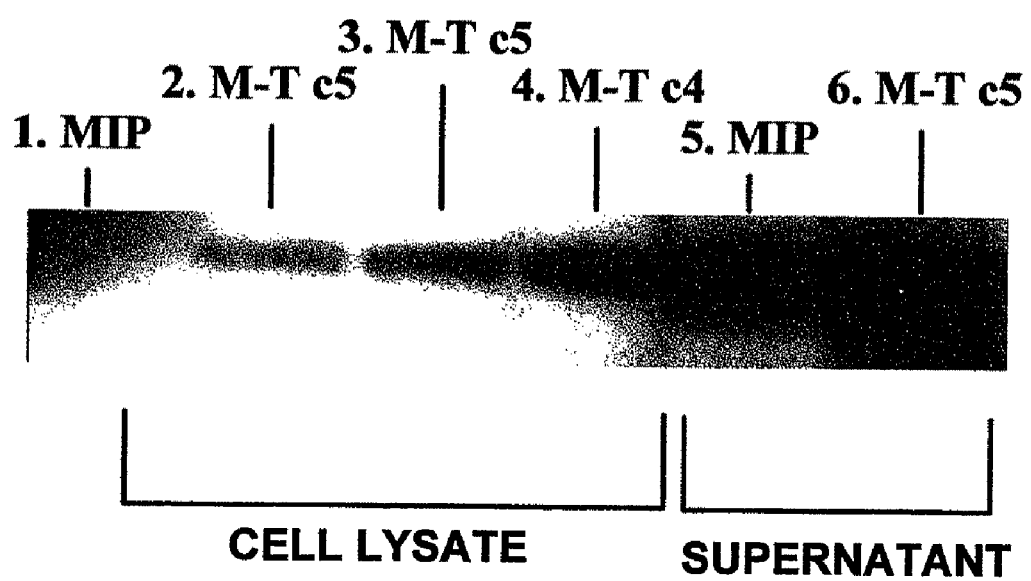
FIG. 7 is a immuno blot assay showing recombinant cells expressing SPARC polypeptide according to one embodiment of the invention.

SPARC Polynucleotide Sensitizes Recombinant Cells to Various Chemotherapy Treatment In order to test this hypothesis, MIP101 cells were transfected with SPARC for the purposes of generating overexpression systems for additional in vitro studies. Two clones overexpressing SPARC (clones 4, 5; FIG. 7) were used for subsequent studies.

Figure 9:
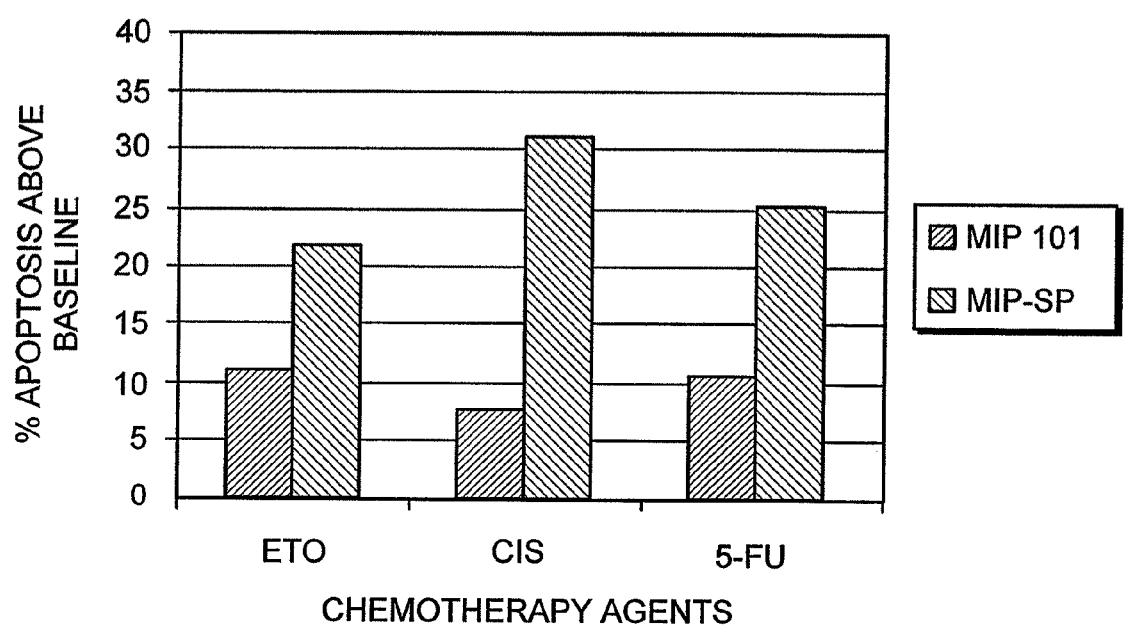
FIG. 9 is a graph showing the percentage of apoptosis of cells following exposure to chemotherapeutic agents according to one embodiment of the invention.
Figure 10:
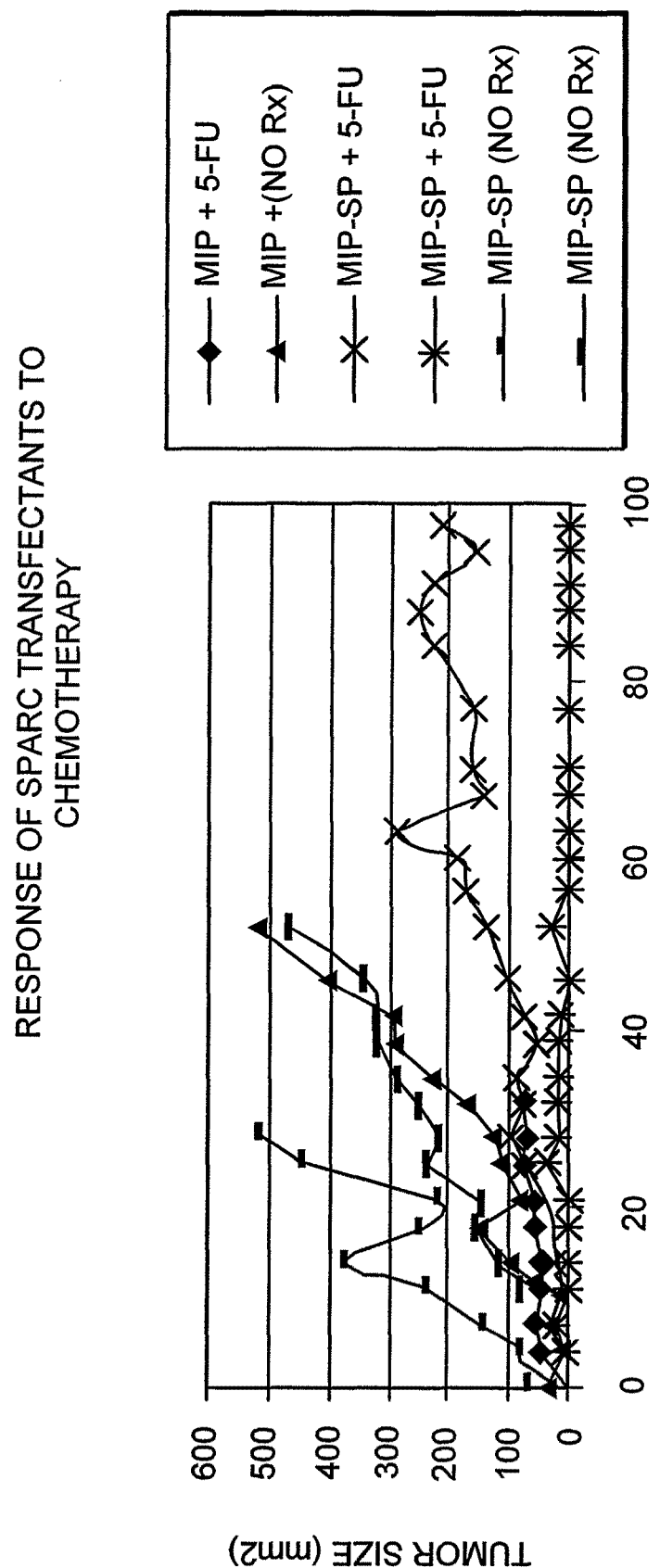
FIG. 10 is a graph showing the response of SPARC transfectants to chemotherapy agents according to one embodiment of the invention.

The sensitivity of the SPARC-transfectants to various chemotherapeutic agents was assessed by colony formation assay, which showed that clones overexpressing SPARC were unable to form tumorigenic colonies at higher concentrations of chemotherapy when compared to the parental cell lines. Similarly, FACS analysis of cell populations induced to undergo apoptosis following exposure to chemotherapeutic agents showed a dramatic shift toward early apoptosis in SPARC-transfectants (FIG. 8D) following a 12-hr exposure to chemotherapy. A smaller population of cells from the parental cell line underwent apoptosis following induction with chemotherapy only (FIG. 8C). Overall, there appeared to be at least a 2-fold increase in the population of SPARC-overexpressing cells undergoing apoptosis in comparison to the parental MIP101 cell line following exposure to various chemotherapeutic agents (FIG. 9). FIG. 10 shows the response of SPARC transfectants to chemotherapy agents.

Example 5

SPARC Sensitizing is Observed In Vivo

Figure 11:
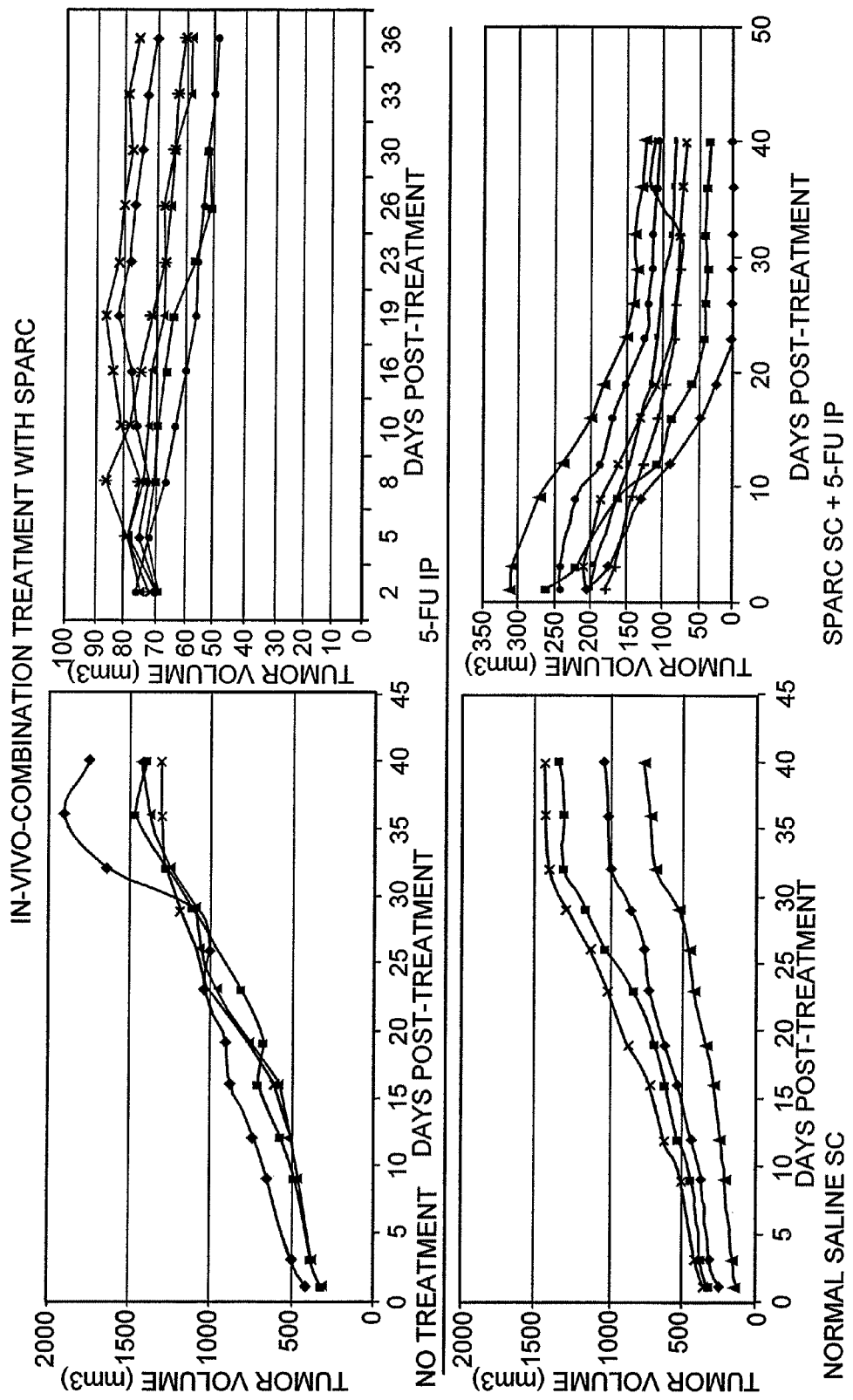
FIG. 11 is a graph presentation showing complete tumor regression in animals transplanted with SPARC-transfectants following 6 cycles of chemotherapy in two animals according to one embodiment of the invention.
Figure 12:
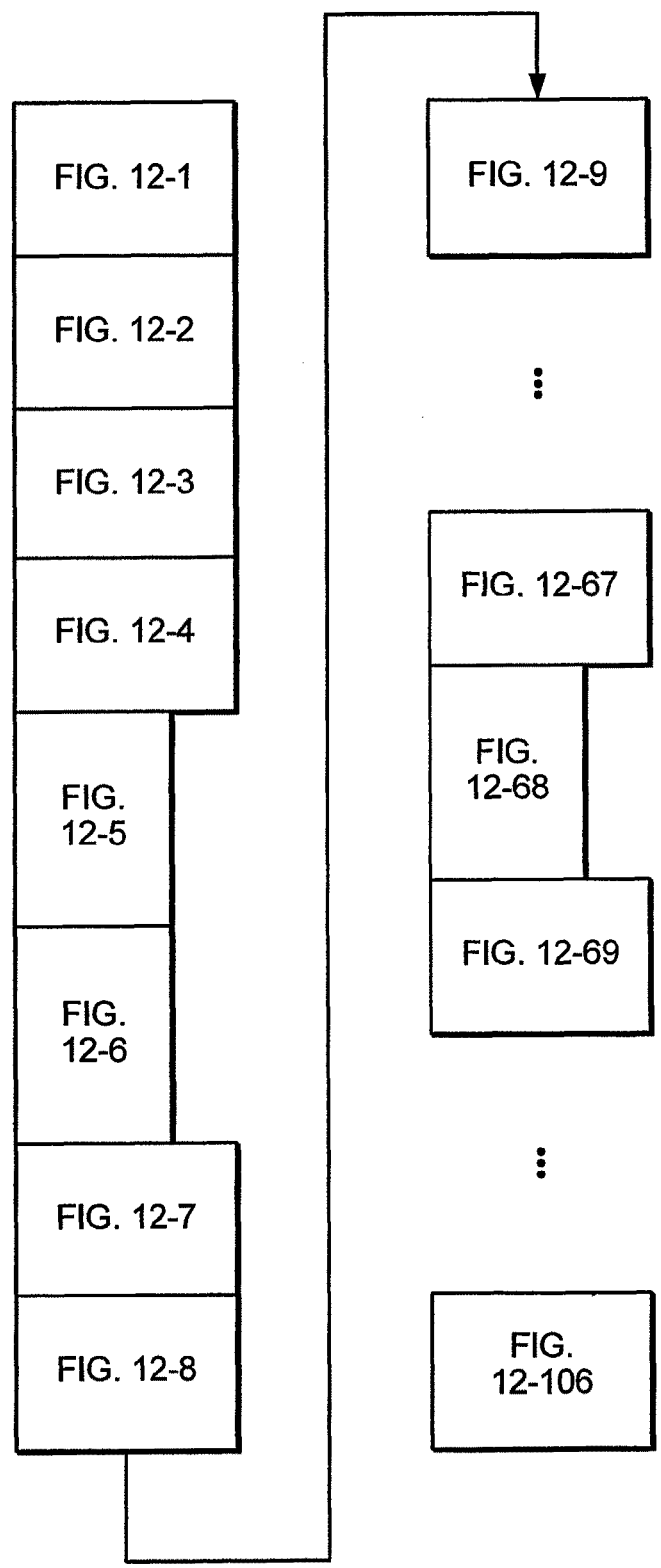
FIG. 12 is a figure containing the polynucleotide and polypeptide sequences of the SPARC family members according to one embodiment of the invention.
Figures 12, 76:

The increased sensitivity to chemotherapy in vitro translated to the in-vivo model system, two of four animals showing complete tumor regression in animals transplanted with SPARC-transfectants following 6 cycles of chemotherapy (FIG. 11). The remaining animals engrafted with SPARC-transfectants had a dramatic reduction in tumor growth rate in comparison to animals engrafted with the parental MIP101. All control animals (xenografts of MIP101 treated with chemotherapy) had tumors >400 mm$^2$ by 50 days post initiation of chemotherapeutic treatment, while animals engrafted with SPARC-transfectant that did not undergo complete tumor regression, had tumors that remained <300 mm$^2$ 140 days post-initiation of chemotherapy (result not shown).

Example 6

Method of Screening for an Agent which Modulates a SPARC Polypeptide Expression

The screening of a modulator of SPARC polypeptide expression can be performed as a simple mammalian cell-based screen. A mammalian tissue culture cell line, e.g., Hela cells are first preincubated with random candidate small molecules. Cell clones are then screened using anti-SPARC western blots or ELISA. Alternatively, a RT-PCR reaction is carried out to examining the modulation on SPARC mRNA expression.

Example 7

Additional Animal Model Therapy

Various animal model therapy was carried out and the results are shown in FIG. 14-.

In FIG. 14, xenograft animals with tumors engrafted with either MIP101 or MIP/SP treated with different chemotherapeutic agent (5-FU or CPT-11) show a more rapid rate of tumor regression of tumor xenografts of MIP/SP in comparison to tumor xenografts of the parental MIP101 cell line (MIP). Two of four animals carrying MIP/SP xenografts had complete tumor regression, while the remaining two had a much slower rate of tumor growth in comparison to the control animals carrying MIP101 exposed to a similar treatment regimen. Representative animals with a tumor xenografts of MIP-SPARC treated with 2 cycles of 5-FU had complete remission by 23 days post-transplant or significantly smaller tumors following only 2 cycles of CPT-11 in comparison to an animal transplanted with a xenograft of the parental MIP101.

In FIG. 15, more animals with xenografts of MIP/SP cells showed evidence of complete tumor regression earlier in the post-radiation treatment period than animals with xenografts of control MIP/Zeo cells. By 15 weeks after radiation therapy, none of the MIP/SP xenograft animals had evidence of tumor, while 30% of MIP/Zeo xenografts continued to harbor tumors (n=10 animals/group; total dose of radiation: 100Gy).

In FIG. 16, combination treatment with SPARC(s) (IP, intraperitoneal) and 5-FU resulted in tumor regression that was significantly greater than treatment with 5-FU alone by 51 days after initiation of treatment. (B) This combination treatment of SPARC(s) (IP) and 5-FU resulted in complete tumor regression in several animals by 84 days post-treatment, while this was not observed in animals treated with 5-FU alone. (mean±SE, n=6 animals/group).

In FIG. 17, combination treatment with SPARC(s) (SC, subcutaneous) and 5-FU resulted in tumor regression that was significantly greater than treatment with 5-FU alone throughout the treatment period. This combination treatment of SPARC(s) (SC) and 5-FU resulted in complete tumor regression in several animals by 42 days post-treatment, while this was not observed in animals treated with 5-FU alone. (mean±SE, n=6 animals/group).

In FIG. 18, animals engrafted with MIP/5FU resistant cells were treated with either 5FU alone or combination SPARC(s) and 5-FU showed that rapid tumor growth continued in animals treated with 5-FU alone, while dramatic tumor regression was observed in animals treated with the combination therapy beginning at 28 days post-treatment. Several animals receiving combination SPARC(s) and 5FU therapy showed complete tumor regression by 117 days post-treatment. (mean±SE, n=6 animals/group).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
<160> NUMBER OF SEQ ID NOS: 83

<210> SEQ ID NO 1
<211> LENGTH: 303
<212> TYPE: PRT
<213> ORGANISM: Homo sapiens

<400> SEQUENCE: 1

Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
            85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140
```

-continued

```
Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
                260                 265                 270

Cys Asp Leu Asp Asn Asp Lys Tyr Ile Ala Leu Asp Glu Trp Ala Gly
            275                 280                 285

Cys Phe Gly Ile Lys Gln Lys Asp Ile Asp Lys Asp Leu Val Ile
        290                 295                 300

<210> SEQ ID NO 2
<211> LENGTH: 2133
<212> TYPE: DNA
<213> ORGANISM: Homo sapiens

<400> SEQUENCE: 2
cgggagagcg cgctctgcct gccgcctgcc tgcctgccac tgagggttcc cagcaccatg     60
agggcctgga tcttctttct cctttgcctg gccggagggg ccttggcagc ccctcagcaa    120
gaagccctgc ctgatgagac agaggtggtg aagaaactg tggcagaggt gactgaggta    180
tctgtgggag ctaatcctgt ccaggtggaa gtaggagaat ttgatgatgg tgcagaggaa    240
accgaagagg aggtggtggc ggaaaatccc tgccagaacc accactgcaa acacggcaag    300
gtgtgcgagc tggatgagaa caacaccccc atgtgcgtgt gccaggaccc caccagctgc    360
ccagccccca ttggcgagtt tgagaaggtg tgcagcaatg acaacaagac cttcgactct    420
tcctgccact tctttgccac aaagtgcacc ctggagggca ccaagaaggg ccacaagctc    480
cacctggact acatcgggcc ttgcaaatac atccccccctt gcctggactc tgagctgacc    540
gaattccccc tgcgcatgcg ggactggctc aagaacgtcc tggtcaccct gtatgagagg    600
gatgaggaca caaaccttct gactgagaag cagaagctgc gggtgaagaa gatccatgag    660
aatgagaagc gcctggaggc aggagaccac cccgtggagc tgctggcccg ggacttcgag    720
aagaactata acatgtacat cttccctgta cactggcagt tcggccagct ggaccagcac    780
cccattgacg ggtacctctc ccacaccgag ctggctccac tgcgtgctcc cctcatcccc    840
atggagcatt gcaccacccg cttttttcgag acctgtgacc tggacaatga caagtacatc    900
gccctggatg agtgggccgg ctgcttcggc atcaagcaga aggatatcga caaggatctt    960
gtgatctaaa tccactcctt ccacagtacc ggattctctc tttaaccctc cccttcgtgt   1020
ttcccccaat gtttaaaatg tttggatggt tgttgttct gcctggagac aaggtgctaa   1080
catagattta agtgaataca ttaacggtgc taaaaatgaa aattctaacc caagacatga   1140
cattcttagc tgtaacttaa ctattaaggc cttttccaca cgcattaata gtcccatttt   1200
tctcttgcca tttgtagctt tgcccattgt cttattggca catgggtgga cacggatctg   1260
```

```
ctgggctctg ccttaaacac acattgcagc ttcaacttttt ctctttagtg ttctgtttga    1320
aactaatact taccgagtca gactttgtgt tcatttcatt tcagggtctt ggctgcctgt    1380
gggcttcccc aggtggcctg gaggtgggca aagggaagta acagacacac gatgttgtca    1440
aggatggttt tgggactaga ggctcagtgg tgggagagat ccctgcagaa tccaccaacc    1500
agaacgtggt ttgcctgagg ctgtaactga gagaaagatt ctggggctgt cttatgaaaa    1560
tatagacatt ctcacataag cccagttcat caccatttcc tcctttacct ttcagtgcag    1620
tttcttttca cattaggctg ttggttcaaa cttttgggag cacggactgt cagttctctg    1680
ggaagtggtc agcgcatcct gcagggcttc tcctcctctg tcttttggag aaccagggct    1740
cttctcaggg gctctaggga ctgccaggct gtttcagcca ggaaggccaa aatcaagagt    1800
gagatgtaga aagttgtaaa atagaaaaag tggagttggt gaatcggttg ttctttcctc    1860
acatttggat gattgtcata aggtttttag catgttcctc cttttcttca ccctcccctt    1920
tgttcttcta ttaatcaaga gaaacttcaa agttaatggg atggtcggat ctcacaggct    1980
gagaactcgt tcacctccaa gcatttcatg aaaaagctgc ttcttattaa tcatacaaac    2040
tctcaccatg atgtgaagag tttcacaaat ctttcaaaat aaaagtaat gacttagaaa    2100 ctgaaaaaaa aaaaaaaaaa aaaaaaaaaa aaa    2133
```

<210> SEQ ID NO 3
<211> LENGTH: 302
<212> TYPE: PRT
<213> ORGANISM: Mus musculus

<400> SEQUENCE: 3

```
Met Arg Ala Trp Ile Phe Phe Leu Leu Cys Leu Ala Gly Arg Ala Leu
1               5                   10                  15

Ala Ala Pro Gln Gln Thr Glu Val Ala Glu Glu Ile Val Glu Glu Glu
            20                  25                  30

Thr Val Val Glu Glu Thr Gly Val Pro Val Gly Ala Asn Pro Val Gln
        35                  40                  45

Val Glu Met Gly Glu Phe Glu Asp Gly Ala Glu Thr Val Glu Glu
    50                  55                  60

Val Val Ala Asp Asn Pro Cys Gln Asn His His Cys Lys His Gly Lys
65                  70                  75                  80

Val Cys Glu Leu Asp Glu Ser Asn Thr Pro Met Cys Val Cys Gln Asp
                85                  90                  95

Pro Thr Ser Cys Pro Ala Pro Ile Gly Glu Phe Glu Lys Val Cys Ser
            100                 105                 110

Asn Asp Asn Lys Thr Phe Asp Ser Ser Cys His Phe Phe Ala Thr Lys
        115                 120                 125

Cys Thr Leu Glu Gly Thr Lys Lys Gly His Lys Leu His Leu Asp Tyr
    130                 135                 140

Ile Gly Pro Cys Lys Tyr Ile Ala Pro Cys Leu Asp Ser Glu Leu Thr
145                 150                 155                 160

Glu Phe Pro Leu Arg Met Arg Asp Trp Leu Lys Asn Val Leu Val Thr
                165                 170                 175

Leu Tyr Glu Arg Asp Glu Gly Asn Asn Leu Leu Thr Glu Lys Gln Lys
            180                 185                 190

Leu Arg Val Lys Lys Ile His Glu Asn Glu Lys Arg Leu Glu Ala Gly
        195                 200                 205

Asp His Pro Val Glu Leu Leu Ala Arg Asp Phe Glu Lys Asn Tyr Asn
    210                 215                 220
```

```
Met Tyr Ile Phe Pro Val His Trp Gln Phe Gly Gln Leu Asp Gln His
225                 230                 235                 240

Pro Ile Asp Gly Tyr Leu Ser His Thr Glu Leu Ala Pro Leu Arg Ala
            245                 250                 255

Pro Leu Ile Pro Met Glu His Cys Thr Thr Arg Phe Phe Glu Thr Cys
                260                 265                 270

Asp Leu Asp Asn Asp Lys Tyr Ile Ala Leu Glu Glu Trp Ala Gly Cys
            275                 280                 285

Phe Gly Ile Lys Glu Gln Asp Ile Asn Lys Asp Leu Val Ile
        290                 295                 300

<210> SEQ ID NO 4
<211> LENGTH: 2079
<212> TYPE: DNA
<213> ORGANISM: Mus musculus

<400> SEQUENCE: 4
```

| | | | | | |
|---|---|---|---|---|---|
| gcattcctgc | agcccttcag | accgccagaa | ctcttctgcc | gcctgcctgc | ctgcctgcct | 60 |
| gcctgcctgt | gccgagagtt | cccagcatca | tgagggcctg | gatcttcttt | ctcctttgcc | 120 |
| tggccgggag | ggccctggca | gcccctcagc | agactgaagt | tgctgaggag | atagtggagg | 180 |
| aggaaaccgt | ggtggaggag | acaggggtac | ctgtgggtgc | caacccagtc | caggtggaaa | 240 |
| tgggagaatt | tgaggacggt | gcagaggaaa | cggtcgagga | ggtggtggct | gacaacccct | 300 |
| gccagaacca | tcattgcaaa | catgcaaggt | gtgtgagctg | gacgagagc | aacaccccca | 360 |
| tgtgtgtgtg | ccaggacccc | accagctgcc | ctgctcccat | ggcgagtttt | gagaaggtat | 420 |
| gcagcaatga | caacaagacc | ttcgactctt | cctgccactt | ctttgccacc | aagtgcaccc | 480 |
| tggagggcac | caagaagggc | cacaagctcc | acctggacta | catcggacca | tgcaaataca | 540 |
| tcgcccctg | cctggattcc | gagctgaccg | aattccctct | gcgcatgcgt | gactggctca | 600 |
| aaaatgtcct | ggtcaccttg | tacgagagag | atgagggcaa | caacctcctc | actgagaagc | 660 |
| agaagctgcg | tgtgaagaag | atccatgaga | tgagaagcg | cctggaggct | ggagaccacc | 720 |
| ccgtggagct | gttggcccga | gacttttgaga | agaactacaa | tatgtacatc | ttccctgtcc | 780 |
| actggcagtt | tggccagctg | gatcagcacc | ctattgatgg | gtacctgtcc | cacactgagc | 840 |
| tggccccact | gcgtgctccc | ctcatcccca | tggaacattg | caccacacgt | ttctttgaga | 900 |
| cctgtgacct | agacaacgac | aagtacattg | ccctggagga | atgggccggc | tgctttggca | 960 |
| tcaaggagca | ggacatcaac | aaggatctgg | tgatctaagt | tcacgcctcc | tgctgcagtc | 1020 |
| ctgaactctc | tccctctgat | gtgtcacccc | tcccattacc | cccttgttta | aaatgtttgg | 1080 |
| atggttggct | gttccgcctg | gggataaggt | gctaacatag | atttaactga | atacattaac | 1140 |
| ggtgctaaaa | aaaaaaaaa | aacaaagtaa | gaaagaaact | agaacccaag | tcacagcatt | 1200 |
| ttcccacata | actctgaggc | catggcccat | ccacagcctc | ctggtcccct | gcactaccca | 1260 |
| gtgtctcact | ggctgtgttg | gaaacggagt | tgcataagct | caccgtccac | aagcacgaga | 1320 |
| tatctctagc | tttcatttca | attttgcatt | tgactcttaa | cactcaccca | gactctgtgc | 1380 |
| ttatttcatt | ttgggggatg | tgggcttttt | cccctggtgg | tttggagtta | ggcagaggga | 1440 |
| agttacagac | acaggtacaa | aatttgggta | aagatactgt | gagacctgag | gacccaccag | 1500 |
| tcagaaccca | catggcaagt | cttagtagcc | taggtcaagg | aaagacagaa | taatccagag | 1560 |
| ctgtggcaca | catgacagac | tcccagcagc | ccgggacctt | gctgtcttct | cgactcttcg | 1620 |
| ggcgtttctt | tccatgtttg | gctgttggtt | ttagttttgg | tgagccatgg | gtgggccaga | 1680 |

```
acatcactca actgcaattg ggctttcagg ttcttgccgg gagctctagg cactgggagg    1740
ctgtttcagg aaagtgagac tcaagaggaa gacagaaaag gttgtaacgt agaggaagtg    1800
agactggtga attggtttga ttttttttcac atctagatgg ctgtcataaa gtttctagca    1860 tgttcccct cacctctccc cacccctgc cacttgaaac cttctactaa tcaagagaaa      1920
cttccaagcc aacggaatgg tcagatctca caggctgaga aattgttccc ctccaagcat    1980
ttcatgaaaa agctgcttct cattaaccat gcaaactctc acagcgatgt gaagagcttg    2040
acaagtcttt caaaataaaa agtaacaact tagaaacgg                            2079

<210> SEQ ID NO 5
<211> LENGTH: 345
<212> TYPE: PRT
<213> ORGANISM: Homo sapiens

<400> SEQUENCE: 5
```

Met Leu Pro Cys Phe Gln Leu Leu Arg Ile Gly Gly Arg Gly Gly
1               5                   10                  15

Asp Leu Tyr Thr Phe His Pro Pro Ala Gly Ala Gly Cys Thr Tyr Arg
            20                  25                  30

Leu Gly His Arg Ala Asp Leu Cys Asp Val Ala Leu Arg Pro Gln Gln
        35                  40                  45

Glu Pro Gly Leu Ile Ser Gly Ile His Ala Glu Leu His Ala Glu Pro
    50                  55                  60

Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
        195                 200                 205

Gly Glu Val Gly Thr Thr Pro Ser Ala Pro Pro Gln Arg Asn Arg Arg
    210                 215                 220

Lys Ser Val His Arg Val Leu Ala Glu Leu Asp Asp Glu Ser Glu Pro
225                 230                 235                 240

Pro Glu Asn Pro Pro Pro Val Leu Met Glu Pro Arg Lys Lys Leu Arg
                245                 250                 255

Val Asp Lys Ala Pro Leu Thr Pro Thr Gly Asn Arg Arg Gly Arg Pro
            260                 265                 270

Arg Lys Tyr Pro Val Ser Ala Pro Met Ala Pro Ala Val Gly Gly
        275                 280                 285

Gly Glu Pro Cys Ala Ala Pro Cys Cys Cys Leu Pro Gln Glu Glu Thr
    290                 295                 300

Val Ala Trp Val Gln Cys Asp Gly Cys Asp Val Trp Phe His Val Ala

```
            305                 310                 315                 320
Cys Val Gly Cys Ser Ile Gln Ala Ala Arg Glu Ala Asp Phe Arg Cys
                325                 330                 335

Pro Gly Cys Arg Ala Gly Ile Gln Thr
            340                 345

<210> SEQ ID NO 6
<211> LENGTH: 265
<212> TYPE: PRT
<213> ORGANISM: Homo sapiens

<400> SEQUENCE: 6

Met His Phe Tyr Arg Leu Phe Leu Gly Ala Thr Arg Arg Phe Leu Asn
1               5                   10                  15

Pro Glu Trp Lys Gly Glu Ile Asp Asn Trp Cys Val Tyr Val Leu Thr
            20                  25                  30

Ser Leu Leu Pro Phe Lys Ile Gln Ser Gln Asp Ile Lys Ala Leu Gln
        35                  40                  45

Lys Glu Leu Glu Gln Phe Ala Lys Leu Leu Lys Gln Lys Arg Ile Thr
    50                  55                  60

Leu Gly Tyr Thr Gln Ala Asp Val Gly Leu Thr Leu Gly Val Leu Phe
65                  70                  75                  80

Gly Lys Val Phe Ser Gln Thr Thr Ile Cys Arg Phe Glu Ala Leu Gln
                85                  90                  95

Leu Ser Phe Lys Asn Met Cys Lys Leu Arg Pro Leu Leu Gln Lys Trp
            100                 105                 110

Val Glu Glu Ala Asp Asn Asn Glu Asn Leu Gln Glu Ile Cys Lys Ala
        115                 120                 125

Glu Thr Leu Val Gln Ala Arg Lys Arg Lys Arg Thr Ser Ile Glu Asn
    130                 135                 140

Arg Val Arg Gly Asn Leu Glu Asn Leu Phe Leu Gln Cys Pro Lys Pro
145                 150                 155                 160

Thr Leu Gln Gln Ile Ser His Ile Ala Gln Gln Leu Gly Leu Glu Lys
                165                 170                 175

Asp Val Val Arg Val Trp Phe Cys Asn Arg Arg Gln Lys Gly Lys Arg
            180                 185                 190

Ser Ser Ser Asp Tyr Ala Gln Arg Glu Asp Phe Glu Ala Ala Gly Ser
        195                 200                 205

Pro Phe Ser Gly Gly Pro Val Ser Phe Pro Leu Ala Pro Gly Pro His
    210                 215                 220

Phe Gly Thr Pro Gly Tyr Gly Ser Pro His Phe Thr Ala Leu Tyr Ser
225                 230                 235                 240

Ser Val Pro Phe Pro Glu Gly Glu Ala Phe Pro Pro Val Ser Val Thr
                245                 250                 255

Thr Leu Gly Ser Pro Met His Ser Asn
            260                 265

<210> SEQ ID NO 7
<211> LENGTH: 14468
<212> TYPE: DNA
<213> ORGANISM: Homo sapiens

<400> SEQUENCE: 7
tctaaggctg ttctgatctc ttcatctgtc ccttcacctg gcccctgtac cccgttcccc      60
tttggacccc ttgaaccctc ccaggacccc cgctcagccc cttcccgccc caaccgact     120 cttcccgaac gtcccttacc aaccgcgaga gccccctact gcgctttggc cacacccct    180
```

```
acgcctcgct cccggccccg cctctgcccc tgaccgcgcc tgcgcaaggc gggcgcccta    240
aagtcctatt tcactctgtt gggaggaggg ggaaaggtgt acgcaggcgc agtggcgtct    300
aaatttgggc ccactaaatg cgtcggagca tctccgcgcc caggcggctc ctcctcactg    360
cggcaacccg ggaaaacttg tgaactaatc agaaaagtg gaaggcggga gatcttgggg     420
cgctgtccaa tggcgcggaa gagaacaaat gagctggcca atcggaacg gcacgggggc     480 gggctcgctc ggcgcgaagt tcgggcccgg gaattccgaa ggaggggtag gcgctgcccg    540
cgcgcagagg ccgcgcccct cctgccccg gcttcttggc tgtcaaacag atgcagcaac     600
gtcggctcct gccgaggagc ccaaggggtc ccgggatccg ccgcacaggc tggcactgct    660
tgaagaggag gctactcgga gactgcgccg cgcgggtaga tccgaaacgg ggctggggcg    720
gagtgggaaa aggccgggta tgccttgcat gatcgcgggg agctccttcc tgtttttatc    780
ccacctagag aagccgggaa gtaggggttt aggtccaatt tgttggagta cttaaggact    840
cgtttgcact ttcttttggg ggatgacagt ggattcattg ccctcggagg ttcaaccagt    900
tatgagtgag ggattggcca gaagatcggg gcgcaggcaa gcaggagtgc tctattagga    960
taagcaagtt tgacaggaag aagctgctct tctccgaatt acacagaggt gatgtgttcg    1020
tattgcacgt agacgtgtgt ataacaggac ctccttcccc gcgccccgcc accccgacac    1080
acacaggagc tgcctaaagt atccttgcct tgcagattgg aggctcccca aatattttgt    1140
gatctgagga tccagctcaa gtgaggtgcc ataggacgtg ttcctgagtt tgcattgcac    1200
ggagaccttc ctggaatttt tcatttgcaa gtcggcttaa ccaattttgc attgagtcct    1260
aggctgcttg cactctgaat ttgggctatt caggtagtgt gctcaaagtt gaaaccgcat    1320
acagcacaac tcaagtttgc atcagactgg gaagcgaact taagccagcg gtgcgtggcc    1380
caggagtggg aaaggaaatg gatgcctgaa gtggaagagg tggtgcagag ggggcaccgc    1440
ccatgctgcc ctgcttccaa ctgctgcgca taggggcgg caggggcggt gatctctaca    1500
ccttccaccc ccccgccggg gctggctgca cctatcgctt gggccacagg gccgacctgt    1560
gtgatgtggc cctgcggccc cagcaggagc ctggcctcat ctctgggatc cacgccgaac    1620
tgcatgccga gccccggggt gatgactgga gggtcagcct ggaagaccac agcagccaag    1680
gtgagcatta agcagggcag cttttgcccct gggtggttga agcgccaggc tggaatgagt    1740
aaggtctcca caagaccctg ctgcctgcct cccatactcc catcagattg gatggatagt    1800
cgtggtccag accttcatct tcccaccaga agtgtgcaca gtcagaagct ctctgccaga    1860
ctgacccttt ttggtcccgt ttagctcata caggacctgg gatatcatca gaaagatatc    1920
acagtgggga tgttctgagg ccactagagg ccaagtttag acttgattca gtttccagct    1980
ttgctgaggc actctgttcc tgggttaggg cagttctatg ttgaataatg ttttaataa     2040 tctgggcatg tctttctccg tgacttgagg cagttagcct cagaaagcct agattcacat    2100
ttgagttttg ccactgcctc ttggtaaagt cagctgtagg agtgttatgg ttattagact    2160
atagtagcca acattcatct agtgcttact gttatgagcc aggccctatt ttaagtgtat    2220
tgaatgtagg tggtactaat attatcctca tttacagtaa aggaaaatga ggcacaaaga    2280
ggttaaggaa cttgtccagg gctgggcatg gtggtttaca cctataatcc agcactttgg    2340
gaggctaagg cagggtggat cacttgagct caggagttcg agaccagcct gggcaacatg    2400
gtgaaaacct gtctctacca aaaaattaat taattttta aaaaagcct gggcgcggtg     2460 gctcacgcct gtaatcccag cactttggga ggccgagatg gcagatcac gaggtcagga    2520 gttcgagacc atcctgacca acatgttgaa accccatctg tgctgaaaaa aaaatacaaa    2580
```

```
aattagccag gtgtggtggc gtgcacctgt aacccagct actcaggagg ctgaagcagc   2640
agaatcactt gaacccggga ggcggaggtt gcagtgagct gagatcgcac cactgcactc   2700
cagcttgggc gacagagcga gactccatct caaacaaaca aacaaaccaa aagcttgccc   2760
agggtcacat aactggtaag tggtagagct aggatctgaa cgagctggag ctgggggaga   2820
gtgagcatgt ttgaaaactg gaccttaggg cggggcacgg tggctcacgc ctgtaatccc   2880
agcactttgg gaggctgagg cgggcagatc aggaggtcag gagtatgaga ccagcctggc   2940
caacatggta aaaccctgtc tctgctaaaa ataaaaaaat tagccagacg tggtggcaca   3000
tgcctgtaat cccagctact caggaggctg aggcaggaga attgcttgaa cctgggaggc   3060
ggttcaagct tgggcaatag agcaaaactc catctcaaaa aaaaaaaag aaagaaaaaa   3120 aaagaagaaa gaaagaaaat tggaccttag gacagtgagg gcagggatcc tttgtaggaa   3180
agcacaagaa acacagactt gttcctagct gacaaggagt gtactgcctg gtacctgtca   3240
cctgctgagg ggcttaggat gtgagggaga atctgactac agtttcatat tcttccccag   3300
aaatcataca gatttctcca ctcctgactc tggtcatttc tgttttttgtc ctccatattt   3360 gcctggtgcc ccaccatcaa caggtacttt ggtcaataat gtccgactcc caagaggtca   3420
caggctggaa ttgagtgatg gagacctcct gacctttggc cctgaagggc cccaggaac    3480 cagcccctcg gagttctact tcatgttcca acaagtacga gtcaagcctc aggactttgc   3540
tgccattacc atcccacggt ctaggggaga agcccgggtt ggggctggtt tccggcctat   3600
gctgccctcc caggggggctc cacagcggcc tctcagcacc ttctccctg ccccaaggc    3660 cacactgatc ctaaactcca taggcagcct cagcaagctc cggccccagc ccctcacctt   3720
ctcccctagt tggggtggac caaagagcct gcctgttccc gccccacctg ggaagtggg    3780 gaccacgcct tctgctccac cccaacgcaa tcggaggaaa tctgttcacc gagtgttggc   3840
ggaactggat gatgagagtg agcctcctga gaacccgcca ccggtcctta tggagcccag   3900
gaagaaactc cgtgtagaca aagccccact gactcccact gggtaagtgg agtcctcact   3960
tggccctctc agtgttttac tgcttttcga ttccttgtat ccctaggctg tgaggaggtc   4020
cccctgcctg gggggatggg cacgggaggt ggaatagatg gaatggcaag acctgggtta   4080
gctctgatag gaaagaaaaa atatgtgcag gagaacatga gaggtggggt ggggcagtgc   4140
ttataaaaca accggagtga gcatgtcctg ctttttacat tcatatggct ttaacccat    4200 tcttctagtg cctaaggatg gggaactttc aggctcacac tagaggtttt taggcccacc   4260
ctatgtgttt ttaaggacag agtccaggct caccttagtt ctcagaccac tgtgcctctg   4320
tggcctcacc ctatgaccag ccataggggtg gcaaggtcta ggccttctcc tacaggtttc   4380
cggtgaccct tgtgtctgtg tcacttcctt cagaaatcga cgtggccgtc ctcggaagta   4440
cccagtgagc gctcccatgg ctcccccctgc agttgggggc gggagccct gtgcagctcc    4500 ttgttgctgc ctgccccagg aagagacagt ggcctgggtt cagtgtgatg gctgtgacgt    4560
ctggttccat gtggcctgtg ttggctgcag catccaggct gccagggagg ccgacttccg    4620
atgcccaggg tgccgggctg gcattcagac ctaaggtcca ccgccaaggc accatcggac    4680
acacctgccc atgagtagac acagcagcga gcaaataggt ctgataaata ccccccttcc    4740
cttccctccc caagagggaa tgactacagg gaagaaggat ggattgatgt ggactcattc    4800
agggcctgga gcagaccctg gtggccaaga cagaagagat ggtttcctgc caaagatatt    4860
gccacctcca ggaaattgcc agtgagctgg aagttcccac tattacaagc cataaggcca    4920
tgttgccatg gacaccagaa tatctgtagt cagagcacct atcagttgca aaagccatgc    4980
```

```
ctgcaaccga tggaaaatgt aagagggagt tcttaaggtt cttggtgcca tcacccaagg   5040
cattctggga aaacctaggg cctggcccca aaacttccct actctgtggc tagtcctgct   5100
gccaacaaaa tcgtagcgac ctggcttttc acagctttgc ttttatttcc aagtcaagga   5160
caagccgctt cattcactcc tgggcattta ctcttcttgt gggtctgtga tattccttgc   5220
tttccaggga gaatgtgctt ggcaaggtct ggagaactaa ttcagaatct taggggaagg   5280
ggagagatgg aaatacaaac ctgcttactg gaaaggtgca aatatatggg ttgagctgga   5340
ggtaggaata caggtaatta aggtttctag tttaagggaa aacagatcta ttgccattta   5400
aataaggtaa ctgggatttg gttaagttca caaagatagc agaagattta tttacaggct   5460
tcacctgtac tgtcagggca agagaaagcc tggtaaacca gctacagcag tttaccagtg   5520
tgatggctgt gacacagctc cactccacgg gtggacacag cagagggcaa ctgggctggc   5580
ctggttcagt gtgaatcaaa ccgcttaacc cacacatggt acatgtgatt ttcttttgtg   5640
agccttacac caagccaaac tattgtcaaa gcatcatttc tatagaaata aagccttatc   5700
ttgacctgtt ctattaaaac ctgccacatc cgcccttttcc tacctagatt taatgagccc   5760 aagtttttt acatggaaga aatgactctg ggcaaagac ccctaatgaa ctagtggcag   5820
agccaggaat aaaacttgag taactaatga gtcacttatg ggcagagtat gcaaaaacct   5880
taagtggaaa ccaaatagac cctggtatca agaaagcaca agtattaat agaagtttct   5940 ggttggggtg atctaggttc aacagaaata agatgatttc taagtataaa gccatttaag   6000
aattccagag taggggtggga aagcaaaaag ccagctctga acaggtaaca gctacatggt   6060
gactgagtct atgggcaaaa gttcttgcat cacaggcttt tgggaactag cctatcacag   6120
ggccctgtac aaataaactt ggctgcaatc ccagctctcc ctctgatgtt gtgtgacctt   6180
aaggagtgta aatggcacct tagtttcagg gtcacttggg tatgagcatt ggatattccc   6240
atccccacct cagtaactga aggacaaacc aagataagtg tgtctatcta ctgtgtccca   6300
agcttcttta tttaagaaaa aagtgataca tgatgtggga ttaaaatcaa gagcatcatt   6360
gaacttcacc ttccctccaa ccagttgccc caaactcccc tgcccccacc ctttgtgttc   6420
ccaattcctt ccttagtgaa tgaagaactt aatcccaaaa accctggcac aaaactccagg   6480 tttttctttcc ctagctcctc ccctcccccct gtccccattt cctagaaggg caggcacctc   6540
agtttgaatg catgggagag cccagagtgg tgacagagac aggggggaaag gcttcccccct   6600 cagggaaagg gaccgaggag tacagtgcag tgaagtgagg gctcccctag cctggggtac   6660
caaaatgggg ccctggggcc agaggaaagg acactggtcc ccctgagaaa ggagacccag   6720
cagcctcaaa atcctctcgt tgtgcatagt cgctgcttga tcgcttgccc ttctggcgcc   6780
ggttacagaa ccacactcgg accacctgcc agtgaatgac agaaaggaga atgacattag   6840
acaatgagct gagagacggg cctgactctg cttggacatt ctatccaaag ccaacagccc   6900
tagagcagtt agaggaggac attagagaat gagctgagac aggcctgact gcttggacat   6960
tctgtccaaa gccaacagcc ctagagcagt tggaggagcc agagctaggg aaagcgaggt   7020
ggtgacaggg gaaagagatg gagcccgcag agagacatgg cactcacatc cttctcgagc   7080
ccaagctgct gggcgatgtg gctgatctgc tgcagtgtgg gtttcgggca ctgcaggaac   7140
aaattctcca ggttgcctct cactcggttc tcgatacttt tcgctttct ctttcgggcc   7200 tgcacgaggg tttctgcttt gcatatctgt gcaggtggga aggggtgac aagggcaagc   7260 tttggacttg ctgagtaaca gcatcacagg ggtctgtgac tagatgtgtc agcagagcca   7320
ggtggtggtg tgaaaaggca ggatcctgga agggttggct ctggacctta tcccagcaga   7380
```

```
actgaggaat tcactccat cccactgaga accactgcac caaagacgga gagctacgag    7440
ccagtgatgg aagcaatgga aattaggcca agaaagggaa ggtccccggg tatcccccctc   7500 ccacccttac ctcctgaaga ttttcattgt tgtcagcttc ctccacccac ttctgcagca    7560
agggccgcag cttacacatg ttcttgaagc taagctgcag agcctcaaag cggcagatgg    7620
tcgtttggct gaataccttc cctgggggag gccagtcaaa agagaagcaa atgagggag    7680 cacgcagggc ccttgtgacc ctgagatcca agcttaccac ctcttcccag agggagctca    7740
aagcccaagc atcttctccc tctccctact cctcttcatg ggtgagggta gagtctgccc    7800
ctgcccctcc ccactaggtt cagggatact ccttagaggg gagatgcggt cagaatctgc    7860 agagggaac ccaccaaata gaaccccag ggtgagcccc acatcggcct gtgtatatcc      7920
cagggtgatc ctcttctgct tcaggagctt ggcaaattgc tcgagttctt tctgcagagc    7980
tttgatgtcc tgggactgga ttttaaaagg cagaagactt gtaagaacat aaacacacca    8040
gttatcaatc tcccctttcc attcgggatt caagaaccta cgtgtggccc caaggaatag    8100
tctgtagaag tgcatctgcc ttccaagctg cccacctaac ttctagaaat aacctaccca    8160
caaatgtcat tcacccattc cctgttcact gactcatgca tgtaacaaag gactactctt    8220
cccccagaaa ctggcacatc caagggatgc agagcatggt gaaaggacag aaagagagac    8280
cctggcctcg aggagaacac ctgtcaggtt atgaaggtta gaagttcttt gctgggcgcg    8340
gtggctcatg cctataattc cagcactttg ggaggccgag gtgggcagat cacgaggtca    8400
ggagttcaag accagcatgg ccaacatggt gaaaccccgt ctctactaaa aacacaaaaa    8460
ttagctgggc acggtggcac gcacctgtaa tcccagctac tcaggaggct gaggcaggag    8520
aatcacttga acccgggagg cggaggttgc agtgagctga gatcacgcca ctgcactcca    8580
gcctgggtga cagagcaaga ctctgtctca agaaaaaaa aaagaagat agttcattta    8640 atacctgcaa aattctctca ctcaagtatc accccagtt taaggatgtt ttgagattag    8700
agaaatagat aagctgctaa gttctgggtt aattaaaaag gaagagcatc atgtctcaga    8760
agctaaattc agtatatact ctccccagct tgctttgagg gtcccacaaa ctataacatg    8820
gcatgcatac acacaaacac agcaaaaaag taacaggtgt cataagaatg gataaagtgc    8880
tttgtgtgta cttactcctc attttttaaa ttgattatcc ctcatcttta ctgtatcttt    8940
ttcactatag aggcatccta attgattttt aaattcaaga gatttatcga gcaccttcta    9000
taagccagcg gctatacaaa gtggacaaag agccctgaca tccagcatga cagaagtgct    9060
attcggcact tgttcttcaa gttgcccact tggatctctt ccaagtgcac tttccttttt    9120
tccctgccct ataacttttt aataataaac ttccactcct gctctgaaaa ataaaaaagt    9180
aaataaaata aaaaatggcc aggcacagtg gctcatgtct gtaaatccta gcactttggg    9240
aggccaaggt gggcagactg cttgagccca agagttagaa agcagcctgg gtaacatagt    9300
gagacccgtg ccgcccttc tcccacccct gctgcctcta tttaaaaaat atatatatat    9360 tatgaaaaa agcaaagcag tccggcgca gtggtcatgc ctgtaatccc ttcactttgg    9420
gaggccaagg tgggtagatc acttgaggtc aggagttcaa gactagcctg gtcaacatag    9480
tgagactctg tctctactaa aaatacaaaa attagctggg catcatggcg ctcccctata    9540
atcccagcta ctcaggaggc tggggcagga gaattgcttg aacctaggag gtggagtttg    9600
cagtgagcca agatcgcacc actgcactcc agcctgaggg acagagtgag actccatctc    9660
aaaaattaaa aaaaaaataa agcagtctat aggagtaggg taaggagggg aaggagatta    9720
tggaggaggg tgacactttt aaagacagag aaggtgattg tttgagcaaa ggacaagagt    9780
```

```
ctaatgtggc aaggccctga agtgggcctt ccagagccca aagctggtct ggtggctagg   9840
tagatcctgt tgcagacata gtgactttgt tttagtccaa gtgaaatgat ctctcaccct   9900
ttttctcccc ccccaagacg gaatctcgtt ctatcgccca ggctggagtg ctgtggcgtg   9960
atcttggctc actgcaatct ccgccttctg ggttcaagct attctgcctc agccgcctga  10020
gtagctggga ctacaggcac ccaccaccat gcccggctaa ttttgtatt tttagtagat  10080
atggggtttc accatgttgg ccaggctggt caggagacct caagtgatct gtccaccttg  10140
gcttcccaaa gtgctgggat tacaggtgtg aaccaccgca cctagcctca ccttttttt  10200
tttttttttg agagtttcgc ttttgttgcc taggctggag tgcactggcg cgatctcggc  10260
tcaccgcaac ctacatctcc caggttcaag cgattctcct gcctcagctt cctgagtagc  10320
tgagattaca ggcatgcgtc accacgccca gctaattttg tattttagt agagatgggg  10380
tttcgccatg ttggtcaggc tggactcgaa ctcccaacct caggtgattc gcctgcctcg  10440
gcctcccaaa gtgcctggcc acccttttta aaacactgac tctagttgac gtgttggcca  10500
cagacagtag ggaggaagca gtataatttg agaagctact gcggtaatcc cagcagagat  10560
gatggtggct gaggccaggg ttaggttgtg attgattcag gatgtttctt aaggatagga  10620
tgtaggacgt gaaagaaact gaggatgact gggtttggcc ttgagcaact gggtgatcag  10680
ggtggagcag ttcagggagc catcacaaga gacagaaaac gcggtagtca tctggtgtct  10740
aaatggcatt taagccttga gggtgggtga gaggaaggaa gggtagatag agcagaggtt  10800
gaaggactga gccctgggc atgccatatg aggctgccgg cggacagagg tgcacagcta  10860
gtgagaaaaa aacaaggcct ttttgtagtc ctgaagcctc aaggaagtgt tcaatggtg  10920
cttgatcata tcaatttcaa ataggctgtt ttcatcccca acttctgctc agccaataac  10980
tcaaactgat aaatgccctc tgctatcctg gattttccaa attctgtttt ggggttttgg  11040
aataaacact ggtccaaatc ctcgcttcat catttagcag ttaaaacccg ttaaatagga  11100
taataatacc tccccctagg agattttgtg ctggttaatg agataatgat gtataaacgg  11160
agcacacagc caggcactta ggaagtggac cacaattgcc agccattatc attcaaggct  11220
cagcagtgac ctcctgcgaa gaggttgggg cttctcggtc actccagaaa ccagtcacac  11280
ctttctgtga ggtctcaagg cttagtattt aatctctaat tgcttacact tgtcgccttg  11340
gaggactgga agatacatct ttaatagtcc tcagcagggc tggatgcctt caatcccgca  11400
gcagctctat atttgcaaat ggcctggaga aatctctcac cattttttctt gtttacaact  11460
ttggaactga ggctgaagtc aatcaaaatc cagctttcta caaggggtgc cagggtgtgc  11520
accttaacac agtggccagt cattggcctg aggcagagat ccggggaaga caagccctat  11580
acttgactgg aggtaaaccc agctcacaac gcgcacacac acagcccaaa caggagatcc  11640
tatcagaaac gagtcacacc ctagactttc aggaacaata atcctggaat gagcactgtt  11700
tttaccctca ggctatgctt aaccctaagg ccaaaatctt gggtctgata agggtcaaat  11760
tttcaagcag gactaagggt gggaaaaggg gctcaaacca accccaagct gggtctggtg  11820
ctgggccagt aatgagtgac cagaccctgg gcaggcctag gagatgtgag agaccctgac  11880
aagggctggg ccagacagag caaaggccag cctgggccag cttccgactc tcccaggccg  11940
ctctgccctc acctgcagtt gtctcttcga aatccagctt ccagttccca cctggcccct  12000
gcctgccagg gctgcctgca gttgatacac acccctccct ggccagggca gctgaccctg  12060
cctgctcctc tcctgggtgc caggtctggg cagctgcagg tgaccacttc cccatcaggc  12120
tgccctgtca tgaccacctc cccacacccc aaccccgtcg aagctcactt gcctcctccg  12180
```

```
ggttttgctc cagcttctcc ttctccagct tcacggcacc aggggtgacg gtgcagggct   12240
ccggggaggc cccatcggag ttgctctcca ccccgactcc tgcttcgccc tcaggctgag   12300
aggtctccaa gccgccttgg ggcactagcc ccactccaac ctggggccca cagtacgcca   12360 tcccccaca gaactcatac ggcgggggc atggggaat cccccacacc tcagagcctg   12420
gcccaacccc cggcccgatt cctggccctc caggagggcc ttggaagctt agccaggtcc   12480
gaggatcaac ccagcccggc tccggccccc ctggcccatc acctccacca cctggagggg   12540
gcgagaaggc aaaatctgaa gccaggtgtc ccgccatggg gaaggaaggc gcccaagcc   12600 gggggcctgg tgaaatgagg gcttgcgaag ggactactca accctctct ccctccccag   12660 tcccacccac tagccttgac ctctggcccc gccccctgga tgggtggagg agagggaggt   12720 gggggagaa actgaggcga aggatgtttg cctaatggtg gtggcaatgg tgtctgtgga   12780
aggggaaaac cggagacac aactggcgcc cctccaggac ctcagtgcag gtcccccaca   12840 gaaactttt ttatttttat tttttaagac agggtctcac tttgttgccc agactggagt   12900
gcagtggagt acaatgatgg ctcaatgtag cctcgatcta ctgggccaaa gcaatccttc   12960
tgctccagcc tcctaagtgg ctgggactac aggcttggac cactgtgccc tgttagtttt   13020 tttatttta gtagagatgg ggccttgcta tgttacccag gctggtcttg aattcctgtc   13080
ctcaagaaat cctcccgcct ctgccgccca gtgtcatgat taaaggcgtg agccaccaca   13140
cccaactttc aactcccaac ccgctccctg gcactctctc aggctctgca catcccagct   13200
gtctggaatc actcccacac ctccatgttc ttcaggaacc caggtgcttg accccctctc   13260
cacagacctc tggcactgtg ccttcagggg ccagtcaccc tctcagctcc tcaaatttat   13320
tgaatgtgtg tgtggcgcta tccctcaatg catcaacagc cataagcaca atggccagct   13380
gctcccttat gccttccccc gatccatcca gaatcctagg cattcccatc ccgatactgg   13440
ccaaatccag ccaccccgca gcctgggtgc ctggcaccat ctgcccagcc tgccaaattt   13500
caccccatct tcaagagtag actgccagac aaggcctccg tgctatatcc ccccacccc   13560 catcccccca cccctccgtc ttccagaatc agactccaga ctctcctcat ctaacagact   13620
aaggggttgg cccctacttc cccttcaagg gaccagactt tggactgatt gggcctcagt   13680
ttcccaacct ttgctgaaac agagtgataa gacacccgct ttgggccccc tccactatgg   13740
aacctgcaca tcaggttcct tgctccctc tcaaccaaaa ctcagacatc taataccacg   13800
gtaggccccg ttctccctcc cccacctccc tggcccaggc ctccagccct aggccctggg   13860
tggggaaaac caggggtgg ggggtgtgga gaaaaaatat ctgacttcag gttcaaagaa   13920
gcctgggagg gactggggga aggggcagg acaatggcct tggctggaca atcccggtcc   13980
ccagaggggg cagctctaac cctaaacaag tgctcaaccc ttgaatgggc ctggatggct   14040
cccctgggga ctgcttcctg ctccccaacc ccccagtccc aatccctca cacagaatcc   14100 ccttcagaga cgctaaaagg agctccagca accccctct gcaatcccct caaagactga   14160
gcctcagacg ggcaccaagg gccccctaca gggacctagg tatctagttc ctccttcctc   14220
tgggggactc aggcgtccag cttcatcgtg catccctccc cgagcccgga agattgaggg   14280
atgtgctttg tttagtgggg ctggctggca gaaagacgca gaggaggtgg cgagtgattt   14340 gtggagggggt gcaggaaggc tgccctaagc tcccctccag ggtctgtttt tctgggcctg   14400
gcctgagtat cctgaggctc atgctgctgg tctagtgctt gattctgttt gcaagagaat   14460
agccaacg                                                             14468
```

```
<210> SEQ ID NO 8
<211> LENGTH: 345
<212> TYPE: PRT
<213> ORGANISM: Homo sapiens

<400> SEQUENCE: 8

Met Leu Pro Cys Phe Gln Leu Leu Arg Ile Gly Gly Gly Arg Gly Gly
1               5                   10                  15

Asp Leu Tyr Thr Phe His Pro Pro Ala Gly Ala Gly Cys Thr Tyr Arg
            20                  25                  30

Leu Gly His Arg Ala Asp Leu Cys Asp Val Ala Leu Arg Pro Gln Gln
        35                  40                  45

Glu Pro Gly Leu Ile Ser Gly Ile His Ala Glu Leu His Ala Glu Pro
    50                  55                  60

Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
        195                 200                 205

Gly Glu Val Gly Thr Thr Pro Ser Ala Pro Pro Gln Arg Asn Arg Arg
    210                 215                 220

Lys Ser Val His Arg Val Leu Ala Glu Leu Asp Asp Glu Ser Glu Pro
225                 230                 235                 240

Leu Glu Asn Pro Pro Pro Val Leu Met Glu Pro Arg Lys Lys Leu Arg
                245                 250                 255

Val Asp Lys Ala Pro Leu Thr Pro Thr Gly Asn Arg Arg Gly Arg Pro
            260                 265                 270

Arg Lys Tyr Pro Val Ser Ala Pro Met Ala Pro Pro Ala Val Gly Gly
        275                 280                 285

Gly Glu Pro Cys Ala Ala Pro Cys Cys Leu Pro Gln Glu Glu Thr
    290                 295                 300

Val Ala Trp Val Gln Cys Asp Gly Cys Asp Val Trp Phe His Val Ala
305                 310                 315                 320

Cys Val Gly Cys Ser Ile Gln Ala Ala Arg Glu Ala Asp Phe Arg Cys
                325                 330                 335

Pro Gly Cys Arg Ala Gly Ile Gln Thr
            340                 345

<210> SEQ ID NO 9
<211> LENGTH: 3021
<212> TYPE: DNA
<213> ORGANISM: Homo sapiens

<400> SEQUENCE: 9
```

```
tcgtctcctg ccgaggagcc caagggtcc cgggatccgc cgcacaggct ggcactgctt    60
gaagaggagg ctactcggag actgcgccgc gcggattgga ggctcccccaa atattttgcg  120
atctgaggat ccagctcaag tgaggtgcca taggacgtgt tcctgagttt gcattgcacg  180
gagaccttcc tggaattttt catttgcaag tcggcttaac caattttgca ttgagtccta  240
ggctgcttgc actctgaatt tgggctattc aggtagtgtg ctcaaagttg aaaccgcata  300
cagcacaact caagtttgca tcagactggg aagcgaactt aagccagcgg tgcgtggccc  360
aggagtggga aaggaaatgg atgcctgaag tggaagaggt ggtgcagagg gggcaccgcc  420
catgctgccc tgcttccaac tgctgcgcat aggggcggc aggggcggtg atctctacac   480
cttccacccc ccgccggggg ctggctgcac ctatcgcttg gccacaggg ccgacctgtg    540
tgatgtggcc ctgcggcccc agcaggagcc tggcctcatc tctgggatcc acgccgaact  600
gcatgccgag ccccggggtg atgactggag ggtcagcctg aagaccaca gcagccaagg    660
tactttggtc aataatgtcc gactcccaag aggtcacagg ctggaattga gtgatggaga  720
cctcctgacc tttggccctg aagggccccc aggaaccagc ccctcggagt tctacttcat  780
gttccaacaa gtacgagtca agcctcagga ctttgctgcc attaccatcc cacggtctag  840
gggagaagcc cgggttgggg ctggtttccg gcctatgctg ccctcccagg gggctccaca  900
gcggcctctc agcaccttct cccctgcccc caaggccaca ctgatcctaa actccatagg  960
cagcctcagc aagctccggc cccagcccct caccttctcc cctagttggg gtggaccaaa 1020
gagcctgcct gttcccgccc cacctgggga agtggggacc acgccttctg ctccacccca 1080
acgcaatcgg aggaaatctg ttcaccgagt gttggcggaa ctggatgatg agagtgagcc 1140
tcttgagaac ccgccaccgg tccttatgga gccaggaag aaactccgtg tagacaaagc  1200
cccactgact cccactggaa atcgacgtgg ccgtcctcgg aagtacccag tgagcgctcc 1260
catggctccc cctgcagttg ggggcgggga gccctgtgca gctccttgtt gctgcctgcc 1320
ccaggaagag acagtggcct gggttcagtg tgatggctgt gacgtctggt tccatgtggc 1380
ctgtgttggc tgcagcatcc aggctgccag ggaggccgac ttccgatgcc cagggtgccg 1440
ggctggcatt cagacctaag gtccaccgcc aaggcaccat cggacacacc tgcccatgag 1500
tagacacagc agcgagcaaa taggtctgat aaataccccc cttcccttcc ctccccagga 1560
gggaatgact acagggaaga aggatggatt gatgtggact cattcagggc ctggagcaga 1620
ccctggtggc caagacagaa gagatggttt cctgccaaag atattgccac ctccaggaaa 1680
ttgccagtga gctggaagtt cccactatta caagccataa ggccatgttg ccatggacac 1740
cagaatatct gtagtcagag cacctatcag ttgcaaaagc catgcctgca accgatggaa 1800
aatgtaagag ggagttctta aggttcttga tggcatcacc caaggcattc tgggaaaacc 1860
tagggcctgg ccccaaaact tccctactct gtggctagtc ctgctgccaa caaaatcgta 1920
gcgacctggc ttttcacagc tttgctttta tttccaagtc aaggacaagc cgcttcattc 1980
actcctgggc atttactctt cttgtgggtc tgtgatattc cttgctttcc agggagaatg 2040
tgcttggcaa ggtctggaga actaattcag aatcttaggg gaaggggaga gatgaaata  2100
caaacctgct tactgaaaag gtgcaaatat atgggttgag ctggaggtag gaatacaggt 2160
aattaaggtt tctggtttaa gggaaaacag atctattgcc atttaaataa ggtaactggg 2220
atttggttaa gttcacaaag ttagcagaag atttatttac aggcttcacc tgtactgtca 2280
gggcaagaga aagcctggta aaccagctac agcagtttac cagtgtgatg gctgtgacac 2340
agctccactc cacgggtgga cacagcagag ggcaactggg ctggcctggt tcagtgtgaa 2400
```

```
tcaaaccgct taacccacac atggtacatg tgattttctt ttgtgagcct tacaccaagc    2460
caaactattg tcaaagcatc atttctatag aaataaagcc ttatcttgac ctgttctatt    2520
aaaacctgcc acatccgccc tttcctacct agatttaatg agcccaagtt ttttacatg    2580 gaagaaatga ctctggggca agacccta atgaactagt ggcagagcca ggaataaaac     2640
ttgagtaact aatgagtcac ttatgggcag agtatgcaaa aaccttaagt ggaaaccaaa   2700
tagaccctgg tatcaagaaa gcacaaagta ttaatagaag tttctggttg gggtgatcta   2760
ggttcaacag aaataagatg atttctaagt ataaagccat tttagaattc cagagtaggg   2820
tgggaaagca aaaagccagc tctgaacagg taacagctac atggtgactg agtctatggg   2880
caaaagttct tgcatcacag gcttttggga actagcctat cacagggccc tgtacaaata   2940
aacttggctg caatcccaaa aaaaaaaaaa aaaaaaaaaa aaaaaaaaaa aaaaaaaaaa   3000
aaaaaaaaaa aaaaaaaaaa a                                             3021
```

<210> SEQ ID NO 10
<211> LENGTH: 359
<212> TYPE: PRT
<213> ORGANISM: Homo sapiens

<400> SEQUENCE: 10

```
Met Leu Pro Cys Phe Gln Leu Leu Arg Ile Gly Gly Arg Gly Gly
1               5                   10                  15

Asp Leu Tyr Thr Phe His Pro Ala Gly Val Gly Cys Thr Tyr Arg
            20                  25                  30

Leu Gly His Arg Ala Asp Leu Cys Asp Val Ala Leu Arg Pro Gln Gln
        35                  40                  45

Glu Pro Gly Leu Ile Ser Gly Ile His Ala Glu Leu His Ala Glu Pro
    50                  55                  60

Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
        195                 200                 205

Gly Glu Val Gly Thr Thr Pro Ser Ala Pro Pro Gln Arg Asn Arg Arg
    210                 215                 220

Lys Ser Val His Arg Val Leu Ala Glu Leu Asp Asp Glu Ser Glu Pro
225                 230                 235                 240

Pro Glu Asn Pro Pro Val Leu Met Glu Pro Arg Lys Lys Leu Arg
                245                 250                 255

Val Asp Lys Ala Pro Leu Thr Pro Thr Gly Asn Ala Arg Gly Arg Pro
```

```
                260               265                270
Arg Lys Tyr Pro Val Ser Ala Pro Met Ala Pro Ala Val Gly Ala
            275                 280                285

Gly Ser Pro Val Gln Leu Leu Val Ala Ala Cys Pro Arg Lys Arg Gln
        290                 295                 300

Trp Pro Gly Phe Ser Val Met Ala Val Thr Ser Gly Ser Met Trp Pro
305                 310                 315                 320

Val Leu Ala Ala Ala Ser Arg Leu Pro Gly Arg Pro Thr Ser Asp Ala
                325                 330                 335

Gln Gly Ala Gly Leu Ala Phe Ser Leu Arg Ser Thr Ala Lys Ala Pro
            340                 345                 350

Ser Asp Thr Pro Ala His Glu
            355

<210> SEQ ID NO 11
<211> LENGTH: 1080
<212> TYPE: DNA
<213> ORGANISM: Homo sapiens

<400> SEQUENCE: 11
atgctgccct gcttccaact gctgcgcata gggggcggca ggggcggtga tctctacacc      60
ttccaccccc ccgccggggt tggctgcacc tatcgcttgg ccacagggc cgacctgtgt     120 gatgtggccc tgcggcccca gcaggagcct ggcctcatct ctgggatcca cgccgaactg     180
catgccgagc ccggggtga tgactggagg gtcagcctgg aagaccacag cagccaaggt     240
actttggtca ataatgtccg actcccaaga ggtcacaggc tggaattgag tgatggagac     300
ctcctgacct ttggccctga agggccccca ggaaccagcc cctcggagtt ctacttcatg     360
ttccaacaag tacgagtcaa gcctcaggac tttgctgcca ttaccatccc acggtctagg     420
ggagaagccc gggttggggc tggtttccgg cctatgctgc cctcccaggg gctccacag     480 cggcctctca gcaccttctc ccctgccccc aaggccacac tgatcctaaa ctccataggc     540
agcctcagca agctccggcc ccagcccctc accttctccc ctagttgggg tggaccaaag     600
agcctgcctg ttcccgcccc acctggggaa gtggggacca cgccttctgc tccaccccaa     660
cgcaatcgga ggaaatctgt tcaccgagtg ttggcggaac tggatgatga gagtgagcct     720
cctgagaacc cgccaccggt cctttatggag cccaggaaga aactccgtgt agacaaagcc     780
ccactgactc ccactggaaa tgcacgtggc cgtcctcgga agtacccagt gagcgctccc     840
atggctcccc ctgcagttgg ggcggggagc cctgtgcagc tccttgttgc tgcctgcccc     900
aggaagagac agtggcctgg gttcagtgtg atggctgtga cgtctggttc catgtggcct     960
gtgttggctg cagcatccag gctgccaggg aggccgactt ccgatgccca gggtgccggg    1020
ctggcattca gcctaaggtc caccgccaag gcaccatcgg acacacctgc ccatgagtag    1080

<210> SEQ ID NO 12
<211> LENGTH: 345
<212> TYPE: PRT
<213> ORGANISM: Homo sapiens

<400> SEQUENCE: 12

Met Leu Pro Cys Phe Gln Leu Leu Arg Ile Gly Gly Gly Arg Gly Gly
1               5                   10                  15

Asp Leu Tyr Thr Phe His Pro Pro Ala Gly Ala Gly Cys Thr Tyr Arg
            20                  25                  30

Leu Gly His Arg Ala Asp Leu Cys Asp Val Ala Leu Arg Pro Gln Gln
        35                  40                  45
```

Glu Pro Gly Leu Ile Ser Gly Ile His Ala Glu Leu His Ala Glu Pro
 50                  55                  60

Arg Gly Asp Asp Trp Arg Val Ser Leu Glu Asp His Ser Ser Gln Gly
 65                  70                  75                  80

Thr Leu Val Asn Asn Val Arg Leu Pro Arg Gly His Arg Leu Glu Leu
                 85                  90                  95

Ser Asp Gly Asp Leu Leu Thr Phe Gly Pro Glu Gly Pro Pro Gly Thr
             100                 105                 110

Ser Pro Ser Glu Phe Tyr Phe Met Phe Gln Gln Val Arg Val Lys Pro
         115                 120                 125

Gln Asp Phe Ala Ala Ile Thr Ile Pro Arg Ser Arg Gly Glu Ala Arg
     130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
        195                 200                 205

Gly Glu Val Gly Thr Thr Pro Ser Ala Pro Pro Gln Arg Asn Arg Arg
    210                 215                 220

Lys Ser Val His Arg Val Leu Ala Glu Leu Asp Asp Glu Ser Glu Pro
225                 230                 235                 240

Pro Glu Asn Pro Pro Val Leu Met Glu Pro Arg Lys Lys Leu Arg
                245                 250                 255

Val Asp Lys Ala Pro Leu Thr Pro Thr Gly Asn Arg Arg Gly Arg Pro
            260                 265                 270

Arg Lys Tyr Pro Val Ser Ala Pro Met Ala Pro Pro Ala Val Gly Gly
        275                 280                 285

Gly Glu Pro Cys Ala Ala Pro Cys Cys Cys Leu Pro Gln Glu Glu Thr
    290                 295                 300

Val Ala Trp Val Gln Cys Asp Gly Cys Asp Val Trp Phe His Val Ala
305                 310                 315                 320

Cys Val Gly Cys Ser Ile Gln Ala Ala Arg Glu Ala Asp Phe Arg Cys
                325                 330                 335

Pro Gly Cys Arg Ala Gly Ile Gln Thr
            340                 345

<210> SEQ ID NO 13
<211> LENGTH: 4651
<212> TYPE: DNA
<213> ORGANISM: Homo sapiens

<400> SEQUENCE: 13
ccgccacccc gacacacaca ggagctgcct aaagtatcct tgccttgcag attggaggct      60
ccccaaatat tttgtgatct gaggatccag ctcaagtgag gtgccatagg acgtgttcct     120
gagtttgcat tgcacggaga ccttcctgga atttttcatt tgcaagtcgg cttaaccaat     180
tttgcattga gtcctaggct gcttgcactc tgaatttggg ctattcaggt agtgtgctca     240
aagttgaaac cgcatacagc acaactcaag tttgcatcag actgggaagc gaacttaagc     300
cagcggtgcg tggcccagga gtgggaaagg aaatggatgc tgaagtggaa agaggtggtg     360 cagaggggc accgcccatg ctgccctgct tccaactgct gcgcataggg ggcggcaggg     420

```
gcggtgatct ctacaccttc caccccccg ccggggctgg ctgcacctat cgcttgggcc    480
acagggccga cctgtgtgat gtggccctgc ggccccagca ggagcctggc ctcatctctg    540
ggatccacgc cgaactgcat gccgagcccc ggggtgatga ctggagggtc agcctggaag    600
accacagcag ccaaggtgag cattaagcag ggcagctttg cccctgggtg gttgaagcgc    660
caggctggaa tgagtaaggt ctccacaaga ccctgctgcc tgcctcccat actcccatca    720
gattggatgg atagtcgtgg tccagacctt catcttccca ccagaagtgt gcacagtcag    780
aagctctctg ccagactgac ccttttggt cccgtttagc tcatacagga cctgggatat    840
catcagaaag atatcacagt ggggatgttc tgaggccact agaggccaag tttagacttg    900
attcagtttc cagctttgct gaggcactct gttcctgggt tagggcagtt ctatgttgaa    960
taatgttttt aataatctgg gcatgtcttt ctccgtgact tgaggcagtt agcctcagaa   1020
agcctagatt cacatttgag ttttgccact gcctcttggt aaagtcagct gtaggagtgt   1080
tatggttatt agactatagt agccaacatt catctagtgc ttactgttat gagccaggcc   1140
ctattttaag tgtattgaat gtaggtggta ctaatattat cctcatttac agtaaaggaa   1200
aatgaggcac aaagaggtta aggaacttgt ccagggctgg gcatggtggt ttacacctat   1260
aatccagcac tttgggaggc taaggcaggg tggatcactt gagctcagga gttcgagacc   1320
agcctgggca acatggtgaa aacctgtctc taccaaaaaa ttaattaatt ttttaaaaaa   1380
agcctgggcg cggtggctca cgcctgtaat cccagcactt tgggaggccg agatgggcag   1440
atcacgaggt caggagttcg agaccatcct gaccaacatg ttgaaacccc atctgtgctg   1500 aaaaaaaat acaaaaatta gccaggtgtg gtggcgtgca cctgtaaccc cagctactca   1560
ggaggctgaa gcagcagaat cacttgaacc cgggaggcgg aggttgcagt gagctgagat   1620
cgcaccactg cactccagct tgggcgacag agcgagactc catctcaaac aaacaaacaa   1680
accaaaagct tgcccagggt cacataactg gtaagtggta gagctaggat ctgaacgagc   1740
tggagctggg ggagagtgag catgtttgaa aactggacct tagggcgggg cacggtggct   1800
cacgcctgta atcccagcac tttgggaggc tgaggcgggc agatcaggag gtcaggagta   1860
tgagaccagc ctggccaaca tggtaaaacc ctgtctctgc taaaaataaa aaaattagcc   1920
agacgtggtg gcacatgcct gtaatcccag ctactcagga ggctgaggca ggagaattgc   1980
ttgaacctgg gaggcggttc aagcttgggc aatagagcaa aactccatct caaaaaaaaa   2040
aaaaagaaag aaaaaaaaag aagaaagaaa gaaaattgga ccttaggaca gtgagggcag   2100
ggatcctttg taggaaagca caagaaacac agacttgttc ctagctgaca aggagtgtac   2160
tgcctggtac ctgtcacctg ctgagggct taggatgtga gggagaatct gactacagtt   2220
tcatattctt ccccagaaat catacagatt tctccactcc tgactctggt catttctgtt   2280
tttgtcctcc atatttgcct ggtgccccac catcaacagg tactttggtc aataatgtcc   2340
gactcccaag aggtcacagg ctggaattga gtgatggaga cctcctgacc tttggccctg   2400
aagggccccc aggaaccagc cctcggagt tctacttcat gttccaacaa gtacgagtca   2460
agcctcagga ctttgctgcc attaccatcc cacggtctag gggagaagcc cgggttgggg   2520
ctggtttccg gcctatgctg ccctcccagg gggctccaca gcggcctctc agcaccttct   2580
cccctgcccc caaggccaca ctgatcctaa actccatagg cagcctcagc aagctccggc   2640
cccagcccct caccttctcc cctagttggg gtggaccaaa gagcctgcct gttcccgccc   2700
cacctgggga agtggggacc acgccttctg ctccaccca acgcaatcgg aggaaatctg   2760
ttcaccgagt gttggcggaa ctggatgatg agagtgagcc tcctgagaac ccgccaccgg   2820
```

```
tccttatgga gcccaggaag aaactccgtg tagacaaagc cccactgact cccactgggt    2880
aagtggagtc ctcacttggc cctctcagtg ttttactgct tttcgattcc ttgtatccct    2940
aggctgtgag gaggtccccc tgcctggggg gatgggcacg ggaggtggaa tagatggaat    3000
ggcaagacct gggttagctc tgataggaaa agaaaaatat gtgcaggaga acatgagagg    3060
tggggtgggg cagtgcttat aaaacaaccg gagtgagcat gtcctgctttt ttacattcat   3120 atggctttaa ccccattctt ctagtgccta aggatgggga actttcaggc tcacactaga   3180
ggttttaggg cccaccctat gtgttttttaa ggacagagtc caggctcacc ttagttctca   3240
gaccactgtg cctctgtggc ctcaccctat gaccagccat agggtggcaa ggtctaggcc    3300
ttctcctaca ggtttccggt gacccttgtg tctgtgtcac ttcagaaatc gacgtggccg    3360
tcctcggaag tacccagtga gcgctcccat ggctccccct gcagttgggg gcggggagcc    3420
ctgtgcagct ccttgttgct gcctgcccca ggaagagaca gtggcctggg ttcagtgtga    3480
tggctgtgac gtctggttcc atgtggcctg tgttggctgc agcatccagg ctgccaggga    3540
ggccgacttc cgatgcccag ggtgccgggc tggcattcag acctaaggtc caccgccaag    3600
gcaccatcgg acacctgc ccatgagtag acacagcagc gagcaaatag gtctgataaa      3660
tacccccctt cccttccctc cccaagaggg aatgactaca gggaagaagg atggattgat    3720
gtggactcat tcagggcctg gagcagaccc tggtggccaa gacagaagag atggtttcct   3780
gccaaagata ttgccacctc caggaaattg ccagtgagct ggaagttccc actattacaa    3840
gccataaggc catgttgcca tggacaccag aatatctgta gtcagagcac ctatcagttg    3900
caaaagccat gcctgcaacc gatggaaaat gtaagaggga gttcttaagg ttcttggtgg    3960
catcacccaa ggcattctgg gaaacctag ggcctggccc caaaacttcc ctactctgtg     4020
gctagtcctg ctgccaacaa aatcgtagcg acctggcttt tcacagcttt gcttttattt    4080
ccaagtcaag gacaagccgc ttcattcact cctgggcatt tactcttctt gtgggtctgt    4140
gatattcctt gctttccagg gagaatgtgc ttggcaaggt ctggagaact aattcagaat    4200
cttaggggaa ggggagagat ggaaatacaa acctgcttac tggaaaggtg caaatatatg    4260
ggttgagctg gaggtaggaa tacaggtaat taaggtttct agtttaaggg aaaacagatc    4320
tattgccatt taaataaggt aactgggatt tggttaagtt cacaaagata gcagaagatt   4380
tatttacagg cttcacctgt actgtcaggg caagagaaag cctggtaaac cagctacagc    4440
agtttaccag tgtgatggct gtgacacagc tccactccac gggtggacac agcagagggc    4500
aactgggctg gcctggttca gtgtgaatca aaccgcttaa cccacacatg gtacatgtga    4560
ttttcttttg tgagccttac accaagccaa actattgtca aagcatcatt tctatagaaa    4620
taaagcctta tcttgacctg ttctattaaa a                                  4651
```

<210> SEQ ID NO 14
<211> LENGTH: 359
<212> TYPE: PRT
<213> ORGANISM: Homo sapiens

<400> SEQUENCE: 14

Met Leu Pro Cys Phe Gln Leu Leu Arg Ile Gly Gly Gly Arg Gly
1               5                   10                  15

Asp Leu Tyr Thr Phe His Pro Pro Ala Gly Val Gly Cys Thr Tyr Arg
                20                  25                  30

Leu Gly His Arg Ala Asp Leu Cys Asp Val Ala Leu Arg Pro Gln Gln
            35                  40                  45

Glu Pro Gly Leu Ile Ser Gly Ile His Ala Glu Leu His Ala Glu Pro

|  | 50 |  |  | 55 |  |  | 60 |  |  |  |
|---|---|---|---|---|---|---|---|---|---|---|
| Arg | Gly | Asp | Asp | Trp | Arg | Val | Ser | Leu | Glu | Asp | His | Ser | Ser | Gln | Gly |
| 65 |  |  |  | 70 |  |  |  | 75 |  |  |  | 80 |

Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
            115                 120                 125

Gln Asp Phe Ala Ala Ile Thr Ile Pro Arg Ser Arg Gly Glu Ala Arg
            130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
            195                 200                 205

Gly Glu Val Gly Thr Thr Pro Ser Ala Pro Pro Gln Arg Asn Arg Arg
210                 215                 220

Lys Ser Val His Arg Val Leu Ala Glu Leu Asp Asp Glu Ser Glu Pro
225                 230                 235                 240

Pro Glu Asn Pro Pro Val Leu Met Glu Pro Arg Lys Lys Leu Arg
                245                 250                 255

Val Asp Lys Ala Pro Leu Thr Pro Thr Gly Asn Ala Arg Gly Arg Pro
            260                 265                 270

Arg Lys Tyr Pro Val Ser Ala Pro Met Ala Pro Ala Val Gly Ala
            275                 280                 285

Gly Ser Pro Val Gln Leu Leu Val Ala Ala Cys Pro Lys Arg Gln
            290                 295                 300

Trp Pro Gly Phe Ser Val Met Ala Val Thr Ser Gly Ser Met Trp Pro
305                 310                 315                 320

Val Leu Ala Ala Ala Ser Arg Leu Pro Gly Arg Pro Thr Ser Asp Ala
                325                 330                 335

Gln Gly Ala Gly Leu Ala Phe Ser Leu Arg Ser Thr Ala Lys Ala Pro
            340                 345                 350

Ser Asp Thr Pro Ala His Glu
        355

<210> SEQ ID NO 15
<211> LENGTH: 5522
<212> TYPE: DNA
<213> ORGANISM: Homo sapiens

<400> SEQUENCE: 15
gaattccgaa ggaggggtag gcgctgcccg cgcgcagagg ccgcgcccct cctggccccg   60
gcttcttggc tgtcaaacag tagcagcaac gtcggctcct gccgaggagc ccaagggtc   120 ccgggatccg ccgcacaggc tggcactgct tgaagaggag gctactcgga gactgcgccg   180
cgcgggtaga tccgaaacgg ggctgggcg gagtggaaa aggccgggta tgccttgcat   240
gatcgcgggg agctccttcc tgttttatc ccacctagag aagccgggaa gtagggttt   300 aggtccaatt tgttggagta cttaaggact cgtttgcact ttcttttggg ggatgacagt   360
ggattcattg ccctcggagg ttcaaccagt tatgagtgag ggattggcca agagatcggg   420

-continued

```
gcgcaggcaa gcaggagtgc tctattagga taagcaagtt tgacaggaag aagctgctct    480
tctccgaatt acacagaggt gatgtgttcg tattgcacgt agacgtgtgt ataacaggac    540
ctccttcccc gcgccccgcc accccgacac acacaggagc tgcctaaagt atccttgcct    600
tgaagattgg aggctcccca aatatttggt gatctgagga tccagctcaa gtgaggtgcc    660
ataggacgtg ttcctgagtt tgcattgcac ggagaccttc ctggaatttt tcatttgcaa    720
gtcggcttaa ccaatttggc attgagtcct aggctgcttg cactctgaat ttgggctatt    780
caggtagtgt gctcaaagtt gagaccgcat acagaacaac tcaagtttgc atcagactgg    840
gaagcgaact taagccagcg gtgcgtggcc caggagtggg aaaggaaatg gatgcctgaa    900
gtggaagagg tggtgcagag ggggcaccgc ccatgctgcc ctgcttccaa ctgctgcgca    960
tagggggcgg caggggcggt gatctctaca ccttccaccc ccccgccggg gttggctgca   1020
cctatcgctt gggccacagg gccgacctgt gtgatgtggc cctgcggccc cagcaggagc   1080
ctggcctcat ctctgggatc cacgccgaac tgcatgccga gccccggggt gatgactgga   1140
gggtcagcct ggaagaccac agcagccaag gtgagcatta agcagggcag cttttgcccct   1200 gggtggttga agcgccaggc tggaatgagt aaggtctcca caagaccttg ctgtctgcct   1260
cccatactcc catcagattg gatggatagt cgtggtccag accttcatct tcccaccaga   1320
agtgtgcaca gtcagaagct ctctgccaga ctgacccttt tggtcccgt ttagctcata   1380 caggacctgg gatatcatca gaaagatatc acagtgggga tgttctgagg ccactagagg   1440
ccaagtttag acttgattca gtttccagct ttgctgaggc actctgttcc tgggttaggg   1500
cagttctatg ttgaataatg ttttttaataa tctgggcatg tctttctccg tgacttgagg   1560
cagttagcct cagaaagcct agattcacat ttgagtttgg ccactgcctc ttggtaaagt   1620
cagctgtagg agtgttatgg ttattagact atagtagcca acattcatct agtgcttact   1680
gttatgagcc aggccctatt ttaagtgtat tgaatgtagg tggtactaat attatcctca   1740
tttacagaaa aggaaaatga ggcacaaaga ggttaaggaa cttgtccagg gctgggcatg   1800
gtggtttaca cctataatcc agcactttgg gaggctaagg cagggtggat cacttgagct   1860
caggagttcg agaccagcct gggcaacatg gtgaaaacct gtctctacca aaaaattaat   1920 tagttttttta aaaaaagcct gggcgcggtg ggtcacgcct gtaatcccag cactttggga   1980
ggccgagatg ggcagatcac gaggtcagga gttcgagacc atcctgacca acatgttgaa   2040
accccatctg tgctgaaaaa aaaaaaccca aattaaccag gtgtggtggc gtgcacctgt   2100
aaccccagct actcaggagg ctgaagcagc agaatcactt gaacccggga ggcggaggtt   2160
ggagtgagct gagatcgcac cactgcactc cagcttgggc gacagagcga gactccatct   2220
caaacaaaca aacaaaccaa aagcttgccc agggtcacat aactggtaag tggtagagct   2280
aggtactgaa cgagctggag ctgggggaga gtgagcatgt ttgaaaactg gaccttaggg   2340
cggggcacgg tccgtcacgc ctgtaatccc agcactttgg gaggctgagg cgggcagatc   2400
aggaggtcag gagtatgaga ccagcctggc caacatggta aaaccctgtc tctcgtaaaa   2460
ataaaaaaat tagccagacg tggtggcaca tgcctgtaat cccagctact caggaggctg   2520
aggcaggaga attgcttgaa cctgggaggc ggagtgcagt gagctgagat tgcactactg   2580
cactccagct tgggcaatag agcaaatctc catctcaaaa aaaaaaaaaa gaaagaaaaa   2640
aaaagaagaa agaaagaatt ttggcccctta ggacagtgag ggcagggttc ctttgtggga   2700
aagcacaaga aacacagatt tgttcctagc tgacaaggaa tgtactgcct ggtacctgtc   2760
acctgctgag gggcttagga tgtgagggag aatctgacca cagtttcata ttcttcccca   2820
```

```
gaaatcatac agatttctcc actcctgact ctggtcaatt ctgttttgt cctccatatt    2880 tgcctggtgc cccaccatca acaggtactt tggtcaataa tgtccgactc ccaagaggtc    2940
acaggctgga attgagtgat ggagacctcc tgacctttgg ccctgaaggg cccccaggaa    3000
ccagcccctc ggagttctac ttcatgttcc aacaagtacg agtcaagcct caggactttg    3060
ctgccattac catcccacgg tctaggggag aagcccgggt tggggctggt ttccggccta    3120
tgctgccctc caggggggct ccacagcggc ctctcagcac cttctcccct gccccaagg    3180 ccacactgat cctaaactcc ataggcagcc tcagcaagct ccggcccag ccctcacct     3240 tctccctag ttggggtgga ccaaagagcc tgcctgttcc cgccccacct ggggaagtgg     3300
ggaccacgcc ttctgctcca ccccaacgca atcggaggaa atctgttcac cgagtgttgg    3360
cggaactgga tgatgagagt gagcctcctg agaacccgcc accggtcctt atggagccca    3420
ggaagaaact ccgtgtagac aaagcccac tgactccac tgggtaagtg gagtcctcac      3480
ttggccctct cagtgtttta ctgcttttcg attccttgta tccctaggct gtgaggaggt    3540 cccccctgcct gggggatgg gcacgggagg tggaatagat ggaatggcaa gacctgggtt   3600
agctctgata gggaaagaaa aatatgtgca ggagaacatg agaggtgggg tggggcagtg    3660
ctataaaaca accggagtga gcatgtcctg ctttttacat tcatatggct ttaaccccac    3720
tttctagtgc ctaaggatgg ggaactttca ggctcacact agaggttttt aggcccaccc    3780
catgtgtttt taaggacaga gtccaggctc accttagttc tcagaccact gtgcctctgt    3840
ggcctcaccc tatgaccagc cataggtgg caaggtctag gccttctcag atttccggtg     3900
acccttgtgt ctctctcact tccttcagaa atgcacgtgg ccgtcctcgg aagtacccag    3960
tgagcgctcc catggctccc cctgcagttg gggcggggag ccctgtgcag ctccttgttg    4020
ctgcctgccc caggaagaga cagtggcctg ggttcagtgt gatggctgtg acgtctggtt    4080
ccatgtggcc tgtgttggct gcagcatcca ggctgccagg gaggccgact tccgatgccc    4140
agggtgccgg gctggcattc agcctaaggt ccaccgccaa ggcaccatcg acacacctg     4200 cccatgagta gacacagcag cgagcaaata ggtctgataa ataccccct tcccttccct     4260 ccccaagagg gaatgactac agggaagaag gatggattga tgtggactca ttcagggcct   4320
ggagcagacc ctggtggcca agacagaaga gatggtttcc ttccaaagat attgccacct   4380
ccaggaaatt gccagtgagc tggaagttcc cactattaca agccataagg ccatgtcgcc   4440
atggacacca gaatatctgt agtcagagca cctatcagtt gcaaaagcca tgcctgcaac   4500
cgatggaaaa tgtaagaggg agttcttaag gttcttggtg gaatcaccca aggtattctg   4560 ggaaaccta gggcctggcc ccaaaacttc cctactctgt ggctagtcct gctgccaaca    4620
aaatcgtagc gacctggctt ttcacagctt tgctttatt tccaagtcaa ggacaagccg    4680
cttcattcac tcctgggcat ttactcttct tgtgggtctg tgatattcct tgctttccag   4740
ggagaatgtg cttggcaagg tctggagaac taattcagaa tcttagggga aggggagaga   4800
tggaaataca aacctgctta ctggaaaggt gcaaatatg ggttgagctg gaggtaggaa    4860
tacaggtaat taaggtttct agtttaaggg aaaacagatc tatttgccat ttaaatatgg   4920
taactgggat ttggttaagt tcacccagat agcagaagat ttatttacag gcttcacctg   4980
tactgtcagg gacaagagaa aagcctggta aaccaagcta cagcagttta ccagtgtgat   5040
ggctctcaca cagctccacc ccccgggtgg acacagcaga gggcacctgg gctggcctgg   5100
ttcagtgtga atcaaaccgc ttaacccaca catggtacat gtgattttct tttgtgagcc   5160
ttacaccaag ccaaactatt gtcaaagcat catttctata gaaataaagc cttatcttga   5220
```

```
cctgttctat taaacctgc cacatccgcc ctttcctacc tagatttaat gagcccaagt    5280
ttttttacat ggaagaaatg actctggggc aaagacccct aatgaactag tggcagagcc    5340
aggaataaaa cttgagtaac taatgagtca cttatgggca gagtatgcaa aaaccttaag    5400
tggaaaccaa atagaccctg gtatcaagaa agcacaaagt attaatagaa gtttctggtt    5460
ggggtgatct aggttcaaca gaataagat gatttctaag tataaagctc aaaattgaat    5520
tc                                                                  5522
```

<210> SEQ ID NO 16
<211> LENGTH: 650
<212> TYPE: PRT
<213> ORGANISM: Mus musculus

<400> SEQUENCE: 16

```
Met Lys Ala Val Leu Leu Leu Cys Ala Leu Gly Thr Ala Val Ala
1               5                   10                  15

Ile Pro Thr Ser Thr Arg Phe Leu Phe Asp His Ser Asn Pro Thr Thr
                20                  25                  30

Ala Thr Leu Val Thr Pro Glu Asp Ala Thr Val Pro Ile Ala Gly Val
            35                  40                  45

Glu Ala Thr Ala Asp Ile Glu Asn His Pro Asn Asp Lys Ala Glu Lys
        50                  55                  60

Pro Ser Ala Leu Asn Ser Glu Glu Thr His Gln Ser Thr Glu
65                  70                  75                  80

Gln Asp Lys Thr Tyr Ser Phe Glu Val Asp Leu Lys Asp Glu Asp
                85                  90                  95

Gly Asp Gly Asp Leu Ser Val Asp Pro Thr Glu Gly Thr Leu Thr Leu
            100                 105                 110

Asp Leu Gln Glu Gly Thr Ser Glu Pro Gln Gln Lys Ser Leu Pro Glu
        115                 120                 125

Asn Gly Asp Phe Pro Ala Thr Val Ser Thr Ser Tyr Val Asp Pro Asn
    130                 135                 140

Gln Arg Ala Asn Ile Thr Lys Gly Lys Glu Ser Gln Glu Gln Pro Val
145                 150                 155                 160

Ser Asp Ser His Gln Gln Pro Asn Glu Ser Ser Lys Gln Thr Gln Asp
                165                 170                 175

Leu Lys Ala Glu Glu Ser Gln Thr Gln Asp Pro Asp Ile Pro Asn Glu
            180                 185                 190

Glu Glu Glu Glu Glu Asp Glu Glu Glu Glu Glu Pro
        195                 200                 205

Glu Asp Ile Gly Ala Pro Ser Asp Asn Gln Glu Gly Lys Glu Pro
    210                 215                 220

Leu Glu Glu Gln Pro Thr Ser Lys Trp Glu Gly Asn Arg Glu Gln Ser
225                 230                 235                 240

Asp Asp Thr Leu Glu Glu Ser Ser Gln Pro Thr Gln Ile Ser Lys Thr
                245                 250                 255

Glu Lys His Gln Ser Gln Gly Asn Gln Gly Gln Glu Ser Asp Ser
            260                 265                 270

Glu Ala Glu Gly Glu Asp Lys Ala Ala Gly Ser Lys Glu His Ile Pro
        275                 280                 285

His Thr Glu Gln Gln Asp Gln Glu Gly Lys Ala Gly Leu Glu Ala Ile
    290                 295                 300

Gly Asn Gln Lys Asp Thr Asp Glu Lys Ala Val Ser Thr Glu Pro Thr
305                 310                 315                 320
```

Asp Ala Ala Val Val Pro Arg Ser His Gly Ala Gly Asp Asn Gly
                325                 330                 335

Gly Gly Asp Asp Ser Lys His Gly Ala Gly Asp Asp Tyr Phe Ile Pro
            340                 345                 350

Ser Gln Glu Phe Leu Glu Ala Glu Arg Met His Ser Leu Ser Tyr Tyr
        355                 360                 365

Leu Lys Tyr Gly Gly Gly Glu Glu Thr Thr Thr Gly Glu Ser Glu Asn
    370                 375                 380

Arg Arg Glu Ala Ala Asp Asn Gln Glu Ala Lys Lys Ala Glu Ser Ser
385                 390                 395                 400

Pro Asn Ala Glu Pro Ser Asp Glu Gly Asn Ser Arg Glu His Ser Ala
                405                 410                 415

Gly Ser Cys Thr Asn Phe Gln Cys Lys Arg Gly His Ile Cys Lys Thr
            420                 425                 430

Asp Pro Gln Gly Lys Pro His Cys Val Cys Gln Asp Pro Glu Thr Cys
        435                 440                 445

Pro Pro Ala Lys Ile Leu Asp Gln Ala Cys Gly Thr Asp Asn Gln Thr
    450                 455                 460

Tyr Ala Ser Ser Cys His Leu Phe Ala Thr Lys Cys Arg Leu Glu Gly
465                 470                 475                 480

Thr Lys Lys Gly His Gln Leu Gln Leu Asp Tyr Phe Gly Ala Cys Lys
                485                 490                 495

Ser Ile Pro Ala Cys Thr Asp Phe Glu Val Ala Gln Phe Pro Leu Arg
            500                 505                 510

Met Arg Asp Trp Leu Lys Asn Ile Leu Met Gln Leu Tyr Glu Pro Asn
        515                 520                 525

Pro Lys His Gly Gly Tyr Leu Asn Glu Lys Gln Arg Ser Lys Val Lys
    530                 535                 540

Lys Ile Tyr Leu Asp Glu Lys Arg Leu Leu Ala Gly Asp His Pro Ile
545                 550                 555                 560

Glu Leu Leu Leu Arg Asp Phe Lys Lys Asn Tyr His Met Tyr Val Tyr
                565                 570                 575

Pro Val His Trp Gln Phe Asn Glu Leu Asp Gln His Pro Ala Asp Arg
            580                 585                 590

Ile Leu Thr His Ser Glu Leu Ala Pro Leu Arg Ala Ser Leu Val Pro
        595                 600                 605

Met Glu His Cys Ile Thr Arg Phe Phe Glu Glu Cys Asp Pro Asn Lys
    610                 615                 620

Asp Lys His Ile Thr Leu Lys Glu Trp Gly His Cys Phe Gly Ile Lys
625                 630                 635                 640

Glu Glu Asp Ile Asp Glu Asn Leu Leu Phe
                645                 650

<210> SEQ ID NO 17
<211> LENGTH: 2797
<212> TYPE: DNA
<213> ORGANISM: Mus musculus

<400> SEQUENCE: 17
ccatcctaat acgactcact atagggctcg agcggccgcc cgggcaggtc tttgctgcaa    60
agctcagcag cacagaggga gcgagatcca ggaatgtgca acagaaacca tgacagcctg   120
aaacaccctg tggtgccaac ctccaaattc tcatctgtca cttcagaccc tgactggctg   180
acagagcagc agaatttcaa ctccaataaa cgtgaatgtg cttttaggca aagcaaccaa   240

```
gctgacgagg gagggggtg gaagagctag ctcctcttgg gcatttgtca aacttttacc      300
tcctggctgt gtgcaaggag gggactcaac ttcggcttca agctaccaag gctctggatc      360
cagccacctc tccgcagatc tagccagcat gaaggctgtg cttctcctcc tgtgcgcctt      420
gggaaccgct gtggcaatcc cgacaagtac aaggtttctc tttgaccact ccaacccaac      480
tactgcaaca ctggtgacac cggaagacgc tacagtcccc attgccgggg ttgaagctac      540
agcagacata gaaaaccatc ccaatgacaa ggctgaaaaa ccttcagcac ttaattcaga      600
agaggaaact catgaacagt caacagagca ggacaaaacc tacagcttcg aggtggacct      660
gaaggatgag gaggatggag atggggattt aagtgtagat ccaacggaag gaacactaac      720
actggatcta caagaaggca caagtgagcc tcaacagaaa agtctcccgg agaacggcga      780
tttccccgcg accgtgtcca cttcctatgt ggatcctaac caacgcgcaa acatcacaaa      840
gggaaaggag agtcaggagc aacctgtaag tgactcacac cagcaaccga atgaaagcag      900
caagcaaacc caagacttaa aggctgaaga aagccagaca caagatccag acattcccaa      960
tgaagaagag gaagaagaag aggacgaaga agaggaagaa gaggaagagc cggaagacat     1020
tggtgccccc agtgataacc aagaggaggg aaaagaacct ctggaggagc agcctaccag     1080
caagtgggaa ggaaacagag agcaatctga tgacaccttg aagagtccca gtcagcccac     1140
tcagataagc aagacagaga agcatcaatc tgagcaagga aaccaagggc aggagagtga     1200
ctctgaggca gaaggagagg acaaggctgc aggcagcaag gaacacattc cacatacaga     1260
gcagcaggac caagaaggga agctggcct tgaagctatt ggcaaccaga aggacactga     1320
tgagaaggcc gtttccacag aacctaccga tgctgccgtg gtgcctagga gtcacggagg     1380
agctggtgat aacggggggcg gggatgactc taagcatggt gcaggcgatg actacttcat     1440
ccccagccag gaattcctag aggccgaaag gatgcattcc ctctcctatt acctcaaata     1500
tggcggcggc gaggagacaa cgactggcga gagtgagaac cggagggagg ctgcagacaa     1560
ccaagaggcc aagaaagctg agagctcacc aaatgctgaa ccttcagatg agggcaactc     1620
aagggagcac agtgctggtt cttgcacgaa cttccaatgt aaaaggggac acatttgcaa     1680
aaccgatcca caagggaaac ctcactgtgt ttgccaagat ccagagactt gtccccctgc     1740
aaaaatccta gatcaggctt gtggcactga caaccaaacc tacgccagct cctgtcacct     1800
gtttgctacc aagtgcaggc tggaggggac caaaaaggga caccaactgc agctggatta     1860
cttcggagct tgcaaatcta ttcctgcttg tacggacttt gaagtggctc agtttccct      1920 gcggatgaga gactggctca aaacatcct catgcagctt tatgaaccaa atcccaaaca     1980
tggcggctat ctcaatgaaa agcaagaag caaagtcaaa aaatttacc tggatgagaa     2040 gagactcttg gctggagacc atcccattga acttctcttg agggacttta agaaaaacta     2100
ccacatgtat gtgtatcctg tgcactggca gtttaatgaa ctggaccagc atcctgcaga     2160
caggatcttg acacactctg aacttgctcc tctgcgagct tccctggtgc ccatggaaca     2220
ctgcataact cgcttctttg aggagtgtga ccccaacaag gataagcaca tcaccttgaa     2280 ggaatgggc cactgctttg gaattaaaga ggaggatata gatgaaaacc tcctcttttg     2340
aattaagatt tgagagaatc ggaactttcc atccacctca cctgctttac ccgcttcaga     2400
aatacgagca gccatgacac tatacattca tatgtagcaa acatgtgtg tgcatgtgag     2460 agaagacaat ggtagtaatt acttctgggt gatatatata tgagccaggc acttaatatt     2520
aacttaggaa atgaaacttt aaaattaagt agagtcaatg tctataaaag actgtcctgt     2580
ctggggacag ttagccacca tggcaatgtc actctgtgca tctgcgttta taattgataa     2640
```

```
ttataaacta ttaaaaaaac aatgttcata ttgtccataa taccttatgc atgctgagga      2700
agtgagatac tgctctttg agataaatat gcctcctttt cagtgtcttg atgtcctaat       2760
aaaaaatcta taaaacctcc ccaaaaaaaa aaaaaaa                               2797
```

<210> SEQ ID NO 18
<211> LENGTH: 650
<212> TYPE: PRT
<213> ORGANISM: Mus musculus

<400> SEQUENCE: 18

```
Met Lys Ala Val Leu Leu Leu Cys Ala Leu Gly Thr Ala Val Ala
1               5                   10                  15

Ile Pro Thr Ser Thr Arg Phe Leu Ser Asp His Ser Asn Pro Thr Thr
                20                  25                  30

Ala Thr Leu Val Thr Pro Glu Asp Ala Thr Val Pro Ile Ala Gly Val
                35                  40                  45

Glu Ala Thr Ala Asp Ile Glu Asn His Pro Asn Asp Lys Ala Glu Lys
        50                  55                  60

Pro Ser Ala Leu Asn Ser Glu Glu Thr His Glu Gln Ser Thr Glu
65                  70                  75                  80

Gln Asp Lys Thr Tyr Ser Phe Glu Val Asp Leu Lys Asp Glu Glu Asp
                85                  90                  95

Gly Asp Gly Asp Leu Ser Val Asp Pro Thr Glu Gly Thr Leu Thr Leu
                100                 105                 110

Asp Leu Gln Glu Gly Thr Ser Glu Pro Gln Gln Lys Ser Leu Pro Glu
                115                 120                 125

Asn Gly Asp Phe Pro Ala Thr Val Ser Thr Ser Tyr Val Asp Pro Asn
        130                 135                 140

Gln Arg Ala Asn Ile Thr Lys Gly Lys Glu Ser Gln Glu Gln Pro Val
145                 150                 155                 160

Ser Asp Ser His Gln Gln Pro Asn Glu Ser Ser Lys Thr Gln Asp
                165                 170                 175

Leu Lys Ala Glu Glu Ser Gln Thr Gln Asp Pro Asp Ile Pro Asn Glu
                180                 185                 190

Glu Glu Glu Glu Glu Glu Glu Glu Glu Glu Glu Glu Glu Glu Pro
                195                 200                 205

Glu Asp Ile Gly Ala Pro Ser Asp Asn Gln Glu Gly Lys Glu Pro
        210                 215                 220

Leu Glu Glu Gln Pro Thr Ser Lys Trp Glu Gly Asn Arg Glu Gln Ser
225                 230                 235                 240

Asp Asp Thr Leu Glu Glu Ser Ser Gln Pro Thr Gln Ile Ser Lys Thr
                245                 250                 255

Glu Lys His Gln Ser Glu Gln Gly Asn Gln Gly Gln Glu Ser Asp Ser
                260                 265                 270

Glu Ala Glu Gly Glu Asp Lys Ala Ser Gly Ser Lys Glu His Ile Pro
        275                 280                 285

His Thr Glu Gln Gln Asp Gln Glu Gly Lys Ala Gly Leu Glu Ala Ile
        290                 295                 300

Gly Asn Gln Lys Asp Thr Asp Glu Lys Ala Val Ser Thr Glu Pro Thr
305                 310                 315                 320

Asp Ala Ala Val Val Pro Arg Ser His Gly Gly Ala Gly Asp Asn Gly
                325                 330                 335

Gly Gly Asp Asp Ser Lys His Gly Ala Gly Asp Asp Tyr Phe Ile Pro
                340                 345                 350
```

```
Ser Gln Glu Phe Leu Glu Ala Glu Arg Met His Ser Leu Ser Tyr Tyr
        355                 360                 365
Leu Lys Tyr Gly Gly Gly Glu Thr Thr Thr Gly Glu Ser Glu Asn
    370                 375                 380
Gln Arg Glu Ala Ala Asp Asn Gln Glu Ala Lys Lys Ala Glu Ser Ser
385                 390                 395                 400
Pro Asn Ala Glu Pro Ser Asp Glu Gly Asn Ser Arg Glu His Ser Ala
                405                 410                 415
Gly Ser Cys Thr Asn Phe Gln Cys Lys Arg Gly His Ile Cys Lys Thr
            420                 425                 430
Asp Pro Gln Gly Lys Pro His Cys Val Cys Gln Asp Pro Glu Thr Cys
        435                 440                 445
Pro Pro Ala Lys Ile Leu Asp Gln Ala Cys Gly Thr Asp Asn Gln Thr
    450                 455                 460
Tyr Ala Ser Ser Cys His Leu Phe Ala Thr Lys Cys Arg Leu Glu Gly
465                 470                 475                 480
Thr Lys Lys Gly His Gln Leu Gln Leu Asp Tyr Phe Gly Ala Cys Lys
                485                 490                 495
Ser Ile Pro Ala Cys Thr Asp Phe Glu Val Ala Gln Phe Pro Leu Arg
            500                 505                 510
Met Arg Asp Trp Leu Lys Asn Ile Leu Met Gln Leu Tyr Glu Pro Asn
        515                 520                 525
Pro Lys His Gly Gly Tyr Leu Asn Glu Lys Gln Arg Ser Lys Val Lys
    530                 535                 540
Lys Ile Tyr Leu Asp Glu Lys Arg Leu Leu Ala Gly Asp His Pro Ile
545                 550                 555                 560
Glu Leu Leu Leu Arg Asp Phe Lys Lys Asn Tyr His Met Tyr Val Tyr
                565                 570                 575
Pro Val His Trp Gln Phe Asn Glu Leu Asp Gln His Pro Ala Asp Arg
            580                 585                 590
Ile Leu Thr His Ser Glu Leu Ala Pro Leu Arg Ala Ser Leu Val Pro
        595                 600                 605
Met Glu His Cys Ile Thr Arg Phe Phe Glu Glu Cys Asp Pro Asn Lys
    610                 615                 620
Asp Lys His Ile Thr Leu Lys Glu Trp Gly His Cys Phe Gly Ile Lys
625                 630                 635                 640
Glu Glu Asp Ile Asp Glu Asn Leu Leu Phe
                645                 650

<210> SEQ ID NO 19
<211> LENGTH: 2734
<212> TYPE: DNA
<213> ORGANISM: Mus musculus

<400> SEQUENCE: 19
cagcacggag ggagcgagat ccaggaatct gcaacagaaa ccatgacagc ctgaaacacc      60
ctgtggtgcc aacctccaaa ttctcatctg tcacttcaga ccctgactgg ctgacagagc     120
agcagaattt caactccaat aaacgtgaat gtgcttctag gcaaagcagc caagctgacg     180
agggaggggg gtggaagagc tagctcctct tgggcatttg tcaaactttt acctcctggc     240
tgtgtgcaag gagggactc aacttcggct tcaagctacc aaggctctgg atccagccac     300
ctctccgcag atctagccag catgaaggct gtgcttctcc tctgtgcgc cttgggaacc     360 gctgtggcaa tcccgacaag tacaaggttt ctctctgacc actccaaccc aactactgca     420
acactggtga caccggaaga cgctacagtc cccattgccg gggttgaagc tacagcagac     480
```

```
atagaaaacc atcccaatga caaggctgaa aaaccttcag cacttaattc agaagaggaa    540
actcatgaac agtcaacaga gcaggacaaa acctacagct tcgaggtgga cctgaaggat    600
gaggaggatg gagatgggga tttaagtgta gatccaacgg aaggaacact aacactggat    660
ctacaagaag gtacaagtga gcctcaacag aaaagtctcc cggaaaacgg ggatttcccc    720
gcgaccgtgt ccacttccta tgtggatcct aaccaacgcg caaacatcac aaagggaaag    780
gagagtcagg agcaacctgt aagtgactca caccagcaac cgaatgaaag cagcaagcaa    840
acccaagact taaaggctga agaaagccag acacaagatc cagacattcc caatgaagaa    900
gaggaagaag aagaggaaga agaagaggaa gaagaggaag agccggaaga cattggtgcc    960
cccagtgata accaagagga gggaaaagaa cctctggagg agcagcctac cagcaagtgg   1020
gaaggaaaca gagagcaatc tgatgacacc ttagaagagt ccagtcagcc cactcagata   1080
agcaagacag agaagcatca atctgagcaa ggaaaccaag ggcaggagag tgactctgag   1140
gcagaaggag aggacaaggc ttcaggcagc aaggaacaca ttccacatac agagcagcag   1200
gaccaagaag ggaaagctgg ccttgaagct attggcaacc agaaggacac tgatgagaag   1260
gccgtttcca cagaacctac cgatgctgcc gtggtgccta ggagtcacgg aggagctggt   1320
gataacgggg gcggggatga ctctaagcat ggtgcaggcg atgactactt catccccagc   1380
caggaattcc tagaggccga aaggatgcat tccctctcct attacctcaa atatggcggg   1440
ggcgaggaga caacgactgg cgagagtgag aaccagaggg aggctgcaga caaccaagag   1500
gccaagaaag ctgagagctc accaaatgct gaaccttcag atgagggcaa ctcaagggag   1560
cacagtgctg gttcttgcac gaacttccaa tgtaaaaggg gacacatttg caaaaccgat   1620
ccacaaggga aacctcactg tgtttgccaa gatccagaga cttgtccccc tgcaaaaatc   1680
ctagatcagg cttgtggcac tgacaaccaa acctacgcca gctcctgtca cctgtttgct   1740
accaagtgca ggctggaggg gaccaaaaag ggacaccaac tgcagctgga ttacttcgga   1800
gcttgcaaat ctattcctgc ttgtacggac tttgaagtgg ctcagtttcc cctgcggatg   1860
agagactggc tcaaaaacat cctcatgcag ctttatgaac caaatcccaa acatggcggc   1920
tatctcaatg aaaagcaaag aagcaaagtc aaaaaaattt acctggatga aagagactc   1980
ttggctggag accatcccat tgaacttctc ttgagggact ttaagaaaaa ctaccacatg   2040
tatgtgtatc ctgtgcactg gcagtttaat gaactggacc agcatcctgc agacaggatc   2100
ttgacacact ctgaacttgc tcctctgcga gcttccctgg tgcccatgga acactgcata   2160
actcgcttct ttgaggagtg tgaccccaac aaggataagc acatcacctt gaaggaatgg   2220
ggccactgct ttggaattaa agaggaggat atagatgaaa acctcctctt ttgaattaag   2280
atttgagaga atcggaactt tccatccacc tcacctgctt taaccgcttc agaaatacga   2340
gcagccatga cactatacat tcatatgtag caaaacattt gtttggcatg tgagagaaga   2400
caatggtagt aattacttct tggtgatata tatatgagcc aggcacttaa tattaactta   2460
ggaaatgaaa ctttaaaatt aagtagagtc aatgtctata aaagactgtc ctgtctgggg   2520
acagttagcc accatggcaa tgtcactctg tgcatctgcg tttataattg ataattataa   2580
actattaaaa aaacaatgtt catattgtcc ataatacctt atgcatgctg aggaagtgag   2640
atactgctct tttgagataa atatgcctcc ttttcagtgt cttggatgtc ctaataaaaa   2700
atctataaaa cccccaaaaa aaaaaaaaaa aaaa                                2734
```

<210> SEQ ID NO 20
<211> LENGTH: 355

<212> TYPE: PRT
<213> ORGANISM: Homo sapiens

<400> SEQUENCE: 20

| Met | Ala | Ala | Pro | Ala | Phe | Glu | Pro | Gly | Arg | Gln | Ser | Asp | Leu | Leu | Val |
| 1 | | | | 5 | | | | | 10 | | | | | 15 | |

| Lys | Leu | Asn | Arg | Leu | Met | Glu | Arg | Cys | Leu | Arg | Asn | Ser | Lys | Cys | Ile |
| | | | 20 | | | | | 25 | | | | | 30 | | |

| Asp | Thr | Glu | Ser | Leu | Cys | Val | Val | Ala | Gly | Lys | Val | Trp | Gln | Ile |
| | | 35 | | | | | 40 | | | | | 45 | | |

| Arg | Val | Asp | Leu | His | Leu | Leu | Asn | His | Asp | Gly | Asn | Ile | Ile | Asp | Ala |
| | | 50 | | | | | 55 | | | | | 60 | | | |

| Ala | Ser | Ile | Ala | Ala | Ile | Val | Ala | Leu | Cys | His | Phe | Arg | Arg | Pro | Asp |
| 65 | | | | | 70 | | | | | 75 | | | | | 80 |

| Val | Ser | Val | Gln | Gly | Asp | Glu | Val | Thr | Leu | Tyr | Thr | Pro | Glu | Glu | Arg |
| | | | | 85 | | | | | 90 | | | | | 95 | |

| Asp | Pro | Val | Pro | Leu | Ser | Ile | His | His | Met | Pro | Ile | Cys | Val | Ser | Phe |
| | | | 100 | | | | | 105 | | | | | 110 | | |

| Ala | Phe | Phe | Gln | Gln | Gly | Thr | Tyr | Leu | Leu | Val | Asp | Pro | Asn | Glu | Arg |
| | | 115 | | | | | 120 | | | | | 125 | | | |

| Glu | Glu | Arg | Val | Met | Asp | Gly | Leu | Leu | Val | Ile | Ala | Met | Asn | Lys | His |
| | 130 | | | | | 135 | | | | | 140 | | | | |

| Arg | Glu | Ile | Cys | Thr | Ile | Gln | Ser | Ser | Gly | Gly | Ile | Met | Leu | Leu | Lys |
| 145 | | | | | 150 | | | | | 155 | | | | | 160 |

| Asp | Gln | Val | Leu | Arg | Cys | Ser | Lys | Ile | Ala | Gly | Val | Lys | Val | Ala | Glu |
| | | | | 165 | | | | | 170 | | | | | 175 | |

| Ile | Thr | Glu | Leu | Ile | Leu | Lys | Ala | Leu | Glu | Asn | Asp | Gln | Lys | Val | Arg |
| | | | 180 | | | | | 185 | | | | | 190 | | |

| Lys | Glu | Gly | Gly | Lys | Phe | Gly | Phe | Ala | Glu | Ser | Ile | Ala | Asn | Gln | Arg |
| | | | 195 | | | | | 200 | | | | | 205 | | |

| Ile | Thr | Ala | Phe | Lys | Met | Glu | Lys | Ala | Pro | Ile | Asp | Thr | Ser | Asp | Val |
| | 210 | | | | | 215 | | | | | 220 | | | | |

| Glu | Glu | Lys | Ala | Glu | Glu | Ile | Ile | Ala | Glu | Ala | Glu | Pro | Pro | Ser | Glu |
| 225 | | | | | 230 | | | | | 235 | | | | | 240 |

| Val | Val | Ser | Thr | Pro | Val | Leu | Trp | Thr | Pro | Gly | Thr | Ala | Gln | Ile | Gly |
| | | | | 245 | | | | | 250 | | | | | 255 | |

| Glu | Gly | Val | Glu | Asn | Ser | Trp | Gly | Asp | Leu | Glu | Asp | Ser | Glu | Lys | Glu |
| | | | 260 | | | | | 265 | | | | | 270 | | |

| Asp | Asp | Glu | Gly | Gly | Asp | Gln | Ala | Ile | Ile | Leu | Asp | Gly | Ile | Lys |
| | | | 275 | | | | | 280 | | | | | 285 | | |

| Met | Asp | Thr | Gly | Val | Glu | Val | Ser | Asp | Ile | Gly | Ser | Gln | Asp | Ala | Pro |
| | 290 | | | | | 295 | | | | | 300 | | | | |

| Ile | Ile | Leu | Ser | Asp | Ser | Glu | Glu | Glu | Met | Ile | Ile | Leu | Glu | Pro |
| 305 | | | | | 310 | | | | | 315 | | | | | 320 |

| Asp | Lys | Asn | Pro | Lys | Lys | Ile | Arg | Thr | Gln | Thr | Thr | Ser | Ala | Lys | Gln |
| | | | | 325 | | | | | 330 | | | | | 335 | |

| Glu | Lys | Ala | Pro | Ser | Lys | Lys | Pro | Val | Lys | Arg | Arg | Lys | Lys | Lys | Arg |
| | | | 340 | | | | | 345 | | | | | 350 | | |

| Ala | Ala | Asn |
| | | 355 |

<210> SEQ ID NO 21
<211> LENGTH: 1542
<212> TYPE: DNA
<213> ORGANISM: Homo sapiens -continued

```
<400> SEQUENCE: 21
cgaccggcac gttcacccca tccctcaggc tttatttatt tttttcgac aggttctttt      60 caaggctcca gtcaccgcag cagttgtcca tgctgtagtt ccactttcc tgtatgggcg     120 ggctggttag gattccactt tcccccaagt gcttagccca gggccagaca aaaagtagtt    180
gcttaagaaa tacttgttga aggaataaat taatgaatga atttgtgctt acagcggctg    240
gatggcagac aaacctatga ttataggaac atcaggatct catttggaac agattacgga   300
tgctgcattg tggaacttgg aaaaacaaga gttcttggac aggtttcctg tgaacttgtg    360
tctccaaaac tcaatcgggc aacagaaggt attcttttt taaccttgaa ctctctcaga     420
tggccgctcc agctttcgaa cctggcaggc agtcagatct cttggtgaag ttgaatcgac    480
tcatggaaaa atgtctaaga aattcgaagt gtatagacac tgagtctctc tgtgttgttg    540
ctggtgaaaa ggtttggcaa atacgtgtag acctacattt attaaatcat gatggaaata   600
ttattgatgc tgccagcatt gctgcaatcg tggccttatg tcatttccga agacctgatg    660
tctctgtcca aggagatgaa gtaacactgt atacacctga gagcgtgat cctgtaccat     720 taagtatcca ccacatgccc atttgtgtca gttttgcctt tttccagcaa ggaacatatt    780
tattggtgga tcccaatgaa cgagaagaac gtgtgatgga tggcttgctg gtgattgcca   840
tgaacaaaca tcgagagatt tgtactatcc agtccagtgg tgggataatg ctactaaaag    900
atcaagttct gagatgcagt aaaatcgctg gtgtgaaagt agcagaaatt acagagctaa    960
tattgaaagc tttggagaat gaccaaaaag taaggaaaga aggtgaaag tttggttttg    1020 cagagtctat agcaaatcaa aggatcacag catttaaaat ggaaaaggcc cctattgata   1080
cctcggatgt agaagaaaaa gcagaagaaa tcattgctga agcagaacct ccttcagaag   1140
ttgtttctac acctgtgcta tggactcctg gaactgccca aattggagag ggagtagaaa   1200
actcctgggg tgatcttgaa gactctgaga aggaagatga tgaaggcggt ggtgatcaag   1260
ctatcattct tgatggtata aaaatggaca ctggagtaga agtctctgat attggaagcc   1320
aagatgctcc cataatactc tcagatagtg aagaagaaga aatgatcatt ttggaaccag   1380
acaagaatcc aaagaaaata agaacacaga ccaccagtgc aaaacaagaa aaagcaccaa   1440
gtaaaaagcc agtgaaaaga agaaaaaaga agagagctgc caattaaagc taacagttgt   1500
atatctgtat ataataactat taaaagggat atttattcca tt                    1542

<210> SEQ ID NO 22
<211> LENGTH: 664
<212> TYPE: PRT
<213> ORGANISM: Homo sapiens

<400> SEQUENCE: 22

Met Lys Thr Gly Pro Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Trp Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Ser Lys Glu Glu Ser
65                  70                  75                  80

His Glu Gln Ser Ala Glu Gln Gly Lys Ser Ser Gln Glu Leu Gly
                85                  90                  95
```

```
Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ile Glu
            115                 120                 125

Pro Gln Glu Lys Lys Leu Ser Glu Asn Thr Asp Phe Leu Ala Pro Gly
        130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Glu Asp Asn Thr Gln Ser
225                 230                 235                 240

Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
            260                 265                 270

Asn Ala Glu Met Glu Glu Glu Asn Ala Ser Asn Val Asn Lys His Ile
        275                 280                 285

Gln Glu Thr Glu Trp Gln Ser Gln Glu Gly Lys Thr Gly Leu Glu Ala
    290                 295                 300

Ile Ser Asn His Lys Glu Thr Glu Glu Lys Thr Val Ser Glu Ala Leu
305                 310                 315                 320

Leu Met Glu Pro Thr Asp Asp Gly Asn Thr Thr Pro Arg Asn His Gly
                325                 330                 335

Val Asp Asp Asp Gly Asp Asp Asp Gly Asp Gly Gly Thr Asp Gly
            340                 345                 350

Pro Arg His Ser Ala Ser Asp Asp Tyr Phe Ile Pro Ser Gln Ala Phe
        355                 360                 365

Leu Glu Ala Glu Arg Ala Gln Ser Ile Ala Tyr His Leu Lys Ile Glu
    370                 375                 380

Glu Gln Arg Glu Lys Val His Glu Asn Glu Asn Ile Gly Thr Thr Glu
385                 390                 395                 400

Pro Gly Glu His Gln Glu Ala Lys Lys Ala Glu Asn Ser Ser Asn Glu
                405                 410                 415

Glu Glu Thr Ser Ser Glu Gly Asn Met Arg Val His Ala Val Asp Ser
            420                 425                 430

Cys Met Ser Phe Gln Cys Lys Arg Gly His Ile Cys Lys Ala Asp Gln
        435                 440                 445

Gln Gly Lys Pro His Cys Val Cys Gln Asp Pro Val Thr Cys Pro Pro
    450                 455                 460

Thr Lys Pro Leu Asp Gln Val Cys Gly Thr Asp Asn Gln Thr Tyr Ala
465                 470                 475                 480

Ser Ser Cys His Leu Phe Ala Thr Lys Cys Arg Leu Glu Gly Thr Lys
                485                 490                 495

Lys Gly His Gln Leu Gln Leu Asp Tyr Phe Gly Ala Cys Lys Ser Ile
            500                 505                 510

Pro Thr Cys Thr Asp Phe Glu Val Ile Gln Phe Pro Leu Arg Met Arg
        515                 520                 525
```

Asp Trp Leu Lys Asn Ile Leu Met Gln Leu Tyr Glu Ala Asn Ser Glu
    530                 535                 540

His Ala Gly Tyr Leu Asn Glu Lys Gln Arg Asn Lys Val Lys Lys Ile
545                 550                 555                 560

Tyr Leu Asp Glu Lys Arg Leu Leu Ala Gly Asp His Pro Ile Asp Leu
                565                 570                 575

Leu Leu Arg Asp Phe Lys Lys Asn Tyr His Met Tyr Val Tyr Pro Val
            580                 585                 590

His Trp Gln Phe Ser Glu Leu Asp Gln His Pro Met Asp Arg Val Leu
        595                 600                 605

Thr His Ser Glu Leu Ala Pro Leu Arg Ala Ser Leu Val Pro Met Glu
    610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
                645                 650                 655

Asp Ile Asp Glu Asn Leu Leu Phe
            660

<210> SEQ ID NO 23
<211> LENGTH: 2808
<212> TYPE: DNA
<213> ORGANISM: Homo sapiens

<400> SEQUENCE: 23
cggcatgaga ggccagcctg ccagggaaat ccaggaatct gcaacaaaaa cgatgacagt    60
ctgaaatact ctctggtgcc aacctccaaa ttctcgtctg tcacttcaga cccccactag   120
ttgacagagc agcagaatat caactccagt agacttgaat gtgcctctgg caaagaagc   180
agagctaacg aggaaaggga tttaaagagt ttttcttggg tgtttgtcaa acttttattc   240
cctgtctgtg tgcagagggg attcaacttc aatttcctgc agtggctctg ggtccagccc   300
cttacttaaa gatctggaaa gcatgaagac tgggcctttt ttcctatgtc tcttgggaac   360
tgcagctgca atcccgacaa atgcaagatt attatctgat cattccaaac caactgctga   420
aacggtagca cctgacaaca ctgcaatccc cagtttatgg gctgaagctg aagaaaatga   480
aaaagaaaca gcagtatcca cagaagacga ttcccaccat aaggctgaaa atcatcagt   540
actaaagtca aaagaggaaa gccatgaaca gtcagcagaa cagggcaaga gttctagcca   600
agagctggga ttgaaggatc aagaggacag tgatggtcac ttaagtgtga atttggagta   660
tgcaccaact gaaggtacat tggacataaa agaagatatg attgagcctc aggagaaaaa   720
actctcagag aacactgatt ttttggctcc tggtgttagt tccttcacag attctaacca   780
acaagaaagt atcacaaaga gagggaaaa ccaagaacaa cctagaaatt attcacatca   840
tcagttgaac aggagcagta acatagcca aggcctaagg gatcaaggaa ccaagagca   900
ggatccaaat atttccaatg gagaagagga agaagaaaaa gagccaggtg aagttggtac   960
ccacaatgat aaccaagaaa gaagacaga attgcccagg gagcatgcta acagcaagca  1020
ggaggaagac aatacccaat ctgatgatat tttggaagag tctgatcaac caactcaagt  1080
aagcaagatg caggaggatg aatttgatca gggtaaccaa gaacaagaag ataactccaa  1140
tgcagaaatg gaagaggaaa atgcatcgaa cgtcaataag cacattcaag aaactgaatg  1200
gcagagtcaa gagggtaaaa ctggcctaga agtatcagc aaccacaaag agacagaaga  1260
aaagactgtt tctgaggctc tgctcatgga acctactgat gatggtaata ccacgcccag  1320

```
aaatcatgga gttgatgatg atggcgatga tgatggcgat gatggcggca ctgatggccc    1380
caggcacagt gcaagtgatg actacttcat cccaagccag gcctttctgg aggccgagag    1440
agctcaatcc attgcctatc acctcaaaat tgaggagcaa agagaaaaag tacatgaaaa    1500
tgaaaatata ggtaccactg agcctggaga gcaccaagag gccaagaaag cagagaactc    1560
atcaaatgag gaggaaacgt caagtgaagg caacatgagg gtgcatgctg tggattcttg    1620
catgagcttc cagtgtaaaa gaggccacat ctgtaaggca gaccaacagg gaaaacctca    1680
ctgtgtctgc caggatccag tgacttgtcc tccaacaaaa ccccttgatc aagtttgtgg    1740
cactgacaat cagacctatg ctagttcctg tcatctattc gctactaaat gcagactgga    1800
ggggaccaaa aaggggcatc aactccagct ggattatttt ggagcctgca atctattcc    1860
tacttgtacg gactttgaag tgattcagtt tcctctacgg atgagagact ggctcaagaa    1920
tatcctcatg cagctttatg aagccaactc tgaacatgct ggttatctaa atgagaagca    1980
gagaaataaa gtcaagaaaa tttacctgga tgaaaagagg cttttggctg gggaccatcc    2040
cattgatctt ctcttaaggg actttaagaa aaactaccac atgtatgtgt atcctgtgca    2100
ctggcagttt agtgaacttg accaacaccc tatggataga gtcttgacac attctgaact    2160
tgctcctctg cgagcatctc tggtgcccat ggaacactgc ataaccctt tctttgagga    2220
gtgtgaccc aacaaggata agcacatcac cctgaaggag tggggccact gctttggaat    2280
taaagaagag gacatagatg aaatctcttt gttttgaacg aagattttaa agaactcaac    2340
tttccagcat cctcctctgt tctaaccact tcagaaatat atgcagctgt gatacttgta    2400
gatttatatt tagcaaaatg ttagcatgta tgacaagaca atgagagtaa ttgcttgaca    2460
acaacctatg caccaggtat ttaacattaa ctttggaaac aaaaatgtac aattaagtaa    2520
agtcaacata tgcaaaatac tgtacattgt gaacagaagt ttaattcata gtaatttcac    2580
tctctgcatt gacttatgag ataattaatg attaaactat taatgataaa aataatgcat    2640
ttgtattgtt cataatatca tgtgcacttc aagaaaatgg aatgctactc ttttgtggtt    2700
tacgtgtatt attttcaata tcttaatacc ctaataaaga gtccataaaa atccaaaaaa    2760
aaaaaaaaaa aaaaaaaaaa aaaaaaaaaa aaaaaaaaaa aaaaaaaa                2808
```

<210> SEQ ID NO 24
<211> LENGTH: 664
<212> TYPE: PRT
<213> ORGANISM: Homo sapiens

<400> SEQUENCE: 24

```
Met Lys Thr Gly Leu Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Arg Ala Glu
        35                  40                  45

Asp Glu Glu Asn Glu Lys Glu Thr Ala Val Ser Thr Glu Asp Asp Ser
    50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Gln Glu Leu Gly
                85                  90                  95

Leu Lys Asp Gln Glu Asp Ser Asp Gly Asp Leu Ser Val Asn Leu Glu
            100                 105                 110

Tyr Ala Pro Ser Glu Gly Thr Leu Asp Ile Lys Glu Asp Met Ser Glu
```

-continued

```
            115                 120                 125
Pro Gln Glu Lys Lys Leu Ser Glu Asn Thr Asp Phe Leu Ala Pro Gly
130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
                180                 185                 190

Gln Asp Pro Asn Ile Ser Asn Gly Glu Glu Glu Glu Lys Glu Pro
                195                 200                 205

Gly Glu Val Gly Thr His Asn Asp Asn Gln Glu Arg Lys Thr Glu Leu
210                 215                 220

Pro Arg Glu His Ala Asn Ser Lys Gln Glu Glu Asp Asn Thr Gln Ser
225                 230                 235                 240

Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
                260                 265                 270

Asn Ala Glu Met Glu Glu Glu Asn Ala Ser Asn Val Asn Lys His Ile
                275                 280                 285

Gln Glu Thr Glu Trp Gln Ser Gln Glu Gly Lys Thr Gly Leu Glu Ala
290                 295                 300

Ile Ser Asn His Lys Glu Thr Glu Glu Lys Thr Val Ser Glu Ala Leu
305                 310                 315                 320

Leu Met Glu Pro Thr Asp Asp Gly Asn Thr Thr Pro Arg Asn His Gly
                325                 330                 335

Val Asp Asp Asp Gly Asp Asp Gly Asp Asp Gly Gly Thr Asp Gly
                340                 345                 350

Pro Arg His Ser Ala Ser Asp Asp Tyr Phe Ile Pro Ser Gln Ala Phe
                355                 360                 365

Leu Glu Ala Glu Arg Ala Gln Ser Ile Ala Tyr His Leu Lys Ile Glu
370                 375                 380

Glu Gln Arg Glu Lys Val His Glu Asn Glu Asn Ile Gly Thr Thr Glu
385                 390                 395                 400

Pro Gly Glu His Gln Glu Ala Lys Lys Ala Glu Asn Ser Ser Asn Glu
                405                 410                 415

Glu Glu Thr Ser Ser Glu Gly Asn Met Arg Val His Ala Val Asp Ser
                420                 425                 430

Cys Met Ser Phe Gln Cys Lys Arg Gly His Ile Cys Lys Ala Asp Gln
                435                 440                 445

Gln Gly Lys Pro His Cys Val Cys Gln Asp Pro Val Thr Cys Pro Pro
                450                 455                 460

Thr Lys Pro Leu Asp Gln Val Cys Gly Thr Asp Asn Gln Thr Tyr Ala
465                 470                 475                 480

Ser Ser Cys His Leu Phe Ala Thr Lys Cys Arg Leu Glu Gly Thr Lys
                485                 490                 495

Lys Gly His Gln Leu Gln Leu Asp Tyr Phe Gly Ala Cys Lys Ser Ile
                500                 505                 510

Pro Thr Cys Thr Asp Phe Glu Val Ile Gln Phe Pro Leu Arg Met Arg
                515                 520                 525

Asp Trp Leu Lys Asn Ile Leu Met Gln Leu Tyr Glu Ala Asn Ser Glu
530                 535                 540
```

```
His Ala Gly Tyr Leu Asn Glu Lys Gln Arg Asn Lys Val Lys Lys Ile
545                 550                 555                 560

Tyr Leu Asp Glu Lys Arg Leu Leu Ala Gly Asp His Pro Ile Asp Leu
                565                 570                 575

Leu Leu Arg Asp Phe Lys Lys Asn Tyr His Met Tyr Val Tyr Pro Val
            580                 585                 590

His Trp Gln Phe Ser Glu Leu Asp Gln His Pro Met Asp Arg Val Leu
        595                 600                 605

Thr His Ser Glu Leu Ala Pro Leu Arg Ala Ser Leu Val Pro Met Glu
    610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
                645                 650                 655

Asp Ile Asp Glu Asn Leu Leu Phe
            660

<210> SEQ ID NO 25
<211> LENGTH: 2645
<212> TYPE: DNA
<213> ORGANISM: Homo sapiens

<400> SEQUENCE: 25
gagcagcaga atttcaactc cagtagactt gaatatgcct ctgggcaaag aagcagagct      60
aacgaggaaa gggatttaaa gagttttttct tgggtgtttg tcaaactttt attccctgtc    120
tgtgtgcaga ggggattcaa cttcaattttt tctgcagtgg ctctgagtcc agccccttac    180
ttaaagatct ggaaagcatg aagactgggc tttttttcct atgtctcttg ggaactgcag    240
ctgcaatccc gacaaatgca agattattat ctgatcattc caaaccaact gctgaaacgg    300
tagcacccga caacactgca atccccagtt aagggctga agatgaagaa atgaaaaag      360 aaacagcagt atccacagaa gacgattccc accataaggc tgaaaaatca tcagtactaa    420
agtcaaaaga ggaaagccat gaacagtcag cagaacaggg caagagttct agccaagagc    480
tgggattgaa ggatcaagag gacagtgatg gtgacttaag tgtgaatttg gagtatgcac    540
catctgaagg tacattggac ataaaagaag atatgagtga gcctcaggag aaaaaactct    600
cagagaacac tgatttttttg gctcctggtg ttagttcctt cacagattct aaccaacaag    660
aaagtatcac aaagagagag gaaaaccaag aacaacctag aaattattca catcatcagt    720
tgaacaggag cagtaaacat agccaaggcc taagggatca aggaaaccaa gagcaggatc    780
caaatatttc caatggagaa gaggaagaag aaaaagagcc aggtgaagtt ggtacccaca    840
atgataacca agaaagaaag acagaattgc ccagggagca tgctaacagc aagcaggagg    900
aagacaatac ccaatctgat gatattttgg aagagtctga tcaaccaact caagtaagca    960
agatgcagga ggatgaattt gatcagggta accaagaaca agaagataac tccaatgcag   1020
aaatggaaga ggaaaatgca tcgaacgtca ataagcacat tcaagaaact gaatggcaga   1080
gtcaagaggg taaaactggc ctagaagcta tcagcaacca caagagaca gaagaaaaga    1140 ctgtttctga ggctctgctc atggaaccta ctgatgatgg taataccacg cccagaaatc    1200
atggagttga tgatgatggc gatgatgatg gcgatgatgg cggcactgat ggccccaggc   1260
acagtgcaag tgatgactac ttcatcccaa gccaggcctt tctggaggcc gagagagctc   1320
aatccattgc ctatcacctc aaaattgagg agcaaagaga aaagtacat gaaaatgaaa    1380 atataggtac cactgagcct ggagagcacc aagaggccaa gaaagcagag aactcatcaa   1440
```

```
atgaggagga acgtcaagt gaaggcaaca tgagggtgca tgctgtggat tcttgcatga    1500
gcttccagtg taaagaggc cacatctgta aggcagacca cagggaaaa cctcactgtg    1560 tctgccagga tccagtgact tgtcctccaa caaaacccct tgatcaagtt tgtggcactg    1620
acaatcagac ctatgctagt tcctgtcatc tattcgctac taaatgcaga ctggagggga    1680
ccaaaaaggg gcatcaactc cagctggatt attttggagc ctgcaaatct attcctactt    1740
gtacggactt tgaagtgatt cagtttcctc tacggatgag agactggctc aagaatatcc    1800
tcatgcagct ttatgaagcc aactctgaac acgctggtta tctaaatgag aagcagagaa    1860
ataaagtcaa gaaaatttac ctggatgaaa agaggctttt ggctggggac catcccattg    1920
accttctctt aagggacttt aagaaaaact accacatgta tgtgtatcct gtgcactggc    1980
agtttagtga acttgaccaa caccctatgg atagagtctt gacacattct gaacttgctc    2040
ctctgcgagc atctctggtg cccatggaac actgcataac ccgtttcttt gaggagtgtg    2100
accccaacaa ggataagcac atcaccctga aggagtgggg ccactgcttt ggaattaaag    2160
aagaggacat agatgaaaat ctcttgtttt gaacgaagat tttaagaac tcaactttcc    2220 agcatcctcc tctgttctaa ccacttcaga aatatatgca gctgtgatac ttgtagattt    2280
atatttagca aaatgttagc atgtatgaca agacaatgag agtaattgct tgacaacaac    2340
ctatgcacca ggtatttaac attaactttg gaaacaaaaa tgtacaatta agtaaagtca    2400
acatatgcaa aatactgtac attgtgaaca gaagtttaat tcatagtaat ttcactctct    2460
gcattgactt atgagataat taatgattaa actattaatg ataaaataa tgcatttgta    2520 ttgttcataa tatcatgtgc acttcaagaa aatggaatgc tactcttttg tggtttacgt    2580
gtattatttt caatatctta ataccctaat aaagagtcca taaaatcca aaaaaaaaa    2640 aaaaa                                                              2645
```

<210> SEQ ID NO 26
<211> LENGTH: 664
<212> TYPE: PRT
<213> ORGANISM: Homo sapiens

<400> SEQUENCE: 26

```
Met Lys Thr Gly Pro Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Trp Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ile Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160
```

-continued

```
Glu Glu Asn Gln Glu Gln Pro Arg Asn Tyr Ser His His Gln Leu Asn
                165                 170                 175
Arg Ser Ser Lys His Ser Gln Gly Leu Arg Asp Gln Gly Asn Gln Glu
            180                 185                 190
Gln Asp Pro Asn Ile Ser Asn Gly Glu Glu Glu Glu Lys Glu Pro
        195                 200                 205
Gly Glu Val Gly Thr His Asn Asp Asn Gln Glu Arg Lys Thr Glu Leu
    210                 215                 220
Pro Arg Glu His Ala Asn Ser Lys Gln Glu Glu Asp Asn Thr Gln Ser
225                 230                 235                 240
Asp Asp Ile Leu Glu Glu Ser Gln Pro Thr Gln Val Ser Lys Met
                245                 250                 255
Gln Glu Asp Glu Phe Asp Gln Gly Asn Gln Glu Gln Glu Asp Asn Ser
            260                 265                 270
Asn Ala Glu Met Glu Glu Asn Ala Ser Asn Val Asn Lys His Ile
        275                 280                 285
Gln Glu Thr Glu Trp Gln Ser Gln Gly Lys Thr Gly Leu Glu Ala
    290                 295                 300
Ile Ser Asn His Lys Glu Thr Glu Lys Thr Val Ser Glu Ala Leu
305                 310                 315                 320
Leu Met Glu Pro Thr Asp Asp Gly Asn Thr Thr Pro Arg Asn His Gly
                325                 330                 335
Val Asp Asp Asp Gly Asp Asp Gly Asp Asp Gly Gly Thr Asp Gly
            340                 345                 350
Pro Arg His Ser Ala Ser Asp Asp Tyr Phe Ile Pro Ser Gln Ala Phe
        355                 360                 365
Leu Glu Ala Glu Arg Ala Gln Ser Ile Ala Tyr His Leu Lys Ile Glu
    370                 375                 380
Glu Gln Arg Glu Lys Val His Glu Asn Glu Asn Ile Gly Thr Thr Glu
385                 390                 395                 400
Pro Gly Glu His Gln Glu Ala Lys Lys Ala Glu Asn Ser Ser Asn Glu
                405                 410                 415
Glu Glu Thr Ser Ser Glu Gly Asn Met Arg Val His Ala Val Asp Ser
            420                 425                 430
Cys Met Ser Phe Gln Cys Lys Arg Gly His Ile Cys Lys Ala Asp Gln
        435                 440                 445
Gln Gly Lys Pro His Cys Val Cys Gln Asp Pro Val Thr Cys Pro Pro
    450                 455                 460
Thr Lys Pro Leu Asp Gln Val Cys Gly Thr Asp Asn Gln Thr Tyr Ala
465                 470                 475                 480
Ser Ser Cys His Leu Phe Ala Thr Lys Cys Arg Leu Glu Gly Thr Lys
                485                 490                 495
Lys Gly His Gln Leu Gln Leu Asp Tyr Phe Gly Ala Cys Lys Ser Ile
            500                 505                 510
Pro Thr Cys Thr Asp Phe Glu Val Ile Gln Phe Pro Leu Arg Met Arg
        515                 520                 525
Asp Trp Leu Lys Asn Ile Leu Met Gln Leu Tyr Glu Ala Asn Ser Glu
    530                 535                 540
His Ala Gly Tyr Leu Asn Glu Lys Gln Arg Asn Lys Val Lys Lys Ile
545                 550                 555                 560
Tyr Leu Asp Glu Lys Arg Leu Leu Ala Gly Asp His Pro Ile Asp Leu
                565                 570                 575
Leu Leu Arg Asp Phe Lys Lys Asn Tyr His Met Tyr Val Tyr Pro Val
            580                 585                 590
```

```
His Trp Gln Phe Ser Glu Leu Asp Gln His Pro Met Asp Arg Val Leu
        595                 600                 605

Thr His Ser Glu Leu Ala Pro Leu Arg Ala Ser Leu Val Pro Met Glu
610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
        645                 650                 655

Asp Ile Asp Glu Asn Leu Leu Phe
        660

<210> SEQ ID NO 27
<211> LENGTH: 2808
<212> TYPE: DNA
<213> ORGANISM: Homo sapiens

<400> SEQUENCE: 27
cggcatgaga ggccagcctg ccagggaaat ccaggaatct gcaacaaaaa cgatgacagt      60
ctgaaatact ctctggtgcc aacctccaaa ttctcgtctg tcacttcaga cccccactag     120
ttgacagagc agcagaatat caactccagt agacttgaat gtgcctctgg gcaaagaagc     180
agagctaacg aggaaaggga tttaaagagt ttttcttggg tgtttgtcaa acttttattc     240
cctgtctgtg tgcagagggg attcaacttc aattttctgc agtggctctg ggtccagccc     300
cttacttaaa gatctggaaa gcatgaagac tgggcctttt ttcctatgtc tcttgggaac     360
tgcagctgca atcccgacaa atgcaagatt attatctgat cattccaaac caactgctga     420
aacggtagca cctgacaaca ctgcaatccc cagtttatgg gctgaagctg aagaaaatga     480
aaaagaaaca gcagtatcca cagaagacga ttcccaccat aaggctgaaa atcatcagt      540
actaaagtca aaagaggaaa gccatgaaca gtcagcagaa cagggcaaga gttctagcca     600
agagctggga ttgaaggatc aagaggacag tgatggtcac ttaagtgtga atttggagta     660
tgcaccaact gaaggtacat tggacataaa agaagatatg attgagcctc aggagaaaaa     720
actctcagag aacactgatt ttttggctcc tggtgttagt ccttcacag attctaacca     780
acaagaaagt atcacaaaga gagggaaaa ccaagaacaa cctagaaatt attcacatca     840
tcagttgaac aggagcagta acatagcca aggcctaagg gatcaaggaa ccaagagca      900
ggatccaaat atttccaatg gagaagagga gaagaaaaa gagccaggtg aagttggtac     960
ccacaatgat aaccaagaaa gaagacaga attgcccagg gagcatgcta acagcaagca    1020
ggaggaagac aataccaat ctgatgatat tttggaagag tctgatcaac aactcaagt     1080
aagcaagatg caggaggatg aatttgatca gggtaaccaa gaacaagaag ataactccaa    1140
tgcagaaatg gaagaggaaa atgcatcgaa cgtcaataag cacattcaag aaactgaatg    1200
gcagagtcaa gagggtaaaa ctggcctaga agctatcagc aaccacaaag agacagaaga    1260
aaagactgtt tctgaggctc tgctcatgga acctactgat gatggtaata ccacgcccag    1320
aaatcatgga gttgatgatg atggcgatga tgatggcgat gatggcggca ctgatggccc    1380
caggcacagt gcaagtgatg actacttcat cccaagccag gcctttctgg aggccgagag    1440
agctcaatcc attgcctatc acctcaaaat tgaggagcaa agagaaaaag tacatgaaaa    1500
tgaaaatata ggtaccactg agcctggaga gcaccaagag gccaagaaag cagagaactc    1560
atcaaatgag gaggaaacgt caagtgaagg caacatgagg gtgcatgctg tggattcttg    1620
catgagcttc cagtgtaaaa gaggccacat ctgtaaggca gaccaacagg gaaaacctca    1680
```

-continued

```
ctgtgtctgc caggatccag tgacttgtcc tccaacaaaa ccccttgatc aagtttgtgg    1740
cactgacaat cagacctatg ctagttcctg tcatctattc gctactaaat gcagactgga    1800
ggggaccaaa aagggcatc aactccagct ggattatttt ggagcctgca aatctattcc     1860
tacttgtacg gactttgaag tgattcagtt tcctctacgg atgagagact ggctcaagaa    1920
tatcctcatg cagctttatg aagccaactc tgaacatgct ggttatctaa atgagaagca    1980
gagaaataaa gtcaagaaaa tttacctgga tgaaaagagg cttttggctg gggaccatcc    2040
cattgatctt ctcttaaggg actttaagaa aaactaccac atgtatgtgt atcctgtgca    2100
ctggcagttt agtgaacttg accaacaccc tatggataga gtcttgacac attctgaact    2160
tgctcctctg cgagcatctc tggtgcccat ggaacactgc ataccccgtt tctttgagga    2220
gtgtgacccc aacaaggata agcacatcac cctgaaggag tggggccact gctttggaat    2280
taaagaagag gacatagatg aaaatctctt gttttgaacg aagattttaa agaactcaac    2340
tttccagcat cctcctctgt tctaaccact tcagaaatat atgcagctgt gatacttgta    2400
gatttatatt tagcaaaatg ttagcatgta tgacaagaca atgagagtaa ttgcttgaca    2460
acaacctatg caccaggtat ttaacattaa ctttggaaac aaaaatgtac aattaagtaa    2520
agtcaacata tgcaaaatac tgtacattgt gaacagaagt ttaattcata gtaatttcac    2580
tctctgcatt gacttatgag ataattaatg attaaactat taatgataaa aataatgcat    2640
ttgtattgtt cataatatca tgtgcacttc aagaaatgg aatgctactc ttttgtggtt     2700
tacgtgtatt attttcaata tcttaatacc ctaataaaga gtccataaaa atccaaaaaa    2760
aaaaaaaaaa aaaaaaaaaa aaaaaaaaaa aaaaaaaaaa aaaaaaaa                 2808
```

<210> SEQ ID NO 28
<211> LENGTH: 676
<212> TYPE: PRT
<213> ORGANISM: Coturnix coturnix

<400> SEQUENCE: 28

```
Met Lys Thr Val Leu Leu Leu Ile Cys Leu Leu Gly Ser Ala Phe Thr
1               5                   10                  15

Thr Pro Thr Asp Pro Leu Asn Tyr Gln Phe Gly Ala His Gly Gln Lys
            20                  25                  30

Thr Ala Glu Lys His Lys Tyr Thr His Ser Glu Met Pro Glu Glu Glu
        35                  40                  45

Asn Thr Gly Phe Val Asn Lys Gly Asp Val Leu Ser Gly His Arg Thr
    50                  55                  60

Ile Lys Ala Glu Val Pro Val Leu Asp Thr Gln Lys Asp Glu Pro Trp
65                  70                  75                  80

Ala Ser Arg Arg Gln Gly Gln Gly Asp Gly Glu His Gln Thr Lys Asn
                85                  90                  95

Ser Leu Arg Ser Ile Asn Phe Leu Thr Leu His Ser Asn Pro Gly Leu
            100                 105                 110

Ala Ser Asp Asn Gln Glu Ser Asn Ser Gly Ser Ser Arg Glu Gln His
        115                 120                 125

Ser Ser Glu His His Gln Pro Arg Arg His Arg Lys His Gly Asn Met
    130                 135                 140

Ala Gly Gln Trp Ala Leu Arg Gly Glu Ser Pro Val Asp Ala Leu Gly
145                 150                 155                 160

Leu Val Arg Glu Arg Asn Thr Trp Lys Tyr Asn Lys Asn Thr Val Gly
                165                 170                 175

Leu Asp Glu Asn Asn Asn Gly Ser Glu Glu Glu Glu Ala Gly Glu Glu
```

```
                    180                 185                 190
Glu Asp Glu Glu Trp Gly Glu Thr Asp Tyr Arg Asp Met Lys His
            195                 200                 205

Arg Ala Arg Gly Thr Ser His Gly Arg Glu Tyr Arg Trp Gln Asn
        210                 215                 220

Glu Asn Ser Arg Pro Ser Gly Glu Phe Leu Arg Asp Ser Ser Leu Pro
225                 230                 235                 240

Val Arg Ile Thr Lys Arg His Gly Glu Lys Phe Ser Met Glu Glu Glu
                245                 250                 255

Ser Gln Glu Lys Leu Tyr Lys Glu Gly Lys Leu Pro Leu Ser Lys Lys
            260                 265                 270

Asn His Asn Glu Asp Gln Gly Glu Lys Arg Gln Ser Glu Glu Ser Lys
        275                 280                 285

Glu His Phe Gln Val Val Asn Gln Arg Lys His Arg Ala Val Thr Lys
    290                 295                 300

Arg Gln Asp Lys Glu Gly Ser Asn Ala Glu Asp Asp Asn Asp Ser
305                 310                 315                 320

Gly Asp Asp Gly Glu Glu Asp Leu Gly Asn Val Trp Arg Glu Ala Val
                325                 330                 335

Tyr Glu Glu Glu Glu Arg Met Gln Ser Asn Asp Gln Asp Ser Ile Thr
            340                 345                 350

Asn Lys Gln Lys Glu Glu Ile Thr Ala Gly Asp Asp Ser Gly Val Tyr
        355                 360                 365

Arg Glu Met Gln Asp Tyr Lys Gly Asp Lys Ile Lys Asp Val Thr His
    370                 375                 380

Ser Glu Asp Asn His Tyr His His Glu Pro Pro Asn Ser Ser Ser Lys
385                 390                 395                 400

Gln Gln Leu Gln Thr Ser Ser Ser Val Glu Ser Met Asn Ser Thr Glu
                405                 410                 415

His Glu Asp Glu Val Lys Thr Thr Gly Gly Ser Tyr His Glu Glu Ser
            420                 425                 430

Ala Arg Asn Ser Thr Gly Lys Ala Leu Pro Asp Leu Cys Arg Asn Phe
        435                 440                 445

His Cys Lys Arg Gly Lys Val Cys Gln Ala Asp Lys Gln Gly Lys Pro
    450                 455                 460

Ser Cys Ile Cys Gln Asp Pro Ala Ala Cys Pro Ser Thr Lys Asp Tyr
465                 470                 475                 480

Lys Arg Val Cys Gly Thr Asp Asn Lys Thr Tyr Asp Gly Thr Cys Gln
                485                 490                 495

Leu Phe Gly Thr Lys Cys Gln Leu Glu Gly Thr Lys Met Gly Arg Gln
            500                 505                 510

Leu His Leu Asp Tyr Met Gly Ala Cys Lys His Ile Pro His Cys Thr
        515                 520                 525

Asp Tyr Glu Val Asn Gln Phe Pro Leu Arg Met Arg Asp Trp Leu Lys
    530                 535                 540

Asn Ile Leu Met Gln Tyr Tyr Glu Arg Asp Gln Asp Thr Ser Ala Phe
545                 550                 555                 560

Leu Thr Glu Lys Gln Arg Asn Lys Val Lys Lys Ile Tyr Leu Asn Glu
                565                 570                 575

Lys Arg Leu Val Ser Gly Glu His Pro Val Glu Leu Leu His Asp
            580                 585                 590

Phe Glu Lys Asn Tyr His Met Tyr Leu Tyr Pro Val His Trp Gln Phe
        595                 600                 605
```

-continued

```
Tyr Gln Leu Asp Gln His Pro Val Asp Arg Ser Leu Thr His Ser Glu
            610                 615                 620
Leu Ala Pro Leu Arg Ala Ser Leu Val Pro Met Glu His Cys Ile Thr
625                 630                 635                 640
Arg Phe Phe Gln Glu Cys Asp Gly Asp Gln Asp Lys Leu Ile Thr Leu
                645                 650                 655
Lys Glu Trp Cys His Cys Phe Ala Ile Lys Glu Glu Asp Ile Asn Glu
            660                 665                 670
Asn Leu Leu Phe
            675

<210> SEQ ID NO 29
<211> LENGTH: 676
<212> TYPE: PRT
<213> ORGANISM: Coturnix coturnix

<400> SEQUENCE: 29

Met Lys Thr Val Leu Leu Ile Cys Leu Leu Gly Ser Ala Phe Thr
1               5                   10                  15
Thr Pro Thr Asp Pro Leu Asn Tyr Gln Phe Gly Ala His Gly Gln Lys
            20                  25                  30
Thr Ala Glu Lys His Lys Tyr Thr His Ser Glu Met Pro Glu Glu Glu
        35                  40                  45
Asn Thr Gly Phe Val Asn Lys Gly Asp Val Leu Ser Gly His Arg Thr
    50                  55                  60
Ile Lys Ala Glu Val Pro Val Leu Asp Thr Gln Lys Asp Glu Pro Trp
65                  70                  75                  80
Ala Ser Arg Arg Gln Gly Gln Gly Asp Gly Glu His Gln Thr Lys Asn
                85                  90                  95
Ser Leu Arg Ser Ile Asn Phe Leu Thr Leu His Ser Asn Pro Gly Leu
            100                 105                 110
Ala Ser Asp Asn Gln Glu Ser Asn Ser Gly Ser Ser Arg Glu Gln His
        115                 120                 125
Ser Ser Glu His His Gln Pro Arg Arg His Arg Lys His Gly Asn Met
    130                 135                 140
Ala Gly Gln Trp Ala Leu Arg Gly Glu Ser Pro Val Asp Ala Leu Gly
145                 150                 155                 160
Leu Val Arg Glu Arg Asn Thr Trp Lys Tyr Asn Lys Asn Thr Val Gly
                165                 170                 175
Leu Asp Glu Asn Asn Asn Gly Ser Glu Glu Glu Ala Gly Glu Glu
            180                 185                 190
Glu Asp Glu Glu Trp Gly Glu Glu Thr Asp Tyr Arg Asp Met Lys His
        195                 200                 205
Arg Ala Arg Gly Thr Ser His Gly Arg Glu Tyr Arg Arg Trp Gln Asn
    210                 215                 220
Glu Asn Ser Arg Pro Ser Gly Phe Leu Arg Asp Ser Ser Leu Pro
225                 230                 235                 240
Val Arg Ile Thr Lys Arg His Gly Glu Lys Phe Ser Met Glu Glu
                245                 250                 255
Ser Gln Glu Lys Leu Tyr Lys Glu Gly Lys Leu Pro Leu Ser Lys Lys
            260                 265                 270
Asn His Asn Glu Asp Gln Gly Glu Lys Arg Gln Ser Glu Glu Ser Lys
        275                 280                 285
Glu His Phe Gln Val Val Asn Gln Arg Lys His Arg Ala Val Thr Lys
    290                 295                 300
```

Arg Gln Asp Lys Glu Gly Ser Asn Ala Glu Glu Asp Asn Asp Ser
305                 310                 315                 320

Gly Asp Asp Gly Glu Glu Asp Leu Gly Asn Val Trp Arg Glu Val
                325                 330                 335

Tyr Glu Glu Glu Arg Met Gln Ser Asn Asp Gln Asp Ser Ile Thr
            340                 345                 350

Asn Lys Gln Lys Glu Glu Ile Thr Ala Gly Asp Asp Ser Gly Val Tyr
        355                 360                 365

Arg Glu Met Gln Asp Tyr Lys Gly Asp Lys Ile Lys Asp Val Thr His
    370                 375                 380

Ser Glu Asp Asn His Tyr His His Glu Pro Asn Ser Ser Ser Lys
385                 390                 395                 400

Gln Gln Leu Gln Thr Ser Ser Ser Val Glu Ser Met Asn Ser Thr Glu
                405                 410                 415

His Glu Asp Glu Val Lys Thr Thr Gly Gly Ser Tyr His Glu Glu Ser
            420                 425                 430

Ala Arg Asn Ser Thr Gly Lys Ala Leu Pro Asp Leu Cys Arg Asn Phe
        435                 440                 445

His Cys Lys Arg Gly Lys Val Cys Gln Ala Asp Lys Gln Gly Lys Pro
    450                 455                 460

Ser Cys Ile Cys Gln Asp Pro Ala Ala Cys Pro Ser Thr Lys Asp Tyr
465                 470                 475                 480

Lys Arg Val Cys Gly Thr Asp Asn Lys Thr Tyr Asp Gly Thr Cys Gln
                485                 490                 495

Leu Phe Gly Thr Lys Cys Gln Leu Glu Gly Thr Lys Met Gly Arg Gln
            500                 505                 510

Leu His Leu Asp Tyr Met Gly Ala Cys Lys His Ile Pro His Cys Thr
        515                 520                 525

Asp Tyr Glu Val Asn Gln Phe Pro Leu Arg Met Arg Asp Trp Leu Lys
    530                 535                 540

Asn Ile Leu Met Gln Tyr Tyr Glu Arg Asp Gln Asp Thr Ser Ala Phe
545                 550                 555                 560

Leu Thr Glu Lys Gln Arg Asn Lys Val Lys Lys Ile Tyr Leu Asn Glu
                565                 570                 575

Lys Arg Leu Val Ser Gly Glu His Pro Val Glu Leu Leu His Asp
            580                 585                 590

Phe Glu Lys Asn Tyr His Met Tyr Leu Tyr Pro Val His Trp Gln Phe
        595                 600                 605

Tyr Gln Leu Asp Gln His Pro Val Asp Arg Ser Leu Thr His Ser Glu
    610                 615                 620

Leu Ala Pro Leu Arg Ala Ser Leu Val Pro Met Glu His Cys Ile Thr
625                 630                 635                 640

Arg Phe Phe Gln Glu Cys Asp Gly Asp Gln Asp Lys Leu Ile Thr Leu
                645                 650                 655

Lys Glu Trp Cys His Cys Phe Ala Ile Lys Glu Glu Asp Ile Asn Glu
            660                 665                 670

Asn Leu Leu Phe
        675

<210> SEQ ID NO 30
<211> LENGTH: 2678
<212> TYPE: DNA
<213> ORGANISM: Coturnix coturnix

<400> SEQUENCE: 30

```
gtcagacctt cctcctcaga agctcacaga aaaacacgct ttctgaaaga ttccacactc     60
aatgccaaaa tataccacag gaaaattttg caaggctcac ggatttccag tgcaccactg    120
gctaaccaag taggagcacc tcttctactg ccatgaaagg aaaccttcaa accctaccac    180
tgagccatta actaccatcc tgtttaagat ctgaaaaaca tgaagactgt attgctcctg    240
atttgtcttc taggatctgc tttcaccact ccaaccgatc cattgaacta ccaatttggg    300
gcccatggac agaaaactgc agagaagcat aaatatactc attctgaaat gccagaggaa    360
gagaacacag ggtttgtaaa caaggtgat gtgctgtctg ccacaggac cataaaagca    420 gaggtaccgg tactggatac acagaaggat gagccctggg cttccagaag acaaggacaa    480
ggtgatggtg agcatcaaac aaaaaacagc ctgaggagca ttaacttcct tactctgcac    540
agtaatccag ggttggcttc tgataaccag gaaagcaact ctggcagcag cagggaacag    600
cacagctctg agcaccacca gcccaggagg cacaggaaac acggcaacat ggctggccag    660
tgggctctga gaggagaaag tccagtggat gctcttggtc tggttcgtga gcgcaacaca    720
tggaaataca ataaaaacac agttggccta gatgaaaaca caatggaag tgaagaagag    780 gaagctgggg aggaagaaga tgaggaatgg ggtgaagaaa ctgattacag ggatatgaaa    840
cacagagccc gtgggacaag ccatggaaga gaatacagaa gatggcaaaa tgaaaacagc    900
cggccatctg gtgaattctt gagagattcc agtctgccag tacgtataac caagagacac    960
ggtgagaaat tcagcatgga ggaggaaagt caggaaaagc tctacaagga aggaaaactc   1020
cctctctcaa agaaaaatca taatgaggat caaggtgaaa aaagacaaag tgaagaaagt   1080
aaagagcatt ttcaagtagt caatcagcgc aaacacagag cagtgacgaa aaggcaggat   1140
aaggagggca gcaatgctga ggaggatgat aatgatagtg gtgatgatgg tgaggaagat   1200
cttggcaatg tctggaggga agcagtctac gaggaagagg aaagaatgca aagcaatgac   1260
caggacagta tcactaacaa gcaaaaagag gaaataactg ctggagatga cagtggagtt   1320
tatagggaga tgcaggatta caaaggtgac aaaaattaaag atgttactca ctctgaagac   1380
aatcattacc accatgagcc ccctaattcc agcagcaagc aacaactgca acaagtagc   1440 tctgttgaga gcatgaattc aacagagcat gaggatgagg ttaagaccac aggaggttca   1500
tatcatgagg aaagtgcaag gaacagcact gggaaggctc tcccggatct ttgtagaaac   1560
ttccactgca aaagaggaaa agtctgccaa gcagacaagc aaggaaaacc cagctgtatt   1620
tgccaagatc ctgctgcttg cccttccacc aaagattata agcgtgtttg tggcactgat   1680
aataagactt acgatggtac gtgccaactc tttggcacca aatgtcaact gaagggaca   1740 aaaatgggac gccagctgca cctggactat atgggtgcct gcaaacacat accccactgt   1800
actgattacg aagtgaatca gttccctctc cgtatgagag actggctcaa aaacatccta   1860
atgcaatatt atgaacgtga tcaggatacg tctgcatttc taaccgaaaa gcaaaggaat   1920
aaggtcaaaa agatataacct gaatgagaag cgtctcgtct ctggtgagca cccagttgag   1980
cttctcctgc atgactttga gaaaaactac acacatgtatc tctatcctgt gcactggcaa   2040
ttttatcagc ttgaccagca cccagttgac agatcactga ctcattcaga gctcgctcct   2100
ttgagagcct ccctcgttcc catggaacac tgcataaccc gtttcttcca ggagtgtgat   2160
ggagaccaag acaaacttat cactttgaaa gagtggtgcc actgctttgc gattaaggaa   2220
gaagacataa atgaaaatct cctgttctga gcccacctga gcagaatccc catgcagcgc   2280
tacagcttgt caaacatgca atgcccattt atgactgcaa ttaacagctc tgttaatttt   2340
caggaataag ttggcataag attcttggag gcagaacaag tcgctcttgg ataacacaag   2400
```

```
tgcctaattg ttacaaattc attaacagca gtagtgttta agagctctaa gtagctcata    2460
cttaaagagt gtttccctct gcacgtacca ataatctctt agtaagacga ctaacttgat    2520
gactgagttg ttcacaaaac ccttccgtag aattatagga tgtggatttt ataatacacc    2580
gataaaaact actttgaaat aggttttctt ttcctgtcgt ttactgtcag tagctctctg    2640
catagaaatg tcaaataaac agatcttgtt ttggtttc                           2678
```

```
<210> SEQ ID NO 31
<211> LENGTH: 306
<212> TYPE: PRT
<213> ORGANISM: Mus musculus

<400> SEQUENCE: 31

Met Trp Lys Arg Trp Leu Ala Leu Ser Leu Val Thr Ile Ala Leu Val
1               5                   10                  15

His Gly Glu Glu Glu Pro Arg Ser Lys Ser Lys Ile Cys Ala Asn Val
            20                  25                  30

Phe Cys Gly Ala Gly Arg Glu Cys Ala Val Thr Glu Lys Gly Glu Pro
        35                  40                  45

Thr Cys Leu Cys Ile Glu Gln Cys Lys Pro His Lys Arg Pro Val Cys
    50                  55                  60

Gly Ser Asn Gly Lys Thr Tyr Leu Asn His Cys Glu Leu His Arg Asp
65                  70                  75                  80

Ala Cys Leu Thr Gly Ser Lys Ile Gln Val Asp Tyr Asp Gly His Cys
                85                  90                  95

Lys Glu Lys Lys Ser Ala Ser Pro Ser Ala Ser Pro Val Val Cys Tyr
            100                 105                 110

Gln Ala Asn Arg Asp Glu Leu Arg Arg Arg Leu Ile Gln Trp Leu Glu
        115                 120                 125

Ala Glu Ile Ile Pro Asp Gly Trp Phe Ser Lys Gly Ser Asn Tyr Ser
    130                 135                 140

Glu Ile Leu Asp Lys Tyr Phe Lys Ser Phe Asp Asn Gly Asp Ser His
145                 150                 155                 160

Leu Asp Ser Ser Glu Phe Leu Lys Phe Val Glu Gln Asn Glu Thr Ala
                165                 170                 175

Ile Asn Ile Thr Thr Tyr Ala Asp Gln Glu Asn Asn Lys Leu Leu Arg
            180                 185                 190

Ser Leu Cys Val Asp Ala Leu Ile Glu Leu Ser Asp Glu Asn Ala Asp
        195                 200                 205

Trp Lys Leu Ser Phe Gln Glu Phe Leu Lys Cys Leu Asn Pro Ser Phe
    210                 215                 220

Asn Pro Pro Glu Lys Lys Cys Ala Leu Glu Asp Glu Thr Tyr Ala Asp
225                 230                 235                 240

Gly Ala Glu Thr Glu Val Asp Cys Asn Arg Cys Val Cys Ser Cys Gly
                245                 250                 255

His Trp Val Cys Thr Ala Met Thr Cys Asp Gly Lys Asn Gln Lys Gly
            260                 265                 270

Val Gln Thr His Thr Glu Glu Lys Thr Gly Tyr Val Gln Glu Leu
        275                 280                 285

Gln Lys His Gln Gly Thr Ala Glu Lys Thr Lys Lys Val Asn Thr Lys
    290                 295                 300

Glu Ile
305

<210> SEQ ID NO 32
```

<211> LENGTH: 3610
<212> TYPE: DNA
<213> ORGANISM: Mus musculus

<400> SEQUENCE: 32

| | | | | | |
|---|---|---|---|---|---|
| gttcctcgga | gcctggtgat | aagcgacgct | cccaccttcg | cctctaactc | gctgccgcca | 60 |
| ccctgcccag | tgtcctccgg | agtcccggac | ccgagcacga | tgtggaaacg | atggctggcg | 120 |
| ctctcgctgg | tgaccatcgc | cctggtccac | ggcgaggagg | aacctagaag | caaatccaag | 180 |
| atctgcgcca | atgtgttttg | tggagctggc | agggaatgtg | ccgtcacaga | aaggggggag | 240 |
| cccacgtgcc | tctgcattga | gcaatgcaaa | cctcacaaga | ggcctgtgtg | tggcagtaat | 300 |
| ggcaagacct | acctcaacca | ctgtgaactt | catagagatg | cctgcctcac | tggatccaag | 360 |
| atccaggttg | attatgatgg | gcactgcaaa | gaaaagaagt | ctgcgagtcc | atctgccagc | 420 |
| ccagttgtct | gctatcaagc | taaccgcgat | gagctccgac | ggcgcctcat | ccagtggctg | 480 |
| gaagctgaga | tcattccaga | tggctggttc | tctaaaggca | gtaactacag | tgagatccta | 540 |
| gacaagtact | ttaagagctt | tgataatggc | gactctcacc | tggactccag | tgaattcctg | 600 |
| aaattcgtgg | agcagaatga | aacagccatc | aacatcacca | cttatgcaga | tcaggagaac | 660 |
| aacaaactgc | tcagaagcct | ctgtgttgac | gccctcattg | aactgtctga | tgagaacgct | 720 |
| gactggaaac | tcagcttcca | agagttcctc | aagtgcctca | acccatcctt | caaccctcct | 780 |
| gagaagaagt | gtgccctgga | ggacgaaacc | tatgcagatg | gagctgagac | tgaggtggac | 840 |
| tgcaatcgct | gtgtctgttc | ctgtggccac | tgggtctgca | cagcaatgac | ctgtgatgga | 900 |
| aagaatcaga | agggggtcca | gacccacaca | gaggaggaga | agacaggata | tgtccaggaa | 960 |
| ctccagaagc | accagggcac | agcagaaaag | accaagaagg | tgaacaccaa | agagatctaa | 1020 |
| gaagaggcac | agagcaccgt | gtccggagcc | cagcgcctcc | tcttcagcgc | tgagcccagt | 1080 |
| acacacagag | tctgcagcaa | tcaccaaatc | actagtattt | gcttgtatgg | cagcgaatct | 1140 |
| tattttgttt | gttttgcaat | aaaggaaatg | agggtggcca | gcctagcgag | ggaaggccac | 1200 |
| aaccttcacc | tgtaggaatg | ctttaagaga | aactaaagga | cacctttggga | cgagaggcaa | 1260 |
| ctaaggaaac | agcatcgggt | tggcagagga | gcagaggcag | gtttgaatga | agcctttctg | 1320 |
| gggtcacagc | agctgcgagg | agaatacagg | aaaagcatag | agaaacattg | aactagccct | 1380 |
| gctggaggaa | gtggggggag | ctttgtaggg | aggaaccctg | ctgctttgac | ccttgtcacc | 1440 |
| actgtcagca | tgacagacct | gcagcaagtc | tgcttctcct | tttggtccca | acaatcacct | 1500 |
| gaacacacag | ccgcccaact | agttacctgt | gtccctcagc | cttgcatgga | gtttcctgga | 1560 |
| ggaggtgttt | aaatgatgca | gacacttatg | tacttcaagc | gccatggaga | cctaaccaaa | 1620 |
| tttttaaaat | acattttct | ttttttttt | ttttgttaac | caaaggtgct | atttctctgt | 1680 |
| aaaagacttt | tttccaagct | gacttcattc | ctcagttatt | accgttatat | tattgttgtt | 1740 |
| ttttaatatt | tcattttttg | actagatatt | aagcttttgt | aattattttt | tcattagtcc | 1800 |
| tactatttca | gaagtgaagg | tgaaggggt | ttgggcattt | ttccaggtac | agggaactct | 1860 |
| gtaacacaaa | cagcccatac | cctgtcacat | attagaccgg | ttgcagttcg | gagctgcacc | 1920 |
| ccaacccaga | gcttctagaa | aatcagctcc | atgccacgaa | gcacaagagg | cccctcagac | 1980 |
| agaagccaca | ggacaaagca | tcttcataga | cagctgttga | gatccaaaca | gttaatttgc | 2040 |
| ttttgtttct | tgtaagaagt | tccaaggatg | gacgctcagg | ctatcccagc | ctgccagcct | 2100 |
| gctgtgatct | gtggctaact | ggcagagtca | gccactgtgg | tccttagctg | ctcctgtttc | 2160 |
| taggtgtcag | tttacttagt | aaactggtaa | gaatgaatct | tggaatttaa | taaatggtag | 2220 |

-continued

```
tttgtggttt agccaactgg tccagaggga gctaccttct ccttaggata gatgaatcta    2280
caccataaga aaaccagcc aggaatagca tggatgggtt ttgctttggt tgaaatgatc     2340
ctagcaggtg actgggtatg aggacttcat ggtcactctg cccaggaaga gagcgtgaag    2400
gacaactagc agcttcctta gggatggtac acatgagtgt gatctctgga gtcagaggtt    2460
tccccacaca catgatgata aaactttttca gatttagagc ggttaaaact ggagatcgaa   2520
tctggattga gaatcagcac tgggggagaa actgttattg aaagtcaatc ctttcttttga  2580
gcctccgaat aaactatgga gattttcctg cataggaaag tgtggaatgt tgagctattg   2640
agatgggagt ggaattcgtc ctaaatagtt tttcctggtc tcatctgaac aagacaatttt  2700
ggctctgcct agtgttctgt gccctccctt tcaaaagctc tgagccccgc tcatgcagtc   2760
cagatttcat cccctctcc aagtgccttg gagagctcac agcagcaatg ccatcatcaa    2820
aagttttgct gctgggaaga aaaaaaaaaa aaaaaagaa aaaaaaagt tttgctggtt     2880
cttggaggtg atgggagagg gcaggagtat caatttgttc aagtagctgc agtgtctgtt   2940
ggccaatcat ctttagaacc ctgtaacact gagtaccaga gggcaagccc acattcctct   3000
tctgctactt cagtgtaact agggcagctg ttgtctgaag caccatagat tcaggtgatc   3060
ctccatagat tcaggtgatc ctccatagat tcaggtgatc cttgaaccgt tcatgaaaag   3120
ctgctaagta gcctggtttg ggagacttgg gttgagattt gcatgggacc aacacgcagg   3180
attacatctt cttcagttcc tagagtcctc tagaagccta tagaacaaga cggcaagctc   3240
tctgggcttg ctctggggtt ttgttctgtg gttttatgtt gttcttgttg ttttattaac   3300
atcagtgtct cttaagatcc aggacccagg gaggtctttt cacatacata taccaggact  3360
cttgggtact actgtcagtc ttggggaagc aggctcctcc atcggcaacc aaatccatgt   3420
gagcactccg aatgccttgg ttagtcctat gacctaaata gttaaacttc agaaaatggt   3480
ttcaacagat ttctgtgccg agtggttttg aaattgcatt tgtatttgct gtgcttctgt   3540
attccatta actgggtttt ttgttacttc tgatttttgt tactattaat aaataaaaat    3600
aaaataaagt                                                          3610
```

<210> SEQ ID NO 33
<211> LENGTH: 439
<212> TYPE: PRT
<213> ORGANISM: Homo sapiens

<400> SEQUENCE: 33

```
Met Pro Ala Ile Ala Val Leu Ala Ala Ala Ala Ala Trp Cys Phe
1               5                   10                  15

Leu Gln Val Glu Ser Arg His Leu Asp Ala Leu Ala Gly Gly Ala Gly
            20                  25                  30

Pro Asn His Gly Asn Phe Leu Asp Asn Asp Gln Trp Leu Ser Thr Val
        35                  40                  45

Ser Gln Tyr Asp Arg Asp Lys Tyr Trp Asn Arg Phe Asp Asp Asp
    50                  55                  60

Tyr Phe Arg Asn Trp Asn Pro Asn Lys Pro Phe Asp Gln Ala Leu Asp
65                  70                  75                  80

Pro Ser Lys Asp Pro Cys Leu Lys Val Lys Cys Ser Pro His Lys Val
                85                  90                  95

Cys Val Thr Gln Asp Tyr Gln Thr Ala Leu Cys Val Ser Arg Lys His
            100                 105                 110

Leu Leu Pro Arg Gln Lys Lys Gly Asn Val Ala Gln Lys His Trp Val
        115                 120                 125
```

```
Gly Pro Ser Asn Leu Val Lys Cys Lys Pro Cys Pro Val Ala Gln Ser
            130                 135                 140

Ala Met Val Cys Gly Ser Asp Gly His Ser Tyr Thr Ser Lys Cys Lys
145                 150                 155                 160

Leu Glu Phe His Ala Cys Ser Thr Gly Lys Ser Leu Ala Thr Leu Cys
                165                 170                 175

Asp Gly Pro Cys Pro Cys Leu Pro Glu Pro Glu Pro Pro Lys His Lys
            180                 185                 190

Ala Glu Arg Ser Ala Cys Thr Asp Lys Glu Leu Arg Asn Leu Ala Ser
            195                 200                 205

Arg Leu Lys Asp Trp Phe Gly Ala Leu His Glu Asp Ala Asn Arg Val
210                 215                 220

Ile Lys Pro Thr Ser Ser Asn Thr Ala Gln Gly Arg Phe Asp Thr Ser
225                 230                 235                 240

Ile Leu Pro Ile Cys Lys Asp Ser Leu Gly Trp Met Phe Asn Lys Leu
                245                 250                 255

Asp Met Asn Tyr Asp Leu Leu Leu Asp Pro Ser Glu Ile Asn Ala Ile
            260                 265                 270

Tyr Leu Asp Lys Tyr Glu Pro Cys Ile Lys Pro Leu Phe Asn Ser Cys
            275                 280                 285

Asp Ser Phe Lys Asp Gly Lys Leu Ser Asn Asn Glu Trp Cys Tyr Cys
            290                 295                 300

Phe Gln Lys Pro Gly Gly Leu Pro Cys Gln Asn Glu Met Asn Arg Ile
305                 310                 315                 320

Gln Lys Leu Ser Lys Gly Lys Ser Leu Leu Gly Ala Phe Ile Pro Arg
                325                 330                 335

Cys Asn Glu Glu Gly Tyr Tyr Lys Ala Thr Gln Cys His Gly Ser Thr
            340                 345                 350

Gly Gln Cys Trp Cys Val Asp Lys Tyr Gly Asn Glu Leu Ala Gly Ser
            355                 360                 365

Arg Lys Gln Gly Ala Val Ser Cys Glu Glu Glu Gln Glu Thr Ser Gly
            370                 375                 380

Asp Phe Gly Ser Gly Gly Ser Val Val Leu Leu Asp Asp Leu Glu Tyr
385                 390                 395                 400

Glu Arg Glu Leu Gly Pro Lys Asp Lys Glu Gly Lys Leu Arg Val His
            405                 410                 415

Thr Arg Ala Val Thr Glu Asp Asp Glu Asp Glu Asp Asp Asp Lys Glu
            420                 425                 430

Asp Glu Val Gly Tyr Ile Trp
            435
```

<210> SEQ ID NO 34
<211> LENGTH: 3484
<212> TYPE: DNA
<213> ORGANISM: Homo sapiens

<400> SEQUENCE: 34

```
cactctctgt tgtccaatgg acacacctgt cgtgttttga gccagcgaga gatgcagtgg      60
aagtgaaaag catggttaca gactccccat gcgacagtac actcttctga agtagcggac     120
gcctggttag cttgacattc tatgcaaaga tccataatgt ggttcctgca gatggcacag     180
ttatcaacca caatatccca ggcccagagg gctactgcat tccactttt  cacttcaaag     240 cgcttcttgc ccgcgccgct gttggtgccg ctcggggtat ccacatccat cgctgcgggc     300
tcacaaagcg gccagacgct cggcggcggc gtgtggcagg agcgcagggg cgcgagccgg     360
```

-continued

```
cgatcagcct tcccggcgac cgtgccgcgg gagctcgagc aactcggact aggggacccg    420
ggccggcccc caagatgccg gcgatcgcgg tgttggcggc ggccgccgcg gcgtggtgct    480
tcctccaagt cgagagccgg cacctggacg cgctcgccgg aggcgcgggc cccaaccacg    540
gcaatttcct agacaatgac cagtggctga gcaccgtctc ccagtacgac cgggacaagt    600
actggaaccg ctttcgagac gatgattatt tcagaaactg gaatcccaac aagccctttg    660
accaagccct ggacccatcc aaggacccct gcctgaaggt aaaatgcagc cctcacaaag    720
tgtgtgtgac ccaggactac cagaccgccc tgtgtgtcag ccgcaagcac ctgctcccca    780
ggcaaaagaa ggggaacgtg gcccagaaac actgggttgg accttcgaat ttggtcaagt    840
gcaagccctg tcccgtggca cagtcagcca tggtctgcgg ctcagatggc cactcctaca    900
catccaagtg caaattggag ttccatgctt gttctactgg caaaagcctc gccaccctct    960
gtgatgggcc ctgtccctgt ctcccagagc ctgagccacc aaagcacaag cagaaagga    1020 gtgcctgcac agacaaggag ttgcggaacc ttgcctcccg gctgaaggat tggtttggag    1080
ctctccacga ggatgcgaac agagtcatca agcccaccag ctccaacaca gcccaaggca    1140
ggtttgacac tagcatcctg cccatctgca aggactccct gggctggatg ttcaacaagt    1200
tggacatgaa ctatgacctc ctgcttgacc cttcagagat caatgccatc tacctggata    1260
agtacgagcc ctgtatcaag cctctttttca actcgtgtga ctccttcaag gatggcaagc    1320
tttctaacaa tgagtggtgc tactgcttcc agaagcctgg aggtctccct tgccagaatg    1380
aaatgaacag aattcagaag ctgagtaagg ggaaaagcct gttgggggcc ttcatacctc    1440
ggtgtaatga ggagggctat tacaaagcca cacagtgcca cggcagcacg gggcagtgct    1500
ggtgtgtgga caaatatggg aatgagttgg ctggctccag gaaacagggt gctgtgagct    1560
gtgaagagga gcaggaaacc tcagggggatt ttggcagtgg tgggtccgtg gtcctgctgg    1620
atgacctaga atatgaacgg gagctgggac caaggacaa agaggggaag ctgagggtgc    1680
acacccgagc cgtgacagag gatgatgagg atgaggatga tgacaaagag gatgaggtcg    1740
ggtacatatg gtagtgccca caagaaagag gacacaagtt ttgcacaaaa ttgcaagtca    1800
cttcctattc ctgcatttgt atctaagact ccaaggcacc aaggtctctt ctccattgtt    1860
gctctctata cccgacctaa ggtttggaag acaactgctt gttcccagag gattctgatt    1920
ttgcatatgt ttgtatggga gaaagggtgt tgtgttttt tttttgttgt tgtttatttt    1980
ttggataggg aagtcattgg cttaattaga gcctccttcc tttctgtgag attttttccaa    2040 caagcatgtg atttacgtgg aattctgaca gtgcagggag ccccccaccct cttaaatgtc    2100 aaagaccctt tttgattacc cacactggtg gttattacag catggttccc agccttacag    2160
tgtctaagtg cttctcttgt gtcctgtaga tgttgtgaaa aagaaaaaaa caaaaaatac    2220
accacactgt actttttccc cctgcccccg ttactgccgg tgattattat taaaaattag    2280 ttttttttcac atcattctat ctggcttcct ataaacaaca gccttaattc agtcaagact    2340 cccctttggga attcattta ttaaaaattg gtgtctggat acttccctgt acatgcataa    2400
atatgcatgc atgtacagaa agactgtatg tgtgtgcctt gcacacacac ccatacctct    2460
cagaaaaagt gtttgggtat cttaaaaact cgaaaacaa tgataaattt ctcagcttgt    2520
ccagacctga aacaaatttt ctggaataag aaatttgtat taaagtcctt ttttgcacta    2580
acagttggct cttgtagcct gcaggctgag gaagtctctt ctctgtgcat cagcagagtt    2640
actgaaagcc tctgattgag aaaaaacctc cgtctgccta aatcacttt ctcgcagaag    2700 ccatgcgact cccacacgac acgggcagct tcacaagcca tctctttcat ttctgcttga    2760
```

-continued

```
agccccttgg ctgcagcaat cctgtctgcc ataggtttct tccttcctta cctactcaag    2820
ggctttttct aaggcatgca cacatatctc ctgttctctg agagtaccat ggtgttcctt    2880
aaaagaagaa aatttctaat tctgaactca atgttttgct tttactccct ttctactgac    2940
aaatcatgat aagggcacaa aagctgtaca gattttttt tttaaccact caatcccaaa    3000
tggaggccta caagaacat cgtaataaca catggaagca aacccgggt ttttaagagc    3060 aaattctgtc cccccctcac tcccccaagt gacaagatac taatgaagaa agttcttcac    3120
catagtgttt gttttaacta aactcattgg agtctagttc caaatttggt agggtcatca    3180
tctctacatt ccttaggatt tctctcccta tcaagctggc ccagatacaa gtaccaaaca    3240
gtagtctctg aagttcccat ttccttcagt accagtctat aagctactgt ccgccactga    3300
ttttcatcta tcagggtgtc ctaatcagaa tcagccaccc aagcaagcct ctctggccca    3360
catatctatc tcttgccttc ccccatgaac ttcagcctgt ccacacaaaa gccacataaa    3420
ctcaagcaag aaatatgttc agccaaaaca tgattatagt ggcagctgac caataccca    3480 cccc                                                                 3484
```

<210> SEQ ID NO 35
<211> LENGTH: 434
<212> TYPE: PRT
<213> ORGANISM: Homo sapiens

<400> SEQUENCE: 35

```
Met Leu Pro Ala Arg Cys Ala Arg Leu Leu Thr Pro His Leu Leu Leu
1               5                   10                  15

Val Leu Val Gln Leu Ser Pro Ala Arg Gly His Arg Thr Thr Gly Pro
            20                  25                  30

Arg Phe Leu Ile Ser Asp Arg Asp Pro Gln Cys Asn Leu His Cys Ser
        35                  40                  45

Arg Thr Gln Pro Lys Pro Ile Cys Ala Ser Asp Gly Arg Ser Tyr Glu
    50                  55                  60

Ser Met Cys Glu Tyr Gln Arg Ala Lys Cys Arg Asp Pro Thr Leu Gly
65                  70                  75                  80

Val Val His Arg Gly Arg Cys Lys Asp Ala Gly Gln Ser Lys Cys Arg
                85                  90                  95

Leu Glu Arg Ala Gln Ala Leu Glu Gln Ala Lys Lys Pro Gln Glu Ala
            100                 105                 110

Val Phe Val Pro Glu Cys Gly Glu Asp Gly Ser Phe Thr Gln Val Gln
        115                 120                 125

Cys His Thr Tyr Thr Gly Tyr Cys Trp Cys Val Thr Pro Asp Gly Lys
    130                 135                 140

Pro Ile Ser Gly Ser Ser Val Gln Asn Lys Thr Pro Val Cys Ser Gly
145                 150                 155                 160

Ser Val Thr Asp Lys Pro Leu Ser Gln Gly Asn Ser Gly Arg Lys Asp
                165                 170                 175

Asp Gly Ser Lys Pro Thr Pro Thr Met Glu Thr Gln Pro Val Phe Asp
            180                 185                 190

Gly Asp Glu Ile Thr Ala Pro Thr Leu Trp Ile Lys His Leu Val Ile
        195                 200                 205

Lys Asp Ser Lys Leu Asn Asn Thr Asn Ile Arg Asn Ser Glu Lys Val
    210                 215                 220

Tyr Ser Cys Asp Gln Glu Arg Gln Ser Ala Leu Glu Glu Ala Gln Gln
225                 230                 235                 240

Asn Pro Arg Glu Gly Ile Val Ile Pro Glu Cys Ala Pro Gly Gly Leu
```

|     |     |     |     |     | 245 |     |     |     |     | 250 |     |     |     |     | 255 |     |
Tyr Lys Pro Val Gln Cys His Gln Ser Thr Gly Tyr Cys Trp Cys Val
            260                     265                     270

Leu Val Asp Thr Gly Arg Pro Leu Pro Gly Thr Ser Thr Arg Tyr Val
            275                     280                     285

Met Pro Ser Cys Glu Ser Asp Ala Arg Ala Lys Thr Thr Glu Ala Asp
            290                     295                     300

Asp Pro Phe Lys Asp Arg Glu Leu Pro Gly Cys Pro Glu Gly Lys Lys
305                     310                     315                     320

Met Glu Phe Ile Thr Ser Leu Leu Asp Ala Leu Thr Thr Asp Met Val
                        325                     330                     335

Gln Ala Ile Asn Ser Ala Ala Pro Thr Gly Gly Gly Arg Phe Ser Glu
            340                     345                     350

Pro Asp Pro Ser His Thr Leu Glu Glu Arg Val Val His Trp Tyr Phe
            355                     360                     365

Ser Gln Leu Asp Ser Asn Ser Ser Asn Asp Ile Asn Lys Arg Glu Met
            370                     375                     380

Lys Pro Phe Lys Arg Tyr Val Lys Lys Ala Lys Pro Lys Lys Cys
385                     390                     395                     400

Ala Arg Arg Phe Thr Asp Tyr Cys Asp Leu Asn Lys Asp Lys Val Ile
                        405                     410                     415

Ser Leu Pro Glu Leu Lys Gly Cys Leu Gly Val Ser Lys Glu Gly Arg
            420                     425                     430

Leu Val

<210> SEQ ID NO 36
<211> LENGTH: 3669
<212> TYPE: DNA
<213> ORGANISM: Homo sapiens

<400> SEQUENCE: 36
gcctgctgcc gcctgggccc cgccgagcgg agctagcgcc gcgcgcagag cacacgctcg      60
cgctccagct cccctcctgc gcggttcatg actgtgtccc ctgaccgcag cctctgcgag     120
cccccgccgc aggaccacgg cccgctcccc gccgcgcga gggccccgag cgaaggaagg      180
aagggaggcg cgctgtgcgc cccgcggagc ccgcgaaccc cgctcgctgc cggctgccca     240
gcctggctgg caccatgctg cccgcgcgct gcgcccgcct gctcacgccc cacttgctgc     300
tggtgttggt gcagctgtcc cctgctcgcg gccaccgcac cacaggcccc aggtttctaa     360
taagtgaccg tgacccacag tgcaacctcc actgctccag gactcaaccc aaacccatct     420
gtgcctctga tggcaggtcc tacgagtcca tgtgtgagta ccagcgagcc aagtgccgag     480
acccgaccct gggcgtggtg catcgaggta gatgcaaaga tgctggccag agcaagtgtc     540
gcctggagcg ggctcaagcc ctggagcaag ccaagaagcc tcaggaagct gtgtttgtcc     600
cagagtgtgg cgaggatggc tcctttaccc aggtgcagtg ccatacttac actgggtact     660
gctggtgtgt caccccggat gggaagccca tcagtggctc ttctgtgcag aataaaaactc    720
ctgtatgttc aggttcagtc accgacaagc ccttgagcca gggtaactca ggaaggaaag    780
atgacgggtc taagccgaca cccacgatgg agacccagcc ggtgttcgat ggagatgaaa    840
tcacagcccc aactctatgg attaaacact tggtgatcaa ggactccaaa ctgaacaaca    900
ccaacataag aaattcagag aaagtctatt cgtgtgacca ggagaggcag agtgccctgg    960
aagaggccca gcagaatccc gtgagggta ttgtcatccc tgaatgtgcc cctggggac    1020
tctataagcc agtgcaatgc caccagtcca ctggctactg ctggtgtgtg ctggtggaca   1080

```
cagggcgccc gctgcctggg acctccacac gctacgtgat gcccagttgt gagagcgacg   1140
ccagggccaa gactacagag gcggatgacc ccttcaagga cagggagcta ccaggctgtc   1200
cagaagggaa gaaatggag tttatcacca gcctactgga tgctctcacc actgacatgg    1260
ttcaggccat taactcagca gcgcccactg gaggtgggag gttctcagag ccagacccca   1320
gccacaccct ggaggagcgg gtagtgcact ggtatttcag ccagctggac agcaatagca   1380
gcaacgacat taacaagcgg gagatgaagc ccttcaagcg ctacgtgaag aagaaagcca   1440
agcccaagaa atgtgcccgg cgtttcaccg actactgtga cctgaacaaa gacaaggtca   1500
tttcactgcc tgagctgaag ggctgcctgg gtgttagcaa agaaggacgc ctcgtctaag   1560
gagcagaaaa cccaagggca ggtggagagt ccagggaggc aggatggatc accagacacc   1620
taaccttcag cgttgcccat ggccctgcca catcccgtgt aacataagtg gtgcccacca   1680
tgtttgcact tttaataact cttacttgcg tgttttgttt ttggtttcat tttaaaacac   1740
caatatctaa taccacagtg ggaaaaggaa agggaagaaa gactttattc tctctcttat   1800 tgtaagttttt tggatctgct actgacaact tttagagggt tttgggggggg tggggagggg  1860 tgttgttggg gcctgagaag aaagagattt atatgctgta tataaatata tatgtaaatt   1920
gtatagttct tttgtacagg cattggcatt gctgtttgtt tatttctctc cctctgcctg   1980
ctgtgggtgg tgggcactct ggacacatag tccagctttc taaaatccag gactctatcc   2040
tgggcctact aaacttctgt ttggagactg acccttgtgt ataaagacgg gagtcctgca   2100
attgtactgc ggactccacg agttcttttc tggtgggagg actatattgc cccatgccat   2160
tagttgtcaa aattgataag tcacttggct ctcggccttg tccagggagg ttgggctaag   2220
gagagatgga aactgccctg ggagaggaag ggagtccaga tcccatgaat agcccacaca   2280
ggtaccggct ctcagagggt ccgtgcattc ctgctctccg gacccccaaa gggcccagca   2340
ttggtgggtg caccagtatc ttagtgaccc tcggagcaaa ttatccacaa aggatttgca   2400
ttacgtcact cgaaacgttt tcatccatgc ttagcatcta ctctgtataa cgcatgagag   2460
gggaggcaaa gaagaaaagg acacacggaa gggcctttaa aaaagtagat atttaatatc   2520
taagcagggg agggacagg acagaaagcc tgcactgagg ggtgcggtgc caacagggaa    2580
actcttcacc tccctgcaaa cctaccagtg aggctcccag agacgcagct gtctcagtgc   2640
ccaggggcag attgggtgtg acctctccac tcctccatct cctgctgttg tcctagtggc   2700
tatcacaggc ctgggtgggt gggttggggg aagtgtcagt caccttgttg gtaacactaa   2760
agttgttttg ttggtttttt aaaaacccaa tactgaggtt cttcctgttc cctcaagttt   2820
tcttatgggc ttccaggctt taagctaatt ccagaagtaa aactgatctt gggtttccta   2880
ttctgcctcc cctagaaggg cagggtgat aacccagcta cagggaaatc ccggcccagc    2940
tttccacagg catcacaggc atcttccgcg gattctaggg tgggctgccc agccttctgg   3000
tctgaggcgc agctccctct gcccaggtgc tgtgcctatt caagtggcct tcaggcagag   3060
cagcaagtgg cccttagcgc ccctttccat aagcagctgt ggtggcagtg agggaggttg   3120
ggtagccctg gactggtccc ctcctcagat caccccttgca aatctggcct catcttgtat   3180
tccaacccga catccctaaa agtacctcca cccgttccgg gtctggaagg cgttggcacc   3240
acaagcactg tccctgtggg aggagcacaa ccttctcggg acaggatctg atggggtctt   3300
gggctaaagg aggtccctgc tgtcctggag aaagtcctag aggttatctc aggaatgact   3360
ggtggccctg ccccaacgtg gaaaggtggg aaggaagcct tctcccatta gccccaatga   3420
gagaactcaa cgtgccggag ctgagtgggc cttgcacgag acactggccc cactttcagg   3480
```

```
cctggaggaa gcatgcacac atggagacgg cgcctgcctg tagatgtttg gatcttcgag    3540
atctccccag gcatcttgtc tcccacagga tcgtgtgtgt aggtggtgtt gtgtggtttt    3600
cctttgtgaa ggagagaggg aaactatttg tagcttgttt tataaaaaat aaaaaatggg    3660
taaatcttg                                                              3669
```

<210> SEQ ID NO 37
<211> LENGTH: 263
<212> TYPE: PRT
<213> ORGANISM: Mus musculus

<400> SEQUENCE: 37

```
Met Leu Pro Cys Phe Gln Leu Leu Arg Ile Gly Gly Arg Gly Gly
1               5                   10                  15

Asp Leu Tyr Thr Phe His Pro Pro Ser Lys Ser Gly Cys Thr Tyr Gly
            20                  25                  30

Leu Gly Cys Arg Ala Asp Leu Cys Asp Val Ala Leu Arg Pro Gln Gln
        35                  40                  45

Glu Pro Gly Leu Ile Ser Gly Val His Ala Glu Leu His Ala Glu Leu
    50                  55                  60

Gln Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Gln Gly Gln Ala Gly Thr
            100                 105                 110

Ser Ser Ser Glu Phe Tyr Phe Met Phe Gln Gln Val Arg Val Lys
        115                 120                 125

Pro Gln Asp Phe Ala Ala Ile Thr Val Pro Arg Ser Lys Gly Glu Ala
    130                 135                 140

Gly Gly Gly Phe Gln Pro Met Leu Pro Pro Gln Gly Ala Pro Gln Arg
145                 150                 155                 160

Pro Leu Ser Thr Leu Ser Ser Ala Pro Lys Ala Thr Leu Ile Leu Asn
                165                 170                 175

Ser Ile Gly Ser Leu Ser Lys Leu Gln Ala Gln Pro Leu Thr Phe Ser
            180                 185                 190

Arg Gly Gly Gly Arg Pro Gln Gly Leu Ala Ile Pro Ser Gln His Gly
        195                 200                 205

Glu Ala Gln Val Ser Pro Ala Pro Pro Thr Arg Asn Arg Arg Lys Ser
    210                 215                 220

Ala His Lys Val Leu Ala Glu Leu Asp Asp Glu Val Ser Pro Gly Pro
225                 230                 235                 240

Leu Ser Val Leu Thr Glu Pro Arg Lys Arg Leu Arg Val Glu Lys Ala
                245                 250                 255

Ala Leu Ile Ala Ser Gly Glu
            260
```

<210> SEQ ID NO 38
<211> LENGTH: 1611
<212> TYPE: DNA
<213> ORGANISM: Mus musculus

<400> SEQUENCE: 38

```
ggaatccctt cctcagttta ccccgcgagc gaaaaaaaga aaggattgtc ggaggctccc     60
ggatgttgag ccgcctgagg atccggcttc actgaggtgc cacaagacgt cttcctggtt    120
```

```
ttgcatcgca tcaggacttt actggaattg cttttaaac ctcatcttga cagcctctgt    180
cttggtgcat atccaggcct ctggcgctct gaatctgcac tgcttaagtt ggcattaggc    240
acaatactta gctgttgaca tcagagagaa ctgaattgaa gcccacggtg catgacccag    300
gagtaggaga gggaatggac ttctgaggtg ggcgaagtgg tgcagagggg cacccccca    360
tgctgccctg tttccagctg ctgcgtatag ggggcggcag gggcggtgac ctctacacct    420
tccacccccc gtccaagtct ggctgcacct atggattggg ctgcagggcc gacctgtgtg    480
atgtggccct gcggcccag caggagcccg gcctcatctc tggagtccat gcggaattgc    540
atgctgaact ccaaggggac gactggaggg tcagcctgga ggatcacagc agccaaggga    600
ctttggtcaa taatgtccga cttccaagag gccacagact ggagttgagt gatggtgacc    660
ttctgacctt tggcccccaa ggtcaagcag gaaccagctc ctcctcagag ttctacttca    720
tgtttcaaca agtccgggtt aaacctcagg actttgcagc cataaccgtc cctcggtcta    780
agggagaagc tgggggcggt ttccaaccta tgctgccccc ccaaggggca cctcagaggc    840
cactcagcac tctctcctct gcccccaagg ccacactgat tctcaattcc atcggcagcc    900
tcagcaaact ccaggcccag cctctcacct tctcccgtgg tggtggcagg ccacagggcc    960
tggctattcc ctctcagcat ggggaagcgc aagtttcgcc tgctccaccc acaagaaacc   1020
ggaggaaatc agctcataaa gtgttggcag agctagatga cgaggtctcc ccaggccccc   1080
tgtccgtcct gacggagccc aggaagaggc tccgggtgga gaaagctgct ctgatagcca   1140
gtggggaatg accacaggga aaggtccatt gctaaagact gactcaaggc tggagaatgc   1200
ttgcaaatga agtgacagaa aagatggttt cctgccaaag atgttgcagc ctccaagttt   1260
ccagtgagct acaagcccag tcacaaggaa taaagccttg cctccatgga tgccaggata   1320
cctgcagtta gagcaccggt cccagaaacc attcctagaa ggtatggttt tattttgctg   1380
aagccagcat ataccaggca agtgctctgc cacaataccc taaccctact catgttcttg   1440
aatggcatcg gctaaagcac cctgaaggac ccagagcaca ttcccaaggc atcctcatgc   1500
caccgctagc tagtatcacc accagctgag tctctgggac tagcttttca gagcttagtc   1560
tttattccca aataaagaat aaactgtttc atccaaaaa aaaaaaaaa a              1611

<210> SEQ ID NO 39
<211> LENGTH: 2133
<212> TYPE: DNA
<213> ORGANISM: Homo sapiens

<400> SEQUENCE: 39
cgggagagcg cgctctgcct gccgcctgcc tgcctgccac tgagggttcc cagcaccatg     60
agggcctgga tcttctttct cctttgcctg gccgggaggg ccttggcagc ccctcagcaa    120
gaagccctgc ctgatgagac agaggtggtg aagaaactg tggcagaggt gactgaggta    180
tctgtgggag ctaatcctgt ccaggtggaa gtaggagaat tgatgatgg tgcagaggaa    240
accgaagagg aggtggtggc ggaaaatccc tgccagaacc accactgcaa acacggcaag    300
gtgtgcgagc tggatgagaa caacacccc atgtgcgtgt gccaggaccc caccagctgc    360
ccagccccca ttggcgagtt tgagaaggtg tgcagcaatg acaacaagac cttcgactct    420
tcctgccact tcttgcccac aaagtgcacc ctggagggca ccaagaaggg ccacaagctc    480
cacctggact acatcgggcc ttgcaaatac atcccccctt gcctggactc tgagctgacc    540
gaattcccc tgcgcatgcg ggactggctc aagaacgtcc tggtcaccct gtatgagagg    600
gatgaggaca caacaccttct gactgagaag cagaagctgc gggtgaagaa gatccatgag    660
```

```
aatgagaagc gcctggaggc aggagaccac cccgtggagc tgctggcccg ggacttcgag      720
aagaactata acatgtacat cttccctgta cactggcagt tcggccagct ggaccagcac      780
cccattgacg ggtacctctc ccacaccgag ctggctccac tgcgtgctcc cctcatcccc      840
atggagcatt gcaccacccg cttttttcgag acctgtgacc tggacaatga caagtacatc      900
gccctggatg agtgggccgg ctgcttcggc atcaagcaga aggatatcga caaggatctt      960
gtgatctaaa tccactcctt ccacagtacc ggattctctc tttaaccctc cccttcgtgt     1020
ttcccccaat gtttaaaatg tttggatggt tgttgttct gcctggagac aaggtgctaa      1080
catagattta agtgaataca ttaacggtgc taaaaatgaa aattctaacc aagacatga      1140 cattcttagc tgtaacttaa ctattaaggc cttttccaca cgcattaata gtcccatttt     1200
tctcttgcca tttgtagctt tgcccattgt cttattggca catgggtgga cacggatctg     1260
ctgggctctg ccttaaacac acattgcagc ttcaactttt ctctttagtg ttctgtttga     1320
aactaatact taccgagtca gactttgtgt tcatttcatt tcagggtctt ggctgcctgt     1380
gggcttcccc aggtggcctg gaggtgggca aagggaagta acagacacac gatgttgtca     1440
aggatggttt tgggactaga ggctcagtgg tgggagagat ccctgcagaa tccaccaacc     1500
agaacgtggt ttgcctgagg ctgtaactga gagaaagatt ctgggctgt cttatgaaaa      1560 tatagacatt ctcacataag cccagttcat caccatttcc tcctttacct ttcagtgcag     1620
tttcttttca cattaggctg ttggttcaaa cttttgggag cacggactgt cagttctctg     1680
ggaagtggtc agcgcatcct gcagggcttc tcctcctctg tcttttggag aaccagggct     1740
cttctcaggg gctctaggga ctgccaggct gtttcagcca ggaaggccaa aatcaagagt     1800
gagatgtaga aagttgtaaa atagaaaaag tggagttggt gaatcggttg ttctttcctc     1860
acatttggat gattgtcata aggttttag catgttcctc ctttcttca ccctcccctt      1920 tgttcttcta ttaatcaaga gaaacttcaa agttaatggg atggtcggat ctcacaggct     1980
gagaactcgt tcacctccaa gcatttcatg aaaaagctgc ttcttattaa tcatacaaac     2040
tctcaccatg atgtgaagag tttcacaaat cttttcaaaat aaaaagtaat gacttagaaa     2100
ctgaaaaaaa aaaaaaaaaa aaaaaaaaaa aaa                                   2133

<210> SEQ ID NO 40
<211> LENGTH: 2678
<212> TYPE: DNA
<213> ORGANISM: Coturnix coturnix

<400> SEQUENCE: 40
gtcagacctt cctcctcaga agctcacaga aaaacacgct ttctgaaaga ttccacactc       60
aatgccaaaa ataccacag gaaaattttg caaggctcac ggatttccag tgcaccactg      120
gctaaccaag taggagcacc tcttctactg ccatgaaagg aaaccttcaa accctaccac      180
tgagccatta actaccatcc tgtttaagat ctgaaaaaca tgaagactgt attgctcctg      240
atttgtcttc taggatctgc tttcaccact ccaaccgatc cattgaacta ccaatttggg      300
gcccatggac agaaaactgc agagaagcat aaatatactc attctgaaat gccagaggaa      360
gagaacacag ggtttgtaaa caaggtgat gtgctgtctg gccacaggac cataaaagca      420
gaggtaccgg tactggatac acagaaggat gagccctggg cttccagaag acaaggacaa      480
ggtgatggtg agcatcaaac aaaaaacagc ctgaggagca ttaacttcct tactctgcac      540
agtaatccag ggttggcttc tgataaccag gaaagcaact ctggcagcag cagggaacag      600
cacagctctg agcaccacca gcccaggagg cacaggaaac acggcaacat ggctggccag      660
```

-continued

```
tgggctctga gaggagaaag tccagtggat gctcttggtc tggttcgtga gcgcaacaca    720
tggaaataca ataaaaacac agttggccta gatgaaaaca acaatggaag tgaagaagag    780
gaagctgggg aggaagaaga tgaggaatgg ggtgaagaaa ctgattacag ggatatgaaa    840
cacagagccc gtgggacaag ccatggaaga gaatacagaa gatggcaaaa tgaaaacagc    900
cggccatctg gtgaattctt gagagattcc agtctgccag tacgtataac aagagacac     960 ggtgagaaat tcagcatgga ggaggaaagt caggaaaagc tctacaagga aggaaaactc    1020
cctctctcaa agaaaaatca taatgaggat caaggtgaaa aaagacaaag tgaagaaagt    1080
aaagagcatt ttcaagtagt caatcagcgc aaacacagag cagtgacgaa aaggcaggat    1140
aaggagggca gcaatgctga ggaggatgat aatgatagtg gtgatgatgg tgaggaagat    1200
cttggcaatg tctggaggga agcagtctac gaggaagagg aaagaatgca aagcaatgac    1260
caggacagta tcactaacaa gcaaaaagag gaaataactg ctggagatga cagtggagtt    1320
tatagggaga tgcaggatta caaggtgac aaaattaaag atgttactca ctctgaagac     1380
aatcattacc accatgagcc ccctaattcc agcagcaagc aacaactgca acaagtagc     1440 tctgttgaga gcatgaattc aacagagcat gaggatgagg ttaagaccac aggaggttca    1500
tatcatgagg aaagtgcaag gaacagcact gggaaggctc tcccggatct ttgtagaaac    1560
ttccactgca aaagaggaaa agtctgccaa gcagacaagc aaggaaaacc cagctgtatt    1620
tgccaagatc ctgctgcttg cccttccacc aaagattata gcgtgtttg tggcactgat     1680 aataagactt acgatggtac gtgccaactc tttggcacca aatgtcaact tgaagggaca    1740
aaaatgggac gccagctgca cctggactat atgggtgcct gcaaacacat accccactgt    1800
actgattacg aagtgaatca gttccctctc cgtatgagag actggctcaa aaacatccta    1860
atgcaatatt atgaacgtga tcaggatacg tctgcatttc taaccgaaaa gcaaaggaat    1920
aaggtcaaaa agatataccct gaatgagaag cgtctcgtct ctggtgagca cccagttgag    1980
cttctcctgc atgactttga gaaaaactac cacatgtatc tctatcctgt gcactggcaa    2040
ttttatcagc ttgaccagca cccagttgac agatcactga ctcattcaga gctcgctcct    2100
ttgagagcct ccctcgttcc catggaacac tgcataaccc gtttcttcca ggagtgtgat    2160
ggagaccaag acaaacttat cactttgaaa gagtggtgcc actgctttgc gattaaggaa    2220
gaagacataa atgaaaatct cctgttctga gcccacctga gcagaatccc catgcagcgc    2280
tacagcttgt caaacatgca atgcccattt atgactgcaa ttaacagctc tgttaatttt    2340
caggaataag ttggcataag attccttgag gcagaacaag tcgctcttgg ataacacaag    2400
tgcctaattg ttacaaattc attaacagca gtagtgttta agagctctaa gtagctcata    2460
cttaaagagt gtttccctct gcacgtacca ataatctctt agtaagacga ctaacttgat    2520
gactgagttg ttcacaaaac ccttccgtag aattatagga tgtggatttt ataatacacc    2580
gataaaaact actttgaaat aggttttctt ttcctgtcgt ttactgtcag tagctctctg    2640
catagaaatg tcaaataaac agatcttgtt ttggtttc                          2678
```

<210> SEQ ID NO 41
<211> LENGTH: 2808
<212> TYPE: DNA
<213> ORGANISM: Homo sapiens

<400> SEQUENCE: 41

```
cggcatgaga ggccagcctg ccagggaaat ccaggaatct gcaacaaaaa cgatgacagt     60
ctgaaatact ctctggtgcc aacctccaaa ttctcgtctg tcacttcaga cccccactag    120
```

```
ttgacagagc agcagaatat caactccagt agacttgaat gtgcctctgg gcaaagaagc    180
agagctaacg aggaaaggga tttaaagagt ttttcttggg tgtttgtcaa acttttattc    240
cctgtctgtg tgcagagggg attcaacttc aatttctgc agtggctctg ggtccagccc     300
cttacttaaa gatctggaaa gcatgaagac tgggcctttt ttcctatgtc tcttgggaac    360
tgcagctgca atcccgacaa atgcaagatt attatctgat cattccaaac caactgctga    420
aacggtagca cctgacaaca ctgcaatccc cagtttatgg gctgaagctg aagaaaatga    480
aaaagaaaca gcagtatcca cagaagacga ttcccaccat aaggctgaaa aatcatcagt    540
actaaagtca aaagaggaaa gccatgaaca gtcagcagaa cagggcaaga gttctagcca    600
agagctggga ttgaaggatc aagaggacag tgatggtcac ttaagtgtga atttggagta    660
tgcaccaact gaaggtacat tggacataaa agaagatatg attgagcctc aggagaaaaa    720
actctcagag aacactgatt ttttggctcc tggtgttagt tccttcacag attctaacca    780
acaagaaagt atcacaaaga gagaggaaaa ccaagaacaa cctagaaatt attcacatca    840
tcagttgaac aggagcagta acatagcca aggcctaagg gatcaaggaa accaagagca     900
ggatccaaat atttccaatg gagaagagga agaagaaaaa gagccaggtg aagttggtac    960
ccacaatgat aaccaagaaa gaaagacaga attgcccagg gagcatgcta acagcaagca    1020
ggaggaagac aatacccaat ctgatgatat tttggaagag tctgatcaac caactcaagt    1080
aagcaagatg caggaggatg aatttgatca gggtaaccaa gaacaagaag ataactccaa    1140
tgcagaaatg gaagaggaaa atgcatcgaa cgtcaataag cacattcaag aaactgaatg    1200
gcagagtcaa gagggtaaaa ctggcctaga agctatcagc aaccacaaag agacagaaga    1260
aaagactgtt tctgaggctc tgctcatgga acctactgat gatggtaata ccacgcccag    1320
aaatcatgga gttgatgatg atggcgatga tgatggcgat gatggcggca ctgatggccc    1380
caggcacagt gcaagtgatg actacttcat cccaagccag gccttttctgg aggccgagag    1440 agctcaatcc attgcctatc acctcaaaat tgaggagcaa agagaaaaag tacatgaaaa    1500
tgaaaatata ggtaccactg agcctggaga gcaccaagag gccaagaaag cagagaactc    1560
atcaaatgag gaggaaacgt caagtgaagg caacatgagg gtgcatgctg tggattcttg    1620
catgagcttc cagtgtaaaa gaggccacat ctgtaaggca gaccaacagg gaaaacctca    1680
ctgtgtctgc caggatccag tgacttgtcc tccaacaaaa ccccttgatc aagtttgtgg    1740
cactgacaat cagacctatg ctagttcctg tcatctattc gctactaaat gcagactgga    1800
ggggaccaaa aaggggcatc aactccagct ggattatttt ggagcctgca atctattcc     1860 tacttgtacg gactttgaag tgattcagtt tcctctacgg atgagagact ggctcaagaa    1920
tatcctcatg cagctttatg aagccaactc tgaacatgct ggttatctaa atgagaagca    1980
gagaaataaa gtcaagaaaa tttacctgga tgaaaagagg cttttggctg gggaccatcc    2040
cattgatctt ctcttaaggg actttaagaa aaactaccac atgtatgtgt atcctgtgca    2100
ctggcagttt agtgaacttg accaacaccc tatggataga gtcttgacac attctgaact    2160
tgctcctctg cgagcatctc tggtgcccat ggaacactgc ataacccgtt tctttgagga    2220
gtgtgacccc aacaaggata agcacatcac cctgaaggag tggggccact gctttggaat    2280
taaagaagag gacatagatg aaaatctctt gttttgaacg aagattttaa agaactcaac    2340
tttccagcat cctcctctgt tctaaccact tcagaaatat atgcagctgt gatacttgta    2400
gatttatatt tagcaaaatg ttagcatgta tgacaagaca atgagagtaa ttgcttgaca    2460
acaacctatg caccaggtat ttaacattaa ctttggaaac aaaaatgtac aattaagtaa    2520
```

```
agtcaacata tgcaaaatac tgtacattgt gaacagaagt ttaattcata gtaatttcac    2580
tctctgcatt gacttatgag ataattaatg attaaactat taatgataaa aataatgcat    2640
ttgtattgtt cataatatca tgtgcacttc aagaaaatgg aatgctactc ttttgtggtt    2700
tacgtgtatt attttcaata tcttaatacc ctaataaaga gtccataaaa atccaaaaaa    2760
aaaaaaaaaa aaaaaaaaaa aaaaaaaaaa aaaaaaaaa aaaaaaaa                  2808

<210> SEQ ID NO 42
<211> LENGTH: 4804
<212> TYPE: DNA
<213> ORGANISM: Homo sapiens

<400> SEQUENCE: 42
agcggccaga cgctcggcgg cggcgtgtgg caggagcgca ggggcgcgag ccggcgatca      60
gccttcccgg cgaccgtgcc gcgggagctc gagcaactcg gactagggga cccgggccgg    120
cccccaagat gccggcgatc gcggtattgg cggcggccgc cgcggcgtgg tgcttcctcc    180
aagtcgagag ccggcacctg gacgcgctcg ccggaggcgc gggccccaac cacggcaatt    240
tcctagacaa tgaccagtgg ctgagcaccg tctcccagta cgaccgggac aagtactgga    300
accgctttcg agacgatgat tatttcagaa actggaatcc caacaagccc tttgaccaag    360
ccctggaccc atccaaggac ccctgcctga aggtaaaatg cagccctcac aaagtgtgtg    420
tgacccagga ctaccagacc gccctgtgtg tcagccgcaa gcacctgctc cccaggcaaa    480
agaaggggaa cgtggcccag aaacactggg ttggaccttc gaatttggtc aagtgcaagc    540
cctgtcccgt ggcacagtca gccatggtct gcggctcaga tggccactcc tacacatcca    600
agtgcaaatt ggagttccat gcttgttcta ctggcaaaag cctcgccacc ctctgtgatg    660
ggccctgtcc ctgtctccca gagcctgagc caccaaagca caggcagaa aggagtgcct    720 gcacagacaa ggagttgcgg aaccttgcct cccggctgaa ggattggttt ggagctctcc    780
acgaggatgc gaacagagtc atcaagccca ccagctccaa cacagcccaa ggcaggtttg    840
acactagcat cctgcccatc tgcaaggact ccctgggctg gatgttcaac aagttggaca    900
tgaactatga cctcctgctt gacccttcag agatcaatgc catctacctg gataagtacg    960
agccctgtat caagcctctt ttcaactcgt gtgactcctt caaggatggc aagctttcta   1020
acaatgagtg gtgctactgc ttccagaagc ctggaggtct cccttgccag aatgaaatga   1080
acagaattca gaagctgagt aaggggaaaa gcctgttggg ggccttcata cctcggtgta   1140
atgaggaggg ctattacaaa gccacacagt gccacggcag cacggggcag tgctggtgtg   1200
tggacaaata tgggaatgag ttggctggct ccaggaaaca gggtgctgtg agctgtgaag   1260
aggagcagga acctcaggg gattttggca gtggtgggtc cgtggtcctg ctggatgacc   1320
tagaatatga acgggagctg gaccaaaagg acaaagaggg gaagctgagg gtgcacaccc   1380
gagccgtgac agaggatgat gaggatgagg atgatgacaa agaggatgag gtcgggtaca   1440
tatggtagtg cccacaagaa agaggacaca agttttgcac aaaattgcaa gtcacttcct   1500
attcctgcat ttgtatctaa gactccaagg caccaaggtc tcttctccat tgttgctctc   1560
tatacccgac ctaaggtttg gaagacaact gcttgttccc agaggattct gattttgcat   1620
atgtttgtat gggagaaagg gtgttgtgtt tttttttttg ttgttgttta ttttttggat   1680
agggaagtca ttggcttaat tagagcctcc ttcctttctg tgagattttt ccaacaagca   1740
tgtgatttac gtggaattct gacagtgcag ggagccccca ccctcttaaa tgtcaaagac   1800 ccttttttgat tacccacact ggtggttatt acagcatggt tccagccctt acagtgtcta   1860
```

```
agtgcttctc ttgtgtcctg tagatgttgt gaaaaagaaa aaaacaaaaa atacaccaca   1920
ctgtactttt tccccctgcc cccgctactg ccggtgatta ttattaaaaa ttagttttt   1980
tcacatcatt atatctggct tcctataaac aacagcctta attcagtcaa gactcccttt   2040
gggaattcat tttattaaaa attggtgtct ggatacttcc ctgtacatgc ataaatatgc   2100
atgcatgtac aggaagactg tatgtgtgtg ccttgcacac acacccatac ctctcagaaa   2160
aagtgggtat attaaaaact cgaaaaacaa tgataaattt ctcagcttgt ccagacctgg   2220
aacaaaattt ctggaataag aaatttgtat taaagtcctt ttttgcacta acagttggct   2280
cttgtagcct gcaggctgag gaagtctctt ctctgtgcat cagcagagtt actgaaagcc   2340
tctgattgag aaaaaacctc cgtctgccta aatcacttt ctcgcagaag ccatgcgact   2400
cccacacgac acgggcagct tcacaagcca tctctttcat ttctgcttga agcccccttg   2460
gctgcagcaa tcctgtctgc cataggtttc ttccttcctt acctactcaa gggcttttc   2520
taaggcatgc acacatatct cctgttctct gagagtacca tggtgttcct taaaagaaga   2580
aaatttctaa ttctgaactc aatgttttgc ttttactccc tttctactga caaatcatga   2640
taagggcaca aaagctgtac agattttttt ttttaaccac tcaatcccaa atggaggcct   2700
acaaagaaca tcgtaataac acatggaagc aaaccctggg ttttttaagag caaattctgt   2760
ccccccctca ctcccccaag tgacaagata ctaatgaaga aagttcttca ccatagtgtt   2820
tgttttaact aaactcattg gagtctagtt ccaaatttgg tagggtcatc atctctacat   2880
tccttaggat ttctctccct atcaagctgg cccagataca agtaccaaac agtagtctct   2940
gaagttcccc catttccttc agtaccagtc tataagctac tgtccgccac tgattttcat   3000
ctatcagggt gtcctaatca gaatcagcca cccaagcaag cctctctggc ccacatatct   3060
atctcttgcc ttcccccatg aacttcagcc tgtccacaca aaagccacat aaactcaagc   3120
aagaaatatg ttcagccaaa acatgattat agtggcagct gaccaatccc ccatcccaaa   3180
ttgaccattt agatgtacca actcaccta aattagcatg ttccaatcca gtcggcattg   3240
cctgaataca gtagcatcat acctatagtt ggtcttagat aagaaatgaa ctacttgata   3300
tagcaaagtc ctttggcttc gtaaataacc ctgaggtttt gtacttactt tccccatagg   3360
aagacagacc ataggcaaac tctgtttgg gatctcaact ccatcacctt tgtttcaata   3420
tttttttct ctcttgaaca aaactgagat aatttagaaa acaggtgctt aattgcaata   3480
aaattactat gaagtatatt aaaaatcacg acattgtaaa atctcacttt agatcatcaa   3540
agaaaaccat tgttactatc tcctttgagc ttaggaaaat gtacaagaga acaaattaaa   3600
attgaaaaat tgatttcact tagaaaaact tctaggaaca gggtgaacca ctgatttaa   3660
tttgcctaat tatcttatga caagtatcaa attaagatga cacttaaaga tccttagcat   3720
taacttaatg atggagaaga gtgctcaaca gacagttccc agtaaggtaa tgagatgcca   3780
ttttccgaga cattcaaga agatattttg attcattaaa acattaaata aaaagccctc   3840
ctcagattgg aaccccaaa tcgatggagt cacattaata atactttca tgcctcactt   3900
tgacatgaca gcattcgatt ttttaaaga tctttaatac tttccatgag tactaaagat   3960
tgtaatgagt taccttatcc ttagaagtag aatgtttgct ttcttcttct tggaaatagt   4020
cctccaaaaa gtccacttgt accagtgaca agaagtcact tgtatagtga ccaagtacac   4080
ataaaatacc gattataaaa atattgtaat aaaccacttc ctcatttgat actggtatta   4140
agctgaatcc tcactaattc acttttgaaa agttcttaat gaacagtttt attcttatac   4200
catgaacagc tctttaata caatttcctt ggtatccaac ttaaatccca gaattttgtt   4260
```

-continued

```
ccaccatggt tagttatttg ccatatgaat gtattcttgt ttctaccaat attctaggca      4320
tgagaatacc ttaatactga gttggagatt ttgtatctgt ttctcctcct ttacgcccat      4380
tttcctaccc acagcagcaa atgacaacgt gtctgtccag gtctgtcccc ctgctcatcc      4440
caggatgcca ctcacatttt tttcttcttt gttaccttg acccacgctg tacaagtaac       4500
atccaagagc ccattctaca agtgggtggt tttggtcttt ttataacttt ttctcaaagt      4560
cactgatgtt tgttcctgtt aaatgtatag cattgtaatg agagcccatc aaatcctgag      4620
tgtcagtttg ttgtccctat tgtagatgaa atagtgatgt agcaaaaacc tagtaaattc      4680
tgaatgcttt tccacgtaga cttatctgga atgtgaacac aactctttgg ttaatagtaa      4740
atgcttaact gtagtcctga gtaggtgcat ttctgtctgt ctcaataaat tttactttgt      4800
ctgc                                                                   4804
```

<210> SEQ ID NO 43
<211> LENGTH: 1370
<212> TYPE: DNA
<213> ORGANISM: Rattus norvegicus

<400> SEQUENCE: 43

```
ctggcctcca actcactgct tccatcctgc ccagtgtcct ctcgagtccc ggacccgagc        60
acgatgtgga aacgctggct ggcgctcgcg ctggtgacca tcgccctggt ccacggcgag       120
gaggaacaaa gaagcaaatc caagatctgc gccaatgtgt tttgtggagc tggccgggaa       180
tgcgccgtca cggagaaggg ggagccaacg tgcctctgca ttgagcaatg caaacctcac       240
aagaggcctg tgtgtggcag taatggcaag acctacctca accattgtga acttcacaga       300
gacgcctgcc tcactggatc caagatccag gttgattatg atgggcactg caaagaaaag       360
aagtctgtga gtccatccgc cagccccgtt gtctgctatc aggctaaccg tgatgagctg       420
cggcgccgga tcatccagtg gctggaagcc gagatcattc cagatggctg gttctctaaa       480
ggcagtaact acagtgagat cctagacaag tactttaaga gctttgataa tggtgactct       540
cacctggact ccagcgaatt cctgaaattc gtggagcaga atgaaacagc cgtcaacatc       600
accgcttacc ccaatcagga gaacaacaaa ctgctcagag gcctctgtgt tgatgccctc       660
attgaactgt ccgatgagaa cgctgactgg aaactcagct ccaagagtt cctcaagtgc        720 ctcaacccat ccttcaaccc tcctgagaag aagtgcgccc tggaggacga aacctatgca       780
gatggagctg agaccgaggt ggactgcaat cgctgtgtct gttcctgtgg acactgggtc       840
tgcacagcga tgacctgtga tggaaagaat cagaagggg tccagaccca cagaggag         900 gagatgacga gatatgccca ggaactccag aagcaccagg gaacagcaga aaagaccaag       960
aaggtgaaca ccaaagagat ctaagaagag gcacgtagca cctcatctgg aacccagcac      1020
ctcctcttca gcgctaagcc cagtatacag cgtctgtggc aatcaccgaa tcaccagtat      1080
ttgcttgtac ggcagcaaat cttatctgtt tgttttgcaa taaaggaagt gagggtggct      1140
ggctagccag ggcaggcagg ccacaacttt cacttctagg aatgctttaa gagacactaa      1200
agggcacctt ggggcaggag gcgagtatcc ggttggcaga ggagcagagg caggtctgaa      1260
tgaaaccttt ctggggtcag ctgtgaggat acaacaggaa aagcatgtga tgttagggg        1320 aacactgagc tggcccctgct ggaggaaata gggggagctt ggtggggagg              1370
```

<210> SEQ ID NO 44
<211> LENGTH: 303
<212> TYPE: PRT
<213> ORGANISM: Homo sapiens -continued

```
<400> SEQUENCE: 44

Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
            260                 265                 270

Cys Asp Leu Asp Asn Asp Lys Tyr Ile Ala Leu Asp Glu Trp Ala Gly
        275                 280                 285

Cys Phe Gly Ile Lys Gln Lys Asp Ile Asp Lys Asp Leu Val Ile
    290                 295                 300

<210> SEQ ID NO 45
<211> LENGTH: 439
<212> TYPE: PRT
<213> ORGANISM: Homo sapiens

<400> SEQUENCE: 45

Met Pro Ala Ile Ala Val Leu Ala Ala Ala Ala Ala Trp Cys Phe
1               5                   10                  15

Leu Gln Val Glu Ser Arg His Leu Asp Ala Leu Ala Gly Gly Ala Gly
            20                  25                  30

Pro Asn His Gly Asn Phe Leu Asp Asn Asp Gln Trp Leu Ser Thr Val
        35                  40                  45

Ser Gln Tyr Asp Arg Asp Lys Tyr Trp Asn Arg Phe Arg Asp Asp
    50                  55                  60

Tyr Phe Arg Asn Trp Asn Pro Asn Lys Pro Phe Asp Gln Ala Leu Asp
```

```
                65                  70                  75                  80
            Pro Ser Lys Asp Pro Cys Leu Lys Val Lys Cys Ser Pro His Lys Val
                                85                  90                  95
            Cys Val Thr Gln Asp Tyr Gln Thr Ala Leu Cys Val Ser Arg Lys His
                            100                 105                 110
            Leu Leu Pro Arg Gln Lys Lys Gly Asn Val Ala Gln Lys His Trp Val
                        115                 120                 125
            Gly Pro Ser Asn Leu Val Lys Cys Lys Pro Cys Pro Val Ala Gln Ser
                    130                 135                 140
            Ala Met Val Cys Gly Ser Asp Gly His Ser Tyr Thr Ser Lys Cys Lys
            145                 150                 155                 160
            Leu Glu Phe His Ala Cys Ser Thr Gly Lys Ser Leu Ala Thr Leu Cys
                            165                 170                 175
            Asp Gly Pro Cys Pro Cys Leu Pro Glu Pro Glu Pro Lys His Lys
                        180                 185                 190
            Ala Glu Arg Ser Ala Cys Thr Asp Lys Glu Leu Arg Asn Leu Ala Ser
                    195                 200                 205
            Arg Leu Lys Asp Trp Phe Gly Ala Leu His Glu Asp Ala Asn Arg Val
                210                 215                 220
            Ile Lys Pro Thr Ser Ser Asn Thr Ala Gln Gly Arg Phe Asp Thr Ser
            225                 230                 235                 240
            Ile Leu Pro Ile Cys Lys Asp Ser Leu Gly Trp Met Phe Asn Lys Leu
                            245                 250                 255
            Asp Met Asn Tyr Asp Leu Leu Leu Asp Pro Ser Glu Ile Asn Ala Ile
                        260                 265                 270
            Tyr Leu Asp Lys Tyr Glu Pro Cys Ile Lys Pro Leu Phe Asn Ser Cys
                    275                 280                 285
            Asp Ser Phe Lys Asp Gly Lys Leu Ser Asn Asn Glu Trp Cys Tyr Cys
                290                 295                 300
            Phe Gln Lys Pro Gly Gly Leu Pro Cys Gln Asn Glu Met Asn Arg Ile
            305                 310                 315                 320
            Gln Lys Leu Ser Lys Gly Lys Ser Leu Leu Gly Ala Phe Ile Pro Arg
                            325                 330                 335
            Cys Asn Glu Glu Gly Tyr Tyr Lys Ala Thr Gln Cys His Gly Ser Thr
                        340                 345                 350
            Gly Gln Cys Trp Cys Val Asp Lys Tyr Gly Asn Glu Leu Ala Gly Ser
                    355                 360                 365
            Arg Lys Gln Gly Ala Val Ser Cys Glu Glu Gln Glu Thr Ser Gly
                370                 375                 380
            Asp Phe Gly Ser Gly Gly Ser Val Val Leu Leu Asp Asp Leu Glu Tyr
            385                 390                 395                 400
            Glu Arg Glu Leu Gly Pro Lys Asp Lys Glu Gly Lys Leu Arg Val His
                            405                 410                 415
            Thr Arg Ala Val Thr Glu Asp Asp Glu Asp Glu Asp Asp Lys Glu
                        420                 425                 430
            Asp Glu Val Gly Tyr Ile Trp
                        435

<210> SEQ ID NO 46
<211> LENGTH: 664
<212> TYPE: PRT
<213> ORGANISM: Homo sapiens

<400> SEQUENCE: 46

Met Lys Thr Gly Pro Phe Phe Leu Cys Leu Leu Gly Thr Ala Ala Ala
```

```
              1               5                  10                 15
    Ile Pro Thr Asn Ala Arg Leu Leu Ser Asp His Ser Lys Pro Thr Ala
                    20                  25                  30
    Glu Thr Val Ala Pro Asp Asn Thr Ala Ile Pro Ser Leu Trp Ala Glu
                    35                  40                  45
    Ala Glu Glu Asn Glu Lys Glu Thr Ala Val Ser Thr Glu Asp Asp Ser
                    50                  55                  60
    His His Lys Ala Glu Lys Ser Ser Val Leu Lys Ser Lys Glu Glu Ser
     65                  70                  75                  80
    His Glu Gln Ser Ala Glu Gln Gly Lys Ser Ser Gln Glu Leu Gly
                            85                  90                  95
    Leu Lys Asp Gln Glu Asp Ser Asp Gly His Leu Ser Val Asn Leu Glu
                    100                 105                 110
    Tyr Ala Pro Thr Glu Gly Thr Leu Asp Ile Lys Glu Asp Met Ile Glu
                    115                 120                 125
    Pro Gln Glu Lys Lys Leu Ser Glu Asn Thr Asp Phe Leu Ala Pro Gly
                    130                 135                 140
    Val Ser Ser Phe Thr Asp Ser Asn Gln Gln Glu Ser Ile Thr Lys Arg
    145                 150                 155                 160
    Glu Glu Asn Gln Glu Gln Pro Arg Asn Tyr Ser His His Gln Leu Asn
                    165                 170                 175
    Arg Ser Ser Lys His Ser Gln Gly Leu Arg Asp Gln Gly Asn Gln Glu
                    180                 185                 190
    Gln Asp Pro Asn Ile Ser Asn Gly Glu Glu Glu Glu Lys Glu Pro
                    195                 200                 205
    Gly Glu Val Gly Thr His Asn Asp Asn Gln Glu Arg Lys Thr Glu Leu
                    210                 215                 220
    Pro Arg Glu His Ala Asn Ser Lys Gln Glu Glu Asp Asn Thr Gln Ser
    225                 230                 235                 240
    Asp Asp Ile Leu Glu Glu Ser Gln Pro Thr Gln Val Ser Lys Met
                    245                 250                 255
    Gln Glu Asp Glu Phe Asp Gln Gly Asn Gln Glu Gln Glu Asp Asn Ser
                    260                 265                 270
    Asn Ala Glu Met Glu Glu Glu Asn Ala Ser Asn Val Asn Lys His Ile
                    275                 280                 285
    Gln Glu Thr Glu Trp Gln Ser Gln Glu Gly Lys Thr Gly Leu Glu Ala
                    290                 295                 300
    Ile Ser Asn His Lys Glu Thr Glu Glu Lys Thr Val Ser Glu Ala Leu
    305                 310                 315                 320
    Leu Met Glu Pro Thr Asp Asp Gly Asn Thr Thr Pro Arg Asn His Gly
                    325                 330                 335
    Val Asp Asp Asp Gly Asp Asp Gly Asp Asp Gly Gly Thr Asp Gly
                    340                 345                 350
    Pro Arg His Ser Ala Ser Asp Asp Tyr Phe Ile Pro Ser Gln Ala Phe
                    355                 360                 365
    Leu Glu Ala Glu Arg Ala Gln Ser Ile Ala Tyr His Leu Lys Ile Glu
                    370                 375                 380
    Glu Gln Arg Glu Lys Val His Glu Asn Glu Asn Ile Gly Thr Thr Glu
    385                 390                 395                 400
    Pro Gly Glu His Gln Glu Ala Lys Lys Ala Glu Asn Ser Ser Asn Glu
                    405                 410                 415
    Glu Glu Thr Ser Ser Gly Asn Met Arg Val His Ala Val Asp Ser
                    420                 425                 430
```

```
Cys Met Ser Phe Gln Cys Lys Arg Gly His Ile Cys Lys Ala Asp Gln
    435                 440                 445

Gln Gly Lys Pro His Cys Val Cys Gln Asp Pro Val Thr Cys Pro Pro
450                 455                 460

Thr Lys Pro Leu Asp Gln Val Cys Gly Thr Asp Asn Gln Thr Tyr Ala
465                 470                 475                 480

Ser Ser Cys His Leu Phe Ala Thr Lys Cys Arg Leu Glu Gly Thr Lys
            485                 490                 495

Lys Gly His Gln Leu Gln Leu Asp Tyr Phe Gly Ala Cys Lys Ser Ile
            500                 505                 510

Pro Thr Cys Thr Asp Phe Glu Val Ile Gln Phe Pro Leu Arg Met Arg
        515                 520                 525

Asp Trp Leu Lys Asn Ile Leu Met Gln Leu Tyr Glu Ala Asn Ser Glu
530                 535                 540

His Ala Gly Tyr Leu Asn Glu Lys Gln Arg Asn Lys Val Lys Lys Ile
545                 550                 555                 560

Tyr Leu Asp Glu Lys Arg Leu Leu Ala Gly Asp His Pro Ile Asp Leu
            565                 570                 575

Leu Leu Arg Asp Phe Lys Lys Asn Tyr His Met Tyr Val Tyr Pro Val
            580                 585                 590

His Trp Gln Phe Ser Glu Leu Asp Gln His Pro Met Asp Arg Val Leu
        595                 600                 605

Thr His Ser Glu Leu Ala Pro Leu Arg Ala Ser Leu Val Pro Met Glu
610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
            645                 650                 655

Asp Ile Asp Glu Asn Leu Leu Phe
660

<210> SEQ ID NO 47
<211> LENGTH: 306
<212> TYPE: PRT
<213> ORGANISM: Rattus norvegicus

<400> SEQUENCE: 47

Met Trp Lys Arg Trp Leu Ala Leu Ala Leu Val Thr Ile Ala Leu Val
1               5                   10                  15

His Gly Glu Glu Glu Gln Arg Ser Lys Ser Lys Ile Cys Ala Asn Val
            20                  25                  30

Phe Cys Gly Ala Gly Arg Glu Cys Ala Val Thr Glu Lys Gly Glu Pro
        35                  40                  45

Thr Cys Leu Cys Ile Glu Gln Cys Lys Pro His Lys Arg Pro Val Cys
    50                  55                  60

Gly Ser Asn Gly Lys Thr Tyr Leu Asn His Cys Glu Leu His Arg Asp
65                  70                  75                  80

Ala Cys Leu Thr Gly Ser Lys Ile Gln Val Asp Tyr Asp Gly His Cys
                85                  90                  95

Lys Glu Lys Lys Ser Val Ser Pro Ser Ala Ser Pro Val Val Cys Tyr
            100                 105                 110

Gln Ala Asn Arg Asp Glu Leu Arg Arg Ile Ile Gln Trp Leu Glu
            115                 120                 125

Ala Glu Ile Ile Pro Asp Gly Trp Phe Ser Lys Gly Ser Asn Tyr Ser
    130                 135                 140
```

```
Glu Ile Leu Asp Lys Tyr Phe Lys Ser Phe Asp Asn Gly Asp Ser His
145                 150                 155                 160

Leu Asp Ser Ser Glu Phe Leu Lys Phe Val Glu Gln Asn Glu Thr Ala
            165                 170                 175

Val Asn Ile Thr Ala Tyr Pro Asn Gln Glu Asn Asn Lys Leu Leu Arg
        180                 185                 190

Gly Leu Cys Val Asp Ala Leu Ile Glu Leu Ser Asp Glu Asn Ala Asp
            195                 200                 205

Trp Lys Leu Ser Phe Gln Glu Phe Leu Lys Cys Leu Asn Pro Ser Phe
210                 215                 220

Asn Pro Pro Glu Lys Lys Cys Ala Leu Glu Asp Glu Thr Tyr Ala Asp
225                 230                 235                 240

Gly Ala Glu Thr Glu Val Asp Cys Asn Arg Cys Val Cys Ser Cys Gly
            245                 250                 255

His Trp Val Cys Thr Ala Met Thr Cys Asp Gly Lys Asn Gln Lys Gly
            260                 265                 270

Val Gln Thr His Thr Glu Glu Met Thr Arg Tyr Ala Gln Glu Leu
    275                 280                 285

Gln Lys His Gln Gly Thr Ala Leu Lys Thr Lys Lys Val Asn Thr Lys
290                 295                 300

Glu Ile
305

<210> SEQ ID NO 48
<211> LENGTH: 676
<212> TYPE: PRT
<213> ORGANISM: Coturnix coturnix

<400> SEQUENCE: 48

Met Lys Thr Val Leu Leu Ile Cys Leu Leu Gly Ser Ala Phe Thr
1               5                   10                  15

Thr Pro Thr Asp Pro Leu Asn Tyr Gln Phe Gly Ala His Gly Gln Lys
            20                  25                  30

Thr Ala Glu Lys His Lys Tyr Thr His Ser Glu Met Pro Glu Glu Glu
        35                  40                  45

Asn Thr Gly Phe Val Asn Lys Gly Asp Val Leu Ser Gly His Arg Thr
50                  55                  60

Ile Lys Ala Glu Val Pro Val Leu Asp Thr Gln Lys Asp Glu Pro Trp
65                  70                  75                  80

Ala Ser Arg Arg Gln Gly Gln Gly Asp Gly Glu His Gln Thr Lys Asn
                85                  90                  95

Ser Leu Arg Ser Ile Asn Phe Leu Thr Leu His Ser Asn Pro Gly Leu
            100                 105                 110

Ala Ser Asp Asn Gln Glu Ser Asn Ser Gly Ser Ser Arg Glu Gln His
        115                 120                 125

Ser Ser Glu His His Gln Pro Arg Arg His Arg Lys His Gly Asn Met
130                 135                 140

Ala Gly Gln Trp Ala Leu Arg Gly Glu Ser Pro Val Asp Ala Leu Gly
145                 150                 155                 160

Leu Val Arg Glu Arg Asn Thr Trp Lys Tyr Asn Lys Asn Thr Val Gly
                165                 170                 175

Leu Asp Glu Asn Asn Asn Gly Ser Glu Glu Glu Ala Gly Glu Glu
            180                 185                 190

Glu Asp Glu Glu Trp Gly Glu Glu Thr Asp Tyr Arg Asp Met Lys His
        195                 200                 205
```

```
Arg Ala Arg Gly Thr Ser His Gly Arg Glu Tyr Arg Arg Trp Gln Asn
    210                 215                 220
Glu Asn Ser Arg Pro Ser Gly Glu Phe Leu Arg Asp Ser Ser Leu Pro
225                 230                 235                 240
Val Arg Ile Thr Lys Arg His Gly Glu Lys Phe Ser Met Glu Glu
            245                 250                 255
Ser Gln Glu Lys Leu Tyr Lys Glu Gly Lys Leu Pro Leu Ser Lys Lys
        260                 265                 270
Asn His Asn Glu Asp Gln Gly Glu Lys Arg Gln Ser Glu Glu Ser Lys
        275                 280                 285
Glu His Phe Gln Val Val Asn Gln Arg Lys His Arg Ala Val Thr Lys
        290                 295                 300
Arg Gln Asp Lys Glu Gly Ser Asn Ala Glu Glu Asp Asn Asp Ser
305                 310                 315                 320
Gly Asp Asp Gly Glu Glu Asp Leu Gly Asn Val Trp Arg Glu Ala Val
                325                 330                 335
Tyr Glu Glu Glu Arg Met Gln Ser Asn Asp Gln Asp Ser Ile Thr
                340                 345                 350
Asn Lys Gln Lys Glu Glu Ile Thr Ala Gly Asp Ser Gly Val Tyr
        355                 360                 365
Arg Glu Met Gln Asp Tyr Lys Gly Asp Lys Ile Lys Asp Val Thr His
        370                 375                 380
Ser Glu Asp Asn His Tyr His His Glu Pro Pro Asn Ser Ser Ser Lys
385                 390                 395                 400
Gln Gln Leu Gln Thr Ser Ser Val Glu Ser Met Asn Ser Thr Glu
                405                 410                 415
His Glu Asp Glu Val Lys Thr Thr Gly Gly Ser Tyr His Glu Glu Ser
                420                 425                 430
Ala Arg Asn Ser Thr Gly Lys Ala Leu Pro Asp Leu Cys Arg Asn Phe
        435                 440                 445
His Cys Lys Arg Gly Lys Val Cys Gln Ala Asp Lys Gln Gly Lys Pro
        450                 455                 460
Ser Cys Ile Cys Gln Asp Pro Ala Ala Cys Pro Ser Thr Lys Asp Tyr
465                 470                 475                 480
Lys Arg Val Cys Gly Thr Asp Asn Lys Thr Tyr Asp Gly Thr Cys Gln
                485                 490                 495
Leu Phe Gly Thr Lys Cys Gln Leu Glu Gly Thr Lys Met Gly Arg Gln
                500                 505                 510
Leu His Leu Asp Tyr Met Gly Ala Cys Lys His Ile Pro His Cys Thr
        515                 520                 525
Asp Tyr Glu Val Asn Gln Phe Pro Leu Arg Met Arg Asp Trp Leu Lys
        530                 535                 540
Asn Ile Leu Met Gln Tyr Tyr Glu Arg Asp Gln Asp Thr Ser Ala Phe
545                 550                 555                 560
Leu Thr Glu Lys Gln Arg Asn Lys Val Lys Lys Ile Tyr Leu Asn Glu
                565                 570                 575
Lys Arg Leu Val Ser Gly Glu His Pro Val Glu Leu Leu His Asp
                580                 585                 590
Phe Glu Lys Asn Tyr His Met Tyr Leu Tyr Pro Val His Trp Gln Phe
        595                 600                 605
Tyr Gln Leu Asp Gln His Pro Val Asp Arg Ser Leu Thr His Ser Glu
        610                 615                 620
Leu Ala Pro Leu Arg Ala Ser Leu Val Pro Met Glu His Cys Ile Thr
625                 630                 635                 640
```

```
Arg Phe Phe Gln Glu Cys Asp Gly Asp Gln Asp Lys Leu Ile Thr Leu
                645                 650                 655
Lys Glu Trp Cys His Cys Phe Ala Ile Lys Glu Glu Asp Ile Asn Glu
        660                 665                 670
Asn Leu Leu Phe
        675

<210> SEQ ID NO 49
<211> LENGTH: 4
<212> TYPE: PRT
<213> ORGANISM: Unknown
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 49

Arg Xaa Lys Arg
1

<210> SEQ ID NO 50
<211> LENGTH: 12
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (4)..(6)
<223> OTHER INFORMATION: n is a, c, g, or t

<400> SEQUENCE: 50
cgcnnnaagc gc                                                         12

<210> SEQ ID NO 51
<211> LENGTH: 6
<212> TYPE: PRT
<213> ORGANISM: Unknown
<220> FEATURE:
<223> OTHER INFORMATION: Synthetic

<400> SEQUENCE: 51

Pro Leu Gly Leu Trp Ala
1               5

<210> SEQ ID NO 52
<211> LENGTH: 18
<212> TYPE: DNA
<213> ORGANISM: Unknown
<220> FEATURE:
<223> OTHER INFORMATION: Synthetic

<400> SEQUENCE: 52
cccctgggcc tgtgggcc                                                   18

<210> SEQ ID NO 53
<211> LENGTH: 6
<212> TYPE: PRT
<213> ORGANISM: Unknown
<220> FEATURE:
<223> OTHER INFORMATION: Synthetic

<400> SEQUENCE: 53

Tyr Glu Val Asp Gly Trp
1               5
```

<210> SEQ ID NO 54
<211> LENGTH: 18
<212> TYPE: DNA
<213> ORGANISM: Unknown
<220> FEATURE:
<223> OTHER INFORMATION: Synthetic

<400> SEQUENCE: 54
tacgaggtgg acggctgg                                                   18

<210> SEQ ID NO 55
<211> LENGTH: 7
<212> TYPE: PRT
<213> ORGANISM: Unknown
<220> FEATURE:
<223> OTHER INFORMATION: Synthetic

<400> SEQUENCE: 55

Val Asp Val Ala Asp Gly Trp
1               5

<210> SEQ ID NO 56
<211> LENGTH: 21
<212> TYPE: DNA
<213> ORGANISM: Unknown
<220> FEATURE:
<223> OTHER INFORMATION: Synthetic

<400> SEQUENCE: 56
gtggacgtgg ccgacggctg g                                               21

<210> SEQ ID NO 57
<211> LENGTH: 7
<212> TYPE: PRT
<213> ORGANISM: Unknown
<220> FEATURE:
<223> OTHER INFORMATION: Synthetic

<400> SEQUENCE: 57

Val Asp Gln Met Asp Gly Trp
1               5

<210> SEQ ID NO 58
<211> LENGTH: 21
<212> TYPE: DNA
<213> ORGANISM: Unknown
<220> FEATURE:
<223> OTHER INFORMATION: Synthetic

<400> SEQUENCE: 58
gtggaccaga tggacggctg g                                               21

<210> SEQ ID NO 59
<211> LENGTH: 6
<212> TYPE: PRT
<213> ORGANISM: Unknown
<220> FEATURE:
<223> OTHER INFORMATION: Synthetic

<400> SEQUENCE: 59

Leu Glu Val Asp Gly Trp
1               5

<210> SEQ ID NO 60
<211> LENGTH: 18
<212> TYPE: DNA

```
<213> ORGANISM: Unknown
<220> FEATURE:
<223> OTHER INFORMATION: Synthetic

<400> SEQUENCE: 60
ctggaggtgg acggctgg                                                   18

<210> SEQ ID NO 61
<211> LENGTH: 6
<212> TYPE: PRT
<213> ORGANISM: Unknown
<220> FEATURE:
<223> OTHER INFORMATION: Synthetic

<400> SEQUENCE: 61

Val Gln Val Asp Gly Trp
1               5

<210> SEQ ID NO 62
<211> LENGTH: 18
<212> TYPE: DNA
<213> ORGANISM: Unknown
<220> FEATURE:
<223> OTHER INFORMATION: Synthetic

<400> SEQUENCE: 62
gtgcaggtgg acggctgg                                                   18

<210> SEQ ID NO 63
<211> LENGTH: 7
<212> TYPE: PRT
<213> ORGANISM: Unknown
<220> FEATURE:
<223> OTHER INFORMATION: Synthetic

<400> SEQUENCE: 63

Val Asp Gln Val Asp Gly Trp
1               5

<210> SEQ ID NO 64
<211> LENGTH: 21
<212> TYPE: DNA
<213> ORGANISM: Unknown
<220> FEATURE:
<223> OTHER INFORMATION: Synthetic

<400> SEQUENCE: 64
gtggaccagg tggacggctg g                                               21

<210> SEQ ID NO 65
<211> LENGTH: 4
<212> TYPE: PRT
<213> ORGANISM: Unknown
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 65

Asp Xaa Xaa Asp
1

<210> SEQ ID NO 66
<211> LENGTH: 12
<212> TYPE: DNA
<213> ORGANISM: Unknown
```

```
<220> FEATURE:
<223> OTHER INFORMATION: Synthetic
<220> FEATURE:
<221> NAME/KEY: misc_feature
<222> LOCATION: (4)..(9)
<223> OTHER INFORMATION: n is a, c, g, or t

<400> SEQUENCE: 66
gacnnnnnng ac                                                              12

<210> SEQ ID NO 67
<211> LENGTH: 4
<212> TYPE: PRT
<213> ORGANISM: Unknown
<220> FEATURE:
<223> OTHER INFORMATION: Synthetic

<400> SEQUENCE: 67

Arg Gly Leu Thr
1

<210> SEQ ID NO 68
<211> LENGTH: 12
<212> TYPE: DNA
<213> ORGANISM: Unknown
<220> FEATURE:
<223> OTHER INFORMATION: Synthetic

<400> SEQUENCE: 68
cgcggcctga cc                                                              12

<210> SEQ ID NO 69
<211> LENGTH: 17
<212> TYPE: PRT
<213> ORGANISM: Unknown
<220> FEATURE:
<223> OTHER INFORMATION: Synthetic

<400> SEQUENCE: 69

Asn Phe Asp Leu Leu Lys Leu Ala Gly Asp Val Glu Ser Asn Pro Gly
1               5                   10                  15

Pro

<210> SEQ ID NO 70
<211> LENGTH: 51
<212> TYPE: DNA
<213> ORGANISM: Unknown
<220> FEATURE:
<223> OTHER INFORMATION: Synthetic

<400> SEQUENCE: 70
aacttcgacc tgctgaagct ggccggcgac gtggagagca accccggccc c                   51

<210> SEQ ID NO 71
<211> LENGTH: 4
<212> TYPE: PRT
<213> ORGANISM: Unknown
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 71
```

Ala Xaa Ala Xaa
1

<210> SEQ ID NO 72
<211> LENGTH: 12
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (4)..(6)
<223> OTHER INFORMATION: can be any of a, t, g, and c
<220> FEATURE:
<221> NAME/KEY: misc_feature
<222> LOCATION: (10)..(12)
<223> OTHER INFORMATION: can be any of a, t, g, and c

<400> SEQUENCE: 72
gccnnngccn nn                                                         12

<210> SEQ ID NO 73
<211> LENGTH: 4
<212> TYPE: PRT
<213> ORGANISM: Unknown
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 73

Leu Thr Lys Xaa
1

<210> SEQ ID NO 74
<211> LENGTH: 10
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t

<400> SEQUENCE: 74 ctgaccaagn                                                            10

<210> SEQ ID NO 75
<211> LENGTH: 9
<212> TYPE: PRT
<213> ORGANISM: Unknown
<220> FEATURE:
<223> OTHER INFORMATION: Synthetic

<400> SEQUENCE: 75

Gly Gly Phe Leu Arg Lys Val Gly Gln
1               5

<210> SEQ ID NO 76
<211> LENGTH: 27
<212> TYPE: DNA
<213> ORGANISM: Unknown
<220> FEATURE:
<223> OTHER INFORMATION: Synthetic

<400> SEQUENCE: 76

```
ggcggcttcc tgcgcaaggt gggccag                                        27
```

<210> SEQ ID NO 77
<211> LENGTH: 17
<212> TYPE: PRT
<213> ORGANISM: Unknown
<220> FEATURE:
<223> OTHER INFORMATION: Synthetic

<400> SEQUENCE: 77

Asn Phe Asp Leu Leu Lys Leu Ala Gly Asp Val Glu Ser Asn Pro Gly
1               5                   10                  15

Pro

<210> SEQ ID NO 78
<211> LENGTH: 23
<212> TYPE: DNA
<213> ORGANISM: Artificial
<220> FEATURE:
<223> OTHER INFORMATION: Synthetic

<400> SEQUENCE: 78

```
cgaagaggag gtggtggcgg aaa                                            23
```

<210> SEQ ID NO 79
<211> LENGTH: 26
<212> TYPE: DNA
<213> ORGANISM: Artificial
<220> FEATURE:
<223> OTHER INFORMATION: Synthetic

<400> SEQUENCE: 79

```
ggttgttgtc ctcatccctc tcatac                                         26
```

<210> SEQ ID NO 80
<211> LENGTH: 24
<212> TYPE: DNA
<213> ORGANISM: Artificial
<220> FEATURE:
<223> OTHER INFORMATION: Synthetic

<400> SEQUENCE: 80

```
ctctctgctc ctcctgttcg acag                                           24
```

<210> SEQ ID NO 81
<211> LENGTH: 24
<212> TYPE: DNA
<213> ORGANISM: Artificial
<220> FEATURE:
<223> OTHER INFORMATION: Synthetic

<400> SEQUENCE: 81

```
aggggtctta ctccttggag gcca                                           24
```

<210> SEQ ID NO 82
<211> LENGTH: 2762
<212> TYPE: DNA
<213> ORGANISM: Unknown
<220> FEATURE:
<223> OTHER INFORMATION: Synthroid
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t

```
<220> FEATURE:
<221> NAME/KEY: misc_feature
<222> LOCATION: (1141)..(1141)
<223> OTHER INFORMATION: n is a, c, g, or t
<220> FEATURE:
<221> NAME/KEY: misc_feature
<222> LOCATION: (1462)..(1462)
<223> OTHER INFORMATION: n is a, c, g, or t
<220> FEATURE:
<221> NAME/KEY: misc_feature
<222> LOCATION: (1525)..(1525)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1759)..(1759)
<223> OTHER INFORMATION: n is a, c, g, or t
<220> FEATURE:
<221> NAME/KEY: misc_feature
<222> LOCATION: (1782)..(1782)
<223> OTHER INFORMATION: n is a, c, g, or t
<220> FEATURE:
<221> NAME/KEY: misc_feature
<222> LOCATION: (1934)..(1934)
<223> OTHER INFORMATION: n is a, c, g, or t
<220> FEATURE:
<221> NAME/KEY: misc_feature
<222> LOCATION: (2521)..(2521)
<223> OTHER INFORMATION: n is a, c, g, or t
<220> FEATURE:
<221> NAME/KEY: misc_feature
<222> LOCATION: (2565)..(2565)
<223> OTHER INFORMATION: n is a, c, g, or t

<400> SEQUENCE: 82
cgggtgagag gccggcctgc cggcgaaccc aggagcttgc aacaaaaacg agggctgcct      60
gcaatattcc ctggcggcga ctgccggatc ctcgtctgtc acntggaaac tttgccaggc     120
tggcgggctc cagggcatta gtggccagtc gactagaatg tgcctctgtc cgagagacag     180
tgctggcgag aggaaatatt taagaagtat ctctgaggta tttgtcaaag tcctgttccc     240
tgtctgaaat gtgagagtg tattgaactt gaatttcttc tgtggatctg gtccagcacc     300
ttaccgaaca ctgggaactg tcaagtgggg gccttttgnc gtaaagtccc tgagaactgc     360
agctatatca ctgcaaatgc caggattaga atcatgttgc aaaccaacgc tgagatggtg     420
tccctcacag caccaacccc agtgcatgtg ccggaactgc acaaactgag agatgaaccc     480
cagcccccac agaaggcgag tctgagcgtg agggtgagca gtcatcagta atacagccaa     540
ggagcaagac cttggatact cagcaaataa ccagattcct gctgagaact ggaaaacgat     600
ctttgccaca gtgaggtcac ttaagtacag ctctggagta tgcaccacct caaggggcac     660
aggatccagg tggaatgact agttaatggg ctttgcaagg aaatcccagg aactcattgt     720
ttggtttgtg aggtgagctc attcgcagac cccaacgaat gcggggtag ccagatgaag      780 gcaaatcggg aatgagctgg aggaaattcg ggtcatcagc tgaagaggag cagtgaatgg     840
ggccaaggac ctgatgaccg agaatatgaa gagcagggtc caaatggctc gagtggtgaa     900
ggagaatgag gatgagggtc atgtgaagtc agtacccacc gtggtgacca cagagagata     960
ctagattgcc cagtacttat actaagaggc accatgagga atacaacttc cagtctgatg    1020
atattttgga agagttcggt cagggaagtc aagcacccta gattttagcg gatgattttc    1080
atgaggttca ccgagcagaa agagataact ccactgcagt aaacagcatg taagtgcttc    1140
nctcatcgta aacccataag aaacaaaagg caggatcagg aggacaacac tggtcaagag    1200
gatattaaaa tcataaagag atggaaggaa gactgtttcg atgcctctga agtggtctat    1260
```

```
tgacgatgat aatagcttgc ccagaaatga ttgggctggt tgcactggca atcagatgga    1320
ggcaatgact gtcggcaatg atagtgaagc ataggaaatt caggattact tcttccacag    1380
aaccagagtt tctcttcaac ccgaggagcc tcatcccctc cttcaatccc cttgaagttc    1440
agcagcaaaa gaagaagtgc anacaatttg ctgttctggt agcatggatt ctacagagta    1500
cgaagatgga gttaagacaa caganaaatc atgatatgag gtggaaatgc caagtgaagg    1560
cacgtgaggc catccctgga tttttgcagn aacttccact gcaaaagagg aaacatcttc    1620
cacgcagatt aacagggaaa atctcgctgt atttgtcagg atcctgcgat ttgtccttct    1680
accaaacgtc ttgatcgagt ttgtggcact gacaatcgga cctgtgctgg tctctgccaa    1740
ctttcgccac taaatgtcna ttgagggat cagaaggggg cntcaacttc agctggttta    1800
tattggtgcc tgcaaactca tacttacctg tacagatttt ggagtgattc agtttccttt    1860
ccggatgaga gactggctca aggatatccc caggcggcat tatgaaggta actccggaca    1920
tactggtttc taantgaaaa gcagagaaat aaggtcaaga atatttactt ggatgaaaag    1980
aggctctttt ctggggaaca cccctttgat cttctcttga agaactttaa gaaaatttac    2040
cacatgtatc tgtatcctgt gcactggaaa ttttgtgagc cttgcccaac acctatagaa    2100
tagacattgt cacattctga gctcagtcca ttgcgagcgt cttggtacct atggaacagt    2160
gcataacccg tttcttttcg gagtgtgacg gcaactaaga taaacttatc actttgagag    2220
agtggtgcca gtgctttggg attaaggaag aggacataaa tgaaaatctc ttgttttgag    2280
cccagattgt ggagaacaca actttcagca ctctctgttt ttaaggattc catgaatatt    2340
taaggctgta atagctagta tgtttatttt caggaataag ttggcataga gtactttgaa    2400
gcagaagaag tcgcttgtaa taacctatgt atccggttgt tagcattaac ttcagtaaca    2460
gaagtggcat ttgaatgaag ttaacataag ctaattagta tatactttaa acagaatttt    2520
ncttcacacg tactttgttc tctgtattaa gttatgagaa acttnatgat tgagttgttc    2580
acaataggaa taacgcatct gtagagttca tctaggatgt gcatttataa gaaaccgaag    2640
ctactgtttt gttatttatg tatattttt caatatctta atgtcctgat aaagagtcca    2700
tcaaaatcta aatagtaatg tcaaaaaaac tgaacttatt tggaataaaa aaaaaaaaaa    2760
aa                                                                  2762
```

<210> SEQ ID NO 83
<211> LENGTH: 636
<212> TYPE: PRT
<213> ORGANISM: Unknown
<220> FEATURE:
<223> OTHER INFORMATION: Synthetic

<400> SEQUENCE: 83

```
Met Lys Thr Gly Leu Leu Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Phe Asp Asn Thr Ala Ile Pro Glu Glu Lys Glu
        35                  40                  45

Thr Ala Val Ser Thr Glu Asp Asp Ser His His Lys Ala Glu Lys Ser
    50                  55                  60

Ser Val Leu Leu Ala Ser Glu Glu Ser His Glu Ala Ser Ala Glu Gln
65                  70                  75                  80

Gly Lys Ser Ser Lys Asp Gln Glu Asp Gly Asp Gly His Leu Ser Val
                85                  90                  95
```

```
Asn Leu Leu Tyr Ala Pro Ser Glu Gly Thr Leu Asp Ile Lys Glu Asp
            100                 105                 110
Met Ile Glu Pro Gln Glu Lys Lys Leu Ser Glu Ser Thr Asp Phe Leu
            115                 120                 125
Ala Phe Thr Asp Ser Asn Gln Gln Glu Ser Ile Thr Lys Arg Glu Glu
            130                 135                 140
Asn Gln Glu Gln Pro Arg Asn Tyr Ser His His Gln Leu Asn Arg Ser
145                 150                 155                 160
Ser Lys His Ser Gln Gly Leu Arg Glu Gln Gly Asn Ile Glu Gln Ile
                165                 170                 175
Ser Asn Gly Glu Glu Glu Lys Glu Pro Gly Glu Val Gly Thr His
                180                 185                 190
Asn Asp Asn Gln Glu Arg Ala Thr Glu Leu Pro Gly Glu His Ala Gly
                195                 200                 205
Ser Glu Gln Glu Glu Ser Asn Thr Gln Ser Asp Asp Ile Leu Glu Glu
            210                 215                 220
Ser Asp Gln Pro Thr Gln Val Ser Lys Met Gln Glu Asp Glu Phe Asp
225                 230                 235                 240
Gln Gly Asn Glu Glu Gln Glu Asp Asn Ser Asn Ala Glu Met Glu Glu
                245                 250                 255
Ser Asn Ala Ser Leu Val Asn Lys Glu Ile Gln Glu Thr Glu Trp Gln
            260                 265                 270
Ser Gln Glu Gly Lys Thr Gly Leu Glu Ala Ile Ser Asn His Lys Glu
            275                 280                 285
Thr Glu Glu Glu Thr Val Ser Glu Ala Leu Pro Thr Asp Asp Gly Asn
            290                 295                 300
Thr Thr Pro Arg Asn Ala Gly Val Asp Asp Gly Asp Asp Gly
305                 310                 315                 320
Asp Asp Gly Gly Thr Asp Gly Pro Arg His Ser Ala Ser Asp Ile
                325                 330                 335
Pro Gly Gln Ala Phe Leu Glu Ala Glu Arg Ala Gln Ser Ile Ala Tyr
                340                 345                 350
His Leu Lys Ile Glu Glu Gln Lys Glu Lys Val Gln Glu Asn Glu Val
            355                 360                 365
Ile Gly Thr Thr Glu Pro Gly Glu His Gln Glu Ala Asn Lys Ala Glu
            370                 375                 380
Asn Ser Ser Asn Glu Glu Glu Thr Ser Ser Glu Glu Gly Asn Met Arg
385                 390                 395                 400
Val Glu Val Asp Ser Cys Met Ser Phe Gln Cys Lys Arg Gly His Ile
                405                 410                 415
Cys Lys Ala Asp Gln Gln Gly Lys Pro His Cys Val Cys Gln Asp Pro
                420                 425                 430
Val Thr Cys Pro Pro Thr Lys Pro Leu Gln Gln Val Cys Gly Thr Asp
            435                 440                 445
Asn Gln Thr Tyr Ala Ser Ser Cys His Leu Phe Ala Thr Lys Cys Arg
    450                 455                 460
Leu Glu Gly Thr Lys Lys Gly His Gln Leu Gln Leu Asp Tyr Phe Gly
465                 470                 475                 480
Ala Cys Lys Ser Ile Pro Thr Cys Thr Asp Phe Glu Val Ile Gln Phe
                485                 490                 495
Pro Leu Arg Met Arg Asp Trp Leu Lys Asn Ile Leu Met Gln Leu Tyr
            500                 505                 510
Glu Ala Asn Ser Glu His Ala Gly Tyr Leu Asn Glu Lys Gln Arg Asn
```

-continued

```
                    515                     520                     525
Lys Val Lys Lys Ile Tyr Leu Asp Glu Lys Arg Leu Leu Ala Gly Asp
    530                     535                     540

His Pro Ile Asp Leu Leu Leu Arg Asp Phe Lys Lys Met His Met Tyr
545                     550                     555                     560

Val Tyr Pro Val His Trp Gln Phe Ser Glu Leu Asp Gln His Pro Met
                565                     570                     575

Asp Arg Val Leu Thr His Ser Glu Leu Ala Pro Leu Arg Ala Ser Leu
            580                     585                     590

Val Pro Met Glu His Cys Ile Thr Arg Glu Phe Glu Glu Cys Asp Pro
        595                     600                     605

Asn Lys Asp Lys His Ile Thr Leu Lys Glu Trp Gly His Cys Phe Gly
    610                     615                     620

Ile Lys Glu Glu Asp Ile Asp Glu Asn Leu Leu Phe
625                     630                     635
```

What is claimed is:

1. A method for in vivo sensitizing a mammal diagnosed with cancer to a chemotherapy agent, said method comprising:
obtaining a tumor sample from the mammal diagnosed with cancer;
determining a tumor SPARC level in the tumor sample;
comparing the tumor SPARC level to historical correlation data to determine if the tumor SPARC level is below a threshold level; and
if the tumor SPARC level is below the threshold level, administering therapeutically effective amounts of an isolated SPARC family polynucleotide and the chemotherapy agent, wherein said isolated SPARC family polynucleotide expresses a polypeptide comprising SEQ ID NO:1.

2. The method of claim 1, wherein the isolated SPARC family polynucleotide is carried in a virus or liposome.

3. The method of claim 1, wherein the isolated SPARC family polynucleotide and the chemotherapy agent are carried in a liposome.

4. The method of claim 1, further comprising administering a pharmaceutically acceptable carrier.

5. The method of claim 1, wherein the chemotherapy agent is one or more of actinomycin D, adriamycin, altretamine, asparaginase, bleomycin, busulphan, capecitabine, carboplatin, carmustine, chlorambucil, cisplatin, CPT-11, cyclophosphamide, cytarabine, dacarbazine, daunorubicin, doxorubicin, epirubicin, etoposide, fludarabine, fluorouracil, gemcitabine, hydroxyurea, idarubicin, fosfamide, irinotecan, liposomal doxorubicin, lomustine, melphalan, mercaptopurine, methotrexate, mitomycin, mitozantrone, oxaliplatin, procarbazine, steroids, streptozocin, taxol, taxotere, taxotere, tamozolomide, thioguanine, thiotepa, tomudex, topotecan, treosulfan, vinblastine, vincristine, vindesine or vinorelbine.

6. The method of claim 5, wherein the chemotherapy agent includes a taxol.

7. The method of claim 5, wherein the chemotherapy agent includes fluorouracil.

8. The method of claim 1, wherein said mammal exhibits resistance to said chemotherapy agent.

9. The method of claim 1, wherein the mammal is a human patient.

10. The method of claim 1, wherein said isolated SPARC family polynucleotide further comprises tissue specific expression elements that limit the expression of the polypeptide comprising SEQ ID NO: 1 to cells of the cancer and cells of the cancer's tissue of origin.

11. The method of claim 10 wherein the tissue specific expression elements are selected from the group consisting of the Immunoglobulin Heavy Chain enhancer; Immunoglobulin Light Chain enhancer; T-Cell Receptor enhancer; HLA DQα enhancer; HLA DQβ enhancers; β-Interferon enhancer; interleukin-2 enhancer; Interleukin-2 Receptor enhancer; MHC Class II HLA-DRα enhancer; β-Actin enhancer; Muscle Creatine Kinase enhancer; the Transthyretin enhancer; Prealbumin enhancer; Elastase I enhancer; Metallothionein enhancer; Collagenase enhancer; Albumin Gene enhancer; α-Fetoprotein enhancer; β-Globin enhancer; c-fos enhancer; Insulin enhancer; Neural Cell Adhesion Molecule (NCAM) enhancer; α₁Antitrypsin enhancer; Mouse or Type I Collagen enhancer; Glucose-Regulated Proteins (GRP94 and GRP78) enhancer; Rat Growth Hormone enhancer; Human Serum Amyloid A (SAA) enhancer; Troponin I (TN I) enhancer; Platelet-Derived Growth Factor enhancer; Duchenne Muscular Dystrophy enhancer; and Gibbon Ape Leukemia Virus enhancer.

* * * * *